United States Patent
Spurbeck et al.

(10) Patent No.: US 11,702,653 B2
(45) Date of Patent: Jul. 18, 2023

(54) CONTROL COMPOSITIONS AND METHODS FOR SEQUENCING

(71) Applicant: BATTELLE MEMORIAL INSTITUTE, Columbus, OH (US)

(72) Inventors: Rachel R. Spurbeck, Columbus, OH (US); Richard Mon Che Chou, Columbus, OH (US); Anthony D. Duong, Columbus, OH (US)

(73) Assignee: BATTELLE MEMORIAL INSTITUTE, Columbus, OH (US)

( * ) Notice: Subject to any disclaimer, the term of this patent is extended or adjusted under 35 U.S.C. 154(b) by 0 days.

(21) Appl. No.: 16/418,521

(22) Filed: May 21, 2019

(65) Prior Publication Data

US 2019/0382757 A1    Dec. 19, 2019

Related U.S. Application Data

(60) Provisional application No. 62/801,520, filed on Feb. 5, 2019, provisional application No. 62/703,266, filed on Jul. 25, 2018, provisional application No. 62/674,533, filed on May 21, 2018.

(51) Int. Cl.
| | | |
|---|---|---|
| C12N 15/10 | (2006.01) | |
| C12N 15/113 | (2010.01) | |
| C12Q 1/6869 | (2018.01) | |
| C12Q 1/6876 | (2018.01) | |

(52) U.S. Cl.
CPC ........ *C12N 15/1089* (2013.01); *C12N 15/113* (2013.01); *C12Q 1/6869* (2013.01); *C12Q 1/6876* (2013.01); *C12Q 2563/185* (2013.01); *C12Q 2600/166* (2013.01)

(58) Field of Classification Search
None
See application file for complete search history.

(56) References Cited

U.S. PATENT DOCUMENTS

| | | |
|---|---|---|
| 2006/0058249 A1 | 3/2006 | Tong et al. |
| 2006/0073506 A1 | 4/2006 | Frederick |
| 2007/0072212 A1 | 3/2007 | Vinayagamoorthy |
| 2008/0254453 A1 | 10/2008 | Shapero |
| 2010/0240064 A1 | 9/2010 | Jeddeloh |
| 2011/0076726 A1 | 3/2011 | Lakey |
| 2012/0208193 A1 | 8/2012 | Okino |
| 2015/0322508 A1 | 11/2015 | Miguel |
| 2016/0257984 A1 | 9/2016 | Hardenbol et al. |
| 2016/0257993 A1 | 9/2016 | Fu et al. |
| 2016/0281182 A1 | 9/2016 | Monpoeho et al. |
| 2017/0275691 A1 | 9/2017 | Christians et al. |
| 2017/0292149 A1 | 10/2017 | Sherwood |
| 2019/0300948 A1 | 10/2019 | Cuppens |
| 2020/0277672 A1 | 9/2020 | Freeman |

FOREIGN PATENT DOCUMENTS

| | | |
|---|---|---|
| EP | 3246412 | 11/2017 |
| WO | 2004083819 | 9/2004 |
| WO | 2009/036525 | 3/2009 |
| WO | WO2011/156795 | 12/2011 |
| WO | 2016179530 | 11/2016 |
| WO | 2017058936 | 4/2017 |
| WO | 2017/165864 | 9/2017 |
| WO | 2017192974 | 11/2017 |
| WO | 2018119301 | 6/2018 |
| WO | 2019/226648 | 11/2019 |

OTHER PUBLICATIONS

Kaifu Chen et al. The Overlooked Fact: Fundamental Need for Spike-In Control for Virtually All Genome-Wide Analyses Molecular and Cellular Biology Mar. 2016 vol. 36 No. 5.*
Qu et al. Development of ERCC RNA Spike-In Control Mixes J Biomol Tech. Oct. 2011; 22(Suppl): S46.*
Wong et al. ANAQUIN: a software toolkit for the analysis of spike-in controls for next generation sequencing Bioinformatics, 33(11), 2017, 1723-1724 doi: 10.1093/bioinformatics/btx038 Advance Access Publication Date: Jan. 27, 2017.*
Quail et al. SASI-Seq: sample assurance Spike-Ins, and highly differentiating 384 barcoding for Illumina sequencing BMC Genomics vol. 15, Article No. 110 (2014) Published: Feb. 7, 2014.*
Chen et al. Effects of GC Bias in Next-Generation-Sequencing Data on De Novo Genome Assembly PLoS ONE 8(4): e62856. doi:10. 1371/journal.pone.0062856.*
Kojima et al Nucleic Acids Research, 2005, vol. 33, No. 17 e150 doi: 10.1093/nar/gni143.*
Dauphin et al Journal of Applied Microbiology 108 (2010) 163-172.*
Hammer et al. FEBS Letters 586 (2012) 2882-2890.*
Zelikin et al. vol. ACSNANO 1 ■ No. 1 ■ 63-69 ■ 2007.*
O'Connell et al. (High Interspecimen Variability in Nucleic Acid Extraction Efficiency Necessitates the Use of Spike-In Control for Accurate qPCR-based Measurement of Plasma Cell-Free DNA Levels, Laboratory Medicine 48:4:332-338, DOI: 10.1093/labmed/lmx043.*
Stoeckel et al. Water Research 42 4820-4827, Jun. 4, 2009.*
Zhang et al. (Results of first proficiency test for KRAS testing with formalin-fixed, paraffin-embedded cell lines in China, Clin Chem Lab Med 2014; 52(12): 1851-1857.*

(Continued)

*Primary Examiner* — Joseph Woitach
(74) *Attorney, Agent, or Firm* — Barnes & Thornburg LLP

(57) ABSTRACT

The invention relates to control compositions for sequencing and for chemical analyses, such as analytical chemistry analyses. More particularly, the invention relates to control compositions for sequencing and for chemical analyses having at least one barcode sequence fragment and at least one universal sequence fragment, and to methods of their use.

16 Claims, 14 Drawing Sheets

Specification includes a Sequence Listing.

(56) References Cited

OTHER PUBLICATIONS

Sundquist et al Identifying and Preventing DNA Contamination in a DNA-Typing Laboratory Promega.com, Sep. 2005.*
Kozarewa et al. Nature Methods 2009; 6:291-295.
Jiang, L. et al., "Synthetic spike-in standards for RNA-seq experiments," Genome Research, 2011, 21(9) 1543-51.

* cited by examiner

| Soil Sample | Count R1 | Count R2 | Raw Read Count | Ccc1 Identification |
|---|---|---|---|---|
| CCC1-ENCAPSULATED | 173,762 | 2 | 250,385 | 69% |
| CCC1-NONENCAPSULATED | 214,749 | 1 | 290,048 | 74% |
| CCC2-ENCAPSULATED | 385 | 0 | 202,662 | 0% |
| CCC2-NONENCAPSULATED | 375 | 0 | 182,636 | 0% |
| CCC1-CCC2-ENCAPSULATED | 83,406 | 1 | 175,396 | 48% |

| Soil Sample | Count R1 | Count R2 | Raw Read Count | CCC2 Identification |
|---|---|---|---|---|
| CCC1-ENCAPSULATED | 1,437 | 0 | 250,385 | 1% |
| CCC1-NONENCAPSULATED | 631 | 0 | 290,048 | 0% |
| CCC2-ENCAPSULATED | 121,097 | 1 | 202,662 | 60% |
| CCC2-NONENCAPSULATED | 122,405 | 1 | 182,636 | 67% |
| CCC1-CCC2-ENCAPSULATED | 53,703 | 1 | 175,396 | 31% |

*FIG. 4*

Low Quantity Standard

High Quantity Standard

CONTROL COMPOSITIONS AND METHODS FOR SEQUENCING

CROSS-REFERENCE TO RELATED APPLICATIONS

This application claims priority under 35 U.S.C. § 119(e) to U.S. Provisional Application Ser. No. 62/674,533 filed on May 21, 2018, U.S. Provisional Application Ser. No. 62/703,266 filed on Jul. 25, 2018 and U.S. Provisional Application Ser. No. 62/801,520 filed on Feb. 5, 2019, the entire disclosures of which are incorporated herein by reference.

SEQUENCE LISTING

The instant application contains a Sequence Listing which has been submitted electronically in ASCII format and is hereby incorporated by reference in its entirety. Said ASCII copy, created on Jul. 10, 2019, is named 920006-295629_SL.txt and is 777,782 bytes in size.

FIELD OF THE DISCLOSURE

The invention relates to control compositions for sequencing and chemical analyses. More particularly, the invention relates to control compositions for sequencing and chemical analyses having at least one barcode sequence fragment and at least one universal sequence fragment, and to methods of their use.

BACKGROUND AND SUMMARY OF THE INVENTION

Sequencing controls are needed that can be used starting after the extraction step (e.g., by spiking the extract with the control constructs) or in every step of analysis of an unknown test sample (e.g., from nucleic acid extraction to nucleic acid purification to library preparation and sequencing). Sample swapping or sample-to-sample contamination can occur during any of these steps, but without a priori knowledge of what is in the sample, one may not know if the samples were contaminated or just contained similar genetic profiles. Also, sequencing controls that can be used both for 1) detection of sample swapping and sample-to-sample contamination, and 2) quantitation are needed.

For quantitation, metagenomic communities are currently analyzed by determining the relative abundance of 16S genes or unique k-mers that can differentiate microbial species and strains. However, the methods used to process the samples can influence the relative abundance of the community members. For example, during DNA extraction, the chemical or physical lysis process can bias the analysis due to different lysis efficiencies for different microbial membranes and cell wall compositions (e.g., fungi typically are underrepresented in metagenomes due to lysis resistance). After DNA extraction, the library preparation method can also add additional bias. As an example, amplification of library molecules relies on polymerases which can bias results towards fifty percent GC content fragments or shorter fragments versus longer molecules, as polymerases tend to amplify shorter fragments and lower GC content or balanced molecules faster than molecules with high GC content.

Analytical chemistry analysis of unknown materials can be confounded by identification of compounds that do not seem to fit with what is expected. These unexpected compounds could be the result of a cross contamination event or may actually be present in the sample. Therefore, spike-in cross contamination and sample swapping controls are also needed for analytical chemistry analyses.

The present invention provides sequencing controls that can be used starting after the extraction step (e.g., by spiking the extract with the control constructs) or in every step of analysis of an unknown test sample (e.g., from nucleic acid extraction to nucleic acid purification to library preparation and sequencing). In one embodiment, nucleic acid constructs comprising a barcode sequence fragment are provided that can be encapsulated in a simulated cell membrane (e.g., a simulated bacterial cell membrane or eukaryotic cell membrane), or embedded directly in the genome of an organism for use as spike-in sequencing controls. In one aspect, the barcode sequence fragment comprises a unique sequence not present in any known genome. In one embodiment, the sequencing controls can be spiked into the unknown test sample prior to or after nucleic acid extraction and then can be detected in the final sequenced samples. In another embodiment, different nucleic acid constructs (i.e., with different barcode sequence fragments) can be spiked into different samples so that cross-contamination of samples or sample swapping can be detected.

In one embodiment, the barcode sequence fragment can be flanked by universal sequence fragments. The universal sequence fragments can add length to the nucleic acid construct and can serve as markers for bioinformatic analysis to identify the beginning and end of the barcode sequence fragment after sequencing. In another illustrative aspect, the barcode sequence fragment may be flanked by primer binding site sequence fragments (i.e., directly or indirectly linked to the barcode sequence fragment) so that the nucleic acid construct comprising the barcode sequence fragment can be amplified during an amplicon sequencing protocol. In another embodiment, primer binding site sequence fragments may be lacking for use of the sequencing controls in whole genome sequencing protocols. In another embodiment, a set of different nucleic acid construct spike-ins with different barcode sequence fragments (e.g., 384 or 96 different barcode sequence fragments) can be used to allow for multiplexing of samples on one sequencing run.

In various embodiments, samples with microorganisms containing nucleic acids (e.g., DNA), or samples with other sources of nucleic acids, may be analyzed by sequencing using the control compositions for sequencing described herein. The samples can be, for example, selected from the group consisting of urine, nasal secretions, nasal washes, inner ear fluids, bronchial lavages, bronchial washes, alveolar lavages, spinal fluid, bone marrow aspirates, sputum, pleural fluids, synovial fluids, pericardial fluids, peritoneal fluids, saliva, tears, gastric secretions, stool, reproductive tract secretions, lymph fluid, whole blood, serum, plasma, a tissue sample, a soil sample, a water sample, a food sample, an air sample, a plant sample, an industrial waste sample, a surface wipe sample, a dust sample, a hair sample, and an animal sample.

In another embodiment, a method is provided for the use of spike-in controls that simultaneously 1) control for cross-contamination and/or sample swapping and 2) allow for quantitation while controlling for different GC content samples (e.g., low, balanced, and high GC content) and/or for different lysis efficiencies. In one aspect, barcoded DNA molecules are produced with different GC contents, using GC content fragments, wherein the barcode sequence fragments and the GC content fragments are flanked by universal sequence fragments, and then the nucleic acid construct is encapsulated in a simulated cell membrane. By using the same type of nucleic acid construct, but with different barcode sequence fragments, different quantities of the encapsulated nucleic acid construct can be spiked-in, and a standard curve for quantitation can be produced. In this embodiment, the barcode sequence fragments can be used to verify that no cross-contamination or sample swapping occurred during sample preparation or processing. Also in this quantitation embodiment, the different GC content fragments (e.g., low, balanced, and high GC content) have the same barcode sequence fragment at each GC percentage (e.g., low, balanced, and high GC content), but at each separate concentration of the nucleic acid construct used to produce the standard curve, the barcode sequence fragments are unique to each concentration used to produce the standard curve. In this embodiment, the encapsulation method can also be varied to control for different resistances to lysis to mimic, for example, Gram positive, Gram negative, and fungal cell walls. In this encapsulation embodiment, the type of encapsulation method can be correlated to a unique barcode sequence fragment in the nucleic acid construct to enable differentiation post sequencing.

The present invention also provides spike-in cross-contamination and sample swapping controls for analytical chemistry analysis of unknown materials. These controls can be used in analytical chemistry procedures, such as mass spectrometry.

The following clauses, and combinations thereof, provide various additional illustrative aspects of the invention described herein. The various embodiments described in any other section of this patent application, including the section titled "DETAILED DESCRIPTION OF ILLUSTRATIVE EMBODIMENTS" and the "EXAMPLES" are applicable to any of the following embodiments of the invention described in the numbered clauses below.

1. A sequencing control composition, said control composition comprising a nucleic acid construct comprising at least one barcode sequence fragment linked at its 5' or 3' end to at least one universal sequence fragment.
2. The control composition of clause 1 wherein the control composition is used to determine if cross-contamination between samples for sequencing has occurred.
3. The control composition of clause 1 wherein the control composition is used to determine if sample swapping has occurred.
4. The control composition of any one of clauses 1 to 3 wherein the nucleic acid construct is a deoxyribonucleic acid construct.
5. The control composition of any one of clauses 1 to 4 wherein the nucleic acid construct comprises at least a first and a second universal sequence fragment.
6. The control composition of clause 5 wherein the first universal sequence fragment is linked to the 5' end of the barcode sequence fragment and the second universal sequence fragment is linked to the 3' end of the barcode sequence fragment.
7. The control composition of any one of clauses 1 to 6 wherein the nucleic acid construct further comprises at least a first and a second primer binding site fragment.
8. The control composition of clause 6 wherein the nucleic acid construct further comprises at least a first and a second primer binding site fragment and wherein the first primer binding site fragment is linked at its 3' end to the 5' end of the first universal sequence fragment and the second primer binding site fragment is linked at its 5' end to the 3' end of the second universal sequence fragment.
9. The control composition of clause 8 wherein the primer binding site fragments range in length from about 15 base pairs to about 30 base pairs.
10. The control composition of clause 8 wherein the nucleic acid construct ranges in length from about 80 base pairs to about 300 base pairs.
11. The control composition of any one of clauses 1 to 6 wherein the sequencing is whole genome sequencing.
12. The control composition of any one of clauses 7 to 10 wherein the sequencing is amplicon sequencing.
13. The control composition of any one of clauses 1 to 12 wherein the sequencing is Next Generation Sequencing.
14. The control composition of any one of clauses 1 to 13 wherein the nucleic acid construct is encapsulated.
15. The control composition of clause 14 wherein the nucleic acid construct is encapsulated in a liposome.
16. The control composition of clause 15 wherein the liposome comprises a lipid selected from the group consisting of cholesterol, a lipopolysaccharide, a peptidoglycan, a PEG, a teichoic acid, a phospholipid, and combinations thereof.
17. The control composition of any one of clauses 1 to 13 wherein the nucleic acid construct is incorporated into the genome of a microorganism.
18. The control composition of any one of clauses 1 to 17 wherein the barcode sequence fragment comprises a unique sequence not present in any known genome.
19. The control composition of any one of clauses 12 to 16 wherein the nucleic acid construct is incorporated into a plasmid.
20. A kit comprising the control composition of any one of clauses 1 to 19.
21. The kit of clause 20 further comprising a reagent for nucleic acid extraction.
22. The kit of clause 20 or 21 further comprising a reagent for nucleic acid purification.
23. The kit of any one of clauses 20 to 22 further comprising a reagent for library preparation.
24. The kit of any one of clauses 20 to 23 further comprising a probe.
25. The kit of any one of clauses 20 to 24 further comprising a reagent for sequencing.
26. The kit of any one of clauses 20 to 25 wherein the kit comprises more than one control composition of any one of clauses 1 to 19 wherein each control composition comprises a different nucleic acid construct wherein the different nucleic acid constructs comprise different barcode sequence fragments.
27. A method for monitoring cross-contamination or sample swapping over all steps of a DNA sequencing protocol including collection of a sample comprising DNA, DNA extraction from the sample, purification of the extracted DNA, library preparation, and sequencing, the method comprising,
   a) spiking the sample with a control composition comprising a nucleic acid construct wherein the nucleic acid construct comprises at least one barcode sequence fragment linked to at least one universal sequence fragment and wherein the nucleic acid construct is a deoxyribonucleic acid construct;
   b) extracting total DNA wherein total DNA comprises the DNA from the sample and DNA from the nucleic acid construct;

c) purifying total DNA;
d) preparing a library from total DNA;
e) sequencing the extracted, purified total DNA; and
f) detecting the nucleic acid construct in total DNA.

28. The method of clause 27 wherein the sample is selected from the group consisting of urine, nasal secretions, nasal washes, inner ear fluids, bronchial lavages, bronchial washes, alveolar lavages, spinal fluid, bone marrow aspirates, sputum, pleural fluids, synovial fluids, pericardial fluids, peritoneal fluids, saliva, tears, gastric secretions, stool, reproductive tract secretions, lymph fluid, whole blood, serum, plasma, a tissue sample, a soil sample, a water sample, a food sample, an air sample, a plant sample, an industrial waste sample, a surface wipe sample, a dust sample, a hair sample, an agricultural sample, and an animal sample.

29. The method of clause 27 or 28 wherein the method is used to determine if cross-contamination between samples has occurred.

30. The method of clause 27 or 28 wherein the method is used to determine if sample swapping has occurred.

31. The method of any one of clauses 27 to 30 wherein the step of preparing the library from total DNA comprises a step of amplifying the nucleic acid construct.

32. The method of any one of clauses 27 to 31 wherein the nucleic acid construct comprises at least a first and a second universal sequence fragment.

33. The method of clause 32 wherein the first universal sequence fragment is linked to the 5' end of the barcode sequence fragment and the second universal sequence fragment is linked to the 3' end of the barcode sequence fragment.

34. The method of any one of clauses 27 to 33 wherein the nucleic acid construct further comprises at least a first and a second primer binding site fragment.

35. The method of clause 34 wherein the nucleic acid construct further comprises at least a first and a second primer binding site fragment and wherein the first primer binding site fragment is linked at its 3' end to the 5' end of the first universal sequence fragment and the second primer binding site fragment is linked at its 5' end to the 3' end of the second universal sequence fragment.

36. The method of clause 35 wherein the primer binding site fragments range in length from about 15 base pairs to about 30 base pairs.

37. The method of clause 35 wherein the nucleic acid construct ranges in length from about 80 base pairs to about 300 base pairs.

38. The method of any one of clauses 27 to 33 wherein the sequencing is whole genome sequencing.

39. The method of any one of clauses 34 to 37 wherein the sequencing is amplicon sequencing.

40. The method of any one of clauses 27 to 39 wherein the sequencing is Next Generation Sequencing.

41. The method of any one of clauses 27 to 40 wherein the nucleic acid construct is encapsulated.

42. The method of clause 41 wherein the nucleic acid construct is encapsulated in a liposome.

43. The method of clause 42 wherein the liposome comprises a lipid selected from the group consisting of cholesterol, a lipopolysaccharide, a peptidoglycan, a PEG, a teichoic acid, a phospholipid, and combinations thereof.

44. The method of any one of clauses 27 to 40 wherein the nucleic acid construct is incorporated into the genome of a microorganism.

45. The method of any one of clauses 27 to 44 wherein the barcode sequence fragment comprises a unique sequence not present in any known genome.

46. The method of any one of clauses 39 to 43 wherein the nucleic acid construct is incorporated into a plasmid.

47. The method of any one of clauses 26 to 33 or 41 to 45 wherein the library preparation step further comprises the step of hybridizing the nucleic acid construct to an immobilized probe before sequencing the nucleic acid construct.

48. The method of clause 47 wherein the probe comprises sequences complementary to the universal sequence fragments in the nucleic acid construct and wherein the probe does not hybridize to the barcode sequence fragment in the nucleic acid construct.

49. The method of any one of clauses 27 to 48 wherein detecting the nucleic acid construct in total DNA comprises
   i) identifying the universal sequence fragment in a sequencing read generated by sequencing the extracted, purified total DNA;
   ii) comparing a sequence fragment adjacent the universal sequence fragment in the sequencing read to the barcode sequence fragment; and
   iii) determining that cross-contamination or sample swapping has occurred in response to the sequence fragment adjacent the universal sequence fragment not matching the barcode sequence fragment.

50. The method of any one of clauses 32 to 48 wherein detecting the nucleic acid construct in total DNA comprises
   i) identifying the first and second universal sequence fragments in a sequencing read generated by sequencing the extracted, purified total DNA;
   ii) comparing a sequence fragment located between the first and second universal sequence fragments in the sequencing read to the barcode sequence fragment; and
   iii) determining that cross-contamination or sample swapping has occurred in response to the sequence fragment located between the first and second universal sequence fragments not matching the barcode sequence fragment.

51. The method of clause 49 or 50, wherein the identifying and comparing steps are performed using a text-matching algorithm.

52. The method of any one of clauses 49 to 51 wherein the identifying step comprises referencing a database of universal sequence fragments that may be included in the nucleic acid construct of the control composition.

53. The method of any one of clauses 49 to 52 wherein the comparing step comprises referencing a database of barcode sequence fragments that may be included in the nucleic acid construct of the control composition.

54. A sequencing control composition, said control composition comprising a nucleic acid construct comprising at least one barcode sequence fragment, at least one universal sequence fragment, and at least one GC content fragment.

55. The control composition of clause 54 wherein one or more of the GC content fragments has a GC content of about 1 to about 40 percent.

56. The control composition of clause 54 wherein one or more of the GC content fragments has a GC content of about 40 to about 60 percent.
57. The control composition of clause 54 wherein one or more of the GC content fragments has a GC content of about 60 to about 100 percent.
58. The control composition of any one of clauses 54 to 57 comprising nucleic acid constructs with GC content fragments with at least two different percent GC contents.
59. The control composition of any one of clauses 54 to 58 comprising nucleic acid constructs with GC content fragments with at least three different percent GC contents.
60. The control composition of any one of clauses 54 to 59 comprising nucleic acid constructs with GC content fragments with at least four different percent GC contents.
61. The control composition of clause 59 wherein the percent GC contents are about 1 to about 40 percent, about 40 percent to about 60 percent, and about 60 percent to about 100 percent.
62. The control composition of any one of clauses 54 to 61 wherein the control composition is used to determine if cross-contamination between samples for sequencing has occurred.
63. The control composition of any one of clauses 54 to 62 wherein the control composition is used to determine if sample swapping has occurred.
64. The control composition of any one of clauses 54 to 63 wherein the GC content fragment is used to control for polymerase, transposase, ligase, or repair enzyme GC content bias.
65. The control composition of any one of clauses 54 to 64 wherein the control composition is used for quantification of nucleic acids during sequencing.
66. The control composition of any one of clauses 54 to 65 wherein the nucleic acid construct is a deoxyribonucleic acid construct.
67. The control composition of any one of clauses 54 to 66 wherein the nucleic acid construct comprises at least a first and a second universal sequence fragment.
68. The control composition of clause 67 wherein the first universal sequence fragment is linked to the 5' end of the barcode sequence fragment, the barcode sequence fragment is between the first universal sequence fragment and the GC content fragment, and the second universal sequence fragment is linked to the 3' end of the GC content fragment.
69. The control composition of any one of clauses 67 to 68 wherein the nucleic acid construct further comprises at least a first and a second primer binding site fragment.
70. The control composition of clause 69 wherein the first primer binding site fragment is linked at its 3' end to the 5' end of the first universal sequence fragment and the second primer binding site fragment is linked at its 5' end to the 3' end of the second universal sequence fragment.
71. The control composition of any one of clauses 69 to 70 wherein the primer binding site fragments range in length from about 15 base pairs to about 30 base pairs.
72. The control composition of any one of clauses 54 to 71 wherein the nucleic acid construct ranges in length from about 80 base pairs to about 300 base pairs.
73. The control composition of any one of clauses 54 to 68 wherein the sequencing is whole genome sequencing.
74. The control composition of any one of clauses 69 to 72 wherein the sequencing is amplicon sequencing.
75. The control composition of any one of clauses 54 to 74 wherein the sequencing is Next Generation Sequencing.
76. The control composition of any one of clauses 54 to 75 wherein the nucleic acid construct is encapsulated.
77. The control composition of clause 76 wherein the nucleic acid construct is encapsulated in a liposome.
78. The control composition of clause 77 wherein the liposome comprises a lipid selected from the group consisting of cholesterol, a lipopolysaccharide, a peptidoglycan, a PEG, a teichoic acid, a phospholipid, and combinations thereof.
79. The control composition of any one of clauses 54 to 78 wherein the barcode sequence fragment comprises a unique sequence not present in any known genome.
80. The control composition of any one of clauses 54 to 75 wherein the nucleic acid construct is incorporated into the genome of a microorganism.
81. The control composition of any one of clauses 74 to 79 wherein the nucleic acid construct is incorporated into a plasmid.
82. A kit comprising the control composition of any one of clauses 54 to 81.
83. The kit of clause 82 further comprising a reagent for nucleic acid extraction.
84. The kit of clause 82 or 83 further comprising a reagent for nucleic acid purification.
85. The kit of any one of clauses 82 to 84 further comprising a reagent for library preparation.
86. The kit of any one of clauses 82 to 85 further comprising a probe.
87. The kit of any one of clauses 82 to 86 further comprising a reagent for sequencing.
88. The kit of any one of clauses 82 to 87 wherein the kit comprises more than one control composition of any one of clauses 54 to 81 wherein each control composition comprises a different nucleic acid construct wherein the different nucleic acid constructs comprise different barcode sequence fragments.
89. The kit of any one of clauses 82 to 88 wherein the kit comprises more than one control composition of any one of clauses 54 to 81 and wherein the nucleic acid construct in each control composition is encapsulated in a different type of liposome.
90. A method for monitoring sample cross-contamination and/or sample swapping and for quantification of nucleic acids during sequencing, the method comprising,
a) extracting DNA from a sample;
b) purifying the DNA;
c) spiking the sample, after DNA extraction and purification and before library preparation, with a control composition comprising a nucleic acid construct wherein the nucleic acid construct comprises at least one barcode sequence fragment, at least one universal sequence fragment, and at least one GC content fragment, and wherein the nucleic acid construct is a deoxyribonucleic acid construct, wherein total DNA is obtained after spiking the sample, and wherein total DNA comprises the DNA from the sample and the DNA from the nucleic acid construct;

d) preparing a library from total DNA;
e) sequencing total DNA; and
f) detecting and quantifying the nucleic acid construct in total DNA.

91. A method for monitoring sample cross-contamination and/or sample swapping and for quantification of nucleic acids during sequencing, the method comprising,
   a) spiking a sample with a control composition comprising a nucleic acid construct wherein the nucleic acid construct comprises at least one barcode sequence fragment, at least one universal sequence fragment, and at least one GC content fragment and wherein the nucleic acid construct is a deoxyribonucleic acid construct;
   b) extracting total DNA from the sample wherein total DNA comprises the DNA from the sample and the DNA from the nucleic acid construct;
   c) purifying total DNA;
   d) preparing a library from total DNA;
   e) sequencing total DNA; and
   f) detecting and quantifying the nucleic acid construct in total DNA.

92. The method of clause 91 wherein sample cross-contamination and/or sample swapping can be monitored over all steps of a DNA sequencing protocol including collection of the sample, extraction of total DNA, purification of the extracted total DNA, library preparation, and sequencing.

93. The method of any one of clauses 90 to 92 wherein the sample is selected from the group consisting of urine, nasal secretions, nasal washes, inner ear fluids, bronchial lavages, bronchial washes, alveolar lavages, spinal fluid, bone marrow aspirates, sputum, pleural fluids, synovial fluids, pericardial fluids, peritoneal fluids, saliva, tears, gastric secretions, stool, reproductive tract secretions, lymph fluid, whole blood, serum, plasma, a tissue sample, a soil sample, a water sample, a food sample, an air sample, a plant sample, an industrial waste sample, a surface wipe sample, a dust sample, a hair sample, an agricultural sample, and an animal sample.

94. The method of any one of clauses 90 to 93 wherein the step of preparing the library from total DNA comprises a step of amplifying the nucleic acid construct.

95. The method of any one of clauses 90 to 94 wherein one of the GC content fragments has a GC content of about 1 to about 40 percent.

96. The method of any one of clauses 90 to 94 wherein one of the GC content fragments has a GC content of about 40 to about 60 percent.

97. The method of any one of clauses 90 to 94 wherein one of the GC content fragments has a GC content of about 60 to about 100 percent.

98. The method of any one of clauses 90 to 97 wherein the control composition comprises nucleic acid constructs with GC content fragments with at least two different percent GC contents.

99. The method of any one of clauses 90 to 98 wherein the control composition comprises nucleic acid constructs with GC content fragments with at least three different percent GC contents.

100. The method of any one of clauses 90 to 99 wherein the control composition comprises nucleic acid constructs with GC content fragments with at least four different percent GC contents.

101. The method of clause 99 wherein the GC contents are about 1 to about 40 percent, about 40 percent to about 60 percent, and about 60 percent to about 100 percent.

102. The method of any one of clauses 90 to 101 wherein the GC content fragment is used to control for polymerase, transposase, ligase, or repair enzyme GC content bias.

103. The method of any one of clauses 90 to 102 wherein the nucleic acid construct is present at at least two different concentrations for use in generating a standard curve for the quantification of nucleic acids during sequencing.

104. The method of any one of clauses 90 to 103 wherein the nucleic acid construct is present at at least three different concentrations for use in generating a standard curve for the quantification of nucleic acids during sequencing.

105. The method of any one of clauses 90 to 104 wherein the nucleic acid construct is present at at least four different concentrations for use in generating a standard curve for the quantification of nucleic acids during sequencing.

106. The method of any one of clauses 90 to 105 wherein the nucleic acid construct is present at at least five different concentrations for use in generating a standard curve for the quantification of nucleic acids during sequencing.

107. The method of any one of clauses 103 to 106 wherein a different bar code sequence fragment is present in the nucleic acid construct at each of the different concentrations of the nucleic acid construct.

108. The method of clause 107 wherein at each of the different concentrations of the nucleic construct, the control composition comprises multiple nucleic acid constructs with different percent GC contents but with the same barcode sequence fragment for the nucleic acid constructs with different percent GC contents.

109. The method of any one of clauses 90 to 108 wherein the barcode sequence fragment comprises a unique sequence not present in any known genome.

110. The method of any one of clauses 90 to 109 wherein the nucleic acid construct comprises at least a first and a second universal sequence fragment.

111. The method of clause 110 wherein the first universal sequence fragment is linked to the 5' end of the barcode sequence fragment, the barcode sequence fragment is between the first universal sequence fragment and the GC content fragment, and the second universal sequence fragment is linked to the 3' end of the GC content fragment.

112. The method of any one of clauses 109 to 111 wherein the nucleic acid construct further comprises at least a first and a second primer binding site fragment.

113. The method of clause 112 wherein the first primer binding site fragment is linked at its 3' end to the 5' end of the first universal sequence fragment and the second primer binding site fragment is linked at its 5' end to the 3' end of the second universal sequence fragment.

114. The method of any one of clauses 112 to 113 wherein the primer binding site fragments range in length from about 15 base pairs to about 30 base pairs.

115. The method of any one of clauses 90 to 114 wherein the nucleic acid construct ranges in length from about 80 base pairs to about 300 base pairs.

116. The method of any one of clauses 90 to 111 wherein the sequencing is whole genome sequencing.

117. The method of any one of clauses 112 to 115 wherein the sequencing is amplicon sequencing.
118. The method of any one of clauses 90 to 117 wherein the sequencing is Next Generation Sequencing.
119. The method of any one of clauses 91 to 118 wherein the nucleic acid construct is encapsulated.
120. The method of clause 119 wherein the nucleic acid construct is encapsulated in a liposome.
121. The method of clause 120 wherein the liposome comprises a lipid selected from the group consisting of cholesterol, a lipopolysaccharide, a peptidoglycan, a PEG, a teichoic acid, a phospholipid, and combinations thereof.
122. The method of any one of clauses 119 to 121 wherein more than one type of control composition is used in the method wherein the nucleic acid construct in each type of control composition is encapsulated in a different type of liposome.
123. The method of clause 122 wherein each type of control composition with the nucleic acid construct encapsulated in a different type of liposome comprises a different barcode sequence fragment.
124. The method of any one of clauses 91 to 118 wherein the nucleic acid construct is incorporated into the genome of a microorganism.
125. The method of any one of clauses 117 to 123 wherein the nucleic acid construct is incorporated into a plasmid.
126. The method of any one of clauses 90 to 111 or 119 to 124 wherein the library preparation step further comprises the step of hybridizing the nucleic acid construct to an immobilized probe before sequencing the nucleic acid construct.
127. The method of clause 126 wherein the probe comprises sequences complementary to the universal sequence fragments in the nucleic acid construct and wherein the probe does not hybridize to the barcode sequence fragment in the nucleic acid construct.
128. The method of any one of clauses 90 to 127 wherein detecting and quantifying the nucleic acid construct in total DNA comprises:
   a) identifying each universal sequence fragment in sequencing reads generated by sequencing the total DNA;
   b) identifying the barcode sequence fragment in each sequencing read identified as including a universal sequence fragment; and
   c) counting the number of occurrences of each unique barcode sequence fragment identified in the sequencing reads generated by sequencing the total DNA.
129. The method of clause 128, wherein the identifying steps are performed using a text-matching algorithm.
130. The method of clause 128 or 129 wherein identifying each universal sequence fragment comprises referencing a database of universal sequence fragments that may be included in the nucleic acid construct of the control composition.
131. The method of any one of clauses 128 to 130 wherein identifying the barcode sequence fragment comprises referencing a database of barcode sequence fragments that may be included in the nucleic acid construct of the control composition.
132. The method of any one of clauses 128 to 131 further comprising comparing the number of occurrences of each unique barcode sequence fragment identified in the sequencing reads generated by sequencing the total DNA to a known concentration of the nucleic acid construct comprising that barcode sequence fragment in the control composition that was used to spike the sample.
133. The method of any one of clauses 128 to 132 further comprising determining that cross-contamination or sample swapping has occurred in response to identifying an unexpected barcode sequence fragment in the sequencing reads generated by sequencing the total DNA.
134. The method of any one of clauses 128 to 133 further comprising identifying the GC content fragment in each sequencing read identified as including a universal sequence fragment and counting the number of occurrences of each unique GC content fragment identified in the sequencing reads generated by sequencing the total DNA.
135. The method of clause 134, further comprising comparing the number of occurrences of each unique GC content fragment identified in the sequencing reads generated by sequencing the total DNA to a known concentration of the nucleic acid construct comprising that GC content fragment in the control composition that was used to spike the sample.
136. A chemical analysis control composition, said control composition comprising a nucleic acid construct comprising at least one barcode sequence fragment linked at its 5' or 3' end to at least one universal sequence fragment.
137. The control composition of clause 136 wherein the control composition is used to determine if cross-contamination between samples for chemical analysis has occurred.
138. The control composition of clause 136 wherein the control composition is used to determine if sample swapping has occurred.
139. The control composition of any one of clauses 136 to 138 wherein the nucleic acid construct is a deoxyribonucleic acid construct.
140. The control composition of any one of clauses 136 to 139 wherein the nucleic acid construct comprises at least a first and a second universal sequence fragment.
141. The control composition of clause 140 wherein the first universal sequence fragment is linked to the 5' end of the barcode sequence fragment and the second universal sequence fragment is linked to the 3' end of the barcode sequence fragment.
142. The control composition of any one of clauses 136 to 141 wherein the nucleic acid construct further comprises at least a first and a second primer binding site fragment.
143. The control composition of clause 142 wherein the nucleic acid construct further comprises at least a first and a second primer binding site fragment and wherein the first primer binding site fragment is linked at its 3' end to the 5' end of the first universal sequence fragment and the second primer binding site fragment is linked at its 5' end to the 3' end of the second universal sequence fragment.
144. The control composition of clause 143 wherein the primer binding site fragments range in length from about 15 base pairs to about 30 base pairs.
145. The control composition of clause 143 wherein the nucleic acid construct ranges in length from about 80 base pairs to about 300 base pairs.
146. The control composition of any one of clauses 136 to 145 wherein the chemical analysis is quantitative and/or qualitative.

147. The control composition of any one of clauses 136 to 146 wherein a small molecule is analyzed and the small molecule is an inorganic compound or an organic compound.
148. The control composition of any one of clauses 136 to 147 wherein the chemical analysis is selected from the group consisting of forensic analysis, environmental analysis, industrial analysis, and medical analysis.
149. The control composition of clause 148 wherein the analysis is forensic analysis and the forensic analysis is selected from the group consisting of stomach content analysis, blood alcohol content analysis, substance abuse analysis, toxin analysis, and poison analysis.
150. The control composition of any one of clauses 136 to 149 wherein the chemical analysis is mass spectrometry.
151. The control composition of any one of clauses 136 to 150 wherein the nucleic acid construct is encapsulated.
152. The control composition of clause 151 wherein the nucleic acid construct is encapsulated in a liposome.
153. The control composition of clause 152 wherein the liposome comprises a lipid selected from the group consisting of cholesterol, a lipopolysaccharide, a peptidoglycan, a PEG, a teichoic acid, a phospholipid, and combinations thereof.
154. The control composition of any one of clauses 136 to 153 wherein the barcode sequence fragment comprises a unique sequence not present in any known genome.
155. The control composition of any one of clauses 136 to 154 wherein the nucleic acid construct is incorporated into a plasmid.
156. A kit comprising the control composition of any one of clauses 136 to 155.
157. The kit of clause 156 further comprising a reagent for nucleic acid extraction.
158. The kit of clause 156 or 157 further comprising a reagent for nucleic acid purification.
159. The kit of any one of clauses 156 to 158 further comprising a reagent for library preparation.
160. The kit of any one of clauses 156 to 159 further comprising a probe.
161. The kit of any one of clauses 156 to 160 further comprising a reagent for sequencing.
162. A method for monitoring cross-contamination or sample swapping during an analytical chemistry protocol, the method comprising,
   a) spiking an analytical chemistry protocol sample with a control composition comprising a nucleic acid construct wherein the nucleic acid construct comprises at least one barcode sequence fragment linked to at least one universal sequence fragment and wherein the nucleic acid construct is a deoxyribonucleic acid construct;
   b) performing the analytical chemistry protocol;
   c) archiving a sample from the analytical chemistry protocol;
   d) extracting total DNA from the archived sample wherein total DNA comprises the DNA from the nucleic acid construct and DNA from the analytical chemistry protocol sample, if any;
   e) purifying total DNA;
   f) preparing a library from total DNA;
   g) sequencing the extracted, purified total DNA; and
   h) detecting the nucleic acid construct in total DNA.
163. The method of clause 162 wherein the sample is selected from the group consisting of urine, nasal secretions, nasal washes, inner ear fluids, bronchial lavages, bronchial washes, alveolar lavages, spinal fluid, bone marrow aspirates, sputum, pleural fluids, synovial fluids, pericardial fluids, peritoneal fluids, saliva, tears, gastric secretions, stool, reproductive tract secretions, lymph fluid, whole blood, serum, plasma, a tissue sample, a soil sample, a water sample, a food sample, an air sample, a plant sample, an industrial waste sample, a surface wipe sample, a dust sample, a hair sample, an agricultural sample, and an animal sample.
164. The method of clause 162 or 163 wherein the method is used to determine if cross-contamination between samples has occurred.
165. The method of clause 162 or 163 wherein the method is used to determine if sample swapping has occurred.
166. The method of any one of clauses 162 to 165 wherein the step of preparing the library from total DNA comprises a step of amplifying the nucleic acid construct.
167. The method of any one of clauses 162 to 166 wherein the nucleic acid construct comprises at least a first and a second universal sequence fragment.
168. The method of clause 167 wherein the first universal sequence fragment is linked to the 5' end of the barcode sequence fragment and the second universal sequence fragment is linked to the 3' end of the barcode sequence fragment.
169. The method of any one of clauses 162 to 168 wherein the nucleic acid construct further comprises at least a first and a second primer binding site fragment.
170. The method of clause 169 wherein the nucleic acid construct further comprises at least a first and a second primer binding site fragment and wherein the first primer binding site fragment is linked at its 3' end to the 5' end of the first universal sequence fragment and the second primer binding site fragment is linked at its 5' end to the 3' end of the second universal sequence fragment.
171. The method of clause 170 wherein the primer binding site fragments range in length from about 15 base pairs to about 30 base pairs.
172. The method of clause 170 wherein the nucleic acid construct ranges in length from about 80 base pairs to about 300 base pairs.
173. The method of any one of clauses 162 to 172 wherein the nucleic acid construct is encapsulated.
174. The method of clause 173 wherein the nucleic acid construct is encapsulated in a liposome.
175. The method of clause 174 wherein the liposome comprises a lipid selected from the group consisting of cholesterol, a lipopolysaccharide, a peptidoglycan, a PEG, a teichoic acid, a phospholipid, and combinations thereof.
176. The method of any one of clauses 162 to 175 wherein the barcode sequence fragment comprises a unique sequence not present in any known genome.
177. The method of any one of clauses 162 to 176 wherein the nucleic acid construct is incorporated into a plasmid.
178. The method of any one of clauses 162 to 177 wherein the chemical analysis is quantitative and/or qualitative.
179. The method of any one of clauses 162 to 178 wherein a small molecule is analyzed and the small molecule is an inorganic compound or an organic compound.
180. The method of any one of clauses 162 to 179 wherein the chemical analysis is selected from the group consisting of forensic analysis, environmental analysis, industrial analysis, and medical analysis.

181. The method of clause 180 wherein the analysis is forensic analysis and the forensic analysis is selected from the group consisting of stomach content analysis, blood alcohol content analysis, substance abuse analysis, toxin analysis, and poison analysis, or combinations thereof.

182. The method of any one of clauses 162 to 180 wherein the analytical chemistry protocol is mass spectrometry.

183. The method of any one of clauses 162 to 182 wherein detecting the nucleic acid construct in total DNA comprises
    i) identifying the universal sequence fragment in a sequencing read generated by sequencing the extracted, purified total DNA;
    ii) comparing a sequence fragment adjacent the universal sequence fragment in the sequencing read to the barcode sequence fragment; and
    iii) determining that cross-contamination or sample swapping has occurred in response to the sequence fragment adjacent the universal sequence fragment not matching the barcode sequence fragment.

184. The method of any one of clauses 167 to 182 wherein detecting the nucleic acid construct in total DNA comprises
    iv) identifying the first and second universal sequence fragments in a sequencing read generated by sequencing the extracted, purified total DNA;
    v) comparing a sequence fragment located between the first and second universal sequence fragments in the sequencing read to the barcode sequence fragment; and
    vi) determining that cross-contamination or sample swapping has occurred in response to the sequence fragment located between the first and second universal sequence fragments not matching the barcode sequence fragment.

185. The method of clause 183 or 184, wherein the identifying and comparing steps are performed using a text-matching algorithm.

186. The method of any one of clauses 183 to 185 wherein the identifying step comprises referencing a database of universal sequence fragments that may be included in the nucleic acid construct of the control composition.

187. The method of any one of clauses 183 to 186 wherein the comparing step comprises referencing a database of barcode sequence fragments that may be included in the nucleic acid construct of the control composition.

BRIEF DESCRIPTION OF THE DRAWINGS

FIG. 4 shows the sequencing results for soil samples in which CCC-1 DNA and CCC-2 DNA were spiked-in prior to extraction either individually or where CCC-1 DNA and CCC-2 DNA were spiked-in together.

DETAILED DESCRIPTION OF ILLUSTRATIVE EMBODIMENTS

Figure 1:
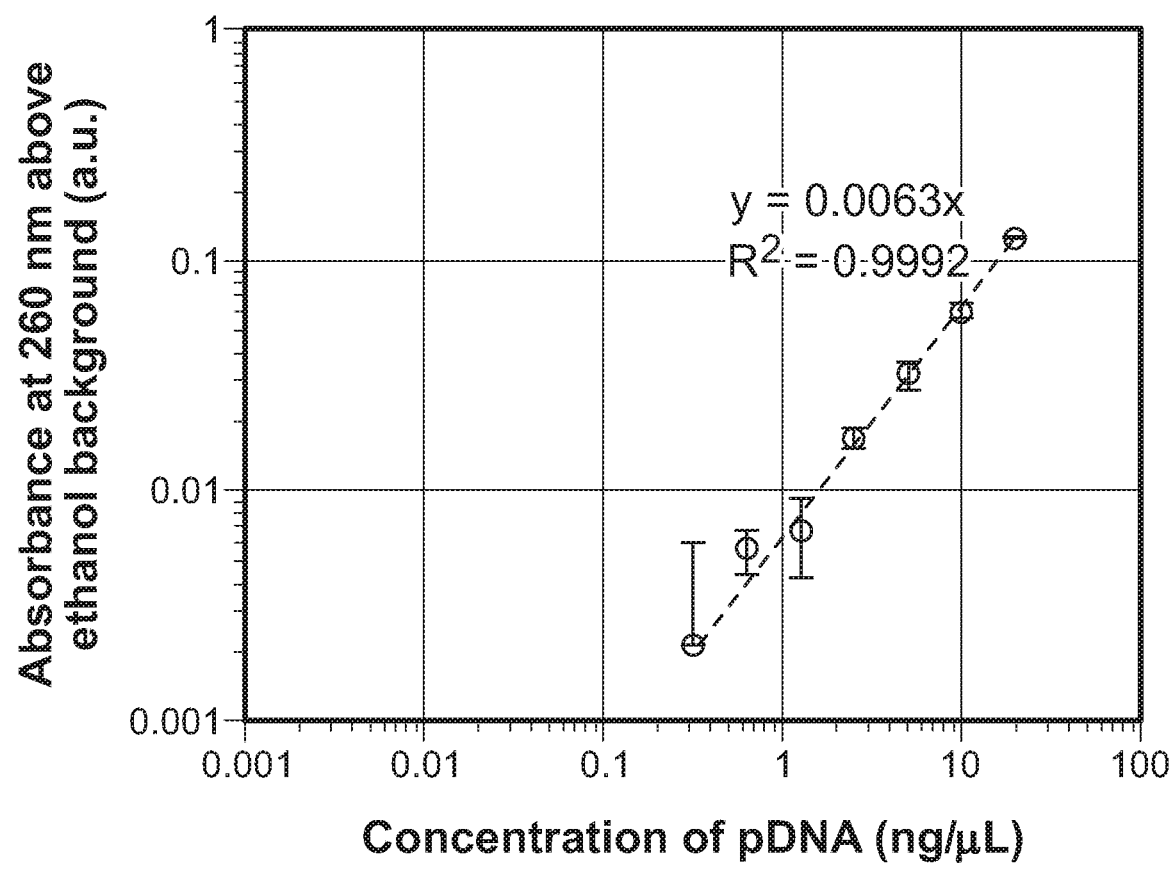
FIG. 1 shows the quantification of CCC DNA (i.e., CCC-1 DNA—for a description see Example 1) via UV absorbance at 260 nm. The curve is linear and CCC DNA (i.e., CCC-1 DNA) can be detected down to a concentration of about 0.3 ng/µL. The absorbance for the sample used in the assays corresponding to FIGS. 2A and B and FIG. 4 was 0.015±0.001. This corresponds to a concentration of ~12±1 ng/µL.

The present invention provides sequencing controls that can be used starting after the extraction step (e.g., by spiking the extract with the control constructs) or in every step of analysis of an unknown test sample (e.g., from nucleic acid extraction to nucleic acid purification to library preparation and sequencing). In one embodiment, nucleic acid constructs comprising a barcode sequence fragment are provided that can be encapsulated in a simulated cell membrane (e.g., a simulated bacterial cell membrane or eukaryotic cell membrane), or embedded directly in the genome of an organism for use as spike-in sequencing controls. In one aspect, the barcode sequence fragment comprises a unique sequence not present in any known genome. In one embodiment, the sequencing controls can be spiked in the unknown test sample prior to or after nucleic acid extraction and then can be detected in the final sequenced samples. In another embodiment, different nucleic acid constructs (i.e., with different barcode sequence fragments) can be spiked in different samples so that cross-contamination of samples or sample swapping can be detected.

In one embodiment, the barcode sequence fragment can be flanked at its 5' or 3' end, or both, by universal sequence fragments. The universal sequence fragments can add length to the nucleic acid construct and can serve as markers for bioinformatic analysis to identify the beginning and end of the barcode sequence fragment after sequencing. In another illustrative aspect, the barcode sequence fragment may be flanked by primer binding site sequence fragments (i.e., directly or indirectly linked to the barcode sequence fragment) so that the nucleic acid construct comprising the barcode sequence fragment can be amplified during an amplicon sequencing protocol. In another embodiment, primer binding site sequence fragments may be lacking for use of the sequencing controls in whole genome sequencing protocols. In another embodiment, a set of different nucleic acid construct spike-ins with different barcode sequence fragments (e.g., 384 or 96 different barcode sequence fragments) can be used to allow for multiplexing of samples on one sequencing run.

In various embodiments, samples with microorganisms containing nucleic acids (e.g., DNA), or samples with other sources of nucleic acids, may be analyzed by sequencing using the control compositions for sequencing described herein. The samples can be, for example, selected from the group consisting of urine, nasal secretions, nasal washes, inner ear fluids, bronchial lavages, bronchial washes, alveolar lavages, spinal fluid, bone marrow aspirates, sputum, pleural fluids, synovial fluids, pericardial fluids, peritoneal fluids, saliva, tears, gastric secretions, stool, reproductive tract secretions, lymph fluid, whole blood, serum, plasma, hair, a tissue sample, a soil sample, a water sample, a food sample, an air sample, a plant sample, an industrial waste sample, a surface wipe sample, and an animal sample.

In another embodiment, compositions and methods are provided for the use of spike-in controls that simultaneously 1) control for cross-contamination and/or sample swapping and 2) allow for quantitation while controlling for different GC content samples (e.g., low, balanced, and high GC content) and/or for different lysis efficiencies. In one aspect, barcoded DNA molecules are produced with different GC contents, using GC content fragments, wherein barcode sequence fragments and GC content fragments are flanked by universal sequence fragments, and then the nucleic acid construct can be encapsulated in a simulated cell membrane. By using the same type of nucleic acid construct, but with different barcode sequence fragments, different quantities of the encapsulated or unencapsulated nucleic acid construct can be spiked-in, and a standard curve for quantitation can be produced. In this embodiment, the barcode sequence fragments can be used to verify that no cross-contamination or sample swapping occurred during sample preparation or processing. In this quantitation embodiment, the different GC content fragments (e.g., low, balanced, and high GC content) have the same barcode sequence fragment at each GC percentage (e.g., low, balanced, and high GC content), but at each separate concentration of the nucleic acid construct used to produce the standard curve, the barcode sequence fragments are unique to each concentration used to produce the standard curve. In this embodiment, the encapsulation method can also be varied to control for different resistances to lysis to mimic, for example, Gram-positive bacterial cell walls, Gram-negative bacterial cell walls, and fungal cell walls. In this encapsulation embodiment, the type of encapsulation method can be correlated to a unique barcode sequence fragment in the nucleic acid construct to enable differentiation post sequencing.

In one embodiment, the nucleic acid construct can be constructed (5' to 3') with a universal sequence fragment, a unique barcode sequence fragment, a GC content fragment (e.g., with high, balanced, or low GC content), and a second universal sequence fragment. In this embodiment, the unique barcode sequence fragment is a sequence that is not present in any known genome. An exemplary GC content fragment can contain about 60 to about 100 percent GC content for high GC content, about 40 to about 60 percent GC content for balanced GC content, and about 1 to about 40 percent GC content for low GC content. In this embodiment, the universal sequence fragments can add length to the nucleic acid construct and can serve as markers for bioinformatic analysis to identify the beginning and end of the nucleic acid construct after sequencing. In alternate embodiments, the universal sequence fragments could be extended as needed to make the total nucleic acid construct longer for different applications such as long read sequencing. In various embodiments, the nucleic acid constructs can either be encapsulated to spike into samples at sample collection and control for full sample preparation and processing or can be unencapsulated and can be spiked in after extraction to control for library preparation. In one aspect, two or more mixtures of three different GC content fragment constructs can be prepared (e.g., a low quantity standard and a high quantity standard with each having a unique barcode sequence fragment so that the high and low quantity standards can be differentiated post-sequencing).

In yet another embodiment, spike-in cross-contamination and sample swapping controls for analytical chemistry analysis of unknown materials are provided. These controls can be used in analytical chemistry procedures, such as mass spectrometry, and any of the nucleic acid constructs described herein can be used.

The following clauses, and combinations thereof, provide various additional illustrative aspects of the invention described herein. The various embodiments described in any other section of this patent application, including the summary portion of the section titled "BACKGROUND AND SUMMARY", the "EXAMPLES", and this "DETAILED DESCRIPTION OF ILLUSTRATIVE EMBODIMENTS" section of the application are applicable to any of the following embodiments of the invention described in the numbered clauses below.

1. A sequencing control composition, said control composition comprising a nucleic acid construct comprising at least one barcode sequence fragment linked at its 5' or 3' end to at least one universal sequence fragment.
2. The control composition of clause 1 wherein the control composition is used to determine if cross-contamination between samples for sequencing has occurred.
3. The control composition of clause 1 wherein the control composition is used to determine if sample swapping has occurred.
4. The control composition of any one of clauses 1 to 3 wherein the nucleic acid construct is a deoxyribonucleic acid construct.
5. The control composition of any one of clauses 1 to 4 wherein the nucleic acid construct comprises at least a first and a second universal sequence fragment.
6. The control composition of clause 5 wherein the first universal sequence fragment is linked to the 5' end of the barcode sequence fragment and the second universal sequence fragment is linked to the 3' end of the barcode sequence fragment.
7. The control composition of any one of clauses 1 to 6 wherein the nucleic acid construct further comprises at least a first and a second primer binding site fragment.
8. The control composition of clause 6 wherein the nucleic acid construct further comprises at least a first and a second primer binding site fragment and wherein the first primer binding site fragment is linked at its 3' end to the 5' end of the first universal sequence fragment and the second primer binding site fragment is linked at its 5' end to the 3' end of the second universal sequence fragment.
9. The control composition of clause 8 wherein the primer binding site fragments range in length from about 15 base pairs to about 30 base pairs.
10. The control composition of clause 8 wherein the nucleic acid construct ranges in length from about 80 base pairs to about 300 base pairs.
11. The control composition of any one of clauses 1 to 6 wherein the sequencing is whole genome sequencing.
12. The control composition of any one of clauses 7 to 10 wherein the sequencing is amplicon sequencing.
13. The control composition of any one of clauses 1 to 12 wherein the sequencing is Next Generation Sequencing.
14. The control composition of any one of clauses 1 to 13 wherein the nucleic acid construct is encapsulated.
15. The control composition of clause 14 wherein the nucleic acid construct is encapsulated in a liposome.
16. The control composition of clause 15 wherein the liposome comprises a lipid selected from the group consisting of cholesterol, a lipopolysaccharide, a peptidoglycan, a PEG, a teichoic acid, a phospholipid, and combinations thereof.
17. The control composition of any one of clauses 1 to 13 wherein the nucleic acid construct is incorporated into the genome of a microorganism.
18. The control composition of any one of clauses 1 to 17 wherein the barcode sequence fragment comprises a unique sequence not present in any known genome.
19. The control composition of any one of clauses 12 to 16 wherein the nucleic acid construct is incorporated into a plasmid.
20. A kit comprising the control composition of any one of clauses 1 to 19.
21. The kit of clause 20 further comprising a reagent for nucleic acid extraction.
22. The kit of clause 20 or 21 further comprising a reagent for nucleic acid purification.
23. The kit of any one of clauses 20 to 22 further comprising a reagent for library preparation.
24. The kit of any one of clauses 20 to 23 further comprising a probe.
25. The kit of any one of clauses 20 to 24 further comprising a reagent for sequencing.
26. The kit of any one of clauses 20 to 25 wherein the kit comprises more than one control composition of any one of clauses 1 to 19 wherein each control composition comprises a different nucleic acid construct wherein the different nucleic acid constructs comprise different barcode sequence fragments.
27. A method for monitoring cross-contamination or sample swapping over all steps of a DNA sequencing protocol including collection of a sample comprising DNA, DNA extraction from the sample, purification of the extracted DNA, library preparation, and sequencing, the method comprising,
    a) spiking the sample with a control composition comprising a nucleic acid construct wherein the nucleic acid construct comprises at least one barcode sequence fragment linked to at least one universal sequence fragment and wherein the nucleic acid construct is a deoxyribonucleic acid construct;

b) extracting total DNA wherein total DNA comprises the DNA from the sample and DNA from the nucleic acid construct;
c) purifying total DNA;
d) preparing a library from total DNA;
e) sequencing the extracted, purified total DNA; and
f) detecting the nucleic acid construct in total DNA.

28. The method of clause 27 wherein the sample is selected from the group consisting of urine, nasal secretions, nasal washes, inner ear fluids, bronchial lavages, bronchial washes, alveolar lavages, spinal fluid, bone marrow aspirates, sputum, pleural fluids, synovial fluids, pericardial fluids, peritoneal fluids, saliva, tears, gastric secretions, stool, reproductive tract secretions, lymph fluid, whole blood, serum, plasma, a tissue sample, a soil sample, a water sample, a food sample, an air sample, a plant sample, an industrial waste sample, a surface wipe sample, a dust sample, a hair sample, an agricultural sample, and an animal sample.

29. The method of clause 27 or 28 wherein the method is used to determine if cross-contamination between samples has occurred.

30. The method of clause 27 or 28 wherein the method is used to determine if sample swapping has occurred.

31. The method of any one of clauses 27 to 30 wherein the step of preparing the library from total DNA comprises a step of amplifying the nucleic acid construct.

32. The method of any one of clauses 27 to 31 wherein the nucleic acid construct comprises at least a first and a second universal sequence fragment.

33. The method of clause 32 wherein the first universal sequence fragment is linked to the 5' end of the barcode sequence fragment and the second universal sequence fragment is linked to the 3' end of the barcode sequence fragment.

34. The method of any one of clauses 27 to 33 wherein the nucleic acid construct further comprises at least a first and a second primer binding site fragment.

35. The method of clause 34 wherein the nucleic acid construct further comprises at least a first and a second primer binding site fragment and wherein the first primer binding site fragment is linked at its 3' end to the 5' end of the first universal sequence fragment and the second primer binding site fragment is linked at its 5' end to the 3' end of the second universal sequence fragment.

36. The method of clause 35 wherein the primer binding site fragments range in length from about 15 base pairs to about 30 base pairs.

37. The method of clause 35 wherein the nucleic acid construct ranges in length from about 80 base pairs to about 300 base pairs.

38. The method of any one of clauses 27 to 33 wherein the sequencing is whole genome sequencing.

39. The method of any one of clauses 34 to 37 wherein the sequencing is amplicon sequencing.

40. The method of any one of clauses 27 to 39 wherein the sequencing is Next Generation Sequencing.

41. The method of any one of clauses 27 to 40 wherein the nucleic acid construct is encapsulated.

42. The method of clause 41 wherein the nucleic acid construct is encapsulated in a liposome.

43. The method of clause 42 wherein the liposome comprises a lipid selected from the group consisting of cholesterol, a lipopolysaccharide, a peptidoglycan, a PEG, a teichoic acid, a phospholipid, and combinations thereof.

44. The method of any one of clauses 27 to 40 wherein the nucleic acid construct is incorporated into the genome of a microorganism.

45. The method of any one of clauses 27 to 44 wherein the barcode sequence fragment comprises a unique sequence not present in any known genome.

46. The method of any one of clauses 39 to 43 wherein the nucleic acid construct is incorporated into a plasmid.

47. The method of any one of clauses 26 to 33 or 41 to 45 wherein the library preparation step further comprises the step of hybridizing the nucleic acid construct to an immobilized probe before sequencing the nucleic acid construct.

48. The method of clause 47 wherein the probe comprises sequences complementary to the universal sequence fragments in the nucleic acid construct and wherein the probe does not hybridize to the barcode sequence fragment in the nucleic acid construct.

49. The method of any one of clauses 27 to 48 wherein detecting the nucleic acid construct in total DNA comprises
   iv) identifying the universal sequence fragment in a sequencing read generated by sequencing the extracted, purified total DNA;
   v) comparing a sequence fragment adjacent the universal sequence fragment in the sequencing read to the barcode sequence fragment; and
   vi) determining that cross-contamination or sample swapping has occurred in response to the sequence fragment adjacent the universal sequence fragment not matching the barcode sequence fragment.

50. The method of any one of clauses 32 to 48 wherein detecting the nucleic acid construct in total DNA comprises
   vii) identifying the first and second universal sequence fragments in a sequencing read generated by sequencing the extracted, purified total DNA;
   viii) comparing a sequence fragment located between the first and second universal sequence fragments in the sequencing read to the barcode sequence fragment; and
   ix) determining that cross-contamination or sample swapping has occurred in response to the sequence fragment located between the first and second universal sequence fragments not matching the barcode sequence fragment.

51. The method of clause 49 or 50, wherein the identifying and comparing steps are performed using a text-matching algorithm.

52. The method of any one of clauses 49 to 51 wherein the identifying step comprises referencing a database of universal sequence fragments that may be included in the nucleic acid construct of the control composition.

53. The method of any one of clauses 49 to 52 wherein the comparing step comprises referencing a database of barcode sequence fragments that may be included in the nucleic acid construct of the control composition.

54. A sequencing control composition, said control composition comprising a nucleic acid construct comprising at least one barcode sequence fragment, at least one universal sequence fragment, and at least one GC content fragment.

55. The control composition of clause 54 wherein one or more of the GC content fragments has a GC content of about 1 to about 40 percent.
56. The control composition of clause 54 wherein one or more of the GC content fragments has a GC content of about 40 to about 60 percent.
57. The control composition of clause 54 wherein one or more of the GC content fragments has a GC content of about 60 to about 100 percent.
58. The control composition of any one of clauses 54 to 57 comprising nucleic acid constructs with GC content fragments with at least two different percent GC contents.
59. The control composition of any one of clauses 54 to 58 comprising nucleic acid constructs with GC content fragments with at least three different percent GC contents.
60. The control composition of any one of clauses 54 to 59 comprising nucleic acid constructs with GC content fragments with at least four different percent GC contents.
61. The control composition of clause 59 wherein the percent GC contents are about 1 to about 40 percent, about 40 percent to about 60 percent, and about 60 percent to about 100 percent.
62. The control composition of any one of clauses 54 to 61 wherein the control composition is used to determine if cross-contamination between samples for sequencing has occurred.
63. The control composition of any one of clauses 54 to 62 wherein the control composition is used to determine if sample swapping has occurred.
64. The control composition of any one of clauses 54 to 63 wherein the GC content fragment is used to control for polymerase, transposase, ligase, or repair enzyme GC content bias.
65. The control composition of any one of clauses 54 to 64 wherein the control composition is used for quantification of nucleic acids during sequencing.
66. The control composition of any one of clauses 54 to 65 wherein the nucleic acid construct is a deoxyribonucleic acid construct.
67. The control composition of any one of clauses 54 to 66 wherein the nucleic acid construct comprises at least a first and a second universal sequence fragment.
68. The control composition of clause 67 wherein the first universal sequence fragment is linked to the 5' end of the barcode sequence fragment, the barcode sequence fragment is between the first universal sequence fragment and the GC content fragment, and the second universal sequence fragment is linked to the 3' end of the GC content fragment.
69. The control composition of any one of clauses 67 to 68 wherein the nucleic acid construct further comprises at least a first and a second primer binding site fragment.
70. The control composition of clause 69 wherein the first primer binding site fragment is linked at its 3' end to the 5' end of the first universal sequence fragment and the second primer binding site fragment is linked at its 5' end to the 3' end of the second universal sequence fragment.
71. The control composition of any one of clauses 69 to 70 wherein the primer binding site fragments range in length from about 15 base pairs to about 30 base pairs.
72. The control composition of any one of clauses 54 to 71 wherein the nucleic acid construct ranges in length from about 80 base pairs to about 300 base pairs.
73. The control composition of any one of clauses 54 to 68 wherein the sequencing is whole genome sequencing.
74. The control composition of any one of clauses 69 to 72 wherein the sequencing is amplicon sequencing.
75. The control composition of any one of clauses 54 to 74 wherein the sequencing is Next Generation Sequencing.
76. The control composition of any one of clauses 54 to 75 wherein the nucleic acid construct is encapsulated.
77. The control composition of clause 76 wherein the nucleic acid construct is encapsulated in a liposome.
78. The control composition of clause 77 wherein the liposome comprises a lipid selected from the group consisting of cholesterol, a lipopolysaccharide, a peptidoglycan, a PEG, a teichoic acid, a phospholipid, and combinations thereof.
79. The control composition of any one of clauses 54 to 78 wherein the barcode sequence fragment comprises a unique sequence not present in any known genome.
80. The control composition of any one of clauses 54 to 75 wherein the nucleic acid construct is incorporated into the genome of a microorganism.
81. The control composition of any one of clauses 74 to 79 wherein the nucleic acid construct is incorporated into a plasmid.
82. A kit comprising the control composition of any one of clauses 54 to 81.
83. The kit of clause 82 further comprising a reagent for nucleic acid extraction.
84. The kit of clause 82 or 83 further comprising a reagent for nucleic acid purification.
85. The kit of any one of clauses 82 to 84 further comprising a reagent for library preparation.
86. The kit of any one of clauses 82 to 85 further comprising a probe.
87. The kit of any one of clauses 82 to 86 further comprising a reagent for sequencing.
88. The kit of any one of clauses 82 to 87 wherein the kit comprises more than one control composition of any one of clauses 54 to 81 wherein each control composition comprises a different nucleic acid construct wherein the different nucleic acid constructs comprise different barcode sequence fragments.
89. The kit of any one of clauses 82 to 88 wherein the kit comprises more than one control composition of any one of clauses 54 to 81 and wherein the nucleic acid construct in each control composition is encapsulated in a different type of liposome.
90. A method for monitoring sample cross-contamination and/or sample swapping and for quantification of nucleic acids during sequencing, the method comprising,
   a) extracting DNA from a sample;
   b) purifying the DNA;
   c) spiking the sample, after DNA extraction and purification and before library preparation, with a control composition comprising a nucleic acid construct wherein the nucleic acid construct comprises at least one barcode sequence fragment, at least one universal sequence fragment, and at least one GC content fragment, and wherein the nucleic acid construct is a deoxyribonucleic acid construct, wherein total DNA is obtained after spiking the sample, and wherein total DNA comprises the DNA from the sample and the DNA from the nucleic acid construct;
d) preparing a library from total DNA;
e) sequencing total DNA; and
f) detecting and quantifying the nucleic acid construct in total DNA.

91. A method for monitoring sample cross-contamination and/or sample swapping and for quantification of nucleic acids during sequencing, the method comprising,
a) spiking a sample with a control composition comprising a nucleic acid construct wherein the nucleic acid construct comprises at least one barcode sequence fragment, at least one universal sequence fragment, and at least one GC content fragment and wherein the nucleic acid construct is a deoxyribonucleic acid construct;
b) extracting total DNA from the sample wherein total DNA comprises the DNA from the sample and the DNA from the nucleic acid construct;
c) purifying total DNA;
d) preparing a library from total DNA;
e) sequencing total DNA; and
f) detecting and quantifying the nucleic acid construct in total DNA.

92. The method of clause 91 wherein sample cross-contamination and/or sample swapping can be monitored over all steps of a DNA sequencing protocol including collection of the sample, extraction of total DNA, purification of the extracted total DNA, library preparation, and sequencing.

93. The method of any one of clauses 90 to 92 wherein the sample is selected from the group consisting of urine, nasal secretions, nasal washes, inner ear fluids, bronchial lavages, bronchial washes, alveolar lavages, spinal fluid, bone marrow aspirates, sputum, pleural fluids, synovial fluids, pericardial fluids, peritoneal fluids, saliva, tears, gastric secretions, stool, reproductive tract secretions, lymph fluid, whole blood, serum, plasma, a tissue sample, a soil sample, a water sample, a food sample, an air sample, a plant sample, an industrial waste sample, a surface wipe sample, a dust sample, a hair sample, an agricultural sample, and an animal sample.

94. The method of any one of clauses 90 to 93 wherein the step of preparing the library from total DNA comprises a step of amplifying the nucleic acid construct.

95. The method of any one of clauses 90 to 94 wherein one of the GC content fragments has a GC content of about 1 to about 40 percent.

96. The method of any one of clauses 90 to 94 wherein one of the GC content fragments has a GC content of about 40 to about 60 percent.

97. The method of any one of clauses 90 to 94 wherein one of the GC content fragments has a GC content of about 60 to about 100 percent.

98. The method of any one of clauses 90 to 97 wherein the control composition comprises nucleic acid constructs with GC content fragments with at least two different percent GC contents.

99. The method of any one of clauses 90 to 98 wherein the control composition comprises nucleic acid constructs with GC content fragments with at least three different percent GC contents.

100. The method of any one of clauses 90 to 99 wherein the control composition comprises nucleic acid constructs with GC content fragments with at least four different percent GC contents.

101. The method of clause 99 wherein the GC contents are about 1 to about 40 percent, about percent to about 60 percent, and about 60 percent to about 100 percent.

102. The method of any one of clauses 90 to 101 wherein the GC content fragment is used to control for polymerase, transposase, ligase, or repair enzyme GC content bias.

103. The method of any one of clauses 90 to 102 wherein the nucleic acid construct is present at at least two different concentrations for use in generating a standard curve for the quantification of nucleic acids during sequencing.

104. The method of any one of clauses 90 to 103 wherein the nucleic acid construct is present at at least three different concentrations for use in generating a standard curve for the quantification of nucleic acids during sequencing.

105. The method of any one of clauses 90 to 104 wherein the nucleic acid construct is present at at least four different concentrations for use in generating a standard curve for the quantification of nucleic acids during sequencing.

106. The method of any one of clauses 90 to 105 wherein the nucleic acid construct is present at at least five different concentrations for use in generating a standard curve for the quantification of nucleic acids during sequencing.

107. The method of any one of clauses 103 to 106 wherein a different bar code sequence fragment is present in the nucleic acid construct at each of the different concentrations of the nucleic acid construct.

108. The method of clause 107 wherein at each of the different concentrations of the nucleic construct, the control composition comprises multiple nucleic acid constructs with different percent GC contents but with the same barcode sequence fragment for the nucleic acid constructs with different percent GC contents.

109. The method of any one of clauses 90 to 108 wherein the barcode sequence fragment comprises a unique sequence not present in any known genome.

110. The method of any one of clauses 90 to 109 wherein the nucleic acid construct comprises at least a first and a second universal sequence fragment.

111. The method of clause 110 wherein the first universal sequence fragment is linked to the 5' end of the barcode sequence fragment, the barcode sequence fragment is between the first universal sequence fragment and the GC content fragment, and the second universal sequence fragment is linked to the 3' end of the GC content fragment.

112. The method of any one of clauses 109 to 111 wherein the nucleic acid construct further comprises at least a first and a second primer binding site fragment.

113. The method of clause 112 wherein the first primer binding site fragment is linked at its 3' end to the 5' end of the first universal sequence fragment and the second primer binding site fragment is linked at its 5' end to the 3' end of the second universal sequence fragment.

114. The method of any one of clauses 112 to 113 wherein the primer binding site fragments range in length from about 15 base pairs to about 30 base pairs.

115. The method of any one of clauses 90 to 114 wherein the nucleic acid construct ranges in length from about 80 base pairs to about 300 base pairs.

116. The method of any one of clauses 90 to 111 wherein the sequencing is whole genome sequencing.
117. The method of any one of clauses 112 to 115 wherein the sequencing is amplicon sequencing.
118. The method of any one of clauses 90 to 117 wherein the sequencing is Next Generation Sequencing.
119. The method of any one of clauses 91 to 118 wherein the nucleic acid construct is encapsulated.
120. The method of clause 119 wherein the nucleic acid construct is encapsulated in a liposome.
121. The method of clause 120 wherein the liposome comprises a lipid selected from the group consisting of cholesterol, a lipopolysaccharide, a peptidoglycan, a PEG, a teichoic acid, a phospholipid, and combinations thereof.
122. The method of any one of clauses 119 to 121 wherein more than one type of control composition is used in the method wherein the nucleic acid construct in each type of control composition is encapsulated in a different type of liposome.
123. The method of clause 122 wherein each type of control composition with the nucleic acid construct encapsulated in a different type of liposome comprises a different barcode sequence fragment.
124. The method of any one of clauses 91 to 118 wherein the nucleic acid construct is incorporated into the genome of a microorganism.
125. The method of any one of clauses 117 to 123 wherein the nucleic acid construct is incorporated into a plasmid.
126. The method of any one of clauses 90 to 111 or 119 to 124 wherein the library preparation step further comprises the step of hybridizing the nucleic acid construct to an immobilized probe before sequencing the nucleic acid construct.
127. The method of clause 126 wherein the probe comprises sequences complementary to the universal sequence fragments in the nucleic acid construct and wherein the probe does not hybridize to the barcode sequence fragment in the nucleic acid construct.
128. The method of any one of clauses 90 to 127 wherein detecting and quantifying the nucleic acid construct in total DNA comprises:
   a) identifying each universal sequence fragment in sequencing reads generated by sequencing the total DNA;
   b) identifying the barcode sequence fragment in each sequencing read identified as including a universal sequence fragment; and
   c) counting the number of occurrences of each unique barcode sequence fragment identified in the sequencing reads generated by sequencing the total DNA.
129. The method of clause 128, wherein the identifying steps are performed using a text-matching algorithm.
130. The method of clause 128 or 129 wherein identifying each universal sequence fragment comprises referencing a database of universal sequence fragments that may be included in the nucleic acid construct of the control composition.
131. The method of any one of clauses 128 to 130 wherein identifying the barcode sequence fragment comprises referencing a database of barcode sequence fragments that may be included in the nucleic acid construct of the control composition.
132. The method of any one of clauses 128 to 131 further comprising comparing the number of occurrences of each unique barcode sequence fragment identified in the sequencing reads generated by sequencing the total DNA to a known concentration of the nucleic acid construct comprising that barcode sequence fragment in the control composition that was used to spike the sample.
133. The method of any one of clauses 128 to 132 further comprising determining that cross-contamination or sample swapping has occurred in response to identifying an unexpected barcode sequence fragment in the sequencing reads generated by sequencing the total DNA.
134. The method of any one of clauses 128 to 133 further comprising identifying the GC content fragment in each sequencing read identified as including a universal sequence fragment and counting the number of occurrences of each unique GC content fragment identified in the sequencing reads generated by sequencing the total DNA.
135. The method of clause 134, further comprising comparing the number of occurrences of each unique GC content fragment identified in the sequencing reads generated by sequencing the total DNA to a known concentration of the nucleic acid construct comprising that GC content fragment in the control composition that was used to spike the sample.
136. A chemical analysis control composition, said control composition comprising a nucleic acid construct comprising at least one barcode sequence fragment linked at its 5' or 3' end to at least one universal sequence fragment.
137. The control composition of clause 136 wherein the control composition is used to determine if cross-contamination between samples for chemical analysis has occurred.
138. The control composition of clause 136 wherein the control composition is used to determine if sample swapping has occurred.
139. The control composition of any one of clauses 136 to 138 wherein the nucleic acid construct is a deoxyribonucleic acid construct.
140. The control composition of any one of clauses 136 to 139 wherein the nucleic acid construct comprises at least a first and a second universal sequence fragment.
141. The control composition of clause 140 wherein the first universal sequence fragment is linked to the 5' end of the barcode sequence fragment and the second universal sequence fragment is linked to the 3' end of the barcode sequence fragment.
142. The control composition of any one of clauses 136 to 141 wherein the nucleic acid construct further comprises at least a first and a second primer binding site fragment.
143. The control composition of clause 142 wherein the nucleic acid construct further comprises at least a first and a second primer binding site fragment and wherein the first primer binding site fragment is linked at its 3' end to the 5' end of the first universal sequence fragment and the second primer binding site fragment is linked at its 5' end to the 3' end of the second universal sequence fragment.
144. The control composition of clause 143 wherein the primer binding site fragments range in length from about 15 base pairs to about 30 base pairs.
145. The control composition of clause 143 wherein the nucleic acid construct ranges in length from about 80 base pairs to about 300 base pairs.

146. The control composition of any one of clauses 136 to 145 wherein the chemical analysis is quantitative and/or qualitative.
147. The control composition of any one of clauses 136 to 146 wherein a small molecule is analyzed and the small molecule is an inorganic compound or an organic compound.
148. The control composition of any one of clauses 136 to 147 wherein the chemical analysis is selected from the group consisting of forensic analysis, environmental analysis, industrial analysis, and medical analysis.
149. The control composition of clause 148 wherein the analysis is forensic analysis and the forensic analysis is selected from the group consisting of stomach content analysis, blood alcohol content analysis, substance abuse analysis, toxin analysis, and poison analysis.
150. The control composition of any one of clauses 136 to 149 wherein the chemical analysis is mass spectrometry.
151. The control composition of any one of clauses 136 to 150 wherein the nucleic acid construct is encapsulated.
152. The control composition of clause 151 wherein the nucleic acid construct is encapsulated in a liposome.
153. The control composition of clause 152 wherein the liposome comprises a lipid selected from the group consisting of cholesterol, a lipopolysaccharide, a peptidoglycan, a PEG, a teichoic acid, a phospholipid, and combinations thereof.
154. The control composition of any one of clauses 136 to 153 wherein the barcode sequence fragment comprises a unique sequence not present in any known genome.
155. The control composition of any one of clauses 136 to 154 wherein the nucleic acid construct is incorporated into a plasmid.
156. A kit comprising the control composition of any one of clauses 136 to 155.
157. The kit of clause 156 further comprising a reagent for nucleic acid extraction.
158. The kit of clause 156 or 157 further comprising a reagent for nucleic acid purification.
159. The kit of any one of clauses 156 to 158 further comprising a reagent for library preparation.
160. The kit of any one of clauses 156 to 159 further comprising a probe.
161. The kit of any one of clauses 156 to 160 further comprising a reagent for sequencing.
162. A method for monitoring cross-contamination or sample swapping during an analytical chemistry protocol, the method comprising,
    a) spiking an analytical chemistry protocol sample with a control composition comprising a nucleic acid construct wherein the nucleic acid construct comprises at least one barcode sequence fragment linked to at least one universal sequence fragment and wherein the nucleic acid construct is a deoxyribonucleic acid construct;
    b) performing the analytical chemistry protocol;
    c) archiving a sample from the analytical chemistry protocol;
    d) extracting total DNA from the archived sample wherein total DNA comprises the DNA from the nucleic acid construct and DNA from the analytical chemistry protocol sample, if any;
    e) purifying total DNA;
    f) preparing a library from total DNA;
    g) sequencing the extracted, purified total DNA; and
    h) detecting the nucleic acid construct in total DNA.
163. The method of clause 162 wherein the sample is selected from the group consisting of urine, nasal secretions, nasal washes, inner ear fluids, bronchial lavages, bronchial washes, alveolar lavages, spinal fluid, bone marrow aspirates, sputum, pleural fluids, synovial fluids, pericardial fluids, peritoneal fluids, saliva, tears, gastric secretions, stool, reproductive tract secretions, lymph fluid, whole blood, serum, plasma, a tissue sample, a soil sample, a water sample, a food sample, an air sample, a plant sample, an industrial waste sample, a surface wipe sample, a dust sample, a hair sample, an agricultural sample, and an animal sample.
164. The method of clause 162 or 163 wherein the method is used to determine if cross-contamination between samples has occurred.
165. The method of clause 162 or 163 wherein the method is used to determine if sample swapping has occurred.
166. The method of any one of clauses 162 to 165 wherein the step of preparing the library from total DNA comprises a step of amplifying the nucleic acid construct.
167. The method of any one of clauses 162 to 166 wherein the nucleic acid construct comprises at least a first and a second universal sequence fragment.
168. The method of clause 167 wherein the first universal sequence fragment is linked to the 5' end of the barcode sequence fragment and the second universal sequence fragment is linked to the 3' end of the barcode sequence fragment.
169. The method of any one of clauses 162 to 168 wherein the nucleic acid construct further comprises at least a first and a second primer binding site fragment.
170. The method of clause 169 wherein the nucleic acid construct further comprises at least a first and a second primer binding site fragment and wherein the first primer binding site fragment is linked at its 3' end to the 5' end of the first universal sequence fragment and the second primer binding site fragment is linked at its 5' end to the 3' end of the second universal sequence fragment.
171. The method of clause 170 wherein the primer binding site fragments range in length from about 15 base pairs to about 30 base pairs.
172. The method of clause 170 wherein the nucleic acid construct ranges in length from about 80 base pairs to about 300 base pairs.
173. The method of any one of clauses 162 to 172 wherein the nucleic acid construct is encapsulated.
174. The method of clause 173 wherein the nucleic acid construct is encapsulated in a liposome.
175. The method of clause 174 wherein the liposome comprises a lipid selected from the group consisting of cholesterol, a lipopolysaccharide, a peptidoglycan, a PEG, a teichoic acid, a phospholipid, and combinations thereof.
176. The method of any one of clauses 162 to 175 wherein the barcode sequence fragment comprises a unique sequence not present in any known genome.
177. The method of any one of clauses 162 to 176 wherein the nucleic acid construct is incorporated into a plasmid.
178. The method of any one of clauses 162 to 177 wherein the chemical analysis is quantitative and/or qualitative.
179. The method of any one of clauses 162 to 178 wherein a small molecule is analyzed and the small molecule is an inorganic compound or an organic compound.

180. The method of any one of clauses 162 to 179 wherein the chemical analysis is selected from the group consisting of forensic analysis, environmental analysis, industrial analysis, and medical analysis.
181. The method of clause 180 wherein the analysis is forensic analysis and the forensic analysis is selected from the group consisting of stomach content analysis, blood alcohol content analysis, substance abuse analysis, toxin analysis, and poison analysis, or combinations thereof.
182. The method of any one of clauses 162 to 180 wherein the analytical chemistry protocol is mass spectrometry.
183. The method of any one of clauses 162 to 182 wherein detecting the nucleic acid construct in total DNA comprises
  iv) identifying the universal sequence fragment in a sequencing read generated by sequencing the extracted, purified total DNA;
  v) comparing a sequence fragment adjacent the universal sequence fragment in the sequencing read to the barcode sequence fragment; and
  vi) determining that cross-contamination or sample swapping has occurred in response to the sequence fragment adjacent the universal sequence fragment not matching the barcode sequence fragment.
184. The method of any one of clauses 167 to 182 wherein detecting the nucleic acid construct in total DNA comprises
  x) identifying the first and second universal sequence fragments in a sequencing read generated by sequencing the extracted, purified total DNA;
  xi) comparing a sequence fragment located between the first and second universal sequence fragments in the sequencing read to the barcode sequence fragment; and
  xii) determining that cross-contamination or sample swapping has occurred in response to the sequence fragment located between the first and second universal sequence fragments not matching the barcode sequence fragment.
185. The method of clause 183 or 184, wherein the identifying and comparing steps are performed using a text-matching algorithm.
186. The method of any one of clauses 183 to 185 wherein the identifying step comprises referencing a database of universal sequence fragments that may be included in the nucleic acid construct of the control composition.
187. The method of any one of clauses 183 to 186 wherein the comparing step comprises referencing a database of barcode sequence fragments that may be included in the nucleic acid construct of the control composition.

Control compositions for sequencing or chemical analyses and methods of their use are provided herein. The polymerase chain reaction (PCR) has been developed to analyze nucleic acids in a laboratory. PCR evolved over the last decade into a new generation of devices and methods known as Next Generation Sequencing (NGS). NGS provides faster detection and amplification of nucleic acids at a cheaper price. The NGS devices and methods allow for rapid sequencing as the nucleic acids are amplified in massively parallel, high-throughput platforms.

NGS, and other sequencing methods, for detection of nucleic acids are powerful techniques, for example, for pathogen detection and identification purposes, including for biosurveillance. However, the field suffers from a lack of standards for use in sequencing methods and devices, including NGS methods and devices. Currently, researchers are able to detect and identify nucleic acids from, for example, pathogens through sequencing, but are unable to monitor sample cross-contamination and sample swapping throughout the sequencing protocol. More effective standards are also needed for monitoring sample cross-contamination and sample swapping after the extraction process, and for quantitation of nucleic acids during sequencing.

Analytical chemistry analysis of unknown materials can be confounded by identification of compounds that do not seem to fit with what is expected. These unexpected compounds could be the result of a cross contamination event or may actually be present in the sample. Therefore, spike-in cross contamination and sample swapping controls are also needed for analytical chemistry analyses.

In one embodiment, control compositions for sequencing or chemical analyses are provided. The control compositions comprise a nucleic acid construct comprising at least one barcode sequence fragment. The barcode sequence fragment comprises a unique sequence not found in any known genome. In one embodiment, the control composition is used to determine if cross-contamination between samples for sequencing or chemical analyses has occurred. In another embodiment, the control composition is used to determine if sample swapping has occurred. In yet another embodiment, the control composition can be used for quantitation of nucleic acids during sequencing. In one aspect, the nucleic acid construct is a deoxyribonucleic acid construct. In another aspect, the nucleic acid construct is a ribonucleic acid. In another embodiment, the nucleic acid construct is incorporated into a plasmid.

In various embodiments, the barcode sequence fragment can be from about 10 to about 35 base pairs in length, about 10 to about 34 base pairs in length, about 10 to about 33 base pairs in length, about 10 to about 32 base pairs in length, about 10 to about 31 base pairs in length, about 10 to about 30 base pairs in length, about 10 to about 29 base pairs in length, about 10 to about 28 base pairs in length, about 10 to about 27 base pairs in length, about 10 to about 26 base pairs in length, about 10 to about 25 base pairs in length, about 10 to about 24 base pairs in length, about 10 to about 15 base pairs in length, about 21 to about 28 base pairs in length, about 21 to about 27 base pairs in length, about 21 to about 26 base pairs in length, about 21 to about 25 base pairs in length, about 22 to about 28 base pairs in length, about 22 to about 27 base pairs in length, about 22 to about 26 base pairs in length, about 22 to about 25 base pairs in length, about 23 to 25 base pairs in length, or about 24 base pairs in length.

Various embodiments of barcode sequence fragments are shown below in Table 1 (labeled barcode sequence fragments). These barcode sequence fragments can be used alone or in combinations of, for example, two or more barcode sequence fragments. Additional barcode sequence fragments are shown in Table 2 between the bolded fragments and within the exemplary nucleic acid constructs having SEQ ID NOS:1 to 384.

TABLE 1

(SEQ ID NOS 775-2938, respectively, in order
of appearance from left to right in each row as shown)

| Barcode Sequence Fragments | Barcode Sequence Fragments | Barcode Sequence Fragments | Barcode Sequence Fragments | Barcode Sequence Fragments | Barcode Sequence Fragments |
|---|---|---|---|---|---|
| TGGTCAACGATA (SEQ ID NO: 775) | CATCGCGTTGAC (SEQ ID NO: 776) | ACGTAACCACGT (SEQ ID NO: 777) | CTTCTTCGCCCT (SEQ ID NO: 778) | GACGGCTATGTT (SEQ ID NO: 779) | GTCATTGGGCTA (SEQ ID NO: 780) |
| ATCGCACAGTAA (SEQ ID NO: 781) | GCACATAGTCGT (SEQ ID NO: 782) | GTCGGAAATTGT (SEQ ID NO: 783) | CAGGCATAACAT (SEQ ID NO: 784) | TCTCTTTCGACA (SEQ ID NO: 785) | AGAGACGCGTAG (SEQ ID NO: 786) |
| GTCGTGTAGCCT (SEQ ID NO: 787) | GGCAAATACACT (SEQ ID NO: 788) | TCTAACGAGTGC (SEQ ID NO: 789) | ATGTGGCGTGTT (SEQ ID NO: 790) | GATTAGGTTCCG (SEQ ID NO: 791) | TTAATGGATCGG (SEQ ID NO: 792) |
| AGCGGAGGTTAG (SEQ ID NO: 793) | GTCATGCTCCAG (SEQ ID NO: 794) | CATCTGGGCAAT (SEQ ID NO: 795) | GTGCGGTTCACT (SEQ ID NO: 796) | CTACTCCACGAG (SEQ ID NO: 797) | ATATTGGCAGCC (SEQ ID NO: 798) |
| ATCCTTTGGTTC (SEQ ID NO: 799) | CCTAGTAAGCTG (SEQ ID NO: 800) | TGTCCGTGGATC (SEQ ID NO: 801) | CCTCACTAGCGA (SEQ ID NO: 802) | GGTGCAGACAGA (SEQ ID NO: 803) | TCGCATGGATAC (SEQ ID NO: 804) |
| TACAGCGCATAC (SEQ ID NO: 805) | TTACCGACGAGT (SEQ ID NO: 806) | ACTCGGCCAACT (SEQ ID NO: 807) | AGCTGATAGTTG (SEQ ID NO: 808) | CCGTACCGTATG (SEQ ID NO: 809) | CAACAATGCCAA (SEQ ID NO: 810) |
| ACCGGTATGTAC (SEQ ID NO: 811) | GCTTAGATGTAG (SEQ ID NO: 812) | GTTGGTTGGCAT (SEQ ID NO: 813) | GCTCTAGTAACG (SEQ ID NO: 814) | ATGTCCGACCAA (SEQ ID NO: 815) | GCCCGACATATA (SEQ ID NO: 816) |
| AATTGTGTCGGA (SEQ ID NO: 817) | AAGACGTAGCGG (SEQ ID NO: 818) | TTCCACACGTGG (SEQ ID NO: 819) | TGGTCCTACAAG (SEQ ID NO: 820) | AGATGGGACTGG (SEQ ID NO: 821) | GATTGAACGCTA (SEQ ID NO: 822) |
| TGCATACACTGG (SEQ ID NO: 823) | TTACCTTACACC (SEQ ID NO: 824) | AACCCAGATGAT (SEQ ID NO: 825) | CGCTATCCAGAC (SEQ ID NO: 826) | GTGCCCACTTGA (SEQ ID NO: 827) | AGTATTCGCGCA (SEQ ID NO: 828) |
| AGTCGAACGAGG (SEQ ID NO: 829) | TGACTAATGGCC (SEQ ID NO: 830) | GTAGTGTCAACA (SEQ ID NO: 831) | GCTTACGTAGGT (SEQ ID NO: 832) | ACCGAACAATCC (SEQ ID NO: 833) | TGCCAACAACAA (SEQ ID NO: 834) |
| ACCAGTGACTCA (SEQ ID NO: 835) | CTCTCTCACTTG (SEQ ID NO: 836) | TGGAGAGGAGAT (SEQ ID NO: 837) | AGTTGGTTACGA (SEQ ID NO: 838) | GTCTACCACGCA (SEQ ID NO: 839) | CTAAAGTAGCAC (SEQ ID NO: 840) |
| GAATACCAAGTC (SEQ ID NO: 841) | ATTGCAAGCAAC (SEQ ID NO: 842) | CGTATAAATGCG (SEQ ID NO: 843) | CTCTACGAACAG (SEQ ID NO: 844) | TCGCGTCCAGTA (SEQ ID NO: 845) | AGTGCTAGGTTA (SEQ ID NO: 846) |
| GTAGATCGTGTA (SEQ ID NO: 847) | CACGTGACATGT (SEQ ID NO: 848) | AATACAGACCTG (SEQ ID NO: 849) | CCTGTGTTGGTG (SEQ ID NO: 850) | GCCTGATTAAGC (SEQ ID NO: 851) | CGGAAACTCCAT (SEQ ID NO: 852) |
| TAACGTGTGTGC (SEQ ID NO: 853) | CACAGTTGAAGT (SEQ ID NO: 854) | GACTCAACCAGT (SEQ ID NO: 855) | GATGGGAGGACT (SEQ ID NO: 856) | ACGTATTCGAAG (SEQ ID NO: 857) | AGGAAAGCCAGA (SEQ ID NO: 858) |
| CATTATGGCGTG (SEQ ID NO: 859) | CTAGGATCACTG (SEQ ID NO: 860) | GGAAGAAGTAGC (SEQ ID NO: 861) | CAGAATCGCTCA (SEQ ID NO: 862) | CGGCTACTATGC (SEQ ID NO: 863) | GTCTGACGGTCT (SEQ ID NO: 864) |
| CCAATACGCCTG (SEQ ID NO: 865) | GATGACCCAAAT (SEQ ID NO: 866) | ATCGATCCACAG (SEQ ID NO: 867) | TGGCACTGGTTA (SEQ ID NO: 868) | AGTTCGGCATTG (SEQ ID NO: 869) | GAAACCAAGCTT (SEQ ID NO: 870) |
| GATCTGCGATCC (SEQ ID NO: 871) | ACCGGAGTAGGA (SEQ ID NO: 872) | ACACCGCACAAT (SEQ ID NO: 873) | GGCAGTGTTAAT (SEQ ID NO: 874) | TTGGGAGCGAAG (SEQ ID NO: 875) | TCATCACGGGCT (SEQ ID NO: 876) |
| CAGCTCATCAGC (SEQ ID NO: 877) | TGAGGACTACCT (SEQ ID NO: 878) | GTCTCCTCCCTT (SEQ ID NO: 879) | AACCCGTCGTCA (SEQ ID NO: 880) | TGTTCGCCCAGA (SEQ ID NO: 881) | TGTTCTGAGACG (SEQ ID NO: 882) |

TABLE 1-continued (SEQ ID NOS 775-2938, respectively, in order
of appearance from left to right in each row as shown)

| Barcode Sequence Fragments | Barcode Sequence Fragments | Barcode Sequence Fragments | Barcode Sequence Fragments | Barcode Sequence Fragments | Barcode Sequence Fragments |
| --- | --- | --- | --- | --- | --- |
| CAAACAACAGCT (SEQ ID NO: 883) | CAATCGGCTTGC (SEQ ID NO: 884) | GTAGCACTCATG (SEQ ID NO: 885) | AGAGGAGTCGAC (SEQ ID NO: 886) | CGCGTATCTCAG (SEQ ID NO: 887) | ATAGCACCAGAT (SEQ ID NO: 888) |
| GCAACACCATCC (SEQ ID NO: 889) | AACACTCGATCG (SEQ ID NO: 890) | CACCTGTAGTAG (SEQ ID NO: 891) | TAAGTCGGCCTA (SEQ ID NO: 892) | CGAAAGCATTCC (SEQ ID NO: 893) | ATCTCGCTGGGT (SEQ ID NO: 894) |
| GCGATATATCGC (SEQ ID NO: 895) | TGACCGGCTGTT (SEQ ID NO: 896) | CACGAGCTACTC (SEQ ID NO: 897) | CAGGGTAGGGTA (SEQ ID NO: 898) | CCGGACAAGAAG (SEQ ID NO: 899) | GCGCGTGTATCT (SEQ ID NO: 900) |
| CGAGCAATCCTA (SEQ ID NO: 901) | GGAGGAGCAATA (SEQ ID NO: 902) | TCTCGATAAGCG (SEQ ID NO: 903) | CATGGGTGTTAC (SEQ ID NO: 904) | CGATCCGATCTG (SEQ ID NO: 905) | AACGCGAAATTC (SEQ ID NO: 906) |
| AGTCGTGCACAT (SEQ ID NO: 907) | AGCGACGAAGAC (SEQ ID NO: 908) | TAGACACCGTGT (SEQ ID NO: 909) | GATGCCTAATGA (SEQ ID NO: 910) | TGCATCGCGTCA (SEQ ID NO: 911) | ATCTGGACGATC (SEQ ID NO: 912) |
| GTATCTGCGCGT (SEQ ID NO: 913) | CTTCCCTAACTC (SEQ ID NO: 914) | AGACAAGCTTCC (SEQ ID NO: 915) | TTATCGGGCATG (SEQ ID NO: 916) | ATGGACCTAGCT (SEQ ID NO: 917) | CCAGCTGGACTT (SEQ ID NO: 918) |
| CGAGGGAAAGTC (SEQ ID NO: 919) | TGGAAGAACGGC (SEQ ID NO: 920) | TCCGCAACCTGA (SEQ ID NO: 921) | TGGACATAAACC (SEQ ID NO: 922) | AGGAATACTCAC (SEQ ID NO: 923) | CTCTAACCTCTA (SEQ ID NO: 924) |
| CAAATTCGGGAT (SEQ ID NO: 925) | GCTAGACACTAC (SEQ ID NO: 926) | TCACTTGGTGCG (SEQ ID NO: 927) | TGACCTCAAGAC (SEQ ID NO: 928) | CTACCTTGAGGA (SEQ ID NO: 929) | CAACCGAGATTA (SEQ ID NO: 930) |
| AGATTGACCAAC (SEQ ID NO: 931) | TTGGATTGAACG (SEQ ID NO: 932) | TTATGTACGGCG (SEQ ID NO: 933) | GCCAAATCGCTC (SEQ ID NO: 934) | CGTGTTATGTGG (SEQ ID NO: 935) | GATTCGAGTGTC (SEQ ID NO: 936) |
| AGTTACGAGCTA (SEQ ID NO: 937) | GATATACCAGTG (SEQ ID NO: 938) | TTGGACGTCCAC (SEQ ID NO: 939) | TCAAAGCTCAAG (SEQ ID NO: 940) | GTACGCACAGTT (SEQ ID NO: 941) | GGTAACCTCTGA (SEQ ID NO: 942) |
| GCATATGCACTG (SEQ ID NO: 943) | AACAAACTGCCA (SEQ ID NO: 944) | TCCAGGGCTATA (SEQ ID NO: 945) | TACCAATCGGTG (SEQ ID NO: 946) | TGGACTCAGCTA (SEQ ID NO: 947) | AGCGAACCTGTT (SEQ ID NO: 948) |
| CAACTCCCGTGA (SEQ ID NO: 949) | GTAGACATGTGT (SEQ ID NO: 950) | GCGTAGAGAGAC (SEQ ID NO: 951) | GTACTCGAACCA (SEQ ID NO: 952) | ACGCGCTAAATC (SEQ ID NO: 953) | ACATGCACATGC (SEQ ID NO: 954) |
| TTGCGTTAGCAG (SEQ ID NO: 955) | TACAGTTACGCG (SEQ ID NO: 956) | GAAACTCCTAGA (SEQ ID NO: 957) | TTCCGGCGATTG (SEQ ID NO: 958) | GACCTGAATACA (SEQ ID NO: 959) | CCTTACCTCCTC (SEQ ID NO: 960) |
| TACGAGCCCTAA (SEQ ID NO: 961) | CAAGCCCTAGTA (SEQ ID NO: 962) | ATCGGGCTTAAC (SEQ ID NO: 963) | GACATGCGGAGA (SEQ ID NO: 964) | ACGTTTGTGGCA (SEQ ID NO: 965) | ACACTGGTCCTG (SEQ ID NO: 966) |
| CACTACGCTAGA (SEQ ID NO: 967) | TAGTGTCGGATC (SEQ ID NO: 968) | TACGCCCATCAG (SEQ ID NO: 969) | CGCACCCATACA (SEQ ID NO: 970) | GCTTAACGTGCC (SEQ ID NO: 971) | AGCTTGAATCAG (SEQ ID NO: 972) |
| TGCAGTCCTCGA (SEQ ID NO: 973) | CTGAGCTCTGCA (SEQ ID NO: 974) | AAGATCGTACTG (SEQ ID NO: 975) | ACATTGAAGCGT (SEQ ID NO: 976) | GAATGGATGGGC (SEQ ID NO: 977) | TAAAGCGAGGAG (SEQ ID NO: 978) |
| ACCATAGCTCCG (SEQ ID NO: 979) | CTTCGACTTTCC (SEQ ID NO: 980) | ACTCATCTTCCA (SEQ ID NO: 981) | GACGACATTTAG (SEQ ID NO: 982) | CATGAACAGTGT (SEQ ID NO: 983) | CGACAACTTGTG (SEQ ID NO: 984) |
| TCGACATCTCTT (SEQ ID NO: 985) | GTCATAAGAACC (SEQ ID NO: 986) | GAGATACAGTTC (SEQ ID NO: 987) | CCAACTACTCGG (SEQ ID NO: 988) | GACTAGTCAGCT (SEQ ID NO: 989) | CGCTGGCTTTAG (SEQ ID NO: 990) |

TABLE 1-continued (SEQ ID NOS 775-2938, respectively, in order of appearance from left to right in each row as shown)

| Barcode Sequence Fragments | Barcode Sequence Fragments | Barcode Sequence Fragments | Barcode Sequence Fragments | Barcode Sequence Fragments | Barcode Sequence Fragments |
|---|---|---|---|---|---|
| GAACACTTTGGA (SEQ ID NO: 991) | GTCCGCAAGTTA (SEQ ID NO: 992) | GCATGCATCCCA (SEQ ID NO: 993) | CCGTTATCAGCG (SEQ ID NO: 994) | CAAGAAATTCGC (SEQ ID NO: 995) | GTGATACCCGCT (SEQ ID NO: 996) |
| GAGCCATCTGTA (SEQ ID NO: 997) | CGTAGAGCTCTC (SEQ ID NO: 998) | GATCTAATCGAG (SEQ ID NO: 999) | TATGGCCAAACC (SEQ ID NO: 1000) | AAGCTCTCCCAG (SEQ ID NO: 1001) | CCAGTTCCAAAG (SEQ ID NO: 1002) |
| TTGGGTACACGT (SEQ ID NO: 1003) | CCTCTGAGAGCT (SEQ ID NO: 1004) | AATCTTGCGCCG (SEQ ID NO: 1005) | TGCCTAAGATCG (SEQ ID NO: 1006) | TGGATCTGTCCG (SEQ ID NO: 1007) | GTCTGGATTGAA (SEQ ID NO: 1008) |
| AAGGCGCTCCTT (SEQ ID NO: 1009) | CCTCGATGCAGT (SEQ ID NO: 1010) | GGAAATCCCATC (SEQ ID NO: 1011) | TTAACTGGAAGC (SEQ ID NO: 1012) | CCTACTCGGTGA (SEQ ID NO: 1013) | GCGCAATAGTAT (SEQ ID NO: 1014) |
| TAATACGGATCG (SEQ ID NO: 1015) | GCGGACTATTCA (SEQ ID NO: 1016) | GACCGTCAATAC (SEQ ID NO: 1017) | ATTCGAGCTGTG (SEQ ID NO: 1018) | ATACCGTCTTTC (SEQ ID NO: 1019) | AGCGTTGTCCAA (SEQ ID NO: 1020) |
| TCGGAATTAGAC (SEQ ID NO: 1021) | CGTGCACAATTG (SEQ ID NO: 1022) | TTGGAACGGCTT (SEQ ID NO: 1023) | GGTCTGTTGAGT (SEQ ID NO: 1024) | AAGGACCGTTTC (SEQ ID NO: 1025) | CGCCTAAACCGT (SEQ ID NO: 1026) |
| TGTGAATTCGGA (SEQ ID NO: 1027) | CGGCCTAAGTTC (SEQ ID NO: 1028) | TCCTAGGTCCGA (SEQ ID NO: 1029) | CTCGTCGACTGA (SEQ ID NO: 1030) | AAGTAGGAAGGA (SEQ ID NO: 1031) | AACACCATCGAC (SEQ ID NO: 1032) |
| CATTCGTGGCGT (SEQ ID NO: 1033) | AGCGCTCACATC (SEQ ID NO: 1034) | TCCTCACTATCA (SEQ ID NO: 1035) | TCTTTCATACCG (SEQ ID NO: 1036) | CGTGCCGCTTAA (SEQ ID NO: 1037) | CTATAGACACGA (SEQ ID NO: 1038) |
| TACTACGTGGCC (SEQ ID NO: 1039) | TGGTTATGGCAC (SEQ ID NO: 1040) | GCCTGCAGTACT (SEQ ID NO: 1041) | CATTCCCGAAAG (SEQ ID NO: 1042) | GCGTCATGCATC (SEQ ID NO: 1043) | CAAGAGCGGATG (SEQ ID NO: 1044) |
| GGCCAGTTCCTA (SEQ ID NO: 1045) | CGAGGTTCTGAT (SEQ ID NO: 1046) | GCCCAAGTTCAC (SEQ ID NO: 1047) | TTGTCAGCTGGA (SEQ ID NO: 1048) | CGTTGGACAAAT (SEQ ID NO: 1049) | CCTTTGGCTGAG (SEQ ID NO: 1050) |
| GATGTTCGCTAG (SEQ ID NO: 1051) | AACTCCTGTGGA (SEQ ID NO: 1052) | ATAAAGAGGAGG (SEQ ID NO: 1053) | ATCTGCGCACCA (SEQ ID NO: 1054) | TTGTTGATGGAG (SEQ ID NO: 1055) | CGACCCATACGT (SEQ ID NO: 1056) |
| CTATCTCCTGTC (SEQ ID NO: 1057) | TAATGGTCGTAG (SEQ ID NO: 1058) | GCGCCGAATCTT (SEQ ID NO: 1059) | CCACGTACGTAA (SEQ ID NO: 1060) | CTTACACTGCTT (SEQ ID NO: 1061) | CTGGATTACGGT (SEQ ID NO: 1062) |
| ACTCACAGGAAT (SEQ ID NO: 1063) | TTGCACCGTCGA (SEQ ID NO: 1064) | ATCCCAGCATGC (SEQ ID NO: 1065) | ACGATATGGTCA (SEQ ID NO: 1066) | AATGCGCGTATA (SEQ ID NO: 1067) | ACCACACGTAGT (SEQ ID NO: 1068) |
| ATGATGAGCCTC (SEQ ID NO: 1069) | TGCTACAGACGT (SEQ ID NO: 1070) | GCTTCCAGACAA (SEQ ID NO: 1071) | GAGACAGTGGAA (SEQ ID NO: 1072) | TGCCATTAGAGC (SEQ ID NO: 1073) | CTAGTGACCTAG (SEQ ID NO: 1074) |
| GTCGACAGAGGA (SEQ ID NO: 1075) | ATGGCCTGACTA (SEQ ID NO: 1076) | ACACAGTCCTGA (SEQ ID NO: 1077) | TCGTAGTAATGG (SEQ ID NO: 1078) | CGAAGGGTTGGA (SEQ ID NO: 1079) | GGATTCGTGTCC (SEQ ID NO: 1080) |
| TGTCGCAAATAG (SEQ ID NO: 1081) | ACGCACATACAA (SEQ ID NO: 1082) | ATTATACGGCGC (SEQ ID NO: 1083) | AGGCTGTACTCC (SEQ ID NO: 1084) | GAGCAACATCCT (SEQ ID NO: 1085) | GTGAGATACCTA (SEQ ID NO: 1086) |
| CATCCCTCTACT (SEQ ID NO: 1087) | TGAGTGGTCTGT (SEQ ID NO: 1088) | ATTCAGATGGCA (SEQ ID NO: 1089) | CGGAAGAGAACA (SEQ ID NO: 1090) | TCGTGTTGTGGC (SEQ ID NO: 1091) | CGCGGTTACTAA (SEQ ID NO: 1092) |
| TATACCGCTGCG (SEQ ID NO: 1093) | GATAGCACTCGT (SEQ ID NO: 1094) | TAAACGCGACTC (SEQ ID NO: 1095) | CTGCGGATATAC (SEQ ID NO: 1096) | ATTTCGACCCGG (SEQ ID NO: 1097) | AGGCCCGTTTAC (SEQ ID NO: 1098) |

TABLE 1-continued (SEQ ID NOS 775-2938, respectively, in order
of appearance from left to right in each row as shown)

| Barcode Sequence Fragments | Barcode Sequence Fragments | Barcode Sequence Fragments | Barcode Sequence Fragments | Barcode Sequence Fragments | Barcode Sequence Fragments |
|---|---|---|---|---|---|
| AGTTGAGGCATT (SEQ ID NO: 1099) | TAGCGCGAACTT (SEQ ID NO: 1100) | CCTCGGGTACTA (SEQ ID NO: 1101) | CTAGCGTGCGTT (SEQ ID NO: 1102) | TGGATTGTGAAC (SEQ ID NO: 1103) | TGTTGTTGGGAA (SEQ ID NO: 1104) |
| ACAATAGACACC (SEQ ID NO: 1105) | CATACACGCACC (SEQ ID NO: 1106) | TTCACCTGTATC (SEQ ID NO: 1107) | ACCATGTAGAAC (SEQ ID NO: 1108) | CCGTTGGACTAC (SEQ ID NO: 1109) | CTGAATCTGGTG (SEQ ID NO: 1110) |
| CGGTCAATTGAC (SEQ ID NO: 1111) | ACCTCAGTCAAG (SEQ ID NO: 1112) | CTCCAGGTCATG (SEQ ID NO: 1113) | TAGCTCACAGCA (SEQ ID NO: 1114) | TCTGGCTACGAC (SEQ ID NO: 1115) | GGCCTCACTGAT (SEQ ID NO: 1116) |
| GTGGAGTCTCAT (SEQ ID NO: 1117) | TCGACCAAACAC (SEQ ID NO: 1118) | CAGGATTCGTAC (SEQ ID NO: 1119) | GTCTTGGGTCGT (SEQ ID NO: 1120) | TCAGGCGTAAAT (SEQ ID NO: 1121) | GTGGTTCGATGT (SEQ ID NO: 1122) |
| GCTCGAAGATTC (SEQ ID NO: 1123) | CCACCCAGTAAC (SEQ ID NO: 1124) | CGCATACGACCT (SEQ ID NO: 1125) | CTGTATGGAGCT (SEQ ID NO: 1126) | TCACGGTGACAT (SEQ ID NO: 1127) | TCGAGAGTTTGC (SEQ ID NO: 1128) |
| AGGCTTACGTGT (SEQ ID NO: 1129) | ATATCGCGATGA (SEQ ID NO: 1130) | GCCTCGTACTGA (SEQ ID NO: 1131) | ATGCAACTCGAA (SEQ ID NO: 1132) | CAAGGTCACCTC (SEQ ID NO: 1133) | TACGACTCTGGC (SEQ ID NO: 1134) |
| TCTCTACCACTC (SEQ ID NO: 1135) | CGCCGGTAATCT (SEQ ID NO: 1136) | ACCAACAGATTG (SEQ ID NO: 1137) | CTAACTGACGCA (SEQ ID NO: 1138) | CTATACGCGAAC (SEQ ID NO: 1139) | GCGTAACTCTCG (SEQ ID NO: 1140) |
| ACTTCCAACTTC (SEQ ID NO: 1141) | CCGATGCCTTGA (SEQ ID NO: 1142) | GTGGCCTACTAC (SEQ ID NO: 1143) | AACGTCCTGTGC (SEQ ID NO: 1144) | GAGGAGTAAAGC (SEQ ID NO: 1145) | CTTTCCCTTCGA (SEQ ID NO: 1146) |
| CTCACCTAGGAA (SEQ ID NO: 1147) | AGCAGGCACGAA (SEQ ID NO: 1148) | TTCCCTTCTCCG (SEQ ID NO: 1149) | AGACGACGTGGA (SEQ ID NO: 1150) | GCAGCATGTTAA (SEQ ID NO: 1151) | AAGATTTGCAGC (SEQ ID NO: 1152) |
| GTGTTGTCGTGC (SEQ ID NO: 1153) | TACGCAGCACTA (SEQ ID NO: 1154) | CATTTGACGACG (SEQ ID NO: 1155) | AAGGTTCCGATA (SEQ ID NO: 1156) | GTTGGGATCCTC (SEQ ID NO: 1157) | AACGGCTGGAAG (SEQ ID NO: 1158) |
| CCACAGATCGAT (SEQ ID NO: 1159) | CGCTTAGTGCTG (SEQ ID NO: 1160) | AAGTGAAGCGAG (SEQ ID NO: 1161) | AGTTTCTGGTGG (SEQ ID NO: 1162) | TTCAGCGATGGT (SEQ ID NO: 1163) | ATCGTCCGCGAT (SEQ ID NO: 1164) |
| TATCGACACAAG (SEQ ID NO: 1165) | CAAAGTTTGCGA (SEQ ID NO: 1166) | TGCCGCCGTAAT (SEQ ID NO: 1167) | TTCCTCCTGCTA (SEQ ID NO: 1168) | ACAATCCCGAGT (SEQ ID NO: 1169) | TCACAGACAATG (SEQ ID NO: 1170) |
| GATTCCGGCTCA (SEQ ID NO: 1171) | TCGAGCCGATCT (SEQ ID NO: 1172) | AACCTCGGATAA (SEQ ID NO: 1173) | CATCTCAGTCGG (SEQ ID NO: 1174) | GTTCTTGGAGAC (SEQ ID NO: 1175) | GAGACTATATGC (SEQ ID NO: 1176) |
| CGTAATTGCCGC (SEQ ID NO: 1177) | CTCATCATGTTC (SEQ ID NO: 1178) | GTGCTTGTGTAG (SEQ ID NO: 1179) | ATATGCGAGACT (SEQ ID NO: 1180) | TAGCCCTGATGC (SEQ ID NO: 1181) | AGAGGGTGATCG (SEQ ID NO: 1182) |
| GGTGACTAGTTC (SEQ ID NO: 1183) | CCAGGGACTTCT (SEQ ID NO: 1184) | CAACTAGACTCG (SEQ ID NO: 1185) | GACCACTGCTGT (SEQ ID NO: 1186) | TTGTCCCAAGCG (SEQ ID NO: 1187) | TAGAGAATGCTC (SEQ ID NO: 1188) |
| ATGGGTTCCGTC (SEQ ID NO: 1189) | GCAATCCTTGCG (SEQ ID NO: 1190) | AGTGCCCTTGGT (SEQ ID NO: 1191) | ATAGACACTCCG (SEQ ID NO: 1192) | TTCGTACTTCGT (SEQ ID NO: 1193) | AGAGCATCCACT (SEQ ID NO: 1194) |
| TAGGCATGCTTG (SEQ ID NO: 1195) | CCTGCTTCCTTC (SEQ ID NO: 1196) | GGAACGACGTGA (SEQ ID NO: 1197) | GAATCGCCGATT (SEQ ID NO: 1198) | CTGCTCAGGCAT (SEQ ID NO: 1199) | ACAGTCTGCATG (SEQ ID NO: 1200) |

TABLE 1-continued (SEQ ID NOS 775-2938, respectively, in order of appearance from left to right in each row as shown)

| Barcode Sequence Fragments | Barcode Sequence Fragments | Barcode Sequence Fragments | Barcode Sequence Fragments | Barcode Sequence Fragments | Barcode Sequence Fragments |
|---|---|---|---|---|---|
| AACTAGTTCAGG (SEQ ID NO: 1201) | CAAGGCACAAGG (SEQ ID NO: 1202) | TGTCAGCTGTCG (SEQ ID NO: 1203) | TAGAAGGCTCCT (SEQ ID NO: 1204) | GACATCTGACAC (SEQ ID NO: 1205) | AATCGGTCCGAT (SEQ ID NO: 1206) |
| ATTCTGCCGAAG (SEQ ID NO: 1207) | GGCCTATAAGTC (SEQ ID NO: 1208) | CTGGTGCTGAAT (SEQ ID NO: 1209) | CGACTAACTAGA (SEQ ID NO: 1210) | CACAACCACAAC (SEQ ID NO: 1211) | CCGTTCAATGGA (SEQ ID NO: 1212) |
| AGCATGTCCCGT (SEQ ID NO: 1213) | TCCATTTCATGC (SEQ ID NO: 1214) | GACAGAGGTGCA (SEQ ID NO: 1215) | TACAACCGAGTA (SEQ ID NO: 1216) | GCACCAATCTGC (SEQ ID NO: 1217) | CTCTCGGCGTAA (SEQ ID NO: 1218) |
| GTACGATATGAC (SEQ ID NO: 1219) | TCGGCGATCATC (SEQ ID NO: 1220) | TCAGACCAACTG (SEQ ID NO: 1221) | CTCATGGTAGCA (SEQ ID NO: 1222) | ATTAGCAGCGTA (SEQ ID NO: 1223) | TCCCTCTGAGAG (SEQ ID NO: 1224) |
| GTGGTGGTTTCC (SEQ ID NO: 1225) | GTTTCACGCGAA (SEQ ID NO: 1226) | AGTGATGTGACT (SEQ ID NO: 1227) | AACGACACGCTT (SEQ ID NO: 1228) | TCCGATAATCGG (SEQ ID NO: 1229) | AAGTTAGTCCGC (SEQ ID NO: 1230) |
| TAGTATGCGCAA (SEQ ID NO: 1231) | ACAAGAACCTTG (SEQ ID NO: 1232) | CTTAGCTACTCT (SEQ ID NO: 1233) | CCTGGCTGAATA (SEQ ID NO: 1234) | CTTTCAGGACCG (SEQ ID NO: 1235) | TCAGATACCAGC (SEQ ID NO: 1236) |
| TGCGCTGAATGT (SEQ ID NO: 1237) | TACTCTCTTAGC (SEQ ID NO: 1238) | TCGGTCCATAGC (SEQ ID NO: 1239) | TTCGGATGTGAA (SEQ ID NO: 1240) | CGTCCTACAGTG (SEQ ID NO: 1241) | TCGAAGACGTAT (SEQ ID NO: 1242) |
| ATGGCTGTCAGT (SEQ ID NO: 1243) | AACTGTTCGCGC (SEQ ID NO: 1244) | CACGTTTATTCC (SEQ ID NO: 1245) | CTAGGTCCGACT (SEQ ID NO: 1246) | GTAACTCAACAG (SEQ ID NO: 1247) | CACTTCTTTGTG (SEQ ID NO: 1248) |
| GTTCTCTTCTCG (SEQ ID NO: 1249) | CGAAGCATCTAC (SEQ ID NO: 1250) | GAAACGGAAACG (SEQ ID NO: 1251) | AGATCCCGTACC (SEQ ID NO: 1252) | CGTGGAAGACGA (SEQ ID NO: 1253) | CGTCGATTGCAC (SEQ ID NO: 1254) |
| CGTAAGATGCCT (SEQ ID NO: 1255) | GTTTGGCCACAC (SEQ ID NO: 1256) | GGTCGTGTCTTG (SEQ ID NO: 1257) | TCTGGTGCATCG (SEQ ID NO: 1258) | GAGAGGGATCAC (SEQ ID NO: 1259) | GTTGCCTCTGAG (SEQ ID NO: 1260) |
| GCGTTCTAGCTG (SEQ ID NO: 1261) | TCAGGTTGCCCA (SEQ ID NO: 1262) | CGTCGTCTAAGA (SEQ ID NO: 1263) | CAGCTGGTTCAA (SEQ ID NO: 1264) | TCGGCTTGGAAT (SEQ ID NO: 1265) | CACCTCCAAGGT (SEQ ID NO: 1266) |
| GTTGTTCTGGGA (SEQ ID NO: 1267) | TCATTCCACTCA (SEQ ID NO: 1268) | CAAGCGTTGTCC (SEQ ID NO: 1269) | GCTGGATTGTCA (SEQ ID NO: 1270) | TGAACAGGTTCA (SEQ ID NO: 1271) | GTAAGCCTCGAT (SEQ ID NO: 1272) |
| GGACTTCCAGCT (SEQ ID NO: 1273) | GTCACATCACGA (SEQ ID NO: 1274) | GACTTATGCCCG (SEQ ID NO: 1275) | TCTTGTTTCTGG (SEQ ID NO: 1276) | GAGAGATCGACG (SEQ ID NO: 1277) | CTCCGCTATAGG (SEQ ID NO: 1278) |
| CTCACAACCGTG (SEQ ID NO: 1279) | CGACATTTCTCT (SEQ ID NO: 1280) | GTGACGTTAGTC (SEQ ID NO: 1281) | TTGAACAAGCCA (SEQ ID NO: 1282) | ATACAAACGCAC (SEQ ID NO: 1283) | ACTGCTATCGCG (SEQ ID NO: 1284) |
| CTGCTATTCCTC (SEQ ID NO: 1285) | GGACGTTAACTA (SEQ ID NO: 1286) | GAGTCTTGGTAA (SEQ ID NO: 1287) | CCAGGTTAATGC (SEQ ID NO: 1288) | GATTCACTGTGG (SEQ ID NO: 1289) | ACCACTTGCCAG (SEQ ID NO: 1290) |
| ATGTCACCGCTG (SEQ ID NO: 1291) | TAGCAGTTGCGT (SEQ ID NO: 1292) | TCGTCGCCAAAC (SEQ ID NO: 1293) | ATTCGTACCTCT (SEQ ID NO: 1294) | GCTTGCCAATCG (SEQ ID NO: 1295) | ACCAGAAATGTC (SEQ ID NO: 1296) |
| TGTAACGCCGAT (SEQ ID NO: 1297) | CACGCTATTGGA (SEQ ID NO: 1298) | AACATGCATGCC (SEQ ID NO: 1299) | TAGCGTTCCAGA (SEQ ID NO: 1300) | CTGACACGAATA (SEQ ID NO: 1301) | ATGCTTGCTCTT (SEQ ID NO: 1302) |
| AGCAGAACATCT (SEQ ID NO: 1303) | AACTTCACTTCC (SEQ ID NO: 1304) | GTCTGTTGAGTG (SEQ ID NO: 1305) | CCAGAAGTGTTC (SEQ ID NO: 1306) | GTTCTAAGGTGA (SEQ ID NO: 1307) | ACAGTTGTACGC (SEQ ID NO: 1308) |

TABLE 1-continued (SEQ ID NOS 775-2938, respectively, in order of appearance from left to right in each row as shown)

| Barcode Sequence Fragments | Barcode Sequence Fragments | Barcode Sequence Fragments | Barcode Sequence Fragments | Barcode Sequence Fragments | Barcode Sequence Fragments |
|---|---|---|---|---|---|
| TGGAGTAGGTGG (SEQ ID NO: 1309) | CCAGTGGATATA (SEQ ID NO: 1310) | TGAGTTCGGTCC (SEQ ID NO: 1311) | ACGATCATCTGG (SEQ ID NO: 1312) | CGTGAATCAACC (SEQ ID NO: 1313) | AGCTACTGCGTC (SEQ ID NO: 1314) |
| TTGGCTCTATTC (SEQ ID NO: 1315) | TGTGTGTAACGC (SEQ ID NO: 1316) | TTACGTGGCGAT (SEQ ID NO: 1317) | ACTGTACATGAG (SEQ ID NO: 1318) | GAGCTAAGTTAC (SEQ ID NO: 1319) | ACTGCCCGATAC (SEQ ID NO: 1320) |
| GATCCCACGTAC (SEQ ID NO: 1321) | CCAATCGTGCAA (SEQ ID NO: 1322) | CAATGCCTCACG (SEQ ID NO: 1323) | TGCCCGGACTTA (SEQ ID NO: 1324) | AGCGATTCCTCG (SEQ ID NO: 1325) | CACAGCGTCCTA (SEQ ID NO: 1326) |
| TACCGCTTCTTC (SEQ ID NO: 1327) | AGGCTAGCAGAG (SEQ ID NO: 1328) | TGTACGGATAAC (SEQ ID NO: 1329) | ATCCCGTACGTG (SEQ ID NO: 1330) | CCAACCCAGATC (SEQ ID NO: 1331) | ACGTCCACTGTG (SEQ ID NO: 1332) |
| TGTGCGATAACA (SEQ ID NO: 1333) | GTCACTCCGAAC (SEQ ID NO: 1334) | AATCAACTAGGC (SEQ ID NO: 1335) | CTTGTTGTTCTG (SEQ ID NO: 1336) | GATTGCTACCAG (SEQ ID NO: 1337) | CGCTAATCGTGA (SEQ ID NO: 1338) |
| GATTATCGACGA (SEQ ID NO: 1339) | CACCGAAATCTG (SEQ ID NO: 1340) | GTGAGGGCAAGT (SEQ ID NO: 1341) | TGACAGAATCCA (SEQ ID NO: 1342) | GGCTCTAACGTA (SEQ ID NO: 1343) | GGCCGTTCGATT (SEQ ID NO: 1344) |
| GCCTAGCCCAAT (SEQ ID NO: 1345) | TGACGTAGAACT (SEQ ID NO: 1346) | CGTGGGCTCATT (SEQ ID NO: 1347) | CACTGTATGAAG (SEQ ID NO: 1348) | AATCTGCACCGA (SEQ ID NO: 1349) | GGAACTTACTCG (SEQ ID NO: 1350) |
| GATGTATGTGGT (SEQ ID NO: 1351) | CTATGCCGGCTA (SEQ ID NO: 1352) | CGTACCAGATCC (SEQ ID NO: 1353) | TGGATGCGCATT (SEQ ID NO: 1354) | CCAGCCTTCAGA (SEQ ID NO: 1355) | CAGTTACCCAAG (SEQ ID NO: 1356) |
| ACTCCTTGTGTT (SEQ ID NO: 1357) | GTGGTATGGGAG (SEQ ID NO: 1358) | ATGTTTAGACGG (SEQ ID NO: 1359) | GCCCATATCAGA (SEQ ID NO: 1360) | CCGTGTTAGACA (SEQ ID NO: 1361) | GAGGGACGCAAT (SEQ ID NO: 1362) |
| GTCACGGACATT (SEQ ID NO: 1363) | TGTACCAACCGA (SEQ ID NO: 1364) | ACATGTCACGTG (SEQ ID NO: 1365) | CGTGTGTGCTCA (SEQ ID NO: 1366) | ACCTCTATTCGT (SEQ ID NO: 1367) | TAGGCCATGTAA (SEQ ID NO: 1368) |
| GCGAGCGAAGTA (SEQ ID NO: 1369) | AGGGTACAGGGT (SEQ ID NO: 1370) | CTTTAGCGCTGG (SEQ ID NO: 1371) | ATCCATGAGCGT (SEQ ID NO: 1372) | GGCAAGGCACAA (SEQ ID NO: 1373) | AACCGTCGCCTA (SEQ ID NO: 1374) |
| ATCTACCGAAGC (SEQ ID NO: 1375) | AGAGTGCTAATC (SEQ ID NO: 1376) | CTGGTCTTACGG (SEQ ID NO: 1377) | TAGACTTCAGAG (SEQ ID NO: 1378) | GCCATTATAGAG (SEQ ID NO: 1379) | TTACGAAGTTGG (SEQ ID NO: 1380) |
| ACTTGGTGTAAG (SEQ ID NO: 1381) | TTGGCGGGTTAT (SEQ ID NO: 1382) | CAAGTCGAATAC (SEQ ID NO: 1383) | TGATTCCCGGTG (SEQ ID NO: 1384) | TAACCGAACCAC (SEQ ID NO: 1385) | AGATAGCTCGCT (SEQ ID NO: 1386) |
| TCTTGGAGGTCA (SEQ ID NO: 1387) | CACGATGGTCAT (SEQ ID NO: 1388) | GCAAGTGTGAGG (SEQ ID NO: 1389) | AGTTCCACGGCT (SEQ ID NO: 1390) | GGTGCGTCACTT (SEQ ID NO: 1391) | CTGGTTGGCATC (SEQ ID NO: 1392) |
| TCACCTCCTTGT (SEQ ID NO: 1393) | GTCACCAATCCG (SEQ ID NO: 1394) | CTCGGTCAACCA (SEQ ID NO: 1395) | GGAAGCTTAACT (SEQ ID NO: 1396) | TGTGCTTGTAGG (SEQ ID NO: 1397) | CTGCTTCTTACA (SEQ ID NO: 1398) |
| GCACACCTGATA (SEQ ID NO: 1399) | CACTAACAAACG (SEQ ID NO: 1400) | ACCCTATTGCGG (SEQ ID NO: 1401) | GGAGACGTTCTT (SEQ ID NO: 1402) | TGACTCTGCGGT (SEQ ID NO: 1403) | GTTCGAGTGAAT (SEQ ID NO: 1404) |
| GCGACAATTACA (SEQ ID NO: 1405) | TTCCAGGCAGAT (SEQ ID NO: 1406) | TCCGTTCGTTTA (SEQ ID NO: 1407) | ATTGCGCTACCG (SEQ ID NO: 1408) | GTACACTGATAG (SEQ ID NO: 1409) | TTCTTCTACCGC (SEQ ID NO: 1410) |
| TCATGCTCCATT (SEQ ID NO: 1411) | TATGGTACCCAG (SEQ ID NO: 1412) | ACCACCGTAACC (SEQ ID NO: 1413) | CCGACCAGCTTA (SEQ ID NO: 1414) | TTACATCCCTTG (SEQ ID NO: 1415) | TCTCTCGATCAT (SEQ ID NO: 1416) |

TABLE 1-continued (SEQ ID NOS 775-2938, respectively, in order
of appearance from left to right in each row as shown)

| Barcode Sequence Fragments | Barcode Sequence Fragments | Barcode Sequence Fragments | Barcode Sequence Fragments | Barcode Sequence Fragments | Barcode Sequence Fragments |
|---|---|---|---|---|---|
| AGCTGTCAAGCT (SEQ ID NO: 1417) | CACGACTTGACA (SEQ ID NO: 1418) | CATTTCGCACTT (SEQ ID NO: 1419) | CAATCCACCGAA (SEQ ID NO: 1420) | GGTGTGAGAAAG (SEQ ID NO: 1421) | AATCCATGACAG (SEQ ID NO: 1422) |
| GAGAGCAACAGA (SEQ ID NO: 1423) | CTTGGAGGCTTA (SEQ ID NO: 1424) | TTAAGCGCCTGA (SEQ ID NO: 1425) | TACGCGTACAGT (SEQ ID NO: 1426) | CTCTTTGTCGAT (SEQ ID NO: 1427) | GGTATTCAAAGC (SEQ ID NO: 1428) |
| TACTCGGGAACT (SEQ ID NO: 1429) | ACGTGGTTCCAC (SEQ ID NO: 1430) | TGCGGGATTCAT (SEQ ID NO: 1431) | CCGTCAAGATGT (SEQ ID NO: 1432) | GTGAACTGGATT (SEQ ID NO: 1433) | GGTCCACCTAAC (SEQ ID NO: 1434) |
| CGTGCTTAGGCT (SEQ ID NO: 1435) | GACGCTTTGCTG (SEQ ID NO: 1436) | CAAACTGCGTTG (SEQ ID NO: 1437) | TACACGCTGATG (SEQ ID NO: 1438) | CCTAACGGTCCA (SEQ ID NO: 1439) | TGATCACTCTTC (SEQ ID NO: 1440) |
| TACCGAAGGTAT (SEQ ID NO: 1441) | ACAGGGTTTGTA (SEQ ID NO: 1442) | TTAGACTCGGAA (SEQ ID NO: 1443) | CGTTTCAAGGAC (SEQ ID NO: 1444) | TGTAGCCGCTTG (SEQ ID NO: 1445) | GGCACGAAAGGT (SEQ ID NO: 1446) |
| CACTCATCATTC (SEQ ID NO: 1447) | GCCTATGAGATC (SEQ ID NO: 1448) | GACCGATAGGGA (SEQ ID NO: 1449) | GCAGAACTTAGT (SEQ ID NO: 1450) | TACCCGACTAAG (SEQ ID NO: 1451) | CATGAGACTGTA (SEQ ID NO: 1452) |
| GTATTTCGGACG (SEQ ID NO: 1453) | CAAACCTATGGC (SEQ ID NO: 1454) | GGCGAACTGAAG (SEQ ID NO: 1455) | ACCCGTTGATGA (SEQ ID NO: 1456) | CGTAGTACCACA (SEQ ID NO: 1457) | GGTCATCACGAT (SEQ ID NO: 1458) |
| TATCTATCCTGC (SEQ ID NO: 1459) | ATCGCTTAAGGC (SEQ ID NO: 1460) | CGGCACTATCAC (SEQ ID NO: 1461) | GACGTAGAACGG (SEQ ID NO: 1462) | CGGAGAGACATG (SEQ ID NO: 1463) | AGTCTAGAGTAC (SEQ ID NO: 1464) |
| TTGCCAAGAGTC (SEQ ID NO: 1465) | ACCATCCAACGA (SEQ ID NO: 1466) | AGGTGGTGGAGT (SEQ ID NO: 1467) | CGGTACCTACCA (SEQ ID NO: 1468) | CCAAAGCCAGTT (SEQ ID NO: 1469) | TGCGCAAAGGAG (SEQ ID NO: 1470) |
| AGTAGCGGAAGA (SEQ ID NO: 1471) | GCAATAGGAGGA (SEQ ID NO: 1472) | ATTCCCAGAACG (SEQ ID NO: 1473) | GCGTTTGCTAGC (SEQ ID NO: 1474) | TACGATGAGTTG (SEQ ID NO: 1475) | GGTTTGCACATG (SEQ ID NO: 1476) |
| GCAATTAGGTAC (SEQ ID NO: 1477) | CCGAACGTCACT (SEQ ID NO: 1478) | AGACGTTGCTAC (SEQ ID NO: 1479) | AGAAACAGCTCT (SEQ ID NO: 1480) | GCTTGGTAGGTT (SEQ ID NO: 1481) | TGGGTTAACACA (SEQ ID NO: 1482) |
| CATACCGTGAGT (SEQ ID NO: 1483) | ACACCAACACCA (SEQ ID NO: 1484) | AGAATAGCGCTT (SEQ ID NO: 1485) | CTCAGACTCAGA (SEQ ID NO: 1486) | CCGGAATCCATA (SEQ ID NO: 1487) | TAGGTTGCTTGG (SEQ ID NO: 1488) |
| ATGTGTGTAGAC (SEQ ID NO: 1489) | CCATCACATAGG (SEQ ID NO: 1490) | AAGCGTACATTG (SEQ ID NO: 1491) | CCGAGTACAATC (SEQ ID NO: 1492) | ATCGGCTTCCGA (SEQ ID NO: 1493) | CAGGAACCAGGA (SEQ ID NO: 1494) |
| CCTGCGAAGTAT (SEQ ID NO: 1495) | CGACACGGAGAA (SEQ ID NO: 1496) | GTTATGACGGAT (SEQ ID NO: 1497) | GATATGAACTGC (SEQ ID NO: 1498) | CACTAGACCCAC (SEQ ID NO: 1499) | TGCTCGATGTGC (SEQ ID NO: 1500) |
| TTCTCTCGACAT (SEQ ID NO: 1501) | GAACCTATGACA (SEQ ID NO: 1502) | AGCCTCATGATG (SEQ ID NO: 1503) | GCAGTCTAAGAT (SEQ ID NO: 1504) | GGAAAGGAGAAT (SEQ ID NO: 1505) | AGGTTTGGCTTG (SEQ ID NO: 1506) |
| GCTCTCCGTAGA (SEQ ID NO: 1507) | ATGCCGGTAATA (SEQ ID NO: 1508) | GTGTATCGCCAC (SEQ ID NO: 1509) | CGGCGCATTATA (SEQ ID NO: 1510) | GAGTATCTGAGT (SEQ ID NO: 1511) | TACTCCAGGCTG (SEQ ID NO: 1512) |
| GTTAAGCTGACC (SEQ ID NO: 1513) | GAACAGCTCTAC (SEQ ID NO: 1514) | CCAAACTCGTCG (SEQ ID NO: 1515) | GGTGCTAATCAC (SEQ ID NO: 1516) | CTCGCTAGATAG (SEQ ID NO: 1517) | TTCGGCATAGTG (SEQ ID NO: 1518) |
| ATGCCATGCCGT (SEQ ID NO: 1519) | GTGAGTCATACC (SEQ ID NO: 1520) | ACGTGAGGAACG (SEQ ID NO: 1521) | CGTTTGGAATGA (SEQ ID NO: 1522) | CCAGGACAGGAA (SEQ ID NO: 1523) | GTGCCATAATCG (SEQ ID NO: 1524) |

TABLE 1-continued (SEQ ID NOS 775-2938, respectively, in order
of appearance from left to right in each row as shown)

| Barcode Sequence Fragments | Barcode Sequence Fragments | Barcode Sequence Fragments | Barcode Sequence Fragments | Barcode Sequence Fragments | Barcode Sequence Fragments |
|---|---|---|---|---|---|
| GACATTGTCACG (SEQ ID NO: 1525) | TGGCCGTTACTG (SEQ ID NO: 1526) | TGAATCGAAGCT (SEQ ID NO: 1527) | GGTTAGAGCGGA (SEQ ID NO: 1528) | AAGGGTTAGTCT (SEQ ID NO: 1529) | TGCAGATCCAAC (SEQ ID NO: 1530) |
| GCCAACAACCAT (SEQ ID NO: 1531) | TAGAGCTGCCAT (SEQ ID NO: 1532) | CTGCAGTAAGTA (SEQ ID NO: 1533) | GTAGTAGACCAT (SEQ ID NO: 1534) | GTGACTAGTGAT (SEQ ID NO: 1535) | TCACTCTTGTAC (SEQ ID NO: 1536) |
| ATCAGTACTAGG (SEQ ID NO: 1537) | ATCTAGTGGCAA (SEQ ID NO: 1538) | TATAGGCTCCGC (SEQ ID NO: 1539) | ATCAAGATACGC (SEQ ID NO: 1540) | GGCCTTCAGTCA (SEQ ID NO: 1541) | TGGTGGAGTTTC (SEQ ID NO: 1542) |
| TCCTCGAGCGAT (SEQ ID NO: 1543) | CCTTCAATGGGA (SEQ ID NO: 1544) | ATCGTGTGTTGG (SEQ ID NO: 1545) | TCTATCTGGCTT (SEQ ID NO: 1546) | ACACGTTTGGGT (SEQ ID NO: 1547) | AGAACACGGAAG (SEQ ID NO: 1548) |
| ACCCAAGCGTTA (SEQ ID NO: 1549) | TTGACGACATCG (SEQ ID NO: 1550) | CTTCCGCAGACA (SEQ ID NO: 1551) | GGAAACAAACGG (SEQ ID NO: 1552) | CGAACGTCTATG (SEQ ID NO: 1553) | TCGAAACATGCA (SEQ ID NO: 1554) |
| TGCAGCAAGATT (SEQ ID NO: 1555) | ACATACTGAGCA (SEQ ID NO: 1556) | GCACTATACGCA (SEQ ID NO: 1557) | GATTGGCATAGT (SEQ ID NO: 1558) | TCATGTGAACGA (SEQ ID NO: 1559) | AACTAAGGACTC (SEQ ID NO: 1560) |
| AGCAACATTGCA (SEQ ID NO: 1561) | GGCTAAACTATG (SEQ ID NO: 1562) | TCTGGGCATTGA (SEQ ID NO: 1563) | GAGTTGTACGAT (SEQ ID NO: 1564) | TCTCCGTTCCCT (SEQ ID NO: 1565) | AACTCAATAGCG (SEQ ID NO: 1566) |
| GATGTGGTGTTA (SEQ ID NO: 1567) | AAGAGCAGAGCC (SEQ ID NO: 1568) | CCAATGATAAGC (SEQ ID NO: 1569) | CTCGAAATGCAA (SEQ ID NO: 1570) | CTGATTACGAGA (SEQ ID NO: 1571) | CTTAGAACGTGC (SEQ ID NO: 1572) |
| CAGAAATGTGTC (SEQ ID NO: 1573) | GGAGAGATCACG (SEQ ID NO: 1574) | TTAAACCGCGCC (SEQ ID NO: 1575) | AGAAGAAAGGCA (SEQ ID NO: 1576) | TCTGAATGGTAG (SEQ ID NO: 1577) | CCGTATATGCGC (SEQ ID NO: 1578) |
| GTAGAGGTAGAG (SEQ ID NO: 1579) | TCAACCCGTGAA (SEQ ID NO: 1580) | CTTGCATACCGG (SEQ ID NO: 1581) | CCACTCTCTCTA (SEQ ID NO: 1582) | CATCGTTGGTCG (SEQ ID NO: 1583) | TATGACGTACGA (SEQ ID NO: 1584) |
| CGTGATCCGCTA (SEQ ID NO: 1585) | GTTTGAAACACG (SEQ ID NO: 1586) | GTGCACGATAAT (SEQ ID NO: 1587) | CCTCCTAATTCA (SEQ ID NO: 1588) | TAGATCCTCGGA (SEQ ID NO: 1589) | TCTCTGAACAGG (SEQ ID NO: 1590) |
| GGTTATTTGGCG (SEQ ID NO: 1591) | AGAGAGACAGGT (SEQ ID NO: 1592) | GGTCTAGGTCTA (SEQ ID NO: 1593) | TTCATGGCCAGC (SEQ ID NO: 1594) | TCGGACAGTGTT (SEQ ID NO: 1595) | CCTTTATAGTCC (SEQ ID NO: 1596) |
| GGATCGTAATAC (SEQ ID NO: 1597) | TCGCCAGTGCAT (SEQ ID NO: 1598) | TCAGGACGTATC (SEQ ID NO: 1599) | ATTGGACACGCT (SEQ ID NO: 1600) | TGATGTGCTAAG (SEQ ID NO: 1601) | TGTAGGTGTGCT (SEQ ID NO: 1602) |
| GCATAGCATCAA (SEQ ID NO: 1603) | GCTCAGGACTCT (SEQ ID NO: 1604) | GAAAGGTGAGAA (SEQ ID NO: 1605) | AATTCACCTCCT (SEQ ID NO: 1606) | CAGTAAATCGCA (SEQ ID NO: 1607) | TCCCACGAAACA (SEQ ID NO: 1608) |
| GTGTTAGATGTG (SEQ ID NO: 1609) | CACTTTGGGTGC (SEQ ID NO: 1610) | GAATATACCTGG (SEQ ID NO: 1611) | ATGAAGCACTGT (SEQ ID NO: 1612) | CAAGTTTCCGCG (SEQ ID NO: 1613) | TACGCTACGACC (SEQ ID NO: 1614) |
| TTAGAGCCATGC (SEQ ID NO: 1615) | TCTAGCCTGGCA (SEQ ID NO: 1616) | GTCGCTTGCACA (SEQ ID NO: 1617) | TTGATGTGAGGT (SEQ ID NO: 1618) | ACATCGTTGACG (SEQ ID NO: 1619) | GTCAGTATGGCT (SEQ ID NO: 1620) |
| TGAACCCTATGG (SEQ ID NO: 1621) | AATGCAATGCGT (SEQ ID NO: 1622) | TCTACCACGAAG (SEQ ID NO: 1623) | TCTTGCGGAGTC (SEQ ID NO: 1624) | ACGAAAGAGCAG (SEQ ID NO: 1625) | CCATATCCCGGA (SEQ ID NO: 1626) |
| AGAGTCTTGCCA (SEQ ID NO: 1627) | CGAATGAGTCAT (SEQ ID NO: 1628) | AATATCGGGATC (SEQ ID NO: 1629) | TTAGTCGTGACG (SEQ ID NO: 1630) | TGATGAACCCGT (SEQ ID NO: 1631) | TCGTACCAGGAT (SEQ ID NO: 1632) |

TABLE 1-continued (SEQ ID NOS 775-2938, respectively, in order
of appearance from left to right in each row as shown)

| Barcode Sequence Fragments | Barcode Sequence Fragments | Barcode Sequence Fragments | Barcode Sequence Fragments | Barcode Sequence Fragments | Barcode Sequence Fragments |
|---|---|---|---|---|---|
| ACAACACTCCGA (SEQ ID NO: 1633) | CAACGCTAGAAT (SEQ ID NO: 1634) | TAGTGCATTCGG (SEQ ID NO: 1635) | TGCCAGACCACT (SEQ ID NO: 1636) | GCTCTTATGCTT (SEQ ID NO: 1637) | AGTGACTGTCAA (SEQ ID NO: 1638) |
| CGATGCTGTTGA (SEQ ID NO: 1639) | ATCAGAGCCCAT (SEQ ID NO: 1640) | TCAATGACCGCA (SEQ ID NO: 1641) | AGGCTCCATGTA (SEQ ID NO: 1642) | CGACCTCGCATA (SEQ ID NO: 1643) | GGTGAGCAAGCA (SEQ ID NO: 1644) |
| ACGACTGCATAA (SEQ ID NO: 1645) | TCTGTAGAGCCA (SEQ ID NO: 1646) | CTATCGGAAGAT (SEQ ID NO: 1647) | ACTACTGAGGAT (SEQ ID NO: 1648) | CTAATTCTCTGC (SEQ ID NO: 1649) | AGTTCATACGGC (SEQ ID NO: 1650) |
| ACGCGAACTAAT (SEQ ID NO: 1651) | CCGACTCTAGGT (SEQ ID NO: 1652) | CGGATTGCTGTA (SEQ ID NO: 1653) | TATCTGGAAGTG (SEQ ID NO: 1654) | GGAAGTGGCCAA (SEQ ID NO: 1655) | TCGCTTTAACCT (SEQ ID NO: 1656) |
| AGCTATGTATGG (SEQ ID NO: 1657) | ATCCTACGAGCA (SEQ ID NO: 1658) | GGTACTGTACCA (SEQ ID NO: 1659) | CAGCTATGGACT (SEQ ID NO: 1660) | GATAATGTGCAC (SEQ ID NO: 1661) | GGCTTACTTGGA (SEQ ID NO: 1662) |
| ACGGGTCATCAT (SEQ ID NO: 1663) | GACAACGAATCT (SEQ ID NO: 1664) | ATCGAATCGAGT (SEQ ID NO: 1665) | TTGCTGGACGCT (SEQ ID NO: 1666) | CTCTGAGGTAAC (SEQ ID NO: 1667) | CCATCCGCAACA (SEQ ID NO: 1668) |
| GAAACATCCCAC (SEQ ID NO: 1669) | TGCGGTTGACTC (SEQ ID NO: 1670) | CTAGCAGTATGA (SEQ ID NO: 1671) | CTACTAGCGGTA (SEQ ID NO: 1672) | ATTTGCTTTGCC (SEQ ID NO: 1673) | CGCAATGAGGGA (SEQ ID NO: 1674) |
| CGTACTCTCGAG (SEQ ID NO: 1675) | TGAGAAGAAAGG (SEQ ID NO: 1676) | GTTAATGGCAGT (SEQ ID NO: 1677) | TACAGGACGGGA (SEQ ID NO: 1678) | TACTGGTAAGAC (SEQ ID NO: 1679) | GCTACAAGCCCT (SEQ ID NO: 1680) |
| TCAGTTCTCGTT (SEQ ID NO: 1681) | TCGGATCTGTGA (SEQ ID NO: 1682) | GTATGGAGCTAT (SEQ ID NO: 1683) | CTCAGGAGACTT (SEQ ID NO: 1684) | TTGAGAAGCACT (SEQ ID NO: 1685) | ATTGAAGTCTGG (SEQ ID NO: 1686) |
| TCGTGCGTGTTG (SEQ ID NO: 1687) | GCCGGTACTCTA (SEQ ID NO: 1688) | CCTTCTGTATAC (SEQ ID NO: 1689) | TCGTTGGGACTA (SEQ ID NO: 1690) | ATAACGGTGTAC (SEQ ID NO: 1691) | GGATTACGCTGT (SEQ ID NO: 1692) |
| GTTATCGCATGG (SEQ ID NO: 1693) | CACAGGATTACC (SEQ ID NO: 1694) | ACGCTGTCGGTT (SEQ ID NO: 1695) | GTCCATGGTTCG (SEQ ID NO: 1696) | TCCCGTAGCATG (SEQ ID NO: 1697) | CAGCAGTCTTCG (SEQ ID NO: 1698) |
| GATCACGAGAGG (SEQ ID NO: 1699) | CGATATCAGTAG (SEQ ID NO: 1700) | CTCGTTTCAGTT (SEQ ID NO: 1701) | TGGCATGTTGGT (SEQ ID NO: 1702) | CAGATGTCGCTA (SEQ ID NO: 1703) | CGTAGCCAACAT (SEQ ID NO: 1704) |
| GTAAATTCAGGC (SEQ ID NO: 1705) | CATAAGGGAGGC (SEQ ID NO: 1706) | GCGAACCTATAC (SEQ ID NO: 1707) | AATCGTAAGGTC (SEQ ID NO: 1708) | TGAGCAACATAC (SEQ ID NO: 1709) | ATACAGCATACG (SEQ ID NO: 1710) |
| AGTGTTTCGGAC (SEQ ID NO: 1711) | TGTGTTACTCCT (SEQ ID NO: 1712) | CTCTCATATGCT (SEQ ID NO: 1713) | CTTACGAGTAGA (SEQ ID NO: 1714) | GGTTCATGAACA (SEQ ID NO: 1715) | CTGAGTGAGTAT (SEQ ID NO: 1716) |
| ACACGCGGTTTA (SEQ ID NO: 1717) | GGTACCTGCAAT (SEQ ID NO: 1718) | CCAGTATCGCGT (SEQ ID NO: 1719) | CAACTGTCAGAC (SEQ ID NO: 1720) | GAGCGAGTTAGG (SEQ ID NO: 1721) | GCTTGTACCGAC (SEQ ID NO: 1722) |
| TGGCAAATCTAG (SEQ ID NO: 1723) | TCGCCTATAAGG (SEQ ID NO: 1724) | TCGTTTCTTCAG (SEQ ID NO: 1725) | TGACTGCGTTAG (SEQ ID NO: 1726) | GCTCAATCAGAA (SEQ ID NO: 1727) | CGCTAGGATGTT (SEQ ID NO: 1728) |
| CACCTTACCTTA (SEQ ID NO: 1729) | AGTGGCACTATC (SEQ ID NO: 1730) | AGTACCTAAGTG (SEQ ID NO: 1731) | GGCTGATGTCAT (SEQ ID NO: 1732) | GACCATGTAGTA (SEQ ID NO: 1733) | GGACAAGTGCGA (SEQ ID NO: 1734) |
| TTAACCTTCCTG (SEQ ID NO: 1735) | TAACCCGATAGA (SEQ ID NO: 1736) | GGATGCAGGATG (SEQ ID NO: 1737) | TGTCCAGTTCGG (SEQ ID NO: 1738) | CACACGCCTGAT (SEQ ID NO: 1739) | GTTCGTATACGG (SEQ ID NO: 1740) |

TABLE 1-continued (SEQ ID NOS 775-2938, respectively, in order
of appearance from left to right in each row as shown)

| Barcode Sequence Fragments | Barcode Sequence Fragments | Barcode Sequence Fragments | Barcode Sequence Fragments | Barcode Sequence Fragments | Barcode Sequence Fragments |
|---|---|---|---|---|---|
| TGCCGTATGCCA (SEQ ID NO: 1741) | GTGTGCTAACGT (SEQ ID NO: 1742) | CCACTTGAGAGT (SEQ ID NO: 1743) | ACTCGTGATAGC (SEQ ID NO: 1744) | TCTTCGCAGCAG (SEQ ID NO: 1745) | CGGGTAGGGTAA (SEQ ID NO: 1746) |
| CGTGACAATAGT (SEQ ID NO: 1747) | CTTGCGGCAATC (SEQ ID NO: 1748) | GCACTTCATTTC (SEQ ID NO: 1749) | GCCCTCAAATGC (SEQ ID NO: 1750) | TCTCATGTGGAG (SEQ ID NO: 1751) | ATGCGCCCGTAT (SEQ ID NO: 1752) |
| CGCTACAACTCG (SEQ ID NO: 1753) | TGAGGTTTGATG (SEQ ID NO: 1754) | AGAATCCACCAC (SEQ ID NO: 1755) | TAAATCACGCGC (SEQ ID NO: 1756) | TTCCATCATGTC (SEQ ID NO: 1757) | CTGTCGTGTCAG (SEQ ID NO: 1758) |
| TTAAGACAGTCG (SEQ ID NO: 1759) | ATTGCTGGTCGA (SEQ ID NO: 1760) | CTCAAGTCAAAG (SEQ ID NO: 1761) | GGCGTGCATTAT (SEQ ID NO: 1762) | GTCCTACACAGC (SEQ ID NO: 1763) | ACGGTGAAAGCG (SEQ ID NO: 1764) |
| TCTGCACTGAGC (SEQ ID NO: 1765) | AAGAAGCCGGAC (SEQ ID NO: 1766) | GTACCTAGCCTG (SEQ ID NO: 1767) | GGTCAATATTGG (SEQ ID NO: 1768) | GAGGTGGGAGTT (SEQ ID NO: 1769) | TCACGTATTCTC (SEQ ID NO: 1770) |
| CGCAGATTAGTA (SEQ ID NO: 1771) | ACGGGATACAGG (SEQ ID NO: 1772) | CACTGAGTACGT (SEQ ID NO: 1773) | AGGTTCTTAGGC (SEQ ID NO: 1774) | TGGCCTAGTCAA (SEQ ID NO: 1775) | GAAGGTGAAGGT (SEQ ID NO: 1776) |
| TGGGTCCCACAT (SEQ ID NO: 1777) | AAGAGTCTCTAG (SEQ ID NO: 1778) | TCAAGCAATACG (SEQ ID NO: 1779) | TAGGTGCAATCA (SEQ ID NO: 1780) | TCCTTCCCTGCT (SEQ ID NO: 1781) | CACATGGGTTTG (SEQ ID NO: 1782) |
| CACTGGTGCATA (SEQ ID NO: 1783) | TCCGTCATGGGT (SEQ ID NO: 1784) | CATGTTGGAACA (SEQ ID NO: 1785) | GTCCAAAGCGTT (SEQ ID NO: 1786) | CTCACTGCTTCT (SEQ ID NO: 1787) | TAGGTAACCGAT (SEQ ID NO: 1788) |
| AACGTAGGCTCT (SEQ ID NO: 1789) | AGATCTATGCAG (SEQ ID NO: 1790) | ATGGGACCTTCA (SEQ ID NO: 1791) | AGATCGTGCCTA (SEQ ID NO: 1792) | TAGGAGAGACAG (SEQ ID NO: 1793) | GGTCGAATTGCT (SEQ ID NO: 1794) |
| AGTTGTAGTCCG (SEQ ID NO: 1795) | GCACAAGGCAAG (SEQ ID NO: 1796) | GCTATTCCTCAT (SEQ ID NO: 1797) | CTCCTCCCTTAC (SEQ ID NO: 1798) | TGTTCCTCTCAC (SEQ ID NO: 1799) | TGTAAACAGGTC (SEQ ID NO: 1800) |
| TCGTCAAACCCG (SEQ ID NO: 1801) | CGGCAAACACTT (SEQ ID NO: 1802) | GTCTCTGAAAGA (SEQ ID NO: 1803) | GAGCATTACATG (SEQ ID NO: 1804) | GCGTTAACCCAA (SEQ ID NO: 1805) | GTTACGTGGTTG (SEQ ID NO: 1806) |
| TAATCGGTGCCA (SEQ ID NO: 1807) | GCGAGTTCCTGT (SEQ ID NO: 1808) | GTTCTGCTTGTT (SEQ ID NO: 1809) | AAGCACGTCTCA (SEQ ID NO: 1810) | CCACACGTTTGG (SEQ ID NO: 1811) | AGGATCAGGGAA (SEQ ID NO: 1812) |
| TTGATCCGGTAG (SEQ ID NO: 1813) | TTCCGAATCGGC (SEQ ID NO: 1814) | GTCAAGACCTCA (SEQ ID NO: 1815) | TAGGGAGACCGA (SEQ ID NO: 1816) | ACAGCATAGCTC (SEQ ID NO: 1817) | TAGGACGGGAGT (SEQ ID NO: 1818) |
| CGGGTGTTTGCT (SEQ ID NO: 1819) | TACCTAGTGAGA (SEQ ID NO: 1820) | TTGTTACGTTCC (SEQ ID NO: 1821) | ATAAGCCCAATG (SEQ ID NO: 1822) | AATGTGGCTCAC (SEQ ID NO: 1823) | GCAACGAACGAG (SEQ ID NO: 1824) |
| TTGACCGCGGTT (SEQ ID NO: 1825) | CGTTCTGGTGGT (SEQ ID NO: 1826) | CAGTTCGAGATA (SEQ ID NO: 1827) | ACGTGCCTTAGA (SEQ ID NO: 1828) | GAGTTCCATTGG (SEQ ID NO: 1829) | TGACGGTTTAGC (SEQ ID NO: 1830) |
| GTGCAACCAATC (SEQ ID NO: 1831) | TTGGTCTCCTCT (SEQ ID NO: 1832) | AATGTCACCAGA (SEQ ID NO: 1833) | TCCTGCTATCTA (SEQ ID NO: 1834) | TCTGATCGAGGT (SEQ ID NO: 1835) | AAGTGTGGTTGT (SEQ ID NO: 1836) |
| GCTTGAGCTTGA (SEQ ID NO: 1837) | CTGCATACTGAG (SEQ ID NO: 1838) | CAGCCTGCAAAT (SEQ ID NO: 1839) | CACGAAAGCAGG (SEQ ID NO: 1840) | CAAGTGAAGGGA (SEQ ID NO: 1841) | CTTCGTTTCGTA (SEQ ID NO: 1842) |
| CGCTGTGGATTA (SEQ ID NO: 1843) | CAGGGCCTTTGT (SEQ ID NO: 1844) | TTGCAAGTACCG (SEQ ID NO: 1845) | TCAGTCCGCAC (SEQ ID NO: 1846) | TGCCCATCAGGT (SEQ ID NO: 1847) | CACCGCTCACAA (SEQ ID NO: 1848) |

TABLE 1-continued (SEQ ID NOS 775-2938, respectively, in order
of appearance from left to right in each row as shown)

| Barcode Sequence Fragments | Barcode Sequence Fragments | Barcode Sequence Fragments | Barcode Sequence Fragments | Barcode Sequence Fragments | Barcode Sequence Fragments |
|---|---|---|---|---|---|
| CTGTCAGTGACC (SEQ ID NO: 1849) | CGATGAATATCG (SEQ ID NO: 1850) | GCTTCTCTCACT (SEQ ID NO: 1851) | TAGCACCTAAAG (SEQ ID NO: 1852) | AGGTTGCTGTAA (SEQ ID NO: 1853) | CTGAACAGTTGC (SEQ ID NO: 1854) |
| ACGATTCGAGTC (SEQ ID NO: 1855) | GTCAATTAGTGG (SEQ ID NO: 1856) | CGAGATAGTTTG (SEQ ID NO: 1857) | GTTTCTTGTTGC (SEQ ID NO: 1858) | TAAGTACTGCAG (SEQ ID NO: 1859) | CGCTCTTAACGG (SEQ ID NO: 1860) |
| GGTTCGGTCCAT (SEQ ID NO: 1861) | AGTACGCAGTCT (SEQ ID NO: 1862) | CGCGTCAAACTA (SEQ ID NO: 1863) | ACCTAAAGCTGC (SEQ ID NO: 1864) | GCCGATTGTAAC (SEQ ID NO: 1865) | GGAGTCTCTTGC (SEQ ID NO: 1866) |
| CTGATCCATCTT (SEQ ID NO: 1867) | AGCAGCTATTGC (SEQ ID NO: 1868) | TTGACACACGAC (SEQ ID NO: 1869) | ACCACGATGCTA (SEQ ID NO: 1870) | CGGTGGAAGCAA (SEQ ID NO: 1871) | AAGTTCCGGCCT (SEQ ID NO: 1872) |
| TATGTGCCGGCT (SEQ ID NO: 1873) | CTCGGATAGATC (SEQ ID NO: 1874) | ATAAGGTCGCCT (SEQ ID NO: 1875) | GCATCTAAAGCC (SEQ ID NO: 1876) | GTTGAAGCACCT (SEQ ID NO: 1877) | GCGCTGTTTAAG (SEQ ID NO: 1878) |
| TGGTCGCATCGT (SEQ ID NO: 1879) | TTCCCGAAACGA (SEQ ID NO: 1880) | TTGCCCTTTGAT (SEQ ID NO: 1881) | CGTTGACACCCA (SEQ ID NO: 1882) | TGTCTTTACCTG (SEQ ID NO: 1883) | GACAATTCCGAA (SEQ ID NO: 1884) |
| TGTAAGACTTGG (SEQ ID NO: 1885) | GAACTTTAGCGC (SEQ ID NO: 1886) | CCTGGAATTAAG (SEQ ID NO: 1887) | CTTGGGTTAGGT (SEQ ID NO: 1888) | CCTTGTTCACCT (SEQ ID NO: 1889) | AGGTCTCCCGAT (SEQ ID NO: 1890) |
| CGGATCTAGTGT (SEQ ID NO: 1891) | TCCTTAGAAGGC (SEQ ID NO: 1892) | TGAGACCCTACA (SEQ ID NO: 1893) | CTACGTGAAATG (SEQ ID NO: 1894) | CAACCACTCGGT (SEQ ID NO: 1895) | ACGATGGTTGAT (SEQ ID NO: 1896) |
| CGATCTTCGAGC (SEQ ID NO: 1897) | GATGGACTTCAA (SEQ ID NO: 1898) | AAGTATCCTGCG (SEQ ID NO: 1899) | GCCAGCTTCATG (SEQ ID NO: 1900) | TCTTAGTCGGGC (SEQ ID NO: 1901) | AGACTTCTCAGG (SEQ ID NO: 1902) |
| GTCGAATTTGCG (SEQ ID NO: 1903) | TACTGAGCCTCG (SEQ ID NO: 1904) | CAAATGGTCGTC (SEQ ID NO: 1905) | GTGCATTCGCCA (SEQ ID NO: 1906) | GTACCGTTGCAA (SEQ ID NO: 1907) | GGATGTCTTCGC (SEQ ID NO: 1908) |
| GCATCAGAGTTA (SEQ ID NO: 1909) | AGAAGGCCTTAT (SEQ ID NO: 1910) | ACACATAAGTCG (SEQ ID NO: 1911) | TGAGAGTCCCTC (SEQ ID NO: 1912) | CTGATAGCACAC (SEQ ID NO: 1913) | TCCTGAACACAG (SEQ ID NO: 1914) |
| GTGGTCATCGTA (SEQ ID NO: 1915) | TGGAGCCTTGTC (SEQ ID NO: 1916) | TACTGCCAGTGA (SEQ ID NO: 1917) | CTCTGTAGCCGA (SEQ ID NO: 1918) | ACAGGTAGAGAG (SEQ ID NO: 1919) | AAGCCTCTACGA (SEQ ID NO: 1920) |
| CTGAAGGGCGAA (SEQ ID NO: 1921) | CTCGATGTAAGC (SEQ ID NO: 1922) | GAGTTTACGGTC (SEQ ID NO: 1923) | GCAGTAACTGTC (SEQ ID NO: 1924) | TGCTCACGTGTG (SEQ ID NO: 1925) | TACTTGCCACGG (SEQ ID NO: 1926) |
| CGCTCACAGAAT (SEQ ID NO: 1927) | AGCTTCGACAGT (SEQ ID NO: 1928) | GGCACACCCTTA (SEQ ID NO: 1929) | CATATAGCCCGA (SEQ ID NO: 1930) | GTAATAATGCCG (SEQ ID NO: 1931) | GCATAAACGACT (SEQ ID NO: 1932) |
| ATTCGGTAGTGC (SEQ ID NO: 1933) | ATACGCATCAAG (SEQ ID NO: 1934) | GTCCAGCTATGA (SEQ ID NO: 1935) | CAGTGCACGTCT (SEQ ID NO: 1936) | CTCGGCACCAAT (SEQ ID NO: 1937) | CTTTGCACTTTG (SEQ ID NO: 1938) |
| CGAGCTGTTACC (SEQ ID NO: 1939) | AGATGTCCGTCA (SEQ ID NO: 1940) | TCGCGCAACTGT (SEQ ID NO: 1941) | CAAGACTGACCT (SEQ ID NO: 1942) | ACTCGAAACCAA (SEQ ID NO: 1943) | TGACACGACATC (SEQ ID NO: 1944) |
| CAACACATGCTG (SEQ ID NO: 1945) | GCACCTGTTGAA (SEQ ID NO: 1946) | ATTCCTCTCCAC (SEQ ID NO: 1947) | CCGATAAAGGTT (SEQ ID NO: 1948) | ACCGTAAGACAT (SEQ ID NO: 1949) | TGTTGACGATGC (SEQ ID NO: 1950) |
| ATTCTCTCACGT (SEQ ID NO: 1951) | CCTAGAGAAACT (SEQ ID NO: 1952) | TGGTTCATCCTT (SEQ ID NO: 1953) | CTTTGTCAGGGC (SEQ ID NO: 1954) | ATCACGGGAGAG (SEQ ID NO: 1955) | GACAAGAAGGTG (SEQ ID NO: 1956) |

TABLE 1-continued (SEQ ID NOS 775-2938, respectively, in order
of appearance from left to right in each row as shown)

| Barcode Sequence Fragments | Barcode Sequence Fragments | Barcode Sequence Fragments | Barcode Sequence Fragments | Barcode Sequence Fragments | Barcode Sequence Fragments |
|---|---|---|---|---|---|
| CGACTCTAAACG (SEQ ID NO: 1957) | GAGGTTCTTGAC (SEQ ID NO: 1958) | AGCACTTTGAGA (SEQ ID NO: 1959) | TCCGAAGACAAT (SEQ ID NO: 1960) | TCACTGCTAGGA (SEQ ID NO: 1961) | GAGTGCTCTAAC (SEQ ID NO: 1962) |
| GTCTTCAGCAAG (SEQ ID NO: 1963) | CTGTAAAGGTTG (SEQ ID NO: 1964) | CCACGGTACTTG (SEQ ID NO: 1965) | ACTTCGGATGCA (SEQ ID NO: 1966) | CTAATCAGAGTG (SEQ ID NO: 1967) | TTGTGTCTCCCT (SEQ ID NO: 1968) |
| CGGATAACCTCC (SEQ ID NO: 1969) | TGAGTCATTGAG (SEQ ID NO: 1970) | ACTAGTTGGACC (SEQ ID NO: 1971) | TAACATCAGGCA (SEQ ID NO: 1972) | TTGGCATTGGCA (SEQ ID NO: 1973) | CGTTACCGGACT (SEQ ID NO: 1974) |
| AGGGTGACTTTA (SEQ ID NO: 1975) | TACGGCAGTTCA (SEQ ID NO: 1976) | GATCAACCCACA (SEQ ID NO: 1977) | TAATGAGATGCC (SEQ ID NO: 1978) | TATAATCCGAGG (SEQ ID NO: 1979) | TGTGCACGCCAT (SEQ ID NO: 1980) |
| GACTTCATGCGA (SEQ ID NO: 1981) | CTCTAGAAGAGT (SEQ ID NO: 1982) | ATGCGAGACTTC (SEQ ID NO: 1983) | ATCGGTGGAATT (SEQ ID NO: 1984) | TCCAGATAGCGT (SEQ ID NO: 1985) | TCCCAGAAGCTC (SEQ ID NO: 1986) |
| GCCTGTCTGCAA (SEQ ID NO: 1987) | TGCACAGTCGCT (SEQ ID NO: 1988) | CGCTTGTGTAGC (SEQ ID NO: 1989) | TATAGTGGGCCT (SEQ ID NO: 1990) | AATCCGGTCACC (SEQ ID NO: 1991) | ACGCTAGATTGA (SEQ ID NO: 1992) |
| ACTGATGGCCTC (SEQ ID NO: 1993) | CATGCGGATCCT (SEQ ID NO: 1994) | ATGAATGCGTCC (SEQ ID NO: 1995) | TCGACGGAGAGA (SEQ ID NO: 1996) | AAGTGCTTGGTA (SEQ ID NO: 1997) | TTACGGCTGGTC (SEQ ID NO: 1998) |
| TTCGATGCCGCA (SEQ ID NO: 1999) | TGCTCCGTAGAA (SEQ ID NO: 2000) | GACTCTGCTCAG (SEQ ID NO: 2001) | ATCTGACATCGG (SEQ ID NO: 2002) | GGTAAAGGGTCG (SEQ ID NO: 2003) | TGCAATGGTACC (SEQ ID NO: 2004) |
| TGTGGCTCGTGT (SEQ ID NO: 2005) | TGATAGGTACAC (SEQ ID NO: 2006) | CACGTACACGTA (SEQ ID NO: 2007) | GATAGGGCCAAG (SEQ ID NO: 2008) | GCTTTCTCAATC (SEQ ID NO: 2009) | AACAGGTCTCTG (SEQ ID NO: 2010) |
| AACTTTCAGGAG (SEQ ID NO: 2011) | CGAGTTCATCGA (SEQ ID NO: 2012) | CAGAGCTAATTG (SEQ ID NO: 2013) | CGGGCTTCATCA (SEQ ID NO: 2014) | ACAGTGCGTCCT (SEQ ID NO: 2015) | GTGCTAATAGGT (SEQ ID NO: 2016) |
| TGCACGTGATAA (SEQ ID NO: 2017) | AAGCAGATTGTC (SEQ ID NO: 2018) | TTATCCAGTCCT (SEQ ID NO: 2019) | CGTAACGTAATG (SEQ ID NO: 2020) | TAGGAACTCACC (SEQ ID NO: 2021) | GCGATCACACCT (SEQ ID NO: 2022) |
| GTTCGGTGTCCA (SEQ ID NO: 2023) | TAGAGGCGTAGG (SEQ ID NO: 2024) | CTAAGACGTCGT (SEQ ID NO: 2025) | TAGCGACCTCAC (SEQ ID NO: 2026) | TGTATTGGACAG (SEQ ID NO: 2027) | AATGGACCGTTC (SEQ ID NO: 2028) |
| AAGACAGCTATC (SEQ ID NO: 2029) | TCAGCGCCGTTA (SEQ ID NO: 2030) | GGCTCAGATTCC (SEQ ID NO: 2031) | ACCCTGGGTATC (SEQ ID NO: 2032) | AGAAAGGGTGTG (SEQ ID NO: 2033) | GTACGTCACTGA (SEQ ID NO: 2034) |
| ATTGACCGGTCA (SEQ ID NO: 2035) | TAGACCGACTCC (SEQ ID NO: 2036) | CTTGGTAGTGCC (SEQ ID NO: 2037) | AGCGAGAAGTGA (SEQ ID NO: 2038) | GCTCACAATGTG (SEQ ID NO: 2039) | TAGCCTGTCGTG (SEQ ID NO: 2040) |
| TTCTCCATCACA (SEQ ID NO: 2041) | GTCAACGCTGTC (SEQ ID NO: 2042) | GTGCTGCGCTTA (SEQ ID NO: 2043) | CTTCAAGATGGA (SEQ ID NO: 2044) | TATTGCAGCAGC (SEQ ID NO: 2045) | ACAGACGACGGA (SEQ ID NO: 2046) |
| CGTAGGTAGAGG (SEQ ID NO: 2047) | ACAGGAGGGTGT (SEQ ID NO: 2048) | AGTAGGAGGCAC (SEQ ID NO: 2049) | GCTGCGTATACC (SEQ ID NO: 2050) | AGATTCGCTCGA (SEQ ID NO: 2051) | TCTATGCGAACG (SEQ ID NO: 2052) |
| ATTTAGGACGAC (SEQ ID NO: 2053) | GCTGTCGTCAAC (SEQ ID NO: 2054) | ACCCGGATTTCG (SEQ ID NO: 2055) | ACAAGGCAAGGC (SEQ ID NO: 2056) | AGCCGGAGAGTA (SEQ ID NO: 2057) | CTATGAGTCCAG (SEQ ID NO: 2058) |
| GGATAGCCAAGG (SEQ ID NO: 2059) | ATAGAGGCCATT (SEQ ID NO: 2060) | CGTCCGTATGAA (SEQ ID NO: 2061) | CGTTAGTGACTG (SEQ ID NO: 2062) | CCTGTAGGTTGC (SEQ ID NO: 2063) | AGTCCTTTATCC (SEQ ID NO: 2064) |

TABLE 1-continued (SEQ ID NOS 775-2938, respectively, in order
of appearance from left to right in each row as shown)

| Barcode Sequence Fragments | Barcode Sequence Fragments | Barcode Sequence Fragments | Barcode Sequence Fragments | Barcode Sequence Fragments | Barcode Sequence Fragments |
|---|---|---|---|---|---|
| TGGTTGGTTACG (SEQ ID NO: 2065) | AAGCTTGAAACC (SEQ ID NO: 2066) | CGATTAGGAATC (SEQ ID NO: 2067) | GCCGTTGATGCT (SEQ ID NO: 2068) | AAGGCCTTTACG (SEQ ID NO: 2069) | AGTTTGCGAGAT (SEQ ID NO: 2070) |
| GTCGTCCAAATG (SEQ ID NO: 2071) | TAAGCGTCTCGA (SEQ ID NO: 2072) | ACGTCTCAGTGC (SEQ ID NO: 2073) | TTCAACCTTTCG (SEQ ID NO: 2074) | CTAGGCAATCAA (SEQ ID NO: 2075) | TCAACGTGCTGC (SEQ ID NO: 2076) |
| CAACGTGCTCCA (SEQ ID NO: 2077) | ATAGCTTCGTGG (SEQ ID NO: 2078) | TAGTAGCACCTG (SEQ ID NO: 2079) | TGGGAGGTGGTA (SEQ ID NO: 2080) | AGGACCTCGTTC (SEQ ID NO: 2081) | GAACCAGTACTC (SEQ ID NO: 2082) |
| TACACAAGTCGC (SEQ ID NO: 2083) | CGGGATCAAATT (SEQ ID NO: 2084) | AGGTCATCTTGG (SEQ ID NO: 2085) | CGCCTGCCAATA (SEQ ID NO: 2086) | CTTGTCTGGAGC (SEQ ID NO: 2087) | TGATAATGCACG (SEQ ID NO: 2088) |
| GCGTCCATGAAT (SEQ ID NO: 2089) | AGTCATCGAATG (SEQ ID NO: 2090) | TGCTGTGACCAC (SEQ ID NO: 2091) | TTGAGCTTGAGC (SEQ ID NO: 2092) | ACCGCATCAATG (SEQ ID NO: 2093) | TAGTGATGACCA (SEQ ID NO: 2094) |
| GTAATGCGTAAC (SEQ ID NO: 2095) | ATCTTGGAGTCG (SEQ ID NO: 2096) | ACACTTCGGCAA (SEQ ID NO: 2097) | TACTAACGCGGT (SEQ ID NO: 2098) | AAGGTCAATCGT (SEQ ID NO: 2099) | ACAGCCACCCAT (SEQ ID NO: 2100) |
| GTCGCCGTACAT (SEQ ID NO: 2101) | AGCACCGGTCTT (SEQ ID NO: 2102) | ACCTCCCGGATA (SEQ ID NO: 2103) | ATCCGCAGTCAC (SEQ ID NO: 2104) | ACCTACTTGTCT (SEQ ID NO: 2105) | TATGTTGACGGC (SEQ ID NO: 2106) |
| GGAATCCGATTA (SEQ ID NO: 2107) | GCAAATCAGCCT (SEQ ID NO: 2108) | GAAGAGGGTTGA (SEQ ID NO: 2109) | AGTGTACCATGA (SEQ ID NO: 2110) | TGTTGGATCGTG (SEQ ID NO: 2111) | CGAGTATACAAC (SEQ ID NO: 2112) |
| CACCCGATGGTT (SEQ ID NO: 2113) | GCAAGCTGTCTC (SEQ ID NO: 2114) | AGTAGACTTACG (SEQ ID NO: 2115) | CCGATTGAATCG (SEQ ID NO: 2116) | ACTGGATCTCGC (SEQ ID NO: 2117) | TACACCTTACCT (SEQ ID NO: 2118) |
| TTCTGAGAGGTA (SEQ ID NO: 2119) | AGCGGCCTATTA (SEQ ID NO: 2120) | TGGAAACCATTG (SEQ ID NO: 2121) | TATATGTGCGAG (SEQ ID NO: 2122) | TCAAGGGACCTT (SEQ ID NO: 2123) | CGTTCAAGCTAG (SEQ ID NO: 2124) |
| ATCCCTACGGAA (SEQ ID NO: 2125) | TCTTCAACTACC (SEQ ID NO: 2126) | AGTCCGAGTTGT (SEQ ID NO: 2127) | CACCCACGTTGA (SEQ ID NO: 2128) | AAGTCGACACAT (SEQ ID NO: 2129) | AACTCGCGCTAC (SEQ ID NO: 2130) |
| GGTTCCATTAGG (SEQ ID NO: 2131) | TGGAATTCGGCT (SEQ ID NO: 2132) | CCGCGATTTCGA (SEQ ID NO: 2133) | TAGTGGGTCAAT (SEQ ID NO: 2134) | AACATTGCAGGT (SEQ ID NO: 2135) | TACCAGGATTGC (SEQ ID NO: 2136) |
| GTGTTCCCAGAA (SEQ ID NO: 2137) | TAAGATGCAGTC (SEQ ID NO: 2138) | ACACACCCTGAC (SEQ ID NO: 2139) | CCTAAACTACGG (SEQ ID NO: 2140) | CCATGAAGTGTA (SEQ ID NO: 2141) | GGTTGTAAGTGT (SEQ ID NO: 2142) |
| CCGAGGTATAAT (SEQ ID NO: 2143) | TGCCGAGTAATC (SEQ ID NO: 2144) | TCACGAGTCACA (SEQ ID NO: 2145) | ACTCCCGTGTGA (SEQ ID NO: 2146) | TCCACAGGGTTC (SEQ ID NO: 2147) | CAACGAACCATC (SEQ ID NO: 2148) |
| AGCGTAATTAGC (SEQ ID NO: 2149) | ACCTTGACAAGA (SEQ ID NO: 2150) | CACAAAGCGATT (SEQ ID NO: 2151) | CTGCAAGCCTGT (SEQ ID NO: 2152) | TCATTAGCGTGG (SEQ ID NO: 2153) | CCATGCTTAGAG (SEQ ID NO: 2154) |
| CTCGTGAATGAC (SEQ ID NO: 2155) | GTAACCACCACC (SEQ ID NO: 2156) | CACCGTGACACT (SEQ ID NO: 2157) | CCAACAGCCAAT (SEQ ID NO: 2158) | ATGTCGAATAGC (SEQ ID NO: 2159) | AATGGCGACTAT (SEQ ID NO: 2160) |
| AGGTGAGTTCTA (SEQ ID NO: 2161) | CATAGCTCGGTC (SEQ ID NO: 2162) | GAAGATCTATCG (SEQ ID NO: 2163) | CGGTTCACATAG (SEQ ID NO: 2164) | CTGACCGTTAAG (SEQ ID NO: 2165) | GACAGGTTGTAT (SEQ ID NO: 2166) |
| CCTGTCCTATCT (SEQ ID NO: 2167) | AACCATGCCAAC (SEQ ID NO: 2168) | GACGGAACAGAC (SEQ ID NO: 2169) | TCAACAGTAGTG (SEQ ID NO: 2170) | TCGGGCTCTTAG (SEQ ID NO: 2171) | GACTATAATGGC (SEQ ID NO: 2172) |

TABLE 1-continued (SEQ ID NOS 775-2938, respectively, in order of appearance from left to right in each row as shown)

| Barcode Sequence Fragments | Barcode Sequence Fragments | Barcode Sequence Fragments | Barcode Sequence Fragments | Barcode Sequence Fragments | Barcode Sequence Fragments |
|---|---|---|---|---|---|
| GGTTTAACACGC (SEQ ID NO: 2173) | TATGGAGCTAGT (SEQ ID NO: 2174) | GGACCGCTTTCA (SEQ ID NO: 2175) | AACACATGGGTT (SEQ ID NO: 2176) | ACTTTAAGGGTG (SEQ ID NO: 2177) | TTCAGGAACTAG (SEQ ID NO: 2178) |
| AGACAGTAGGAG (SEQ ID NO: 2179) | ACTACCTCTTCA (SEQ ID NO: 2180) | CACGGTCCTATG (SEQ ID NO: 2181) | ATCGTAGTGGTC (SEQ ID NO: 2182) | TGGACCACTAGT (SEQ ID NO: 2183) | CAACAGGTAACT (SEQ ID NO: 2184) |
| GCCACGACTTAC (SEQ ID NO: 2185) | GATGATAACCCA (SEQ ID NO: 2186) | GAATGACGTTTG (SEQ ID NO: 2187) | CGAGTCACGATT (SEQ ID NO: 2188) | AACCAGCAGATT (SEQ ID NO: 2189) | TAGTTGAGCTGA (SEQ ID NO: 2190) |
| ATTGTTCCTACC (SEQ ID NO: 2191) | GGCCCAATATAA (SEQ ID NO: 2192) | ACTTACGCCACG (SEQ ID NO: 2193) | AGTGCGTTCTAG (SEQ ID NO: 2194) | ATCGAGGATCTA (SEQ ID NO: 2195) | GTCTCAAAGCAC (SEQ ID NO: 2196) |
| GCCGTAAACTTG (SEQ ID NO: 2197) | TTGTATGACAGG (SEQ ID NO: 2198) | ACGCCTTTCTTA (SEQ ID NO: 2199) | TTCTTAACGCCT (SEQ ID NO: 2200) | TAGCTGGCGTTC (SEQ ID NO: 2201) | AGTTGCCTGAAC (SEQ ID NO: 2202) |
| GCAGATTTCCAG (SEQ ID NO: 2203) | GGTAAGTTTGAC (SEQ ID NO: 2204) | TTGGTGCCTGTG (SEQ ID NO: 2205) | ACCCAGTATGGT (SEQ ID NO: 2206) | CACAAGTATCGA (SEQ ID NO: 2207) | TGGTAGTCTGAA (SEQ ID NO: 2208) |
| AGATGATCAGTC (SEQ ID NO: 2209) | CTACCACGGTAC (SEQ ID NO: 2210) | CATCGGATCTGA (SEQ ID NO: 2211) | CGTTAAGTCAGC (SEQ ID NO: 2212) | GATTGTGCAACC (SEQ ID NO: 2213) | GCATGTCGAAAT (SEQ ID NO: 2214) |
| GAGACGTGTTCT (SEQ ID NO: 2215) | CGGTCTGTCTGA (SEQ ID NO: 2216) | CATGTCTTCCAT (SEQ ID NO: 2217) | TCACAACACCGC (SEQ ID NO: 2218) | CTACAGGGTCTC (SEQ ID NO: 2219) | CCTATGCACGGT (SEQ ID NO: 2220) |
| TATCACCGGCAC (SEQ ID NO: 2221) | GTACATGTCGCC (SEQ ID NO: 2222) | GTTACAGTTGGC (SEQ ID NO: 2223) | AGCAAGGTCTTC (SEQ ID NO: 2224) | GTACCAGGTACT (SEQ ID NO: 2225) | GCGTGGTCATTA (SEQ ID NO: 2226) |
| TATGCCAGAGAT (SEQ ID NO: 2227) | TTCTAGAGTGCG (SEQ ID NO: 2228) | CGGACTCGTTAC (SEQ ID NO: 2229) | TCTAAACCCTCT (SEQ ID NO: 2230) | GTATACCCTTCT (SEQ ID NO: 2231) | AGTCACATCCGC (SEQ ID NO: 2232) |
| AGGTCCAAATCA (SEQ ID NO: 2233) | ACGGATGTTATG (SEQ ID NO: 2234) | TCTCGCACTGGA (SEQ ID NO: 2235) | CCTGATCACACG (SEQ ID NO: 2236) | TAGGTCTAGGTC (SEQ ID NO: 2237) | AGCGTCTGAACT (SEQ ID NO: 2238) |
| ACCGTGCTCACA (SEQ ID NO: 2239) | TTGAGGCTACAA (SEQ ID NO: 2240) | TTCTGGTCTTGT (SEQ ID NO: 2241) | AAGCTGCCTAGT (SEQ ID NO: 2242) | GACAGTAGCTTC (SEQ ID NO: 2243) | ATCGCGACTGCT (SEQ ID NO: 2244) |
| CTCCCTTTGTGT (SEQ ID NO: 2245) | GTAGGAACCGGA (SEQ ID NO: 2246) | GTCCACTTGGAC (SEQ ID NO: 2247) | ATTTGTGGGTAG (SEQ ID NO: 2248) | TGAACGTTGGAT (SEQ ID NO: 2249) | TGGAGGTTCTCA (SEQ ID NO: 2250) |
| AGCTGCACCTAA (SEQ ID NO: 2251) | ACATCTAGCAGA (SEQ ID NO: 2252) | GATTTAGAGGCT (SEQ ID NO: 2253) | TACATGGAGCAT (SEQ ID NO: 2254) | AGTGTGAACGTT (SEQ ID NO: 2255) | TGCTTGTAGGCA (SEQ ID NO: 2256) |
| CCTTGACCGATG (SEQ ID NO: 2257) | CCGACATTGTAG (SEQ ID NO: 2258) | GTCAGCCGTTAA (SEQ ID NO: 2259) | GCCTCAGCAGTT (SEQ ID NO: 2260) | ATGGTCACAAAC (SEQ ID NO: 2261) | CTTAAATGGGCA (SEQ ID NO: 2262) |
| CTATCATCCTCA (SEQ ID NO: 2263) | CATGTAAGGCTC (SEQ ID NO: 2264) | ACGGTTTCTGGA (SEQ ID NO: 2265) | CATCTTCTGATC (SEQ ID NO: 2266) | ACATAGCGGTTC (SEQ ID NO: 2267) | GGTATCACCCTG (SEQ ID NO: 2268) |
| ACTCTAGCCGGT (SEQ ID NO: 2269) | TGCAAGCTAAGT (SEQ ID NO: 2270) | GCAGCCATATTG (SEQ ID NO: 2271) | CAGGTTGTGCCT (SEQ ID NO: 2272) | GCTGTTTGACCG (SEQ ID NO: 2273) | CGCCTTGATAAG (SEQ ID NO: 2274) |
| CGATAGGCCTTA (SEQ ID NO: 2275) | GTGTGTGCCATA (SEQ ID NO: 2276) | ATAGGTGTGCTA (SEQ ID NO: 2277) | GGTTGCCCTGTA (SEQ ID NO: 2278) | CGAATACTGACA (SEQ ID NO: 2279) | CGTTTATCCGTT (SEQ ID NO: 2280) |

TABLE 1-continued (SEQ ID NOS 775-2938, respectively, in order
of appearance from left to right in each row as shown)

| Barcode Sequence Fragments | Barcode Sequence Fragments | Barcode Sequence Fragments | Barcode Sequence Fragments | Barcode Sequence Fragments | Barcode Sequence Fragments |
|---|---|---|---|---|---|
| AATGACCTCGTG (SEQ ID NO: 2281) | TGACAACCGAAT (SEQ ID NO: 2282) | ACCTAGCTAGTG (SEQ ID NO: 2283) | TGGTTTCGAAGA (SEQ ID NO: 2284) | TATCCTGGTTTC (SEQ ID NO: 2285) | TTGTACTCACTC (SEQ ID NO: 2286) |
| CTTAGGCATGTG (SEQ ID NO: 2287) | TAGGCTCGTGCT (SEQ ID NO: 2288) | GTCCTGACACTG (SEQ ID NO: 2289) | TGCGTTCTAGCG (SEQ ID NO: 2290) | CATTGTCCCTAT (SEQ ID NO: 2291) | TTCCCACCCATT (SEQ ID NO: 2292) |
| CCAGATATAGCA (SEQ ID NO: 2293) | CTCCTTAAGGCG (SEQ ID NO: 2294) | GGACTCAACTAA (SEQ ID NO: 2295) | AGTCCACTGGTA (SEQ ID NO: 2296) | ACCGACGCTTGT (SEQ ID NO: 2297) | GCCGCATTCGAT (SEQ ID NO: 2298) |
| GAGAGTCCACTT (SEQ ID NO: 2299) | TTGCCTGGGTCA (SEQ ID NO: 2300) | ATACGGGTTCGT (SEQ ID NO: 2301) | GAACTCGCTATG (SEQ ID NO: 2302) | CTGTGATCGGAT (SEQ ID NO: 2303) | |
| GAACGGGACGTA (SEQ ID NO: 2304) | CAATTCTGCTTC (SEQ ID NO: 2305) | CCTTTCACCTGT (SEQ ID NO: 2306) | GGTAGTTCATAG (SEQ ID NO: 2307) | ATGTACACCGGT (SEQ ID NO: 2308) | |
| ACGTGTAGGCTT (SEQ ID NO: 2309) | ACTGGCAAACCT (SEQ ID NO: 2310) | ATCAGCCAGCTC (SEQ ID NO: 2311) | AGGATGGGATGC (SEQ ID NO: 2312) | TAAGCTAAACCG (SEQ ID NO: 2313) | |
| GGTCTCCTACAG (SEQ ID NO: 2314) | AATCAGAGCTTG (SEQ ID NO: 2315) | GCTCCACAACGT (SEQ ID NO: 2316) | CAGTGATACTGC (SEQ ID NO: 2317) | CATTGGGAGTTC (SEQ ID NO: 2318) | |
| ACTGACTTAAGG (SEQ ID NO: 2319) | CAATGTAGACAC (SEQ ID NO: 2320) | AAGGAGTGCGCA (SEQ ID NO: 2321) | GAGGATACTACT (SEQ ID NO: 2322) | GATCGGTTAATG (SEQ ID NO: 2323) | |
| GATGCTGCCGTT (SEQ ID NO: 2324) | TGGCGATACGTT (SEQ ID NO: 2325) | AGGGAAAGGATC (SEQ ID NO: 2326) | GCATCGTCTGGT (SEQ ID NO: 2327) | CAGCGACTGTTA (SEQ ID NO: 2328) | |
| TTCCTAGGCCAG (SEQ ID NO: 2329) | GCCTTACGATAG (SEQ ID NO: 2330) | ACGACGCATTTG (SEQ ID NO: 2331) | TATGGGTAGCTA (SEQ ID NO: 2332) | GAGCCCAAAGAG (SEQ ID NO: 2333) | |
| ATTAAGCCTGGA (SEQ ID NO: 2334) | TACCTGTGTCTT (SEQ ID NO: 2335) | CGTCACTCCAAG (SEQ ID NO: 2336) | AGGTATTACCGA (SEQ ID NO: 2337) | CGATCACCACAA (SEQ ID NO: 2338) | |
| TGGCTTTCTATC (SEQ ID NO: 2339) | AACGAGGCAACG (SEQ ID NO: 2340) | TTACACAAAGGC (SEQ ID NO: 2341) | TGTCAAAGTGAC (SEQ ID NO: 2342) | CTAGAGCTCCCA (SEQ ID NO: 2343) | |
| ACAGCTCAAACA (SEQ ID NO: 2344) | GAAGACAGCGAC (SEQ ID NO: 2345) | GTATAGTCCGTG (SEQ ID NO: 2346) | GTAACGGCTCTA (SEQ ID NO: 2347) | GAACGCAATTCC (SEQ ID NO: 2348) | |
| GAGCGTATCCAT (SEQ ID NO: 2349) | ACACCTGCGATC (SEQ ID NO: 2350) | TCGTAAGCCGTC (SEQ ID NO: 2351) | GTGTACATAACG (SEQ ID NO: 2352) | ATCCGTCTGACG (SEQ ID NO: 2353) | |
| ATGGGCGAATGG (SEQ ID NO: 2354) | GGCGTTGCATTC (SEQ ID NO: 2355) | TGACGCCTCCAA (SEQ ID NO: 2356) | TGCTGCTCAACG (SEQ ID NO: 2357) | TGAAATGTCCCG (SEQ ID NO: 2358) | |
| GATCTCTGGGTA (SEQ ID NO: 2359) | ACTAGCGTTCAG (SEQ ID NO: 2360) | TTCTCGGTTCTC (SEQ ID NO: 2361) | CGGATGCAAGAG (SEQ ID NO: 2362) | ATTCGCCAAGAA (SEQ ID NO: 2363) | |
| CATCATACGGGT (SEQ ID NO: 2364) | TTGCGACAAAGT (SEQ ID NO: 2365) | GCTACTGGTATG (SEQ ID NO: 2366) | TGACATTCACGG (SEQ ID NO: 2367) | TACGTGATCCCG (SEQ ID NO: 2368) | |
| TACGGATTATGG (SEQ ID NO: 2369) | TGCGAGTATATG (SEQ ID NO: 2370) | GAATCCTCACCG (SEQ ID NO: 2371) | CACATATTGGGC (SEQ ID NO: 2372) | TGGGTAGATCTC (SEQ ID NO: 2373) | |

TABLE 1-continued (SEQ ID NOS 775-2938, respectively, in order
of appearance from left to right in each row as shown)

| Barcode Sequence Fragments | Barcode Sequence Fragments | Barcode Sequence Fragments | Barcode Sequence Fragments | Barcode Sequence Fragments | Barcode Sequence Fragments |
|---|---|---|---|---|---|
| ATAGCGAACTCA (SEQ ID NO: 2374) | TACCACAACGAA (SEQ ID NO: 2375) | CCTGACACACAC (SEQ ID NO: 2376) | TTCAATAGGGAC (SEQ ID NO: 2377) | AGCAATCGGTAT (SEQ ID NO: 2378) | |
| TAACGCTGTGTG (SEQ ID NO: 2379) | TCTGGAACGGTT (SEQ ID NO: 2380) | CAGCGTTTAGCC (SEQ ID NO: 2381) | ATAGCCGATGTC (SEQ ID NO: 2382) | GTTGGACGAAGG (SEQ ID NO: 2383) | |
| AACCAAACTCGA (SEQ ID NO: 2384) | GTACTACCTCGG (SEQ ID NO: 2385) | GGTATGGCTACT (SEQ ID NO: 2386) | ATGCGTAATGCA (SEQ ID NO: 2387) | ACACTATGAAGC (SEQ ID NO: 2388) | |
| GCCGTCTCGTAA (SEQ ID NO: 2389) | TTCCTGTTAACC (SEQ ID NO: 2390) | ACAATGTCACAG (SEQ ID NO: 2391) | ACTCCGATAGAC (SEQ ID NO: 2392) | ACGGAAATCCCT (SEQ ID NO: 2393) | |
| CTGGGTATCTCG (SEQ ID NO: 2394) | CTATCCAAGTGG (SEQ ID NO: 2395) | GCCATAGTGTGT (SEQ ID NO: 2396) | GCTGAGCCTTTG (SEQ ID NO: 2397) | GGTTTCTATCCT (SEQ ID NO: 2398) | |
| GACTACCCGTTG (SEQ ID NO: 2399) | CAGTCTAGTACG (SEQ ID NO: 2400) | GGTCCCGAAATT (SEQ ID NO: 2401) | AACAGAGAGAGC (SEQ ID NO: 2402) | ACGCAATGTCTG (SEQ ID NO: 2403) | |
| GCGTTGCAAACT (SEQ ID NO: 2404) | GTGTCCGGATTC (SEQ ID NO: 2405) | TCTGCGAGTCTG (SEQ ID NO: 2406) | AATTCCGAACGC (SEQ ID NO: 2407) | TCGGTTACGCTG (SEQ ID NO: 2408) | |
| AACCGCATAAGT (SEQ ID NO: 2409) | TGTGGTGATGTA (SEQ ID NO: 2410) | ATGTAGGCTTAG (SEQ ID NO: 2411) | TTAGTACGCAGA (SEQ ID NO: 2412) | AAGCCATTGAAC (SEQ ID NO: 2413) | |
| ACCTTACACCTT (SEQ ID NO: 2414) | CTTTCGTTCAAC (SEQ ID NO: 2415) | TGCTTCCAATTC (SEQ ID NO: 2416) | GAATCTGACAAC (SEQ ID NO: 2417) | CGATTGTTCCGG (SEQ ID NO: 2418) | |
| GTAGGTGCTTAC (SEQ ID NO: 2419) | CCGAAGATTCTG (SEQ ID NO: 2420) | GCCGAGATAATT (SEQ ID NO: 2421) | CACACTGAAGTC (SEQ ID NO: 2422) | CCTAAGAGCATC (SEQ ID NO: 2423) | |
| CGCATTTGGATG (SEQ ID NO: 2424) | GTTGGCGTTACA (SEQ ID NO: 2425) | TCGAGTATCGAA (SEQ ID NO: 2426) | ACTATCAGTGGC (SEQ ID NO: 2427) | GATGGTTTCAGC (SEQ ID NO: 2428) | |
| ATAACATGTGCG (SEQ ID NO: 2429) | GAAGTAGCGAGC (SEQ ID NO: 2430) | GCCCTATCTTCT (SEQ ID NO: 2431) | AGACTCAGACTC (SEQ ID NO: 2432) | TAATTGCAGAGC (SEQ ID NO: 2433) | |
| CTTGAGAAATCG (SEQ ID NO: 2434) | TTGCGGACCCTA (SEQ ID NO: 2435) | AGGTACGCAATT (SEQ ID NO: 2436) | GACCTTTCAAGG (SEQ ID NO: 2437) | TACCGGCTTGCA (SEQ ID NO: 2438) | |
| CTACACAGCACA (SEQ ID NO: 2439) | GCGGAAACATGG (SEQ ID NO: 2440) | GTCCCTATTATC (SEQ ID NO: 2441) | CAAGCAGGTGAG (SEQ ID NO: 2442) | AGTCGGCATCTC (SEQ ID NO: 2443) | |
| GAAATGCTACGT (SEQ ID NO: 2444) | AACGTTAGTGTG (SEQ ID NO: 2445) | TGGGACATATCC (SEQ ID NO: 2446) | GGAGAACGACAC (SEQ ID NO: 2447) | ATATACCTGCGG (SEQ ID NO: 2448) | |
| TCTGAGGTTGCC (SEQ ID NO: 2449) | TGCATGACAGTC (SEQ ID NO: 2450) | GAACGATCATGT (SEQ ID NO: 2451) | CAGCTTCGACTG (SEQ ID NO: 2452) | TGTCTGACGCAA (SEQ ID NO: 2453) | |
| GATCATTCTCTC (SEQ ID NO: 2454) | TCAATCGCTTTC (SEQ ID NO: 2455) | TTCAGACCAGCC (SEQ ID NO: 2456) | ATCTTTCCCTGA (SEQ ID NO: 2457) | CATATCCAGCCG (SEQ ID NO: 2458) | |
| AGACATACCGTA (SEQ ID NO: 2459) | CTACCGATTGCG (SEQ ID NO: 2460) | ACGCATCGCACT (SEQ ID NO: 2461) | CTCCGAACAACA (SEQ ID NO: 2462) | TCTCACTGTTCC (SEQ ID NO: 2463) | |

TABLE 1-continued (SEQ ID NOS 775-2938, respectively, in order of appearance from left to right in each row as shown)

| Barcode Sequence Fragments | Barcode Sequence Fragments | Barcode Sequence Fragments | Barcode Sequence Fragments | Barcode Sequence Fragments | Barcode Sequence Fragments |
|---|---|---|---|---|---|
| GATCCTCATGCG (SEQ ID NO: 2464) | TCACCCAAGGTA (SEQ ID NO: 2465) | CAGTAGCGATAT (SEQ ID NO: 2466) | GGTCACACATCA (SEQ ID NO: 2467) | GCTATGGAACTC (SEQ ID NO: 2468) | |
| ATTATCGTCCCT (SEQ ID NO: 2469) | AGCCAGTCATAC (SEQ ID NO: 2470) | GGATACTCGCAT (SEQ ID NO: 2471) | AGAACTTGACGT (SEQ ID NO: 2472) | CTCCACATTCCT (SEQ ID NO: 2473) | |
| CCAGACCGCTAT (SEQ ID NO: 2474) | TAACGGCGCTCT (SEQ ID NO: 2475) | CTAAGTTGCAAG (SEQ ID NO: 2476) | CTTGAACCCGAC (SEQ ID NO: 2477) | TACGTTTGGCGA (SEQ ID NO: 2478) | |
| AGCTCTAGAAAC (SEQ ID NO: 2479) | GTTTGCTCGAGA (SEQ ID NO: 2480) | CGCGATATCGTC (SEQ ID NO: 2481) | GACGTGTCCATC (SEQ ID NO: 2482) | AATCGCCCTTGG (SEQ ID NO: 2483) | |
| TCCATCGACGTG (SEQ ID NO: 2484) | CAAACGCACTAA (SEQ ID NO: 2485) | CTGATGTACACG (SEQ ID NO: 2486) | AGAGCCAAGAGC (SEQ ID NO: 2487) | CGGCGATGAAAG (SEQ ID NO: 2488) | |
| CGATGTGTGGTT (SEQ ID NO: 2489) | GAACAAAGAGCG (SEQ ID NO: 2490) | AGGCATCTGCTC (SEQ ID NO: 2491) | TGGGAATGTTGT (SEQ ID NO: 2492) | CCGCTACGTGAT (SEQ ID NO: 2493) | |
| GCGAAGTTGGGA (SEQ ID NO: 2494) | GCTAAGTGATGT (SEQ ID NO: 2495) | AGACCTGACCCT (SEQ ID NO: 2496) | CAATCATAGGTG (SEQ ID NO: 2497) | CTGGTAAGTCCA (SEQ ID NO: 2498) | |
| GCATTCGGCGTT (SEQ ID NO: 2499) | AAGGGACAAGTG (SEQ ID NO: 2500) | CATCGACGAGTT (SEQ ID NO: 2501) | ATAAGTAACCGC (SEQ ID NO: 2502) | AGAGCTCCTCTG (SEQ ID NO: 2503) | |
| CGCCATTGTGCA (SEQ ID NO: 2504) | AGTGTCGATTCG (SEQ ID NO: 2505) | GGAGTTGAGGTG (SEQ ID NO: 2506) | GACTTGGTAAAC (SEQ ID NO: 2507) | GACAAACCTTGC (SEQ ID NO: 2508) | |
| TCCAACTGCAGA (SEQ ID NO: 2509) | CTATTAAGCGGC (SEQ ID NO: 2510) | AGCATCCCTAAG (SEQ ID NO: 2511) | AATCACGGTGCT (SEQ ID NO: 2512) | CATTAGCTGGAA (SEQ ID NO: 2513) | |
| TAAAGACCCGTA (SEQ ID NO: 2514) | CCTACCATTGTT (SEQ ID NO: 2515) | CAGACGAGGAAC (SEQ ID NO: 2516) | ACGACCTACGCT (SEQ ID NO: 2517) | CCACAACGATCA (SEQ ID NO: 2518) | |
| TGTATCTTCACC (SEQ ID NO: 2519) | GAGTCCGTTGCT (SEQ ID NO: 2520) | TCGCTACAGATG (SEQ ID NO: 2521) | GATGTCATAGCC (SEQ ID NO: 2522) | CCGGTGTGATTC (SEQ ID NO: 2523) | |
| GACTGACTCGTC (SEQ ID NO: 2524) | GATAACTGTACG (SEQ ID NO: 2525) | TCGGTGTACCAA (SEQ ID NO: 2526) | TGTTGCGTTTCT (SEQ ID NO: 2527) | ATAGTGTTCGGC (SEQ ID NO: 2528) | |
| TCGTGGATAGCT (SEQ ID NO: 2529) | TAAACCTGGACA (SEQ ID NO: 2530) | AACACGGTTTGA (SEQ ID NO: 2531) | GCATACTACAGC (SEQ ID NO: 2532) | TAATCTCGCCGG (SEQ ID NO: 2533) | |
| GACGCACTAACT (SEQ ID NO: 2534) | CCGAATTGACAA (SEQ ID NO: 2535) | CTTGTGCGACAA (SEQ ID NO: 2536) | GAGGTATTCTGA (SEQ ID NO: 2537) | CAGATCCCAACC (SEQ ID NO: 2538) | |
| GGCGATTTACGT (SEQ ID NO: 2539) | CTGGCATCTAGC (SEQ ID NO: 2540) | AGAGTAAGCCGG (SEQ ID NO: 2541) | ATGTTCCTCATC (SEQ ID NO: 2542) | AGAGATTATGCC (SEQ ID NO: 2543) | |
| TAAGGCATCGCT (SEQ ID NO: 2544) | GGTGGTCGTTCT (SEQ ID NO: 2545) | AGACACCAATGT (SEQ ID NO: 2546) | CGGTATAGCAAT (SEQ ID NO: 2547) | TGAATACCTGGC (SEQ ID NO: 2548) | |
| ACCCATACAGCC (SEQ ID NO: 2549) | ACTATGGGCTAA (SEQ ID NO: 2550) | AATACGTCAAGC (SEQ ID NO: 2551) | CTTGGCCTGTAG (SEQ ID NO: 2552) | CTCCCACTAGAG (SEQ ID NO: 2553) | |

TABLE 1-continued (SEQ ID NOS 775-2938, respectively, in order of appearance from left to right in each row as shown)

| Barcode Sequence Fragments | Barcode Sequence Fragments | Barcode Sequence Fragments | Barcode Sequence Fragments | Barcode Sequence Fragments | Barcode Sequence Fragments |
|---|---|---|---|---|---|
| CGCACTACGCAT (SEQ ID NO: 2554) | GCATTGAGTTCG (SEQ ID NO: 2555) | ATGGCAATTCAG (SEQ ID NO: 2556) | ATCAAACGCATG (SEQ ID NO: 2557) | AGCCCTGCTACA (SEQ ID NO: 2558) | |
| CAGTCGTTAAGA (SEQ ID NO: 2559) | GTTGCTGAGTCC (SEQ ID NO: 2560) | CAGTGTCATGAA (SEQ ID NO: 2561) | CGGTCCTGAGTT (SEQ ID NO: 2562) | CCTTATAGAAGG (SEQ ID NO: 2563) | |
| CTACGAAAGCCT (SEQ ID NO: 2564) | CTATGGTGAACC (SEQ ID NO: 2565) | CGGTGACCTACT (SEQ ID NO: 2566) | CTCGAGCGTACT (SEQ ID NO: 2567) | GGCCAAGGAAGT (SEQ ID NO: 2568) | |
| ATAATTGCCGAG (SEQ ID NO: 2569) | GGACCAAGGGAT (SEQ ID NO: 2570) | ACATCCCTACTT (SEQ ID NO: 2571) | TTAAGGACTGAC (SEQ ID NO: 2572) | CCTCTACTCTAA (SEQ ID NO: 2573) | |
| GGCATGTTATCG (SEQ ID NO: 2574) | GTATTGGTCAGA (SEQ ID NO: 2575) | TGAAGCACACTA (SEQ ID NO: 2576) | GTGGAAGAGACA (SEQ ID NO: 2577) | GAGTCGATCTTG (SEQ ID NO: 2578) | |
| AGGCACAGTAGG (SEQ ID NO: 2579) | AGAACCGTCATA (SEQ ID NO: 2580) | GTGAATGTTCGA (SEQ ID NO: 2581) | TAACTAGGACGT (SEQ ID NO: 2582) | GACCTACCGCAT (SEQ ID NO: 2583) | |
| CTACTTACATCC (SEQ ID NO: 2584) | AACTGGAACCCT (SEQ ID NO: 2585) | AGTCGCTACACA (SEQ ID NO: 2586) | GAAAGAGTCTCT (SEQ ID NO: 2587) | ATGTAATAGGCC (SEQ ID NO: 2588) | |
| CTCTTCTGATCA (SEQ ID NO: 2589) | ATACTCGGCTGC (SEQ ID NO: 2590) | AACCACTAACCG (SEQ ID NO: 2591) | TCACCGGAATCC (SEQ ID NO: 2592) | GACTCGCAACTA (SEQ ID NO: 2593) | |
| ATGCTAACCACG (SEQ ID NO: 2594) | ACGCTTAACGAC (SEQ ID NO: 2595) | TTCGCTAACCTT (SEQ ID NO: 2596) | CGACTGCAGCTT (SEQ ID NO: 2597) | CTGACGATCCGT (SEQ ID NO: 2598) | |
| ACCAATCTCGGC (SEQ ID NO: 2599) | AGCTTACCGACC (SEQ ID NO: 2600) | GACACTCACCGT (SEQ ID NO: 2601) | GTTACCCGAGCT (SEQ ID NO: 2602) | GTGCGAGGACAA (SEQ ID NO: 2603) | |
| TATCCAAGCGCA (SEQ ID NO: 2604) | AGGGCTATAGTT (SEQ ID NO: 2605) | TCAGAGTAGACT (SEQ ID NO: 2606) | CCTAGGTCCCAA (SEQ ID NO: 2607) | GCAGAGAGGCTA (SEQ ID NO: 2608) | |
| GTACTGAAGATC (SEQ ID NO: 2609) | TGTCTCGCAAGC (SEQ ID NO: 2610) | GACCAAATGTCC (SEQ ID NO: 2611) | TTGAGTGGTCTG (SEQ ID NO: 2612) | TCCTTGTCCTTG (SEQ ID NO: 2613) | |
| TCGCCGTGTACA (SEQ ID NO: 2614) | CAGCCGCATATC (SEQ ID NO: 2615) | GATGCAACTTCG (SEQ ID NO: 2616) | CGACGAGATTAT (SEQ ID NO: 2617) | CTACAATTGAGG (SEQ ID NO: 2618) | |
| AACTGCGATATG (SEQ ID NO: 2619) | GATACGTTCGCA (SEQ ID NO: 2620) | CACCACAGAATC (SEQ ID NO: 2621) | AGTACTGCCTGC (SEQ ID NO: 2622) | GTTGACCATCGC (SEQ ID NO: 2623) | |
| CTTCCAACTCAT (SEQ ID NO: 2624) | CCAAGATTCGCC (SEQ ID NO: 2625) | GGAGCTCTGTAT (SEQ ID NO: 2626) | GAAGTCCACACT (SEQ ID NO: 2627) | CAATGAGGGAGA (SEQ ID NO: 2628) | |
| GAGATCGCCTAT (SEQ ID NO: 2629) | GAGGCTGATTTA (SEQ ID NO: 2630) | CCTTAAGGGCAT (SEQ ID NO: 2631) | GTAGAATGCTCC (SEQ ID NO: 2632) | AAGCAACGGTGG (SEQ ID NO: 2633) | |
| TGTACATCGCCG (SEQ ID NO: 2634) | GAGTTAGCATCA (SEQ ID NO: 2635) | GCTGCTACAAGT (SEQ ID NO: 2636) | ACACCCTATCGG (SEQ ID NO: 2637) | CTCCAATGACGC (SEQ ID NO: 2638) | |
| TGTTAAGCAGCA (SEQ ID NO: 2639) | TGTAGTATAGGC (SEQ ID NO: 2640) | GTAAACGACTTG (SEQ ID NO: 2641) | AGGAGGATAAAG (SEQ ID NO: 2642) | ATGGAAGGTGGC (SEQ ID NO: 2643) | |

TABLE 1-continued (SEQ ID NOS 775-2938, respectively, in order
of appearance from left to right in each row as shown)

| Barcode Sequence Fragments | Barcode Sequence Fragments | Barcode Sequence Fragments | Barcode Sequence Fragments | Barcode Sequence Fragments | Barcode Sequence Fragments |
|---|---|---|---|---|---|
| ACGGCGTTATGT (SEQ ID NO: 2644) | CTCACGCAATGC (SEQ ID NO: 2645) | CGCCCTCTTCTT (SEQ ID NO: 2646) | GCATGGGTTATC (SEQ ID NO: 2647) | CCGGCTTATGTG (SEQ ID NO: 2648) | |
| ACTTTGCTTTGC (SEQ ID NO: 2649) | GTCCCGTGAAAT (SEQ ID NO: 2650) | ACTAGACGACTA (SEQ ID NO: 2651) | GTTCCCAACGGT (SEQ ID NO: 2652) | CTGTGCAACGTC (SEQ ID NO: 2653) | |
| CAAAGCGGTATT (SEQ ID NO: 2654) | GGACAGTGTATT (SEQ ID NO: 2655) | AGGTTAAGTGCT (SEQ ID NO: 2656) | GTCAGAGTATTG (SEQ ID NO: 2657) | AGTCAATGGCCT (SEQ ID NO: 2658) | |
| CGAAACTACGTA (SEQ ID NO: 2659) | ACACGACTATAG (SEQ ID NO: 2660) | ATATCCTGGGAC (SEQ ID NO: 2661) | ATGACAGAACCT (SEQ ID NO: 2662) | GGAACACATGTT (SEQ ID NO: 2663) | |
| GAGGACCAGCAA (SEQ ID NO: 2664) | GTGTAGGTGCTT (SEQ ID NO: 2665) | TTGTAGCCGACA (SEQ ID NO: 2666) | ACAAGTGCTGCT (SEQ ID NO: 2667) | AGCGCATATCCA (SEQ ID NO: 2668) | |
| AATAGCATGTCG (SEQ ID NO: 2669) | TGAACTAGCGTC (SEQ ID NO: 2670) | TCAGAAGCTCAA (SEQ ID NO: 2671) | AATAGTCGTGAC (SEQ ID NO: 2672) | TGCAACTTGCAG (SEQ ID NO: 2673) | |
| CGGAGTAATCCT (SEQ ID NO: 2674) | TCCGAGTCACCA (SEQ ID NO: 2675) | ACTGTGACGTCC (SEQ ID NO: 2676) | TACAAGTGGTCC (SEQ ID NO: 2677) | GTGTGGCAGAAG (SEQ ID NO: 2678) | |
| CTGTGTCCATGG (SEQ ID NO: 2679) | TCCTCTTTGGTC (SEQ ID NO: 2680) | TTGCAGTGCAAC (SEQ ID NO: 2681) | GCTGGTCTAGTC (SEQ ID NO: 2682) | GTGACCCTGTCA (SEQ ID NO: 2683) | |
| CTTCGCGGATGT (SEQ ID NO: 2684) | TCCACCCTCTAT (SEQ ID NO: 2685) | TGTCATGGCTGA (SEQ ID NO: 2686) | GGCATCCTGGTT (SEQ ID NO: 2687) | CACGCAGTCTAC (SEQ ID NO: 2688) | |
| ATAGGCTGTAGT (SEQ ID NO: 2689) | TCGTGACGCTAA (SEQ ID NO: 2690) | TTCGTGAGGATA (SEQ ID NO: 2691) | GTGCCTCAGGTT (SEQ ID NO: 2692) | TTCACTGTGCGG (SEQ ID NO: 2693) | |
| TGTGTAGCCATG (SEQ ID NO: 2694) | ACGGCTAGTTCC (SEQ ID NO: 2695) | TCCCAACCTAGG (SEQ ID NO: 2696) | ATTACAGCGACA (SEQ ID NO: 2697) | AACGAATACCAC (SEQ ID NO: 2698) | |
| AAGGGCGCTGAA (SEQ ID NO: 2699) | GCACTGGCATAT (SEQ ID NO: 2700) | TAGAATCAACGC (SEQ ID NO: 2701) | ATGCAGAGATCT (SEQ ID NO: 2702) | ATGGTTCACCCG (SEQ ID NO: 2703) | |
| GTTTCCGTGGTG (SEQ ID NO: 2704) | GGCATTAGTTGA (SEQ ID NO: 2705) | CACAATACACCG (SEQ ID NO: 2706) | CGTATGCCGTAC (SEQ ID NO: 2707) | TAGCGGAAGACG (SEQ ID NO: 2708) | |
| AGGAACCAGACG (SEQ ID NO: 2709) | CGGTAGTTGATC (SEQ ID NO: 2710) | GTATGACTAGCA (SEQ ID NO: 2711) | AGCCGACTCTGT (SEQ ID NO: 2712) | CCTCATGCTATT (SEQ ID NO: 2713) | |
| TAATGCCCAGGT (SEQ ID NO: 2714) | TGAAAGCGGCGA (SEQ ID NO: 2715) | ATGCTCTAGAGA (SEQ ID NO: 2716) | CTATTCTTGGCT (SEQ ID NO: 2717) | CCATCTTACCAT (SEQ ID NO: 2718) | |
| TATGAACGTCCG (SEQ ID NO: 2719) | GGTTACGGTTAC (SEQ ID NO: 2720) | AGCTAGCGTTCA (SEQ ID NO: 2721) | TCGGTAGCAACT (SEQ ID NO: 2722) | TATGCTCTCTCA (SEQ ID NO: 2723) | |
| CCACATTGGGTC (SEQ ID NO: 2724) | ACATCAGGTCAC (SEQ ID NO: 2725) | GGTCTTAGCACC (SEQ ID NO: 2726) | CCAAATGATGAC (SEQ ID NO: 2727) | CGTGTAGTAGAT (SEQ ID NO: 2728) | |
| TCAGTCAGATGA (SEQ ID NO: 2729) | GTTGATACGATG (SEQ ID NO: 2730) | TACCATCCATCT (SEQ ID NO: 2731) | GCAGGTAACATT (SEQ ID NO: 2732) | ACATGGGCGGAA (SEQ ID NO: 2733) | |

TABLE 1-continued (SEQ ID NOS 775-2938, respectively, in order
of appearance from left to right in each row as shown)

| Barcode Sequence Fragments | Barcode Sequence Fragments | Barcode Sequence Fragments | Barcode Sequence Fragments | Barcode Sequence Fragments | Barcode Sequence Fragments |
|---|---|---|---|---|---|
| AAGTCACACACA (SEQ ID NO: 2734) | CAGACACTTCCG (SEQ ID NO: 2735) | AGGGATGGACCA (SEQ ID NO: 2736) | GCACGTTCTACG (SEQ ID NO: 2737) | CCGCTGATGTCA (SEQ ID NO: 2738) | |
| GCTGTGATTCGA (SEQ ID NO: 2739) | TCACCATCCGAG (SEQ ID NO: 2740) | ACTAATACGCGA (SEQ ID NO: 2741) | GACTGGAGATGG (SEQ ID NO: 2742) | ACGAGTTTACCG (SEQ ID NO: 2743) | |
| CTAGCTATGGAC (SEQ ID NO: 2744) | ACCCACCACTAG (SEQ ID NO: 2745) | TCATACAGCCAG (SEQ ID NO: 2746) | ACTAAGTACCCG (SEQ ID NO: 2747) | GGAGATTGGAGA (SEQ ID NO: 2748) | |
| CTTGACGAGGTT (SEQ ID NO: 2749) | CAGAAGGTGTGG (SEQ ID NO: 2750) | GGAGGCCATAAG (SEQ ID NO: 2751) | TAAGTGAGTACC (SEQ ID NO: 2752) | AAGCCCAGCATT (SEQ ID NO: 2753) | |
| ACCTGGGAATAT (SEQ ID NO: 2754) | GAAGCTTGAATC (SEQ ID NO: 2755) | GTCCGATCCTAG (SEQ ID NO: 2756) | ATCGACAACACC (SEQ ID NO: 2757) | GGTGAAACCTAT (SEQ ID NO: 2758) | |
| CTCTGCCTAATT (SEQ ID NO: 2759) | ACTAGGATCAGT (SEQ ID NO: 2760) | CTGTGGGATTCA (SEQ ID NO: 2761) | AGCACACTACAC (SEQ ID NO: 2762) | TGGTAAGAGTCT (SEQ ID NO: 2763) | |
| ATATGACCCAGC (SEQ ID NO: 2764) | GCTCCTTAGAAG (SEQ ID NO: 2765) | TTGTCTACCTAC (SEQ ID NO: 2766) | GAATGTTGCGCT (SEQ ID NO: 2767) | GCGCTTAGAATA (SEQ ID NO: 2768) | |
| CTCTATTCCACC (SEQ ID NO: 2769) | TCCCATTCCCAT (SEQ ID NO: 2770) | GAAGGCTCCTTA (SEQ ID NO: 2771) | CGCGCAAGTATT (SEQ ID NO: 2772) | AGGTGTATCACC (SEQ ID NO: 2773) | |
| ATTGAGTGAGTC (SEQ ID NO: 2774) | TGGCGTCATTCG (SEQ ID NO: 2775) | AGATTACAACCG (SEQ ID NO: 2776) | ATAGTTAGGGCT (SEQ ID NO: 2777) | ATTGTCAAGCAG (SEQ ID NO: 2778) | |
| TTATGGTACGGA (SEQ ID NO: 2779) | AATCCTCGGAGT (SEQ ID NO: 2780) | TCTTCTGCCCTA (SEQ ID NO: 2781) | GTTCAACAGCTG (SEQ ID NO: 2782) | TTCGCAGATACG (SEQ ID NO: 2783) | |
| GCTAGTTATGGA (SEQ ID NO: 2784) | CTGGACGCATTA (SEQ ID NO: 2785) | TGAAGTCACAGT (SEQ ID NO: 2786) | TCAGCAAATGGT (SEQ ID NO: 2787) | CATAGGCCATCA (SEQ ID NO: 2788) | |
| CAGATTAACCAG (SEQ ID NO: 2789) | ACCGATTAGGTA (SEQ ID NO: 2790) | CTTAGTGCAGAA (SEQ ID NO: 2791) | AGGGACTTCAAT (SEQ ID NO: 2792) | CCTTGGAATCGC (SEQ ID NO: 2793) | |
| GGCTGCATACTC (SEQ ID NO: 2794) | ATGTGCTGCTCG (SEQ ID NO: 2795) | CATCAGTACGCC (SEQ ID NO: 2796) | GAAGTGTATCTG (SEQ ID NO: 2797) | CACTTGCTCTCT (SEQ ID NO: 2798) | |
| TTGGTAAAGTGC (SEQ ID NO: 2799) | TACGTACGAAAC (SEQ ID NO: 2800) | TAGAACACCATG (SEQ ID NO: 2801) | TCCTGTGCGAGT (SEQ ID NO: 2802) | GCAACTTCGGTA (SEQ ID NO: 2803) | |
| AAGTGGCTATCC (SEQ ID NO: 2804) | ATCACATTCTCC (SEQ ID NO: 2805) | CCGCATGACCTA (SEQ ID NO: 2806) | CCAACGTAACCA (SEQ ID NO: 2807) | GCCAATCCAACA (SEQ ID NO: 2808) | |
| AACCGATGTACC (SEQ ID NO: 2809) | AGCCTGGTACCT (SEQ ID NO: 2810) | GAGAATGGAAAG (SEQ ID NO: 2811) | AAGGTGGACAAG (SEQ ID NO: 2812) | CTGGAACATTAG (SEQ ID NO: 2813) | |
| TCGATTGGCCGT (SEQ ID NO: 2814) | GCTAAAGTCGTA (SEQ ID NO: 2815) | AACCCTAACTGG (SEQ ID NO: 2816) | CAATTGCGTGCA (SEQ ID NO: 2817) | TTAGCCCAGCGT (SEQ ID NO: 2818) | |
| GCATTACTGGAC (SEQ ID NO: 2819) | TCTCAGCGCGTA (SEQ ID NO: 2820) | TCCATACCGGAA (SEQ ID NO: 2821) | ACCAGCTCAGAT (SEQ ID NO: 2822) | AATGGTTCAGCA (SEQ ID NO: 2823) | |

TABLE 1-continued (SEQ ID NOS 775-2938, respectively, in order of appearance from left to right in each row as shown)

| Barcode Sequence Fragments | Barcode Sequence Fragments | Barcode Sequence Fragments | Barcode Sequence Fragments | Barcode Sequence Fragments | Barcode Sequence Fragments |
|---|---|---|---|---|---|
| TTGGGCCACATA (SEQ ID NO: 2824) | GACCCTAGACCT (SEQ ID NO: 2825) | GTTCAGACTAGC (SEQ ID NO: 2826) | ACGGTACCCTAC (SEQ ID NO: 2827) | CAGCAAGAGGAC (SEQ ID NO: 2828) | |
| CACACAAAGTCA (SEQ ID NO: 2829) | TATTCAGCGGAC (SEQ ID NO: 2830) | GACACCACAATA (SEQ ID NO: 2831) | TCATAGGGTAGT (SEQ ID NO: 2832) | CTAGTACAAGCC (SEQ ID NO: 2833) | |
| GCCAAGGATAGG (SEQ ID NO: 2834) | GTTCCGGATTAG (SEQ ID NO: 2835) | CGATTTAGGCCA (SEQ ID NO: 2836) | ATGGAGTTGTTG (SEQ ID NO: 2837) | AGAGCGGAACAA (SEQ ID NO: 2838) | |
| CGCCACGTGTAT (SEQ ID NO: 2839) | GCGTGTAATTAG (SEQ ID NO: 2840) | AGGATATTCGTG (SEQ ID NO: 2841) | CGTATCTCAGGA (SEQ ID NO: 2842) | GCAGTTGCCTCA (SEQ ID NO: 2843) | |
| GCAACCGATTGT (SEQ ID NO: 2844) | CTGTAGCTTGGC (SEQ ID NO: 2845) | CAATACGACCGT (SEQ ID NO: 2846) | TAGTTCGGTGAC (SEQ ID NO: 2847) | CGCGCCTTAAAC (SEQ ID NO: 2848) | |
| CATGTGCTTAGG (SEQ ID NO: 2849) | ATGCCTCGTAAG (SEQ ID NO: 2850) | GCCATGTGTGTA (SEQ ID NO: 2851) | CCATGGCTGTGT (SEQ ID NO: 2852) | TCCGCGCAAGTT (SEQ ID NO: 2853) | |
| GTTCCTCCATTA (SEQ ID NO: 2854) | ACCTATGGTGAA (SEQ ID NO: 2855) | GACTCCTAGACC (SEQ ID NO: 2856) | CTAGTCGCTGGT (SEQ ID NO: 2857) | TAACCACCAACG (SEQ ID NO: 2858) | |
| ACCTGTCCTTTC (SEQ ID NO: 2859) | CTGTTACAGCGA (SEQ ID NO: 2860) | AAGGCAAGAAGA (SEQ ID NO: 2861) | TCCAAGCGTCAC (SEQ ID NO: 2862) | TGCGTCAGCTAC (SEQ ID NO: 2863) | |
| GTTCACGCCCAA (SEQ ID NO: 2864) | CAGTCAGGCCTT (SEQ ID NO: 2865) | ACGAGGAGTCGA (SEQ ID NO: 2866) | GCTTCATTTCTG (SEQ ID NO: 2867) | CGAAATGCATGT (SEQ ID NO: 2868) | |
| CGATCGAACACT (SEQ ID NO: 2869) | ACTGAGCTGCAT (SEQ ID NO: 2870) | GCGGTACTACTA (SEQ ID NO: 2871) | AACTTGGCCGTA (SEQ ID NO: 2872) | ATGATCGGTACA (SEQ ID NO: 2873) | |
| CATGCCAACATG (SEQ ID NO: 2874) | ACGAAGTCTACC (SEQ ID NO: 2875) | TCAGCTGACTAG (SEQ ID NO: 2876) | CATACGATACAG (SEQ ID NO: 2877) | TTACCCGCACAG (SEQ ID NO: 2878) | |
| GAGTACAGTCTA (SEQ ID NO: 2879) | ACCGTCTTTCTC (SEQ ID NO: 2880) | ACCTGATCCGCA (SEQ ID NO: 2881) | GGTTGAGAAGAG (SEQ ID NO: 2882) | CCTGTTAGCGAA (SEQ ID NO: 2883) | |
| CCTACATGAGAC (SEQ ID NO: 2884) | AGTCTGTCTGCG (SEQ ID NO: 2885) | CAAGCTAGCTGT (SEQ ID NO: 2886) | CTGGGAGTTGTT (SEQ ID NO: 2887) | GCTCCGACCATA (SEQ ID NO: 2888) | |
| TCCGTGGTATAG (SEQ ID NO: 2889) | CCGCACTCAAGT (SEQ ID NO: 2890) | GTGGATAAACTC (SEQ ID NO: 2891) | ATCATCTCGGCG (SEQ ID NO: 2892) | ACAAATCGTTGG (SEQ ID NO: 2893) | |
| TCTACGGCACGT (SEQ ID NO: 2894) | TGTGGAAACTCC (SEQ ID NO: 2895) | GGTACAATGATC (SEQ ID NO: 2896) | ATTACCCACAGG (SEQ ID NO: 2897) | GAAGGAAAGTAG (SEQ ID NO: 2898) | |
| ATGCTGCAACAC (SEQ ID NO: 2899) | TTAGGCAGGTTC (SEQ ID NO: 2900) | ACTGTCGCAGTA (SEQ ID NO: 2901) | CACATCAGCGCT (SEQ ID NO: 2902) | ACAAACATGGTC (SEQ ID NO: 2903) | |
| TTCTCATGGAGG (SEQ ID NO: 2904) | TAAGACTACTGG (SEQ ID NO: 2905) | CATCCTGAGCAA (SEQ ID NO: 2906) | TGACCATAGTGA (SEQ ID NO: 2907) | GGACTATCGTTG (SEQ ID NO: 2908) | |
| CATAGTGATTGG (SEQ ID NO: 2909) | CGCGAAGTTTCA (SEQ ID NO: 2910) | CAACATCGTAGC (SEQ ID NO: 2911) | GATAAGCGCCTT (SEQ ID NO: 2912) | GCTATATCCAGG (SEQ ID NO: 2913) | |

TABLE 1-continued (SEQ ID NOS 775-2938, respectively, in order
of appearance from left to right in each row as shown)

| Barcode Sequence Fragments | Barcode Sequence Fragments | Barcode Sequence Fragments | Barcode Sequence Fragments | Barcode Sequence Fragments | Barcode Sequence Fragments |
|---|---|---|---|---|---|
| GCTATCAAGACA (SEQ ID NO: 2914) | CGATACACTGCC (SEQ ID NO: 2915) | GGCAATCATCTG (SEQ ID NO: 2916) | TAGTCTAAGGGT (SEQ ID NO: 2917) | TATTCCCACGTT (SEQ ID NO: 2918) | |
| CCGTGACAACTC (SEQ ID NO: 2919) | TTGAAATCCCGG (SEQ ID NO: 2920) | TATCGCGCGATA (SEQ ID NO: 2921) | AATTAGGCGTGT (SEQ ID NO: 2922) | CCATTAGTTCCT (SEQ ID NO: 2923) | |
| CGTTCCTTGTTA (SEQ ID NO: 2924) | GTTAGGGAGCGA (SEQ ID NO: 2925) | TACGGTCTGGAT (SEQ ID NO: 2926) | TGCTCTTGCTCT (SEQ ID NO: 2927) | TAACCTTCGCTT (SEQ ID NO: 2928) | |
| GGAATTATCGGT (SEQ ID NO: 2929) | TTACTGTGGCCG (SEQ ID NO: 2930) | TCGTTCAGGACC (SEQ ID NO: 2931) | TCCACTAGAGCA (SEQ ID NO: 2932) | GTAATCTGCCGA (SEQ ID NO: 2933) | |
| CATCAAGCATAG (SEQ ID NO: 2934) | ATATAAGGCCCA (SEQ ID NO: 2935) | TGATCCGGGTAT (SEQ ID NO: 2936) | CATTGCAAAGCA (SEQ ID NO: 2937) | GGTGGCATGGAA (SEQ ID NO: 2938) | |

TABLE 2

| | forward primer binding site fragment | 5' universal sequence fragment | barcode sequence fragment | 3' universal sequence fragment | reverse primer binding site fragment |
|---|---|---|---|---|---|
| (SEQ ID NO: 1) | CCTACGGGAGGCATCAG | GCAGATCTCG | CCTACGGGAGGCATCAG | AGTCAGTCAGCC | GGATTAGATACCCTAGTAGTC |
| (SEQ ID NO: 2) | CCTACGGGAGGCATCAG | GCAGATCTCG | CCTACGGGAGGCATCAG | AGTCAGTCAGCC | GGATTAGATACCCTAGTAGTC |
| (SEQ ID NO: 3) | CCTACGGGAGGCATCAG | GCAGATCTCG | CCTACGGGAGGCATCAG | AGTCAGTCAGCC | GGATTAGATACCCTAGTAGTC |
| (SEQ ID NO: 4) | CCTACGGGAGGCATCAG | GCAGATCTCG | CCTACGGGAGGCATCAG | AGTCAGTCAGCC | GGATTAGATACCCTAGTAGTC |
| (SEQ ID NO: 5) | CCTACGGGAGGCATCAG | GCAGATCTCG | CCTACGGGAGGCATCAG | AGTCAGTCAGCC | GGATTAGATACCCTAGTAGTC |
| (SEQ ID NO: 6) | CCTACGGGAGGCATCAG | GCAGATCTCG | CCTACGGGAGGCATCAG | AGTCAGTCAGCC | GGATTAGATACCCTAGTAGTC |
| (SEQ ID NO: 7) | CCTACGGGAGGCATCAG | GCAGATCTCG | CCTACGGGAGGCATCAG | AGTCAGTCAGCC | GGATTAGATACCCTAGTAGTC |
| (SEQ ID NO: 8) | CCTACGGGAGGCATCAG | GCAGATCTCG | CCTACGGGAGGCATCAG | AGTCAGTCAGCC | GGATTAGATACCCTAGTAGTC |
| (SEQ ID NO: 9) | CCTACGGGAGGCATCAG | GCAGATCTCG | CCTACGGGAGGCATCAG | AGTCAGTCAGCC | GGATTAGATACCCTAGTAGTC |
| (SEQ ID NO: 10) | CCTACGGGAGGCATCAG | GCAGATCTCG | CCTACGGGAGGCATCAG | AGTCAGTCAGCC | GGATTAGATACCCTAGTAGTC |
| (SEQ ID NO: 11) | CCTACGGGAGGCATCAG | GCAGATCTCG | CCTACGGGAGGCATCAG | AGTCAGTCAGCC | GGATTAGATACCCTAGTAGTC |
| (SEQ ID NO: 12) | CCTACGGGAGGCATCAG | GCAGATCTCG | CCTACGGGAGGCATCAG | AGTCAGTCAGCC | GGATTAGATACCCTAGTAGTC |
| (SEQ ID NO: 13) | CCTACGGGAGGCATCAG | GCAGATCTCG | CCTACGGGAGGCATCAG | AGTCAGTCAGCC | GGATTAGATACCCTAGTAGTC |
| (SEQ ID NO: 14) | CCTACGGGAGGCATCAG | GCAGATCTCG | CCTACGGGAGGCATCAG | AGTCAGTCAGCC | GGATTAGATACCCTAGTAGTC |
| (SEQ ID NO: 15) | CCTACGGGAGGCATCAG | GCAGATCTCG | CCTACGGGAGGCATCAG | AGTCAGTCAGCC | GGATTAGATACCCTAGTAGTC |
| (SEQ ID NO: 16) | CCTACGGGAGGCATCAG | GCAGATCTCG | CCTACGGGAGGCATCAG | AGTCAGTCAGCC | GGATTAGATACCCTAGTAGTC |
| (SEQ ID NO: 17) | CCTACGGGAGGCATCAG | GCAGATCTCG | CCTACGGGAGGCATCAG | AGTCAGTCAGCC | GGATTAGATACCCTAGTAGTC |
| (SEQ ID NO: 18) | CCTACGGGAGGCATCAG | GCAGATCTCG | CCTACGGGAGGCATCAG | AGTCAGTCAGCC | GGATTAGATACCCTAGTAGTC |
| (SEQ ID NO: 19) | CCTACGGGAGGCATCAG | GCAGATCTCG | CCTACGGGAGGCATCAG | AGTCAGTCAGCC | GGATTAGATACCCTAGTAGTC |
| (SEQ ID NO: 20) | CCTACGGGAGGCATCAG | GCAGATCTCG | CCTACGGGAGGCATCAG | AGTCAGTCAGCC | GGATTAGATACCCTAGTAGTC |
| (SEQ ID NO: 21) | CCTACGGGAGGCATCAG | GCAGATCTCG | CCTACGGGAGGCATCAG | AGTCAGTCAGCC | GGATTAGATACCCTAGTAGTC |
| (SEQ ID NO: 22) | CCTACGGGAGGCATCAG | GCAGATCTCG | CCTACGGGAGGCATCAG | AGTCAGTCAGCC | GGATTAGATACCCTAGTAGTC |

TABLE 2-continued

| | forward primer binding site fragment | 5' universal sequence fragment | barcode sequence fragment | 3' universal sequence fragment | reverse primer binding site fragment |
|---|---|---|---|---|---|
| (SEQ ID NO: 23) | CCTACGGGAGGCATCAG | GCAGATCTCG | CCTACGGGAGGCATCAG | AGTCAGTCAGCC | GGATTAGATACCCTAGTAGTC |
| (SEQ ID NO: 24) | CCTACGGGAGGCATCAG | GCAGATCTCG | CCTACGGGAGGCATCAG | AGTCAGTCAGCC | GGATTAGATACCCTAGTAGTC |
| (SEQ ID NO: 25) | CCTACGGGAGGCATCAG | GCAGATCTCG | CCTACGGGAGGCATCAG | AGTCAGTCAGCC | GGATTAGATACCCTAGTAGTC |
| (SEQ ID NO: 26) | CCTACGGGAGGCATCAG | GCAGATCTCG | CCTACGGGAGGCATCAG | AGTCAGTCAGCC | GGATTAGATACCCTAGTAGTC |
| (SEQ ID NO: 27) | CCTACGGGAGGCATCAG | GCAGATCTCG | CCTACGGGAGGCATCAG | AGTCAGTCAGCC | GGATTAGATACCCTAGTAGTC |
| (SEQ ID NO: 28) | CCTACGGGAGGCATCAG | GCAGATCTCG | CCTACGGGAGGCATCAG | AGTCAGTCAGCC | GGATTAGATACCCTAGTAGTC |
| (SEQ ID NO: 29) | CCTACGGGAGGCATCAG | GCAGATCTCG | CCTACGGGAGGCATCAG | AGTCAGTCAGCC | GGATTAGATACCCTAGTAGTC |
| (SEQ ID NO: 30) | CCTACGGGAGGCATCAG | GCAGATCTCG | CCTACGGGAGGCATCAG | AGTCAGTCAGCC | GGATTAGATACCCTAGTAGTC |
| (SEQ ID NO: 31) | CCTACGGGAGGCATCAG | GCAGATCTCG | CCTACGGGAGGCATCAG | AGTCAGTCAGCC | GGATTAGATACCCTAGTAGTC |
| (SEQ ID NO: 32) | CCTACGGGAGGCATCAG | GCAGATCTCG | CCTACGGGAGGCATCAG | AGTCAGTCAGCC | GGATTAGATACCCTAGTAGTC |
| (SEQ ID NO: 33) | CCTACGGGAGGCATCAG | GCAGATCTCG | CCTACGGGAGGCATCAG | AGTCAGTCAGCC | GGATTAGATACCCTAGTAGTC |
| (SEQ ID NO: 34) | CCTACGGGAGGCATCAG | GCAGATCTCG | CCTACGGGAGGCATCAG | AGTCAGTCAGCC | GGATTAGATACCCTAGTAGTC |
| (SEQ ID NO: 35) | CCTACGGGAGGCATCAG | GCAGATCTCG | CCTACGGGAGGCATCAG | AGTCAGTCAGCC | GGATTAGATACCCTAGTAGTC |
| (SEQ ID NO: 36) | CCTACGGGAGGCATCAG | GCAGATCTCG | CCTACGGGAGGCATCAG | AGTCAGTCAGCC | GGATTAGATACCCTAGTAGTC |
| (SEQ ID NO: 37) | CCTACGGGAGGCATCAG | GCAGATCTCG | CCTACGGGAGGCATCAG | AGTCAGTCAGCC | GGATTAGATACCCTAGTAGTC |
| (SEQ ID NO: 38) | CCTACGGGAGGCATCAG | GCAGATCTCG | CCTACGGGAGGCATCAG | AGTCAGTCAGCC | GGATTAGATACCCTAGTAGTC |
| (SEQ ID NO: 39) | CCTACGGGAGGCATCAG | GCAGATCTCG | CCTACGGGAGGCATCAG | AGTCAGTCAGCC | GGATTAGATACCCTAGTAGTC |
| (SEQ ID NO: 40) | CCTACGGGAGGCATCAG | GCAGATCTCG | CCTACGGGAGGCATCAG | AGTCAGTCAGCC | GGATTAGATACCCTAGTAGTC |
| (SEQ ID NO: 41) | CCTACGGGAGGCATCAG | GCAGATCTCG | CCTACGGGAGGCATCAG | AGTCAGTCAGCC | GGATTAGATACCCTAGTAGTC |
| (SEQ ID NO: 42) | CCTACGGGAGGCATCAG | GCAGATCTCG | CCTACGGGAGGCATCAG | AGTCAGTCAGCC | GGATTAGATACCCTAGTAGTC |
| (SEQ ID NO: 43) | CCTACGGGAGGCATCAG | GCAGATCTCG | CCTACGGGAGGCATCAG | AGTCAGTCAGCC | GGATTAGATACCCTAGTAGTC |
| (SEQ ID NO: 44) | CCTACGGGAGGCATCAG | GCAGATCTCG | CCTACGGGAGGCATCAG | AGTCAGTCAGCC | GGATTAGATACCCTAGTAGTC |
| (SEQ ID NO: 45) | CCTACGGGAGGCATCAG | GCAGATCTCG | CCTACGGGAGGCATCAG | AGTCAGTCAGCC | GGATTAGATACCCTAGTAGTC |
| (SEQ ID NO: 46) | CCTACGGGAGGCATCAG | GCAGATCTCG | CCTACGGGAGGCATCAG | AGTCAGTCAGCC | GGATTAGATACCCTAGTAGTC |
| (SEQ ID NO: 47) | CCTACGGGAGGCATCAG | GCAGATCTCG | CCTACGGGAGGCATCAG | AGTCAGTCAGCC | GGATTAGATACCCTAGTAGTC |
| (SEQ ID NO: 48) | CCTACGGGAGGCATCAG | GCAGATCTCG | CCTACGGGAGGCATCAG | AGTCAGTCAGCC | GGATTAGATACCCTAGTAGTC |
| (SEQ ID NO: 49) | CCTACGGGAGGCATCAG | GCAGATCTCG | CCTACGGGAGGCATCAG | AGTCAGTCAGCC | GGATTAGATACCCTAGTAGTC |
| (SEQ ID NO: 50) | CCTACGGGAGGCATCAG | GCAGATCTCG | CCTACGGGAGGCATCAG | AGTCAGTCAGCC | GGATTAGATACCCTAGTAGTC |
| (SEQ ID NO: 51) | CCTACGGGAGGCATCAG | GCAGATCTCG | CCTACGGGAGGCATCAG | AGTCAGTCAGCC | GGATTAGATACCCTAGTAGTC |
| (SEQ ID NO: 52) | CCTACGGGAGGCATCAG | GCAGATCTCG | CCTACGGGAGGCATCAG | AGTCAGTCAGCC | GGATTAGATACCCTAGTAGTC |
| (SEQ ID NO: 53) | CCTACGGGAGGCATCAG | GCAGATCTCG | CCTACGGGAGGCATCAG | AGTCAGTCAGCC | GGATTAGATACCCTAGTAGTC |
| (SEQ ID NO: 54) | CCTACGGGAGGCATCAG | GCAGATCTCG | CCTACGGGAGGCATCAG | AGTCAGTCAGCC | GGATTAGATACCCTAGTAGTC |
| (SEQ ID NO: 55) | CCTACGGGAGGCATCAG | GCAGATCTCG | CCTACGGGAGGCATCAG | AGTCAGTCAGCC | GGATTAGATACCCTAGTAGTC |
| (SEQ ID NO: 56) | CCTACGGGAGGCATCAG | GCAGATCTCG | CCTACGGGAGGCATCAG | AGTCAGTCAGCC | GGATTAGATACCCTAGTAGTC |
| (SEQ ID NO: 57) | CCTACGGGAGGCATCAG | GCAGATCTCG | CCTACGGGAGGCATCAG | AGTCAGTCAGCC | GGATTAGATACCCTAGTAGTC |
| (SEQ ID NO: 58) | CCTACGGGAGGCATCAG | GCAGATCTCG | CCTACGGGAGGCATCAG | AGTCAGTCAGCC | GGATTAGATACCCTAGTAGTC |
| (SEQ ID NO: 59) | CCTACGGGAGGCATCAG | GCAGATCTCG | CCTACGGGAGGCATCAG | AGTCAGTCAGCC | GGATTAGATACCCTAGTAGTC |

TABLE 2-continued

| | forward primer binding site fragment | 5' universal sequence fragment | barcode sequence fragment | 3' universal sequence fragment | reverse primer binding site fragment |
|---|---|---|---|---|---|
| (SEQ ID NO: 60) | CCTACGGGAGGCATCAG | GCAGATCTCG | CCTACGGGAGGCATCAG | AGTCAGTCAGCC | GGATTAGATACCCTAGTAGTC |
| (SEQ ID NO: 61) | CCTACGGGAGGCATCAG | GCAGATCTCG | CCTACGGGAGGCATCAG | AGTCAGTCAGCC | GGATTAGATACCCTAGTAGTC |
| (SEQ ID NO: 62) | CCTACGGGAGGCATCAG | GCAGATCTCG | CCTACGGGAGGCATCAG | AGTCAGTCAGCC | GGATTAGATACCCTAGTAGTC |
| (SEQ ID NO: 63) | CCTACGGGAGGCATCAG | GCAGATCTCG | CCTACGGGAGGCATCAG | AGTCAGTCAGCC | GGATTAGATACCCTAGTAGTC |
| (SEQ ID NO: 64) | CCTACGGGAGGCATCAG | GCAGATCTCG | CCTACGGGAGGCATCAG | AGTCAGTCAGCC | GGATTAGATACCCTAGTAGTC |
| (SEQ ID NO: 65) | CCTACGGGAGGCATCAG | GCAGATCTCG | CCTACGGGAGGCATCAG | AGTCAGTCAGCC | GGATTAGATACCCTAGTAGTC |
| (SEQ ID NO: 66) | CCTACGGGAGGCATCAG | GCAGATCTCG | CCTACGGGAGGCATCAG | AGTCAGTCAGCC | GGATTAGATACCCTAGTAGTC |
| (SEQ ID NO: 67) | CCTACGGGAGGCATCAG | GCAGATCTCG | CCTACGGGAGGCATCAG | AGTCAGTCAGCC | GGATTAGATACCCTAGTAGTC |
| (SEQ ID NO: 68) | CCTACGGGAGGCATCAG | GCAGATCTCG | CCTACGGGAGGCATCAG | AGTCAGTCAGCC | GGATTAGATACCCTAGTAGTC |
| (SEQ ID NO: 69) | CCTACGGGAGGCATCAG | GCAGATCTCG | CCTACGGGAGGCATCAG | AGTCAGTCAGCC | GGATTAGATACCCTAGTAGTC |
| (SEQ ID NO: 70) | CCTACGGGAGGCATCAG | GCAGATCTCG | CCTACGGGAGGCATCAG | AGTCAGTCAGCC | GGATTAGATACCCTAGTAGTC |
| (SEQ ID NO: 71) | CCTACGGGAGGCATCAG | GCAGATCTCG | CCTACGGGAGGCATCAG | AGTCAGTCAGCC | GGATTAGATACCCTAGTAGTC |
| (SEQ ID NO: 72) | CCTACGGGAGGCATCAG | GCAGATCTCG | CCTACGGGAGGCATCAG | AGTCAGTCAGCC | GGATTAGATACCCTAGTAGTC |
| (SEQ ID NO: 73) | CCTACGGGAGGCATCAG | GCAGATCTCG | CCTACGGGAGGCATCAG | AGTCAGTCAGCC | GGATTAGATACCCTAGTAGTC |
| (SEQ ID NO: 74) | CCTACGGGAGGCATCAG | GCAGATCTCG | CCTACGGGAGGCATCAG | AGTCAGTCAGCC | GGATTAGATACCCTAGTAGTC |
| (SEQ ID NO: 75) | CCTACGGGAGGCATCAG | GCAGATCTCG | CCTACGGGAGGCATCAG | AGTCAGTCAGCC | GGATTAGATACCCTAGTAGTC |
| (SEQ ID NO: 76) | CCTACGGGAGGCATCAG | GCAGATCTCG | CCTACGGGAGGCATCAG | AGTCAGTCAGCC | GGATTAGATACCCTAGTAGTC |
| (SEQ ID NO: 77) | CCTACGGGAGGCATCAG | GCAGATCTCG | CCTACGGGAGGCATCAG | AGTCAGTCAGCC | GGATTAGATACCCTAGTAGTC |
| (SEQ ID NO: 78) | CCTACGGGAGGCATCAG | GCAGATCTCG | CCTACGGGAGGCATCAG | AGTCAGTCAGCC | GGATTAGATACCCTAGTAGTC |
| (SEQ ID NO: 79) | CCTACGGGAGGCATCAG | GCAGATCTCG | CCTACGGGAGGCATCAG | AGTCAGTCAGCC | GGATTAGATACCCTAGTAGTC |
| (SEQ ID NO: 80) | CCTACGGGAGGCATCAG | GCAGATCTCG | CCTACGGGAGGCATCAG | AGTCAGTCAGCC | GGATTAGATACCCTAGTAGTC |
| (SEQ ID NO: 81) | CCTACGGGAGGCATCAG | GCAGATCTCG | CCTACGGGAGGCATCAG | AGTCAGTCAGCC | GGATTAGATACCCTAGTAGTC |
| (SEQ ID NO: 82) | CCTACGGGAGGCATCAG | GCAGATCTCG | CCTACGGGAGGCATCAG | AGTCAGTCAGCC | GGATTAGATACCCTAGTAGTC |
| (SEQ ID NO: 83) | CCTACGGGAGGCATCAG | GCAGATCTCG | CCTACGGGAGGCATCAG | AGTCAGTCAGCC | GGATTAGATACCCTAGTAGTC |
| (SEQ ID NO: 84) | CCTACGGGAGGCATCAG | GCAGATCTCG | CCTACGGGAGGCATCAG | AGTCAGTCAGCC | GGATTAGATACCCTAGTAGTC |
| (SEQ ID NO: 85) | CCTACGGGAGGCATCAG | GCAGATCTCG | CCTACGGGAGGCATCAG | AGTCAGTCAGCC | GGATTAGATACCCTAGTAGTC |
| (SEQ ID NO: 86) | CCTACGGGAGGCATCAG | GCAGATCTCG | CCTACGGGAGGCATCAG | AGTCAGTCAGCC | GGATTAGATACCCTAGTAGTC |
| (SEQ ID NO: 87) | CCTACGGGAGGCATCAG | GCAGATCTCG | CCTACGGGAGGCATCAG | AGTCAGTCAGCC | GGATTAGATACCCTAGTAGTC |
| (SEQ ID NO: 88) | CCTACGGGAGGCATCAG | GCAGATCTCG | CCTACGGGAGGCATCAG | AGTCAGTCAGCC | GGATTAGATACCCTAGTAGTC |
| (SEQ ID NO: 89) | CCTACGGGAGGCATCAG | GCAGATCTCG | CCTACGGGAGGCATCAG | AGTCAGTCAGCC | GGATTAGATACCCTAGTAGTC |
| (SEQ ID NO: 90) | CCTACGGGAGGCATCAG | GCAGATCTCG | CCTACGGGAGGCATCAG | AGTCAGTCAGCC | GGATTAGATACCCTAGTAGTC |
| (SEQ ID NO: 91) | CCTACGGGAGGCATCAG | GCAGATCTCG | CCTACGGGAGGCATCAG | AGTCAGTCAGCC | GGATTAGATACCCTAGTAGTC |
| (SEQ ID NO: 92) | CCTACGGGAGGCATCAG | GCAGATCTCG | CCTACGGGAGGCATCAG | AGTCAGTCAGCC | GGATTAGATACCCTAGTAGTC |
| (SEQ ID NO: 93) | CCTACGGGAGGCATCAG | GCAGATCTCG | CCTACGGGAGGCATCAG | AGTCAGTCAGCC | GGATTAGATACCCTAGTAGTC |
| (SEQ ID NO: 94) | CCTACGGGAGGCATCAG | GCAGATCTCG | CCTACGGGAGGCATCAG | AGTCAGTCAGCC | GGATTAGATACCCTAGTAGTC |
| (SEQ ID NO: 95) | CCTACGGGAGGCATCAG | GCAGATCTCG | CCTACGGGAGGCATCAG | AGTCAGTCAGCC | GGATTAGATACCCTAGTAGTC |
| (SEQ ID NO: 96) | CCTACGGGAGGCATCAG | GCAGATCTCG | CCTACGGGAGGCATCAG | AGTCAGTCAGCC | GGATTAGATACCCTAGTAGTC |
| (SEQ ID NO: 97) | CCTACGGGAGGCATCAG | GCAGATCTCG | CCTACGGGAGGCATCAG | AGTCAGTCAGCC | GGATTAGATACCCTAGTAGTC |

TABLE 2-continued

| | forward primer binding site fragment | 5' universal sequence fragment | barcode sequence fragment | 3' universal sequence fragment | reverse primer binding site fragment |
|---|---|---|---|---|---|
| (SEQ ID NO: 98) | CCTACGGGAGGCATCAG | GCAGATCTCG | CCTACGGGAGGCATCAG | AGTCAGTCAGCC | GGATTAGATACCCTAGTAGTC |
| (SEQ ID NO: 99) | CCTACGGGAGGCATCAG | GCAGATCTCG | CCTACGGGAGGCATCAG | AGTCAGTCAGCC | GGATTAGATACCCTAGTAGTC |
| (SEQ ID NO: 100) | CCTACGGGAGGCATCAG | GCAGATCTCG | CCTACGGGAGGCATCAG | AGTCAGTCAGCC | GGATTAGATACCCTAGTAGTC |
| (SEQ ID NO: 101) | CCTACGGGAGGCATCAG | GCAGATCTCG | CCTACGGGAGGCATCAG | AGTCAGTCAGCC | GGATTAGATACCCTAGTAGTC |
| (SEQ ID NO: 102) | CCTACGGGAGGCATCAG | GCAGATCTCG | CCTACGGGAGGCATCAG | AGTCAGTCAGCC | GGATTAGATACCCTAGTAGTC |
| (SEQ ID NO: 103) | CCTACGGGAGGCATCAG | GCAGATCTCG | CCTACGGGAGGCATCAG | AGTCAGTCAGCC | GGATTAGATACCCTAGTAGTC |
| (SEQ ID NO: 104) | CCTACGGGAGGCATCAG | GCAGATCTCG | CCTACGGGAGGCATCAG | AGTCAGTCAGCC | GGATTAGATACCCTAGTAGTC |
| (SEQ ID NO: 105) | CCTACGGGAGGCATCAG | GCAGATCTCG | CCTACGGGAGGCATCAG | AGTCAGTCAGCC | GGATTAGATACCCTAGTAGTC |
| (SEQ ID NO: 106) | CCTACGGGAGGCATCAG | GCAGATCTCG | CCTACGGGAGGCATCAG | AGTCAGTCAGCC | GGATTAGATACCCTAGTAGTC |
| (SEQ ID NO: 107) | CCTACGGGAGGCATCAG | GCAGATCTCG | CCTACGGGAGGCATCAG | AGTCAGTCAGCC | GGATTAGATACCCTAGTAGTC |
| (SEQ ID NO: 108) | CCTACGGGAGGCATCAG | GCAGATCTCG | CCTACGGGAGGCATCAG | AGTCAGTCAGCC | GGATTAGATACCCTAGTAGTC |
| (SEQ ID NO: 109) | CCTACGGGAGGCATCAG | GCAGATCTCG | CCTACGGGAGGCATCAG | AGTCAGTCAGCC | GGATTAGATACCCTAGTAGTC |
| (SEQ ID NO: 110) | CCTACGGGAGGCATCAG | GCAGATCTCG | CCTACGGGAGGCATCAG | AGTCAGTCAGCC | GGATTAGATACCCTAGTAGTC |
| (SEQ ID NO: 111) | CCTACGGGAGGCATCAG | GCAGATCTCG | CCTACGGGAGGCATCAG | AGTCAGTCAGCC | GGATTAGATACCCTAGTAGTC |
| (SEQ ID NO: 112) | CCTACGGGAGGCATCAG | GCAGATCTCG | CCTACGGGAGGCATCAG | AGTCAGTCAGCC | GGATTAGATACCCTAGTAGTC |
| (SEQ ID NO: 113) | CCTACGGGAGGCATCAG | GCAGATCTCG | CCTACGGGAGGCATCAG | AGTCAGTCAGCC | GGATTAGATACCCTAGTAGTC |
| (SEQ ID NO: 114) | CCTACGGGAGGCATCAG | GCAGATCTCG | CCTACGGGAGGCATCAG | AGTCAGTCAGCC | GGATTAGATACCCTAGTAGTC |
| (SEQ ID NO: 115) | CCTACGGGAGGCATCAG | GCAGATCTCG | CCTACGGGAGGCATCAG | AGTCAGTCAGCC | GGATTAGATACCCTAGTAGTC |
| (SEQ ID NO: 116) | CCTACGGGAGGCATCAG | GCAGATCTCG | CCTACGGGAGGCATCAG | AGTCAGTCAGCC | GGATTAGATACCCTAGTAGTC |
| (SEQ ID NO: 117) | CCTACGGGAGGCATCAG | GCAGATCTCG | CCTACGGGAGGCATCAG | AGTCAGTCAGCC | GGATTAGATACCCTAGTAGTC |
| (SEQ ID NO: 118) | CCTACGGGAGGCATCAG | GCAGATCTCG | CCTACGGGAGGCATCAG | AGTCAGTCAGCC | GGATTAGATACCCTAGTAGTC |
| (SEQ ID NO: 119) | CCTACGGGAGGCATCAG | GCAGATCTCG | CCTACGGGAGGCATCAG | AGTCAGTCAGCC | GGATTAGATACCCTAGTAGTC |
| (SEQ ID NO: 120) | CCTACGGGAGGCATCAG | GCAGATCTCG | CCTACGGGAGGCATCAG | AGTCAGTCAGCC | GGATTAGATACCCTAGTAGTC |
| (SEQ ID NO: 121) | CCTACGGGAGGCATCAG | GCAGATCTCG | CCTACGGGAGGCATCAG | AGTCAGTCAGCC | GGATTAGATACCCTAGTAGTC |
| (SEQ ID NO: 122) | CCTACGGGAGGCATCAG | GCAGATCTCG | CCTACGGGAGGCATCAG | AGTCAGTCAGCC | GGATTAGATACCCTAGTAGTC |
| (SEQ ID NO: 123) | CCTACGGGAGGCATCAG | GCAGATCTCG | CCTACGGGAGGCATCAG | AGTCAGTCAGCC | GGATTAGATACCCTAGTAGTC |
| (SEQ ID NO: 124) | CCTACGGGAGGCATCAG | GCAGATCTCG | CCTACGGGAGGCATCAG | AGTCAGTCAGCC | GGATTAGATACCCTAGTAGTC |
| (SEQ ID NO: 125) | CCTACGGGAGGCATCAG | GCAGATCTCG | CCTACGGGAGGCATCAG | AGTCAGTCAGCC | GGATTAGATACCCTAGTAGTC |
| (SEQ ID NO: 126) | CCTACGGGAGGCATCAG | GCAGATCTCG | CCTACGGGAGGCATCAG | AGTCAGTCAGCC | GGATTAGATACCCTAGTAGTC |
| (SEQ ID NO: 127) | CCTACGGGAGGCATCAG | GCAGATCTCG | CCTACGGGAGGCATCAG | AGTCAGTCAGCC | GGATTAGATACCCTAGTAGTC |
| (SEQ ID NO: 128) | CCTACGGGAGGCATCAG | GCAGATCTCG | CCTACGGGAGGCATCAG | AGTCAGTCAGCC | GGATTAGATACCCTAGTAGTC |
| (SEQ ID NO: 129) | CCTACGGGAGGCATCAG | GCAGATCTCG | CCTACGGGAGGCATCAG | AGTCAGTCAGCC | GGATTAGATACCCTAGTAGTC |
| (SEQ ID NO: 130) | CCTACGGGAGGCATCAG | GCAGATCTCG | CCTACGGGAGGCATCAG | AGTCAGTCAGCC | GGATTAGATACCCTAGTAGTC |
| (SEQ ID NO: 131) | CCTACGGGAGGCATCAG | GCAGATCTCG | CCTACGGGAGGCATCAG | AGTCAGTCAGCC | GGATTAGATACCCTAGTAGTC |
| (SEQ ID NO: 132) | CCTACGGGAGGCATCAG | GCAGATCTCG | CCTACGGGAGGCATCAG | AGTCAGTCAGCC | GGATTAGATACCCTAGTAGTC |
| (SEQ ID NO: 133) | CCTACGGGAGGCATCAG | GCAGATCTCG | CCTACGGGAGGCATCAG | AGTCAGTCAGCC | GGATTAGATACCCTAGTAGTC |
| (SEQ ID NO: 134) | CCTACGGGAGGCATCAG | GCAGATCTCG | CCTACGGGAGGCATCAG | AGTCAGTCAGCC | GGATTAGATACCCTAGTAGTC |

TABLE 2-continued

| | forward primer binding site fragment | 5' universal sequence fragment | barcode sequence fragment | 3' universal sequence fragment | reverse primer binding site fragment |
|---|---|---|---|---|---|
| (SEQ ID NO: 135) | CCTACGGGAGGCATCAG | GCAGATCTCG | CCTACGGGAGGCATCAG | AGTCAGTCAGCC | GGATTAGATACCCTAGTAGTC |
| (SEQ ID NO: 136) | CCTACGGGAGGCATCAG | GCAGATCTCG | CCTACGGGAGGCATCAG | AGTCAGTCAGCC | GGATTAGATACCCTAGTAGTC |
| (SEQ ID NO: 137) | CCTACGGGAGGCATCAG | GCAGATCTCG | CCTACGGGAGGCATCAG | AGTCAGTCAGCC | GGATTAGATACCCTAGTAGTC |
| (SEQ ID NO: 138) | CCTACGGGAGGCATCAG | GCAGATCTCG | CCTACGGGAGGCATCAG | AGTCAGTCAGCC | GGATTAGATACCCTAGTAGTC |
| (SEQ ID NO: 139) | CCTACGGGAGGCATCAG | GCAGATCTCG | CCTACGGGAGGCATCAG | AGTCAGTCAGCC | GGATTAGATACCCTAGTAGTC |
| (SEQ ID NO: 140) | CCTACGGGAGGCATCAG | GCAGATCTCG | CCTACGGGAGGCATCAG | AGTCAGTCAGCC | GGATTAGATACCCTAGTAGTC |
| (SEQ ID NO: 141) | CCTACGGGAGGCATCAG | GCAGATCTCG | CCTACGGGAGGCATCAG | AGTCAGTCAGCC | GGATTAGATACCCTAGTAGTC |
| (SEQ ID NO: 142) | CCTACGGGAGGCATCAG | GCAGATCTCG | CCTACGGGAGGCATCAG | AGTCAGTCAGCC | GGATTAGATACCCTAGTAGTC |
| (SEQ ID NO: 143) | CCTACGGGAGGCATCAG | GCAGATCTCG | CCTACGGGAGGCATCAG | AGTCAGTCAGCC | GGATTAGATACCCTAGTAGTC |
| (SEQ ID NO: 144) | CCTACGGGAGGCATCAG | GCAGATCTCG | CCTACGGGAGGCATCAG | AGTCAGTCAGCC | GGATTAGATACCCTAGTAGTC |
| (SEQ ID NO: 145) | CCTACGGGAGGCATCAG | GCAGATCTCG | CCTACGGGAGGCATCAG | AGTCAGTCAGCC | GGATTAGATACCCTAGTAGTC |
| (SEQ ID NO: 146) | CCTACGGGAGGCATCAG | GCAGATCTCG | CCTACGGGAGGCATCAG | AGTCAGTCAGCC | GGATTAGATACCCTAGTAGTC |
| (SEQ ID NO: 147) | CCTACGGGAGGCATCAG | GCAGATCTCG | CCTACGGGAGGCATCAG | AGTCAGTCAGCC | GGATTAGATACCCTAGTAGTC |
| (SEQ ID NO: 148) | CCTACGGGAGGCATCAG | GCAGATCTCG | CCTACGGGAGGCATCAG | AGTCAGTCAGCC | GGATTAGATACCCTAGTAGTC |
| (SEQ ID NO: 149) | CCTACGGGAGGCATCAG | GCAGATCTCG | CCTACGGGAGGCATCAG | AGTCAGTCAGCC | GGATTAGATACCCTAGTAGTC |
| (SEQ ID NO: 150) | CCTACGGGAGGCATCAG | GCAGATCTCG | CCTACGGGAGGCATCAG | AGTCAGTCAGCC | GGATTAGATACCCTAGTAGTC |
| (SEQ ID NO: 151) | CCTACGGGAGGCATCAG | GCAGATCTCG | CCTACGGGAGGCATCAG | AGTCAGTCAGCC | GGATTAGATACCCTAGTAGTC |
| (SEQ ID NO: 152) | CCTACGGGAGGCATCAG | GCAGATCTCG | CCTACGGGAGGCATCAG | AGTCAGTCAGCC | GGATTAGATACCCTAGTAGTC |
| (SEQ ID NO: 153) | CCTACGGGAGGCATCAG | GCAGATCTCG | CCTACGGGAGGCATCAG | AGTCAGTCAGCC | GGATTAGATACCCTAGTAGTC |
| (SEQ ID NO: 154) | CCTACGGGAGGCATCAG | GCAGATCTCG | CCTACGGGAGGCATCAG | AGTCAGTCAGCC | GGATTAGATACCCTAGTAGTC |
| (SEQ ID NO: 155) | CCTACGGGAGGCATCAG | GCAGATCTCG | CCTACGGGAGGCATCAG | AGTCAGTCAGCC | GGATTAGATACCCTAGTAGTC |
| (SEQ ID NO: 156) | CCTACGGGAGGCATCAG | GCAGATCTCG | CCTACGGGAGGCATCAG | AGTCAGTCAGCC | GGATTAGATACCCTAGTAGTC |
| (SEQ ID NO: 157) | CCTACGGGAGGCATCAG | GCAGATCTCG | CCTACGGGAGGCATCAG | AGTCAGTCAGCC | GGATTAGATACCCTAGTAGTC |
| (SEQ ID NO: 158) | CCTACGGGAGGCATCAG | GCAGATCTCG | CCTACGGGAGGCATCAG | AGTCAGTCAGCC | GGATTAGATACCCTAGTAGTC |
| (SEQ ID NO: 159) | CCTACGGGAGGCATCAG | GCAGATCTCG | CCTACGGGAGGCATCAG | AGTCAGTCAGCC | GGATTAGATACCCTAGTAGTC |
| (SEQ ID NO: 160) | CCTACGGGAGGCATCAG | GCAGATCTCG | CCTACGGGAGGCATCAG | AGTCAGTCAGCC | GGATTAGATACCCTAGTAGTC |
| (SEQ ID NO: 161) | CCTACGGGAGGCATCAG | GCAGATCTCG | CCTACGGGAGGCATCAG | AGTCAGTCAGCC | GGATTAGATACCCTAGTAGTC |
| (SEQ ID NO: 162) | CCTACGGGAGGCATCAG | GCAGATCTCG | CCTACGGGAGGCATCAG | AGTCAGTCAGCC | GGATTAGATACCCTAGTAGTC |
| (SEQ ID NO: 163) | CCTACGGGAGGCATCAG | GCAGATCTCG | CCTACGGGAGGCATCAG | AGTCAGTCAGCC | GGATTAGATACCCTAGTAGTC |
| (SEQ ID NO: 164) | CCTACGGGAGGCATCAG | GCAGATCTCG | CCTACGGGAGGCATCAG | AGTCAGTCAGCC | GGATTAGATACCCTAGTAGTC |
| (SEQ ID NO: 165) | CCTACGGGAGGCATCAG | GCAGATCTCG | CCTACGGGAGGCATCAG | AGTCAGTCAGCC | GGATTAGATACCCTAGTAGTC |
| (SEQ ID NO: 166) | CCTACGGGAGGCATCAG | GCAGATCTCG | CCTACGGGAGGCATCAG | AGTCAGTCAGCC | GGATTAGATACCCTAGTAGTC |
| (SEQ ID NO: 167) | CCTACGGGAGGCATCAG | GCAGATCTCG | CCTACGGGAGGCATCAG | AGTCAGTCAGCC | GGATTAGATACCCTAGTAGTC |
| (SEQ ID NO: 168) | CCTACGGGAGGCATCAG | GCAGATCTCG | CCTACGGGAGGCATCAG | AGTCAGTCAGCC | GGATTAGATACCCTAGTAGTC |
| (SEQ ID NO: 169) | CCTACGGGAGGCATCAG | GCAGATCTCG | CCTACGGGAGGCATCAG | AGTCAGTCAGCC | GGATTAGATACCCTAGTAGTC |
| (SEQ ID NO: 170) | CCTACGGGAGGCATCAG | GCAGATCTCG | CCTACGGGAGGCATCAG | AGTCAGTCAGCC | GGATTAGATACCCTAGTAGTC |
| (SEQ ID NO: 171) | CCTACGGGAGGCATCAG | GCAGATCTCG | CCTACGGGAGGCATCAG | AGTCAGTCAGCC | GGATTAGATACCCTAGTAGTC |
| (SEQ ID NO: 172) | CCTACGGGAGGCATCAG | GCAGATCTCG | CCTACGGGAGGCATCAG | AGTCAGTCAGCC | GGATTAGATACCCTAGTAGTC |

TABLE 2-continued

| | forward primer binding site fragment | 5' universal sequence fragment | barcode sequence fragment | 3' universal sequence fragment | reverse primer binding site fragment |
|---|---|---|---|---|---|
| (SEQ ID NO: 173) | CCTACGGGAGGCATCAG | GCAGATCTCG | CCTACGGGAGGCATCAG | AGTCAGTCAGCC | GGATTAGATACCCTAGTAGTC |
| (SEQ ID NO: 174) | CCTACGGGAGGCATCAG | GCAGATCTCG | CCTACGGGAGGCATCAG | AGTCAGTCAGCC | GGATTAGATACCCTAGTAGTC |
| (SEQ ID NO: 175) | CCTACGGGAGGCATCAG | GCAGATCTCG | CCTACGGGAGGCATCAG | AGTCAGTCAGCC | GGATTAGATACCCTAGTAGTC |
| (SEQ ID NO: 176) | CCTACGGGAGGCATCAG | GCAGATCTCG | CCTACGGGAGGCATCAG | AGTCAGTCAGCC | GGATTAGATACCCTAGTAGTC |
| (SEQ ID NO: 177) | CCTACGGGAGGCATCAG | GCAGATCTCG | CCTACGGGAGGCATCAG | AGTCAGTCAGCC | GGATTAGATACCCTAGTAGTC |
| (SEQ ID NO: 178) | CCTACGGGAGGCATCAG | GCAGATCTCG | CCTACGGGAGGCATCAG | AGTCAGTCAGCC | GGATTAGATACCCTAGTAGTC |
| (SEQ ID NO: 179) | CCTACGGGAGGCATCAG | GCAGATCTCG | CCTACGGGAGGCATCAG | AGTCAGTCAGCC | GGATTAGATACCCTAGTAGTC |
| (SEQ ID NO: 180) | CCTACGGGAGGCATCAG | GCAGATCTCG | CCTACGGGAGGCATCAG | AGTCAGTCAGCC | GGATTAGATACCCTAGTAGTC |
| (SEQ ID NO: 181) | CCTACGGGAGGCATCAG | GCAGATCTCG | CCTACGGGAGGCATCAG | AGTCAGTCAGCC | GGATTAGATACCCTAGTAGTC |
| (SEQ ID NO: 182) | CCTACGGGAGGCATCAG | GCAGATCTCG | CCTACGGGAGGCATCAG | AGTCAGTCAGCC | GGATTAGATACCCTAGTAGTC |
| (SEQ ID NO: 183) | CCTACGGGAGGCATCAG | GCAGATCTCG | CCTACGGGAGGCATCAG | AGTCAGTCAGCC | GGATTAGATACCCTAGTAGTC |
| (SEQ ID NO: 184) | CCTACGGGAGGCATCAG | GCAGATCTCG | CCTACGGGAGGCATCAG | AGTCAGTCAGCC | GGATTAGATACCCTAGTAGTC |
| (SEQ ID NO: 185) | CCTACGGGAGGCATCAG | GCAGATCTCG | CCTACGGGAGGCATCAG | AGTCAGTCAGCC | GGATTAGATACCCTAGTAGTC |
| (SEQ ID NO: 186) | CCTACGGGAGGCATCAG | GCAGATCTCG | CCTACGGGAGGCATCAG | AGTCAGTCAGCC | GGATTAGATACCCTAGTAGTC |
| (SEQ ID NO: 187) | CCTACGGGAGGCATCAG | GCAGATCTCG | CCTACGGGAGGCATCAG | AGTCAGTCAGCC | GGATTAGATACCCTAGTAGTC |
| (SEQ ID NO: 188) | CCTACGGGAGGCATCAG | GCAGATCTCG | CCTACGGGAGGCATCAG | AGTCAGTCAGCC | GGATTAGATACCCTAGTAGTC |
| (SEQ ID NO: 189) | CCTACGGGAGGCATCAG | GCAGATCTCG | CCTACGGGAGGCATCAG | AGTCAGTCAGCC | GGATTAGATACCCTAGTAGTC |
| (SEQ ID NO: 190) | CCTACGGGAGGCATCAG | GCAGATCTCG | CCTACGGGAGGCATCAG | AGTCAGTCAGCC | GGATTAGATACCCTAGTAGTC |
| (SEQ ID NO: 191) | CCTACGGGAGGCATCAG | GCAGATCTCG | CCTACGGGAGGCATCAG | AGTCAGTCAGCC | GGATTAGATACCCTAGTAGTC |
| (SEQ ID NO: 192) | CCTACGGGAGGCATCAG | GCAGATCTCG | CCTACGGGAGGCATCAG | AGTCAGTCAGCC | GGATTAGATACCCTAGTAGTC |
| (SEQ ID NO: 193) | CCTACGGGAGGCATCAG | GCAGATCTCG | CCTACGGGAGGCATCAG | AGTCAGTCAGCC | GGATTAGATACCCTAGTAGTC |
| (SEQ ID NO: 194) | CCTACGGGAGGCATCAG | GCAGATCTCG | CCTACGGGAGGCATCAG | AGTCAGTCAGCC | GGATTAGATACCCTAGTAGTC |
| (SEQ ID NO: 195) | CCTACGGGAGGCATCAG | GCAGATCTCG | CCTACGGGAGGCATCAG | AGTCAGTCAGCC | GGATTAGATACCCTAGTAGTC |
| (SEQ ID NO: 196) | CCTACGGGAGGCATCAG | GCAGATCTCG | CCTACGGGAGGCATCAG | AGTCAGTCAGCC | GGATTAGATACCCTAGTAGTC |
| (SEQ ID NO: 197) | CCTACGGGAGGCATCAG | GCAGATCTCG | CCTACGGGAGGCATCAG | AGTCAGTCAGCC | GGATTAGATACCCTAGTAGTC |
| (SEQ ID NO: 198) | CCTACGGGAGGCATCAG | GCAGATCTCG | CCTACGGGAGGCATCAG | AGTCAGTCAGCC | GGATTAGATACCCTAGTAGTC |
| (SEQ ID NO: 199) | CCTACGGGAGGCATCAG | GCAGATCTCG | CCTACGGGAGGCATCAG | AGTCAGTCAGCC | GGATTAGATACCCTAGTAGTC |
| (SEQ ID NO: 200) | CCTACGGGAGGCATCAG | GCAGATCTCG | CCTACGGGAGGCATCAG | AGTCAGTCAGCC | GGATTAGATACCCTAGTAGTC |
| (SEQ ID NO: 201) | CCTACGGGAGGCATCAG | GCAGATCTCG | CCTACGGGAGGCATCAG | AGTCAGTCAGCC | GGATTAGATACCCTAGTAGTC |
| (SEQ ID NO: 202) | CCTACGGGAGGCATCAG | GCAGATCTCG | CCTACGGGAGGCATCAG | AGTCAGTCAGCC | GGATTAGATACCCTAGTAGTC |
| (SEQ ID NO: 203) | CCTACGGGAGGCATCAG | GCAGATCTCG | CCTACGGGAGGCATCAG | AGTCAGTCAGCC | GGATTAGATACCCTAGTAGTC |
| (SEQ ID NO: 204) | CCTACGGGAGGCATCAG | GCAGATCTCG | CCTACGGGAGGCATCAG | AGTCAGTCAGCC | GGATTAGATACCCTAGTAGTC |
| (SEQ ID NO: 205) | CCTACGGGAGGCATCAG | GCAGATCTCG | CCTACGGGAGGCATCAG | AGTCAGTCAGCC | GGATTAGATACCCTAGTAGTC |
| (SEQ ID NO: 206) | CCTACGGGAGGCATCAG | GCAGATCTCG | CCTACGGGAGGCATCAG | AGTCAGTCAGCC | GGATTAGATACCCTAGTAGTC |
| (SEQ ID NO: 207) | CCTACGGGAGGCATCAG | GCAGATCTCG | CCTACGGGAGGCATCAG | AGTCAGTCAGCC | GGATTAGATACCCTAGTAGTC |
| (SEQ ID NO: 208) | CCTACGGGAGGCATCAG | GCAGATCTCG | CCTACGGGAGGCATCAG | AGTCAGTCAGCC | GGATTAGATACCCTAGTAGTC |
| (SEQ ID NO: 209) | CCTACGGGAGGCATCAG | GCAGATCTCG | CCTACGGGAGGCATCAG | AGTCAGTCAGCC | GGATTAGATACCCTAGTAGTC |

TABLE 2-continued

| | forward primer binding site fragment | 5' universal sequence fragment | barcode sequence fragment | 3' universal sequence fragment | reverse primer binding site fragment |
|---|---|---|---|---|---|
| (SEQ ID NO: 210) | CCTACGGGAGGCATCAG | GCAGATCTCG | CCTACGGGAGGCATCAG | AGTCAGTCAGCC | GGATTAGATACCCTAGTAGTC |
| (SEQ ID NO: 211) | CCTACGGGAGGCATCAG | GCAGATCTCG | CCTACGGGAGGCATCAG | AGTCAGTCAGCC | GGATTAGATACCCTAGTAGTC |
| (SEQ ID NO: 212) | CCTACGGGAGGCATCAG | GCAGATCTCG | CCTACGGGAGGCATCAG | AGTCAGTCAGCC | GGATTAGATACCCTAGTAGTC |
| (SEQ ID NO: 213) | CCTACGGGAGGCATCAG | GCAGATCTCG | CCTACGGGAGGCATCAG | AGTCAGTCAGCC | GGATTAGATACCCTAGTAGTC |
| (SEQ ID NO: 214) | CCTACGGGAGGCATCAG | GCAGATCTCG | CCTACGGGAGGCATCAG | AGTCAGTCAGCC | GGATTAGATACCCTAGTAGTC |
| (SEQ ID NO: 215) | CCTACGGGAGGCATCAG | GCAGATCTCG | CCTACGGGAGGCATCAG | AGTCAGTCAGCC | GGATTAGATACCCTAGTAGTC |
| (SEQ ID NO: 216) | CCTACGGGAGGCATCAG | GCAGATCTCG | CCTACGGGAGGCATCAG | AGTCAGTCAGCC | GGATTAGATACCCTAGTAGTC |
| (SEQ ID NO: 217) | CCTACGGGAGGCATCAG | GCAGATCTCG | CCTACGGGAGGCATCAG | AGTCAGTCAGCC | GGATTAGATACCCTAGTAGTC |
| (SEQ ID NO: 218) | CCTACGGGAGGCATCAG | GCAGATCTCG | CCTACGGGAGGCATCAG | AGTCAGTCAGCC | GGATTAGATACCCTAGTAGTC |
| (SEQ ID NO: 219) | CCTACGGGAGGCATCAG | GCAGATCTCG | CCTACGGGAGGCATCAG | AGTCAGTCAGCC | GGATTAGATACCCTAGTAGTC |
| (SEQ ID NO: 220) | CCTACGGGAGGCATCAG | GCAGATCTCG | CCTACGGGAGGCATCAG | AGTCAGTCAGCC | GGATTAGATACCCTAGTAGTC |
| (SEQ ID NO: 221) | CCTACGGGAGGCATCAG | GCAGATCTCG | CCTACGGGAGGCATCAG | AGTCAGTCAGCC | GGATTAGATACCCTAGTAGTC |
| (SEQ ID NO: 222) | CCTACGGGAGGCATCAG | GCAGATCTCG | CCTACGGGAGGCATCAG | AGTCAGTCAGCC | GGATTAGATACCCTAGTAGTC |
| (SEQ ID NO: 223) | CCTACGGGAGGCATCAG | GCAGATCTCG | CCTACGGGAGGCATCAG | AGTCAGTCAGCC | GGATTAGATACCCTAGTAGTC |
| (SEQ ID NO: 224) | CCTACGGGAGGCATCAG | GCAGATCTCG | CCTACGGGAGGCATCAG | AGTCAGTCAGCC | GGATTAGATACCCTAGTAGTC |
| (SEQ ID NO: 225) | CCTACGGGAGGCATCAG | GCAGATCTCG | CCTACGGGAGGCATCAG | AGTCAGTCAGCC | GGATTAGATACCCTAGTAGTC |
| (SEQ ID NO: 226) | CCTACGGGAGGCATCAG | GCAGATCTCG | CCTACGGGAGGCATCAG | AGTCAGTCAGCC | GGATTAGATACCCTAGTAGTC |
| (SEQ ID NO: 227) | CCTACGGGAGGCATCAG | GCAGATCTCG | CCTACGGGAGGCATCAG | AGTCAGTCAGCC | GGATTAGATACCCTAGTAGTC |
| (SEQ ID NO: 228) | CCTACGGGAGGCATCAG | GCAGATCTCG | CCTACGGGAGGCATCAG | AGTCAGTCAGCC | GGATTAGATACCCTAGTAGTC |
| (SEQ ID NO: 229) | CCTACGGGAGGCATCAG | GCAGATCTCG | CCTACGGGAGGCATCAG | AGTCAGTCAGCC | GGATTAGATACCCTAGTAGTC |
| (SEQ ID NO: 230) | CCTACGGGAGGCATCAG | GCAGATCTCG | CCTACGGGAGGCATCAG | AGTCAGTCAGCC | GGATTAGATACCCTAGTAGTC |
| (SEQ ID NO: 231) | CCTACGGGAGGCATCAG | GCAGATCTCG | CCTACGGGAGGCATCAG | AGTCAGTCAGCC | GGATTAGATACCCTAGTAGTC |
| (SEQ ID NO: 232) | CCTACGGGAGGCATCAG | GCAGATCTCG | CCTACGGGAGGCATCAG | AGTCAGTCAGCC | GGATTAGATACCCTAGTAGTC |
| (SEQ ID NO: 233) | CCTACGGGAGGCATCAG | GCAGATCTCG | CCTACGGGAGGCATCAG | AGTCAGTCAGCC | GGATTAGATACCCTAGTAGTC |
| (SEQ ID NO: 234) | CCTACGGGAGGCATCAG | GCAGATCTCG | CCTACGGGAGGCATCAG | AGTCAGTCAGCC | GGATTAGATACCCTAGTAGTC |
| (SEQ ID NO: 235) | CCTACGGGAGGCATCAG | GCAGATCTCG | CCTACGGGAGGCATCAG | AGTCAGTCAGCC | GGATTAGATACCCTAGTAGTC |
| (SEQ ID NO: 236) | CCTACGGGAGGCATCAG | GCAGATCTCG | CCTACGGGAGGCATCAG | AGTCAGTCAGCC | GGATTAGATACCCTAGTAGTC |
| (SEQ ID NO: 237) | CCTACGGGAGGCATCAG | GCAGATCTCG | CCTACGGGAGGCATCAG | AGTCAGTCAGCC | GGATTAGATACCCTAGTAGTC |
| (SEQ ID NO: 238) | CCTACGGGAGGCATCAG | GCAGATCTCG | CCTACGGGAGGCATCAG | AGTCAGTCAGCC | GGATTAGATACCCTAGTAGTC |
| (SEQ ID NO: 239) | CCTACGGGAGGCATCAG | GCAGATCTCG | CCTACGGGAGGCATCAG | AGTCAGTCAGCC | GGATTAGATACCCTAGTAGTC |
| (SEQ ID NO: 240) | CCTACGGGAGGCATCAG | GCAGATCTCG | CCTACGGGAGGCATCAG | AGTCAGTCAGCC | GGATTAGATACCCTAGTAGTC |
| (SEQ ID NO: 241) | CCTACGGGAGGCATCAG | GCAGATCTCG | CCTACGGGAGGCATCAG | AGTCAGTCAGCC | GGATTAGATACCCTAGTAGTC |
| (SEQ ID NO: 242) | CCTACGGGAGGCATCAG | GCAGATCTCG | CCTACGGGAGGCATCAG | AGTCAGTCAGCC | GGATTAGATACCCTAGTAGTC |
| (SEQ ID NO: 243) | CCTACGGGAGGCATCAG | GCAGATCTCG | CCTACGGGAGGCATCAG | AGTCAGTCAGCC | GGATTAGATACCCTAGTAGTC |
| (SEQ ID NO: 244) | CCTACGGGAGGCATCAG | GCAGATCTCG | CCTACGGGAGGCATCAG | AGTCAGTCAGCC | GGATTAGATACCCTAGTAGTC |
| (SEQ ID NO: 245) | CCTACGGGAGGCATCAG | GCAGATCTCG | CCTACGGGAGGCATCAG | AGTCAGTCAGCC | GGATTAGATACCCTAGTAGTC |
| (SEQ ID NO: 246) | CCTACGGGAGGCATCAG | GCAGATCTCG | CCTACGGGAGGCATCAG | AGTCAGTCAGCC | GGATTAGATACCCTAGTAGTC |
| (SEQ ID NO: 247) | CCTACGGGAGGCATCAG | GCAGATCTCG | CCTACGGGAGGCATCAG | AGTCAGTCAGCC | GGATTAGATACCCTAGTAGTC |

TABLE 2-continued

| | forward primer binding site fragment | 5' universal sequence fragment | barcode sequence fragment | 3' universal sequence fragment | reverse primer binding site fragment |
|---|---|---|---|---|---|
| (SEQ ID NO: 248) | CCTACGGGAGGCATCAG | GCAGATCTCG | CCTACGGGAGGCATCAG | AGTCAGTCAGCC | GGATTAGATACCCTAGTAGTC |
| (SEQ ID NO: 249) | CCTACGGGAGGCATCAG | GCAGATCTCG | CCTACGGGAGGCATCAG | AGTCAGTCAGCC | GGATTAGATACCCTAGTAGTC |
| (SEQ ID NO: 250) | CCTACGGGAGGCATCAG | GCAGATCTCG | CCTACGGGAGGCATCAG | AGTCAGTCAGCC | GGATTAGATACCCTAGTAGTC |
| (SEQ ID NO: 251) | CCTACGGGAGGCATCAG | GCAGATCTCG | CCTACGGGAGGCATCAG | AGTCAGTCAGCC | GGATTAGATACCCTAGTAGTC |
| (SEQ ID NO: 252) | CCTACGGGAGGCATCAG | GCAGATCTCG | CCTACGGGAGGCATCAG | AGTCAGTCAGCC | GGATTAGATACCCTAGTAGTC |
| (SEQ ID NO: 253) | CCTACGGGAGGCATCAG | GCAGATCTCG | CCTACGGGAGGCATCAG | AGTCAGTCAGCC | GGATTAGATACCCTAGTAGTC |
| (SEQ ID NO: 254) | CCTACGGGAGGCATCAG | GCAGATCTCG | CCTACGGGAGGCATCAG | AGTCAGTCAGCC | GGATTAGATACCCTAGTAGTC |
| (SEQ ID NO: 255) | CCTACGGGAGGCATCAG | GCAGATCTCG | CCTACGGGAGGCATCAG | AGTCAGTCAGCC | GGATTAGATACCCTAGTAGTC |
| (SEQ ID NO: 256) | CCTACGGGAGGCATCAG | GCAGATCTCG | CCTACGGGAGGCATCAG | AGTCAGTCAGCC | GGATTAGATACCCTAGTAGTC |
| (SEQ ID NO: 257) | CCTACGGGAGGCATCAG | GCAGATCTCG | CCTACGGGAGGCATCAG | AGTCAGTCAGCC | GGATTAGATACCCTAGTAGTC |
| (SEQ ID NO: 258) | CCTACGGGAGGCATCAG | GCAGATCTCG | CCTACGGGAGGCATCAG | AGTCAGTCAGCC | GGATTAGATACCCTAGTAGTC |
| (SEQ ID NO: 259) | CCTACGGGAGGCATCAG | GCAGATCTCG | CCTACGGGAGGCATCAG | AGTCAGTCAGCC | GGATTAGATACCCTAGTAGTC |
| (SEQ ID NO: 260) | CCTACGGGAGGCATCAG | GCAGATCTCG | CCTACGGGAGGCATCAG | AGTCAGTCAGCC | GGATTAGATACCCTAGTAGTC |
| (SEQ ID NO: 261) | CCTACGGGAGGCATCAG | GCAGATCTCG | CCTACGGGAGGCATCAG | AGTCAGTCAGCC | GGATTAGATACCCTAGTAGTC |
| (SEQ ID NO: 262) | CCTACGGGAGGCATCAG | GCAGATCTCG | CCTACGGGAGGCATCAG | AGTCAGTCAGCC | GGATTAGATACCCTAGTAGTC |
| (SEQ ID NO: 263) | CCTACGGGAGGCATCAG | GCAGATCTCG | CCTACGGGAGGCATCAG | AGTCAGTCAGCC | GGATTAGATACCCTAGTAGTC |
| (SEQ ID NO: 264) | CCTACGGGAGGCATCAG | GCAGATCTCG | CCTACGGGAGGCATCAG | AGTCAGTCAGCC | GGATTAGATACCCTAGTAGTC |
| (SEQ ID NO: 265) | CCTACGGGAGGCATCAG | GCAGATCTCG | CCTACGGGAGGCATCAG | AGTCAGTCAGCC | GGATTAGATACCCTAGTAGTC |
| (SEQ ID NO: 266) | CCTACGGGAGGCATCAG | GCAGATCTCG | CCTACGGGAGGCATCAG | AGTCAGTCAGCC | GGATTAGATACCCTAGTAGTC |
| (SEQ ID NO: 267) | CCTACGGGAGGCATCAG | GCAGATCTCG | CCTACGGGAGGCATCAG | AGTCAGTCAGCC | GGATTAGATACCCTAGTAGTC |
| (SEQ ID NO: 268) | CCTACGGGAGGCATCAG | GCAGATCTCG | CCTACGGGAGGCATCAG | AGTCAGTCAGCC | GGATTAGATACCCTAGTAGTC |
| (SEQ ID NO: 269) | CCTACGGGAGGCATCAG | GCAGATCTCG | CCTACGGGAGGCATCAG | AGTCAGTCAGCC | GGATTAGATACCCTAGTAGTC |
| (SEQ ID NO: 270) | CCTACGGGAGGCATCAG | GCAGATCTCG | CCTACGGGAGGCATCAG | AGTCAGTCAGCC | GGATTAGATACCCTAGTAGTC |
| (SEQ ID NO: 271) | CCTACGGGAGGCATCAG | GCAGATCTCG | CCTACGGGAGGCATCAG | AGTCAGTCAGCC | GGATTAGATACCCTAGTAGTC |
| (SEQ ID NO: 272) | CCTACGGGAGGCATCAG | GCAGATCTCG | CCTACGGGAGGCATCAG | AGTCAGTCAGCC | GGATTAGATACCCTAGTAGTC |
| (SEQ ID NO: 273) | CCTACGGGAGGCATCAG | GCAGATCTCG | CCTACGGGAGGCATCAG | AGTCAGTCAGCC | GGATTAGATACCCTAGTAGTC |
| (SEQ ID NO: 274) | CCTACGGGAGGCATCAG | GCAGATCTCG | CCTACGGGAGGCATCAG | AGTCAGTCAGCC | GGATTAGATACCCTAGTAGTC |
| (SEQ ID NO: 275) | CCTACGGGAGGCATCAG | GCAGATCTCG | CCTACGGGAGGCATCAG | AGTCAGTCAGCC | GGATTAGATACCCTAGTAGTC |
| (SEQ ID NO: 276) | CCTACGGGAGGCATCAG | GCAGATCTCG | CCTACGGGAGGCATCAG | AGTCAGTCAGCC | GGATTAGATACCCTAGTAGTC |
| (SEQ ID NO: 277) | CCTACGGGAGGCATCAG | GCAGATCTCG | CCTACGGGAGGCATCAG | AGTCAGTCAGCC | GGATTAGATACCCTAGTAGTC |
| (SEQ ID NO: 278) | CCTACGGGAGGCATCAG | GCAGATCTCG | CCTACGGGAGGCATCAG | AGTCAGTCAGCC | GGATTAGATACCCTAGTAGTC |
| (SEQ ID NO: 279) | CCTACGGGAGGCATCAG | GCAGATCTCG | CCTACGGGAGGCATCAG | AGTCAGTCAGCC | GGATTAGATACCCTAGTAGTC |
| (SEQ ID NO: 280) | CCTACGGGAGGCATCAG | GCAGATCTCG | CCTACGGGAGGCATCAG | AGTCAGTCAGCC | GGATTAGATACCCTAGTAGTC |
| (SEQ ID NO: 281) | CCTACGGGAGGCATCAG | GCAGATCTCG | CCTACGGGAGGCATCAG | AGTCAGTCAGCC | GGATTAGATACCCTAGTAGTC |
| (SEQ ID NO: 282) | CCTACGGGAGGCATCAG | GCAGATCTCG | CCTACGGGAGGCATCAG | AGTCAGTCAGCC | GGATTAGATACCCTAGTAGTC |
| (SEQ ID NO: 283) | CCTACGGGAGGCATCAG | GCAGATCTCG | CCTACGGGAGGCATCAG | AGTCAGTCAGCC | GGATTAGATACCCTAGTAGTC |
| (SEQ ID NO: 284) | CCTACGGGAGGCATCAG | GCAGATCTCG | CCTACGGGAGGCATCAG | AGTCAGTCAGCC | GGATTAGATACCCTAGTAGTC |

TABLE 2-continued

| | forward primer binding site fragment | 5' universal sequence fragment | barcode sequence fragment | 3' universal sequence fragment | reverse primer binding site fragment |
|---|---|---|---|---|---|
| (SEQ ID NO: 285) | CCTACGGGAGGCATCAG | GCAGATCTCG | CCTACGGGAGGCATCAG | AGTCAGTCAGCC | GGATTAGATACCCTAGTAGTC |
| (SEQ ID NO: 286) | CCTACGGGAGGCATCAG | GCAGATCTCG | CCTACGGGAGGCATCAG | AGTCAGTCAGCC | GGATTAGATACCCTAGTAGTC |
| (SEQ ID NO: 287) | CCTACGGGAGGCATCAG | GCAGATCTCG | CCTACGGGAGGCATCAG | AGTCAGTCAGCC | GGATTAGATACCCTAGTAGTC |
| (SEQ ID NO: 288) | CCTACGGGAGGCATCAG | GCAGATCTCG | CCTACGGGAGGCATCAG | AGTCAGTCAGCC | GGATTAGATACCCTAGTAGTC |
| (SEQ ID NO: 289) | CCTACGGGAGGCATCAG | GCAGATCTCG | CCTACGGGAGGCATCAG | AGTCAGTCAGCC | GGATTAGATACCCTAGTAGTC |
| (SEQ ID NO: 290) | CCTACGGGAGGCATCAG | GCAGATCTCG | CCTACGGGAGGCATCAG | AGTCAGTCAGCC | GGATTAGATACCCTAGTAGTC |
| (SEQ ID NO: 291) | CCTACGGGAGGCATCAG | GCAGATCTCG | CCTACGGGAGGCATCAG | AGTCAGTCAGCC | GGATTAGATACCCTAGTAGTC |
| (SEQ ID NO: 292) | CCTACGGGAGGCATCAG | GCAGATCTCG | CCTACGGGAGGCATCAG | AGTCAGTCAGCC | GGATTAGATACCCTAGTAGTC |
| (SEQ ID NO: 293) | CCTACGGGAGGCATCAG | GCAGATCTCG | CCTACGGGAGGCATCAG | AGTCAGTCAGCC | GGATTAGATACCCTAGTAGTC |
| (SEQ ID NO: 294) | CCTACGGGAGGCATCAG | GCAGATCTCG | CCTACGGGAGGCATCAG | AGTCAGTCAGCC | GGATTAGATACCCTAGTAGTC |
| (SEQ ID NO: 295) | CCTACGGGAGGCATCAG | GCAGATCTCG | CCTACGGGAGGCATCAG | AGTCAGTCAGCC | GGATTAGATACCCTAGTAGTC |
| (SEQ ID NO: 296) | CCTACGGGAGGCATCAG | GCAGATCTCG | CCTACGGGAGGCATCAG | AGTCAGTCAGCC | GGATTAGATACCCTAGTAGTC |
| (SEQ ID NO: 297) | CCTACGGGAGGCATCAG | GCAGATCTCG | CCTACGGGAGGCATCAG | AGTCAGTCAGCC | GGATTAGATACCCTAGTAGTC |
| (SEQ ID NO: 298) | CCTACGGGAGGCATCAG | GCAGATCTCG | CCTACGGGAGGCATCAG | AGTCAGTCAGCC | GGATTAGATACCCTAGTAGTC |
| (SEQ ID NO: 299) | CCTACGGGAGGCATCAG | GCAGATCTCG | CCTACGGGAGGCATCAG | AGTCAGTCAGCC | GGATTAGATACCCTAGTAGTC |
| (SEQ ID NO: 300) | CCTACGGGAGGCATCAG | GCAGATCTCG | CCTACGGGAGGCATCAG | AGTCAGTCAGCC | GGATTAGATACCCTAGTAGTC |
| (SEQ ID NO: 301) | CCTACGGGAGGCATCAG | GCAGATCTCG | CCTACGGGAGGCATCAG | AGTCAGTCAGCC | GGATTAGATACCCTAGTAGTC |
| (SEQ ID NO: 302) | CCTACGGGAGGCATCAG | GCAGATCTCG | CCTACGGGAGGCATCAG | AGTCAGTCAGCC | GGATTAGATACCCTAGTAGTC |
| (SEQ ID NO: 303) | CCTACGGGAGGCATCAG | GCAGATCTCG | CCTACGGGAGGCATCAG | AGTCAGTCAGCC | GGATTAGATACCCTAGTAGTC |
| (SEQ ID NO: 304) | CCTACGGGAGGCATCAG | GCAGATCTCG | CCTACGGGAGGCATCAG | AGTCAGTCAGCC | GGATTAGATACCCTAGTAGTC |
| (SEQ ID NO: 305) | CCTACGGGAGGCATCAG | GCAGATCTCG | CCTACGGGAGGCATCAG | AGTCAGTCAGCC | GGATTAGATACCCTAGTAGTC |
| (SEQ ID NO: 306) | CCTACGGGAGGCATCAG | GCAGATCTCG | CCTACGGGAGGCATCAG | AGTCAGTCAGCC | GGATTAGATACCCTAGTAGTC |
| (SEQ ID NO: 307) | CCTACGGGAGGCATCAG | GCAGATCTCG | CCTACGGGAGGCATCAG | AGTCAGTCAGCC | GGATTAGATACCCTAGTAGTC |
| (SEQ ID NO: 308) | CCTACGGGAGGCATCAG | GCAGATCTCG | CCTACGGGAGGCATCAG | AGTCAGTCAGCC | GGATTAGATACCCTAGTAGTC |
| (SEQ ID NO: 309) | CCTACGGGAGGCATCAG | GCAGATCTCG | CCTACGGGAGGCATCAG | AGTCAGTCAGCC | GGATTAGATACCCTAGTAGTC |
| (SEQ ID NO: 310) | CCTACGGGAGGCATCAG | GCAGATCTCG | CCTACGGGAGGCATCAG | AGTCAGTCAGCC | GGATTAGATACCCTAGTAGTC |
| (SEQ ID NO: 311) | CCTACGGGAGGCATCAG | GCAGATCTCG | CCTACGGGAGGCATCAG | AGTCAGTCAGCC | GGATTAGATACCCTAGTAGTC |
| (SEQ ID NO: 312) | CCTACGGGAGGCATCAG | GCAGATCTCG | CCTACGGGAGGCATCAG | AGTCAGTCAGCC | GGATTAGATACCCTAGTAGTC |
| (SEQ ID NO: 313) | CCTACGGGAGGCATCAG | GCAGATCTCG | CCTACGGGAGGCATCAG | AGTCAGTCAGCC | GGATTAGATACCCTAGTAGTC |
| (SEQ ID NO: 314) | CCTACGGGAGGCATCAG | GCAGATCTCG | CCTACGGGAGGCATCAG | AGTCAGTCAGCC | GGATTAGATACCCTAGTAGTC |
| (SEQ ID NO: 315) | CCTACGGGAGGCATCAG | GCAGATCTCG | CCTACGGGAGGCATCAG | AGTCAGTCAGCC | GGATTAGATACCCTAGTAGTC |
| (SEQ ID NO: 316) | CCTACGGGAGGCATCAG | GCAGATCTCG | CCTACGGGAGGCATCAG | AGTCAGTCAGCC | GGATTAGATACCCTAGTAGTC |
| (SEQ ID NO: 317) | CCTACGGGAGGCATCAG | GCAGATCTCG | CCTACGGGAGGCATCAG | AGTCAGTCAGCC | GGATTAGATACCCTAGTAGTC |
| (SEQ ID NO: 318) | CCTACGGGAGGCATCAG | GCAGATCTCG | CCTACGGGAGGCATCAG | AGTCAGTCAGCC | GGATTAGATACCCTAGTAGTC |
| (SEQ ID NO: 319) | CCTACGGGAGGCATCAG | GCAGATCTCG | CCTACGGGAGGCATCAG | AGTCAGTCAGCC | GGATTAGATACCCTAGTAGTC |
| (SEQ ID NO: 320) | CCTACGGGAGGCATCAG | GCAGATCTCG | CCTACGGGAGGCATCAG | AGTCAGTCAGCC | GGATTAGATACCCTAGTAGTC |
| (SEQ ID NO: 321) | CCTACGGGAGGCATCAG | GCAGATCTCG | CCTACGGGAGGCATCAG | AGTCAGTCAGCC | GGATTAGATACCCTAGTAGTC |
| (SEQ ID NO: 322) | CCTACGGGAGGCATCAG | GCAGATCTCG | CCTACGGGAGGCATCAG | AGTCAGTCAGCC | GGATTAGATACCCTAGTAGTC |

TABLE 2-continued

| | forward primer binding site fragment | 5' universal sequence fragment | barcode sequence fragment | 3' universal sequence fragment | reverse primer binding site fragment |
|---|---|---|---|---|---|
| (SEQ ID NO: 323) | CCTACGGGAGGCATCAG | GCAGATCTCG | CCTACGGGAGGCATCAG | AGTCAGTCAGCC | GGATTAGATACCCTAGTAGTC |
| (SEQ ID NO: 324) | CCTACGGGAGGCATCAG | GCAGATCTCG | CCTACGGGAGGCATCAG | AGTCAGTCAGCC | GGATTAGATACCCTAGTAGTC |
| (SEQ ID NO: 325) | CCTACGGGAGGCATCAG | GCAGATCTCG | CCTACGGGAGGCATCAG | AGTCAGTCAGCC | GGATTAGATACCCTAGTAGTC |
| (SEQ ID NO: 326) | CCTACGGGAGGCATCAG | GCAGATCTCG | CCTACGGGAGGCATCAG | AGTCAGTCAGCC | GGATTAGATACCCTAGTAGTC |
| (SEQ ID NO: 327) | CCTACGGGAGGCATCAG | GCAGATCTCG | CCTACGGGAGGCATCAG | AGTCAGTCAGCC | GGATTAGATACCCTAGTAGTC |
| (SEQ ID NO: 328) | CCTACGGGAGGCATCAG | GCAGATCTCG | CCTACGGGAGGCATCAG | AGTCAGTCAGCC | GGATTAGATACCCTAGTAGTC |
| (SEQ ID NO: 329) | CCTACGGGAGGCATCAG | GCAGATCTCG | CCTACGGGAGGCATCAG | AGTCAGTCAGCC | GGATTAGATACCCTAGTAGTC |
| (SEQ ID NO: 330) | CCTACGGGAGGCATCAG | GCAGATCTCG | CCTACGGGAGGCATCAG | AGTCAGTCAGCC | GGATTAGATACCCTAGTAGTC |
| (SEQ ID NO: 331) | CCTACGGGAGGCATCAG | GCAGATCTCG | CCTACGGGAGGCATCAG | AGTCAGTCAGCC | GGATTAGATACCCTAGTAGTC |
| (SEQ ID NO: 332) | CCTACGGGAGGCATCAG | GCAGATCTCG | CCTACGGGAGGCATCAG | AGTCAGTCAGCC | GGATTAGATACCCTAGTAGTC |
| (SEQ ID NO: 333) | CCTACGGGAGGCATCAG | GCAGATCTCG | CCTACGGGAGGCATCAG | AGTCAGTCAGCC | GGATTAGATACCCTAGTAGTC |
| (SEQ ID NO: 334) | CCTACGGGAGGCATCAG | GCAGATCTCG | CCTACGGGAGGCATCAG | AGTCAGTCAGCC | GGATTAGATACCCTAGTAGTC |
| (SEQ ID NO: 335) | CCTACGGGAGGCATCAG | GCAGATCTCG | CCTACGGGAGGCATCAG | AGTCAGTCAGCC | GGATTAGATACCCTAGTAGTC |
| (SEQ ID NO: 336) | CCTACGGGAGGCATCAG | GCAGATCTCG | CCTACGGGAGGCATCAG | AGTCAGTCAGCC | GGATTAGATACCCTAGTAGTC |
| (SEQ ID NO: 337) | CCTACGGGAGGCATCAG | GCAGATCTCG | CCTACGGGAGGCATCAG | AGTCAGTCAGCC | GGATTAGATACCCTAGTAGTC |
| (SEQ ID NO: 338) | CCTACGGGAGGCATCAG | GCAGATCTCG | CCTACGGGAGGCATCAG | AGTCAGTCAGCC | GGATTAGATACCCTAGTAGTC |
| (SEQ ID NO: 339) | CCTACGGGAGGCATCAG | GCAGATCTCG | CCTACGGGAGGCATCAG | AGTCAGTCAGCC | GGATTAGATACCCTAGTAGTC |
| (SEQ ID NO: 340) | CCTACGGGAGGCATCAG | GCAGATCTCG | CCTACGGGAGGCATCAG | AGTCAGTCAGCC | GGATTAGATACCCTAGTAGTC |
| (SEQ ID NO: 341) | CCTACGGGAGGCATCAG | GCAGATCTCG | CCTACGGGAGGCATCAG | AGTCAGTCAGCC | GGATTAGATACCCTAGTAGTC |
| (SEQ ID NO: 342) | CCTACGGGAGGCATCAG | GCAGATCTCG | CCTACGGGAGGCATCAG | AGTCAGTCAGCC | GGATTAGATACCCTAGTAGTC |
| (SEQ ID NO: 343) | CCTACGGGAGGCATCAG | GCAGATCTCG | CCTACGGGAGGCATCAG | AGTCAGTCAGCC | GGATTAGATACCCTAGTAGTC |
| (SEQ ID NO: 344) | CCTACGGGAGGCATCAG | GCAGATCTCG | CCTACGGGAGGCATCAG | AGTCAGTCAGCC | GGATTAGATACCCTAGTAGTC |
| (SEQ ID NO: 345) | CCTACGGGAGGCATCAG | GCAGATCTCG | CCTACGGGAGGCATCAG | AGTCAGTCAGCC | GGATTAGATACCCTAGTAGTC |
| (SEQ ID NO: 346) | CCTACGGGAGGCATCAG | GCAGATCTCG | CCTACGGGAGGCATCAG | AGTCAGTCAGCC | GGATTAGATACCCTAGTAGTC |
| (SEQ ID NO: 347) | CCTACGGGAGGCATCAG | GCAGATCTCG | CCTACGGGAGGCATCAG | AGTCAGTCAGCC | GGATTAGATACCCTAGTAGTC |
| (SEQ ID NO: 348) | CCTACGGGAGGCATCAG | GCAGATCTCG | CCTACGGGAGGCATCAG | AGTCAGTCAGCC | GGATTAGATACCCTAGTAGTC |
| (SEQ ID NO: 349) | CCTACGGGAGGCATCAG | GCAGATCTCG | CCTACGGGAGGCATCAG | AGTCAGTCAGCC | GGATTAGATACCCTAGTAGTC |
| (SEQ ID NO: 350) | CCTACGGGAGGCATCAG | GCAGATCTCG | CCTACGGGAGGCATCAG | AGTCAGTCAGCC | GGATTAGATACCCTAGTAGTC |
| (SEQ ID NO: 351) | CCTACGGGAGGCATCAG | GCAGATCTCG | CCTACGGGAGGCATCAG | AGTCAGTCAGCC | GGATTAGATACCCTAGTAGTC |
| (SEQ ID NO: 352) | CCTACGGGAGGCATCAG | GCAGATCTCG | CCTACGGGAGGCATCAG | AGTCAGTCAGCC | GGATTAGATACCCTAGTAGTC |
| (SEQ ID NO: 353) | CCTACGGGAGGCATCAG | GCAGATCTCG | CCTACGGGAGGCATCAG | AGTCAGTCAGCC | GGATTAGATACCCTAGTAGTC |
| (SEQ ID NO: 354) | CCTACGGGAGGCATCAG | GCAGATCTCG | CCTACGGGAGGCATCAG | AGTCAGTCAGCC | GGATTAGATACCCTAGTAGTC |
| (SEQ ID NO: 355) | CCTACGGGAGGCATCAG | GCAGATCTCG | CCTACGGGAGGCATCAG | AGTCAGTCAGCC | GGATTAGATACCCTAGTAGTC |
| (SEQ ID NO: 356) | CCTACGGGAGGCATCAG | GCAGATCTCG | CCTACGGGAGGCATCAG | AGTCAGTCAGCC | GGATTAGATACCCTAGTAGTC |
| (SEQ ID NO: 357) | CCTACGGGAGGCATCAG | GCAGATCTCG | CCTACGGGAGGCATCAG | AGTCAGTCAGCC | GGATTAGATACCCTAGTAGTC |
| (SEQ ID NO: 358) | CCTACGGGAGGCATCAG | GCAGATCTCG | CCTACGGGAGGCATCAG | AGTCAGTCAGCC | GGATTAGATACCCTAGTAGTC |
| (SEQ ID NO: 359) | CCTACGGGAGGCATCAG | GCAGATCTCG | CCTACGGGAGGCATCAG | AGTCAGTCAGCC | GGATTAGATACCCTAGTAGTC |

TABLE 2-continued

| | forward primer binding site fragment | 5' universal sequence fragment | barcode sequence fragment | 3' universal sequence fragment | reverse primer binding site fragment |
|---|---|---|---|---|---|
| (SEQ ID NO: 360) | CCTACGGGAGGCATCAG | GCAGATCTCG | CCTACGGGAGGCATCAG | AGTCAGTCAGCC | GGATTAGATACCCTAGTAGTC |
| (SEQ ID NO: 361) | CCTACGGGAGGCATCAG | GCAGATCTCG | CCTACGGGAGGCATCAG | AGTCAGTCAGCC | GGATTAGATACCCTAGTAGTC |
| (SEQ ID NO: 362) | CCTACGGGAGGCATCAG | GCAGATCTCG | CCTACGGGAGGCATCAG | AGTCAGTCAGCC | GGATTAGATACCCTAGTAGTC |
| (SEQ ID NO: 363) | CCTACGGGAGGCATCAG | GCAGATCTCG | CCTACGGGAGGCATCAG | AGTCAGTCAGCC | GGATTAGATACCCTAGTAGTC |
| (SEQ ID NO: 364) | CCTACGGGAGGCATCAG | GCAGATCTCG | CCTACGGGAGGCATCAG | AGTCAGTCAGCC | GGATTAGATACCCTAGTAGTC |
| (SEQ ID NO: 365) | CCTACGGGAGGCATCAG | GCAGATCTCG | CCTACGGGAGGCATCAG | AGTCAGTCAGCC | GGATTAGATACCCTAGTAGTC |
| (SEQ ID NO: 366) | CCTACGGGAGGCATCAG | GCAGATCTCG | CCTACGGGAGGCATCAG | AGTCAGTCAGCC | GGATTAGATACCCTAGTAGTC |
| (SEQ ID NO: 367) | CCTACGGGAGGCATCAG | GCAGATCTCG | CCTACGGGAGGCATCAG | AGTCAGTCAGCC | GGATTAGATACCCTAGTAGTC |
| (SEQ ID NO: 368) | CCTACGGGAGGCATCAG | GCAGATCTCG | CCTACGGGAGGCATCAG | AGTCAGTCAGCC | GGATTAGATACCCTAGTAGTC |
| (SEQ ID NO: 369) | CCTACGGGAGGCATCAG | GCAGATCTCG | CCTACGGGAGGCATCAG | AGTCAGTCAGCC | GGATTAGATACCCTAGTAGTC |
| (SEQ ID NO: 370) | CCTACGGGAGGCATCAG | GCAGATCTCG | CCTACGGGAGGCATCAG | AGTCAGTCAGCC | GGATTAGATACCCTAGTAGTC |
| (SEQ ID NO: 371) | CCTACGGGAGGCATCAG | GCAGATCTCG | CCTACGGGAGGCATCAG | AGTCAGTCAGCC | GGATTAGATACCCTAGTAGTC |
| (SEQ ID NO: 372) | CCTACGGGAGGCATCAG | GCAGATCTCG | CCTACGGGAGGCATCAG | AGTCAGTCAGCC | GGATTAGATACCCTAGTAGTC |
| (SEQ ID NO: 373) | CCTACGGGAGGCATCAG | GCAGATCTCG | CCTACGGGAGGCATCAG | AGTCAGTCAGCC | GGATTAGATACCCTAGTAGTC |
| (SEQ ID NO: 374) | CCTACGGGAGGCATCAG | GCAGATCTCG | CCTACGGGAGGCATCAG | AGTCAGTCAGCC | GGATTAGATACCCTAGTAGTC |
| (SEQ ID NO: 375) | CCTACGGGAGGCATCAG | GCAGATCTCG | CCTACGGGAGGCATCAG | AGTCAGTCAGCC | GGATTAGATACCCTAGTAGTC |
| (SEQ ID NO: 376) | CCTACGGGAGGCATCAG | GCAGATCTCG | CCTACGGGAGGCATCAG | AGTCAGTCAGCC | GGATTAGATACCCTAGTAGTC |
| (SEQ ID NO: 377) | CCTACGGGAGGCATCAG | GCAGATCTCG | CCTACGGGAGGCATCAG | AGTCAGTCAGCC | GGATTAGATACCCTAGTAGTC |
| (SEQ ID NO: 378) | CCTACGGGAGGCATCAG | GCAGATCTCG | CCTACGGGAGGCATCAG | AGTCAGTCAGCC | GGATTAGATACCCTAGTAGTC |
| (SEQ ID NO: 379) | CCTACGGGAGGCATCAG | GCAGATCTCG | CCTACGGGAGGCATCAG | AGTCAGTCAGCC | GGATTAGATACCCTAGTAGTC |
| (SEQ ID NO: 380) | CCTACGGGAGGCATCAG | GCAGATCTCG | CCTACGGGAGGCATCAG | AGTCAGTCAGCC | GGATTAGATACCCTAGTAGTC |
| (SEQ ID NO: 381) | CCTACGGGAGGCATCAG | GCAGATCTCG | CCTACGGGAGGCATCAG | AGTCAGTCAGCC | GGATTAGATACCCTAGTAGTC |
| (SEQ ID NO: 382) | CCTACGGGAGGCATCAG | GCAGATCTCG | CCTACGGGAGGCATCAG | AGTCAGTCAGCC | GGATTAGATACCCTAGTAGTC |
| (SEQ ID NO: 383) | CCTACGGGAGGCATCAG | GCAGATCTCG | CCTACGGGAGGCATCAG | AGTCAGTCAGCC | GGATTAGATACCCTAGTAGTC |
| (SEQ ID NO: 384) | CCTACGGGAGGCATCAG | GCAGATCTCG | CCTACGGGAGGCATCAG | AGTCAGTCAGCC | GGATTAGATACCCTAGTAGTC |

In one illustrative aspect, the control composition for sequencing or chemical analyses comprises a nucleic acid construct comprising at least one barcode sequence fragment linked at its 5' or 3' end to at least one universal sequence fragment. In another embodiment, the nucleic acid construct comprises at least a first and a second universal sequence fragment, and the first universal sequence fragment can be linked to the 5' end of the barcode sequence fragment and the second universal sequence fragment can be linked to the 3' end of the barcode sequence fragment. In one aspect, the universal sequence fragments can be extended as needed to make the nucleic acid construct longer for different applications such as whole genome sequencing where short inserts may be lost.

In yet another embodiment, a universal sequence fragment is not included in the nucleic acid construct (e.g., for microarray applications). In this microarray embodiment, primer binding site fragments are also not included. The complimentary sequence to each barcode sequence fragment may be spotted onto the microarray alongside nucleic acid sequences of interest to detect the barcode sequence fragments. The barcode sequence fragment detected would be in a fixed location that would identify which barcode sequence fragment was present.

In various embodiments, the universal sequence fragments can be from about 10 base pairs in length to about 270 base pairs in length, from about 10 base pairs in length to about 260 base pairs in length, from about 10 base pairs in length to about 250 base pairs in length, from about 10 base pairs in length to about 240 base pairs in length, from about 10 base pairs in length to about 230 base pairs in length, from about 10 base pairs in length to about 220 base pairs in length, from about 10 base pairs in length to about 210 base pairs in length, from about 10 base pairs in length to about 200 base pairs in length, from about 10 base pairs in length to about 190 base pairs in length, from about 10 base pairs in length to about 180 base pairs in length, from about 10 base pairs in length to about 170 base pairs in length, from about base pairs in length to about 160 base pairs in length, from about 10 base pairs in length to about 150 base pairs in length, from about 10 base pairs in length to about 140 base pairs in length, from about 10 base pairs in length to about 130 base pairs in length, from about 10 base pairs in length to about 120 base pairs in length, from about 10 base pairs in length to about 110 base pairs in length, from about 10 base pairs in length to about 100 base pairs in length, from about 10 base pairs in length to about 90 base pairs in length, from about 10 base pairs in length to about 80 base pairs in length, from about 10 base pairs in length to about 70 base pairs in length, from about 10 base pairs in length to about 60 base pairs in length, from about 10 base pairs in length to about 50 base pairs in length, from about 10 base pairs in length to about 40 base pairs in length, from about 10 base pairs in length to about 30 base pairs in length, from about 10 base pairs in length to about 20 base pairs in length, from about 10 base pairs in length to about 15 base pairs in length, from about 8 base pairs in length to about 15 base pairs in length, or from about 8 base pairs in length to about 12 base pairs in length.

Figure 5:
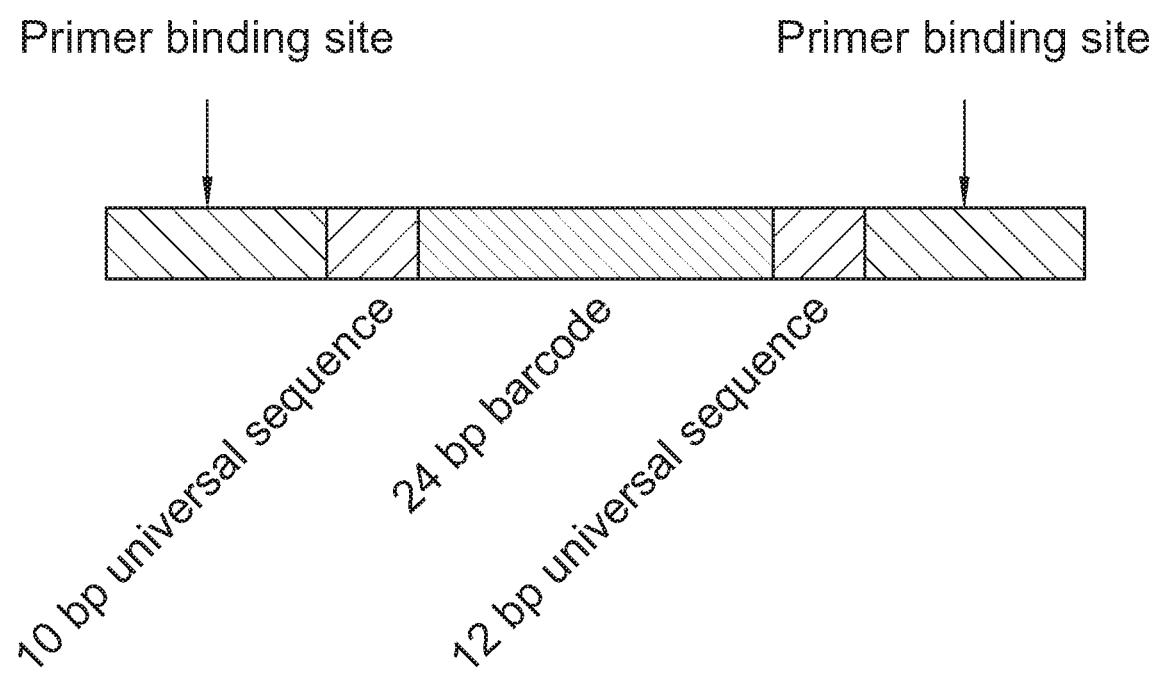
FIG. 5 shows schematically an exemplary nucleic acid construct as described herein comprising the unique barcode sequence fragment (e.g., 24 bases) that is not present in any known genome. The exemplary nucleic acid construct also comprises 10 bp and 12 bp universal sequence fragments and primer binding sites at the 5' and 3' ends of the nucleic acid construct.
Figure 7A:
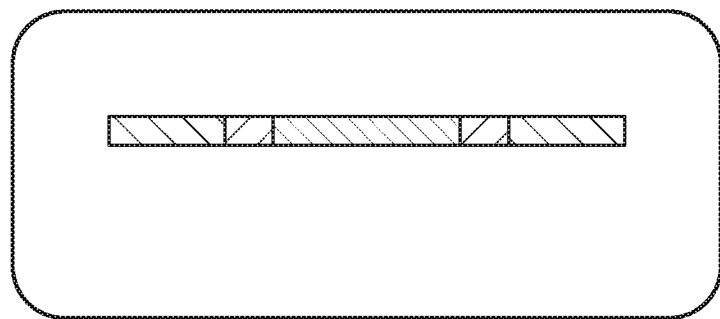
FIGS. 7A-7B show schematically the direct encapsulation of exemplary nucleic acid constructs as described herein without a plasmid or genome backbone. In various embodiments, the nucleic acid construct comprises (FIG. 7A) or lacks (FIG. 7B) primer binding site sequence fragments.
Figure 7B:
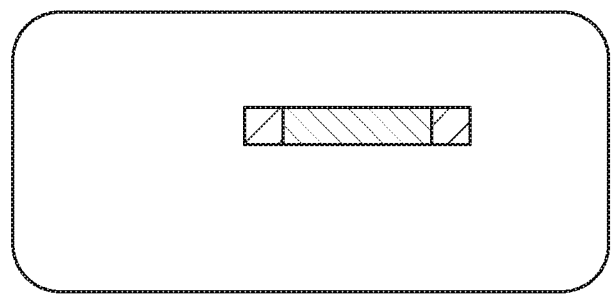

In embodiments for amplicon sequencing or chemical analyses involving amplicon sequencing to detect the nucleic acid construct of the control composition, the nucleic acid construct can further comprise at least a first and a second primer binding site fragment. In this aspect, the primers can be any primers of interest. In this embodiment, the first primer binding site fragment is linked at its 3' end to the 5' end of the first universal sequence fragment and the second primer binding site fragment is linked at its 5' end to the 3' end of the second universal sequence fragment (see FIG. 5 for an example). In embodiments for whole genome sequencing, the nucleic acid construct may lack primer binding site fragments (see FIG. 7B for an example). In embodiments where primer binding site fragments are included in the nucleic acid construct, the primer binding site fragments can range in length from about 15 base pairs to about 28 base pairs, from about 15 base pairs to about 26 base pairs, from about 15 base pairs to about 24 base pairs, from about 15 base pairs to about 22 base pairs, from about 15 base pairs to about 20 base pairs, from about 16 base pairs to about 22 base pairs, from about 16 base pairs to about 20 base pairs, from about 17 base pairs to about 20 base pairs, or can be about 18 base pairs.

In all of the various embodiments described above, the entire nucleic acid construct, not including plasmid sequence if a plasmid is present, can range in length from about 80 base pairs to about 300 base pairs, from about 80 base pairs to about 290 base pairs, from about 80 base pairs to about 280 base pairs, from about 80 base pairs to about 270 base pairs, from about 80 base pairs to about 260 base pairs, from about 80 base pairs to about 250 base pairs, from about 80 base pairs to about 240 base pairs, from about 80 base pairs to about 230 base pairs, from about 80 base pairs to about 220 base pairs, from about 80 base pairs to about 210 base pairs, from about 80 base pairs to about 200 base pairs, from about 80 base pairs to about 190 base pairs, from about 80 base pairs to about 180 base pairs, from about 80 base pairs to about 170 base pairs, or from about 80 base pairs to about 160 base pairs.

Various embodiments of the nucleic acid constructs, including the forward and reverse primer binding site fragments, the 5' and 3' universal sequence fragments, and the barcode sequence fragment are shown in Table 2 above having SEQ ID NOS:1 to 384. The corresponding full sequences are also shown as SEQ ID NOS:385 to 768 in Table 3 below. These embodiments have primer binding site sequence fragments similar to the nucleic acid construct exemplified in FIG. 5.

TABLE 3

|  | full sequence |
|---|---|
| (SEQ ID NO: 385) | CCTACGGGAGGCATCAGGCAGATCTCGTCCCTTGTCTCCACGAGACTGATTAGTCAGTCAGCCGGATTAGATACCCTAGTAGTC |
| (SEQ ID NO: 386) | CCTACGGGAGGCATCAGGCAGATCTCGGCTGTACGGATTATCACCAGGTGTAGTCAGTCAGCCGGATTAGATACCCTAGTAGTC |
| (SEQ ID NO: 387) | CCTACGGGAGGCATCAGGCAGATCTCGTGGTCAACGATACATCGCGTTGACAGTCAGTCAGCCGGATTAGATACCCTAGTAGTC |
| (SEQ ID NO: 388) | CCTACGGGAGGCATCAGGCAGATCTCGATCGCACAGTAAGCACATAGTCGTAGTCAGTCAGCCGGATTAGATACCCTAGTAGTC |
| (SEQ ID NO: 389) | CCTACGGGAGGCATCAGGCAGATCTCGGTCGTGTAGCCTGGCAAATACACTAGTCAGTCAGCCGGATTAGATACCCTAGTAGTC |
| (SEQ ID NO: 390) | CCTACGGGAGGCATCAGGCAGATCTCGAGCGGAGGTTAGGTCATGCTCCAGAGTCAGTCAGCCGGATTAGATACCCTAGTAGTC |
| (SEQ ID NO: 391) | CCTACGGGAGGCATCAGGCAGATCTCGATCCTTTGGTTCCCTAGTAAGCTGAGTCAGTCAGCCGGATTAGATACCCTAGTAGTC |
| (SEQ ID NO: 392) | CCTACGGGAGGCATCAGGCAGATCTCGTACAGCGCATACTTACCGACGAGTAGTCAGTCAGCCGGATTAGATACCCTAGTAGTC |
| (SEQ ID NO: 393) | CCTACGGGAGGCATCAGGCAGATCTCGACCGGTATGTACGCTTAGATGTAGAGTCAGTCAGCCGGATTAGATACCCTAGTAGTC |
| (SEQ ID NO: 394) | CCTACGGGAGGCATCAGGCAGATCTCGAATTGTGTCGGAAAGACGTAGCGGAGTCAGTCAGCCGGATTAGATACCCTAGTAGTC |
| (SEQ ID NO: 395) | CCTACGGGAGGCATCAGGCAGATCTCGTGCATACACTGGTTACCTTACACCAGTCAGTCAGCCGGATTAGATACCCTAGTAGTC |
| (SEQ ID NO: 396) | CCTACGGGAGGCATCAGGCAGATCTCGAGTCGAACGAGGTGACTAATGGCCAGTCAGTCAGCCGGATTAGATACCCTAGTAGTC |
| (SEQ ID NO: 397) | CCTACGGGAGGCATCAGGCAGATCTCGACCAGTGACTCACTCTCTCACTTGAGTCAGTCAGCCGGATTAGATACCCTAGTAGTC |
| (SEQ ID NO: 398) | CCTACGGGAGGCATCAGGCAGATCTCGGAATACCAAGTCATTGCAAGCAACAGTCAGTCAGCCGGATTAGATACCCTAGTAGTC |
| (SEQ ID NO: 399) | CCTACGGGAGGCATCAGGCAGATCTCGGTAGATCGTGTACACGTGACATGTAGTCAGTCAGCCGGATTAGATACCCTAGTAGTC |
| (SEQ ID NO: 400) | CCTACGGGAGGCATCAGGCAGATCTCGTAACGTGTGTGCCACAGTTGAAGTAGTCAGTCAGCCGGATTAGATACCCTAGTAGTC |
| (SEQ ID NO: 401) | CCTACGGGAGGCATCAGGCAGATCTCGCATTATGGCGTGCTAGGATCACTGAGTCAGTCAGCCGGATTAGATACCCTAGTAGTC |

TABLE 3-continued

| | full sequence |
|---|---|
| (SEQ ID NO: 402) | CCTACGGGAGGCATCAGGCAGATCTCGCCAATACGCCTGGATGACCCAAATAGTCAGTCAGCCGGATTAGATACCCTAGTAGTC |
| (SEQ ID NO: 403) | CCTACGGGAGGCATCAGGCAGATCTCGGATCTGCGATCCACCGGAGTAGGAAGTCAGTCAGCCGGATTAGATACCCTAGTAGTC |
| (SEQ ID NO: 404) | CCTACGGGAGGCATCAGGCAGATCTCGCAGCTCATCAGCTGAGGACTACCTAGTCAGTCAGCCGGATTAGATACCCTAGTAGTC |
| (SEQ ID NO: 405) | CCTACGGGAGGCATCAGGCAGATCTCGCAAACAACAGCTCAATCGGCTTGCAGTCAGTCAGCCGGATTAGATACCCTAGTAGTC |
| (SEQ ID NO: 406) | CCTACGGGAGGCATCAGGCAGATCTCGGCAACACCATCCAACACTCGATCGAGTCAGTCAGCCGGATTAGATACCCTAGTAGTC |
| (SEQ ID NO: 407) | CCTACGGGAGGCATCAGGCAGATCTCGGCGATATATCGCTGACCGGCTGTTAGTCAGTCAGCCGGATTAGATACCCTAGTAGTC |
| (SEQ ID NO: 408) | CCTACGGGAGGCATCAGGCAGATCTCGCGAGCAATCCTAGGAGGAGCAATAAGTCAGTCAGCCGGATTAGATACCCTAGTAGTC |
| (SEQ ID NO: 409) | CCTACGGGAGGCATCAGGCAGATCTCGAGTCGTGCACATAGCGACGAAGACAGTCAGTCAGCCGGATTAGATACCCTAGTAGTC |
| (SEQ ID NO: 410) | CCTACGGGAGGCATCAGGCAGATCTCGGTATCTGCGCGTCTTCCCTAACTCAGTCAGTCAGCCGGATTAGATACCCTAGTAGTC |
| (SEQ ID NO: 411) | CCTACGGGAGGCATCAGGCAGATCTCGCGAGGGAAAGTCTGGAAGAACGGCAGTCAGTCAGCCGGATTAGATACCCTAGTAGTC |
| (SEQ ID NO: 412) | CCTACGGGAGGCATCAGGCAGATCTCGCAAATTCGGGATGCTAGACACTACAGTCAGTCAGCCGGATTAGATACCCTAGTAGTC |
| (SEQ ID NO: 413) | CCTACGGGAGGCATCAGGCAGATCTCGAGATTGACCAACTTGGATTGAACGAGTCAGTCAGCCGGATTAGATACCCTAGTAGTC |
| (SEQ ID NO: 414) | CCTACGGGAGGCATCAGGCAGATCTCGAGTTACGAGCTAGATATACCAGTGAGTCAGTCAGCCGGATTAGATACCCTAGTAGTC |
| (SEQ ID NO: 415) | CCTACGGGAGGCATCAGGCAGATCTCGGCATATGCACTGAACAAACTGCCAAGTCAGTCAGCCGGATTAGATACCCTAGTAGTC |
| (SEQ ID NO: 416) | CCTACGGGAGGCATCAGGCAGATCTCGCAACTCCCGTGAGTAGACATGTGTAGTCAGTCAGCCGGATTAGATACCCTAGTAGTC |
| (SEQ ID NO: 417) | CCTACGGGAGGCATCAGGCAGATCTCGTTGCGTTAGCAGTACAGTTACGCGAGTCAGTCAGCCGGATTAGATACCCTAGTAGTC |
| (SEQ ID NO: 418) | CCTACGGGAGGCATCAGGCAGATCTCGTACGAGCCCTAACAAGCCCTAGTAAGTCAGTCAGCCGGATTAGATACCCTAGTAGTC |
| (SEQ ID NO: 419) | CCTACGGGAGGCATCAGGCAGATCTCGCACTACGCTAGATAGTGTCGGATCAGTCAGTCAGCCGGATTAGATACCCTAGTAGTC |
| (SEQ ID NO: 420) | CCTACGGGAGGCATCAGGCAGATCTCGTGCAGTCCTCGACTGAGCTCTGCAAGTCAGTCAGCCGGATTAGATACCCTAGTAGTC |
| (SEQ ID NO: 421) | CCTACGGGAGGCATCAGGCAGATCTCGACCATAGCTCCGCTTCGACTTTCCAGTCAGTCAGCCGGATTAGATACCCTAGTAGTC |
| (SEQ ID NO: 422) | CCTACGGGAGGCATCAGGCAGATCTCGTCGACATCTCTTGTCATAAGAACCAGTCAGTCAGCCGGATTAGATACCCTAGTAGTC |
| (SEQ ID NO: 423) | CCTACGGGAGGCATCAGGCAGATCTCGGAACACTTTGGAGTCCGCAAGTTAAGTCAGTCAGCCGGATTAGATACCCTAGTAGTC |
| (SEQ ID NO: 424) | CCTACGGGAGGCATCAGGCAGATCTCGGAGCCATCTGTACGTAGAGCTCTCAGTCAGTCAGCCGGATTAGATACCCTAGTAGTC |
| (SEQ ID NO: 425) | CCTACGGGAGGCATCAGGCAGATCTCGTTGGGTACACGTCCTCTGAGAGCTAGTCAGTCAGCCGGATTAGATACCCTAGTAGTC |
| (SEQ ID NO: 426) | CCTACGGGAGGCATCAGGCAGATCTCGAAGGCGCTCCTTCCTCGATGCAGTAGTCAGTCAGCCGGATTAGATACCCTAGTAGTC |
| (SEQ ID NO: 427) | CCTACGGGAGGCATCAGGCAGATCTCGTAATACGGATCGGCGGACTATTCAAGTCAGTCAGCCGGATTAGATACCCTAGTAGTC |
| (SEQ ID NO: 428) | CCTACGGGAGGCATCAGGCAGATCTCGTCGGAATTAGACCGTGCACAATTGAGTCAGTCAGCCGGATTAGATACCCTAGTAGTC |
| (SEQ ID NO: 429) | CCTACGGGAGGCATCAGGCAGATCTCGTGTGAATTCGGACGGCCTAAGTTCAGTCAGTCAGCCGGATTAGATACCCTAGTAGTC |
| (SEQ ID NO: 430) | CCTACGGGAGGCATCAGGCAGATCTCGCATTCGTGGCGTAGCGCTCACATCAGTCAGTCAGCCGGATTAGATACCCTAGTAGTC |
| (SEQ ID NO: 431) | CCTACGGGAGGCATCAGGCAGATCTCGTACTACGTGGCCTGGTTATGGCACAGTCAGTCAGCCGGATTAGATACCCTAGTAGTC |
| (SEQ ID NO: 432) | CCTACGGGAGGCATCAGGCAGATCTCGGGCCAGTTCCTACGAGGTTCTGATAGTCAGTCAGCCGGATTAGATACCCTAGTAGTC |
| (SEQ ID NO: 433) | CCTACGGGAGGCATCAGGCAGATCTCGGATGTTCGCTAGAACTCCTGTGGAAGTCAGTCAGCCGGATTAGATACCCTAGTAGTC |
| (SEQ ID NO: 434) | CCTACGGGAGGCATCAGGCAGATCTCGCTATCTCCTGTCTAATGGTCGTAGAGTCAGTCAGCCGGATTAGATACCCTAGTAGTC |
| (SEQ ID NO: 435) | CCTACGGGAGGCATCAGGCAGATCTCGACTCACAGGAATTTGCACCGTCGAAGTCAGTCAGCCGGATTAGATACCCTAGTAGTC |
| (SEQ ID NO: 436) | CCTACGGGAGGCATCAGGCAGATCTCGATGATGAGCCTCTGCTACAGACGTAGTCAGTCAGCCGGATTAGATACCCTAGTAGTC |
| (SEQ ID NO: 437) | CCTACGGGAGGCATCAGGCAGATCTCGGTCGACAGAGGAATGGCCTGACTAAGTCAGTCAGCCGGATTAGATACCCTAGTAGTC |
| (SEQ ID NO: 438) | CCTACGGGAGGCATCAGGCAGATCTCGTGTCGCAAATAGACGCACATACAAAGTCAGTCAGCCGGATTAGATACCCTAGTAGTC |
| (SEQ ID NO: 439) | CCTACGGGAGGCATCAGGCAGATCTCGCATCCCTCTACTTGAGTGGTCTGTAGTCAGTCAGCCGGATTAGATACCCTAGTAGTC |
| (SEQ ID NO: 440) | CCTACGGGAGGCATCAGGCAGATCTCGTATACCGCTGCGGATAGCACTCGTAGTCAGTCAGCCGGATTAGATACCCTAGTAGTC |

TABLE 3-continued full sequence (SEQ ID NO: 441) CCTACGGGAGGCATCAGGCAGATCTCGAGTTGAGGCATTTAGCGCGAACTTAGTCAGTCAGCCGGATTAGATACCCTAGTAGTC
(SEQ ID NO: 442) CCTACGGGAGGCATCAGGCAGATCTCGACAATAGACACCCATACACGCACCAGTCAGTCAGCCGGATTAGATACCCTAGTAGTC
(SEQ ID NO: 443) CCTACGGGAGGCATCAGGCAGATCTCGCGGTCAATTGACACCTCAGTCAAGAGTCAGTCAGCCGGATTAGATACCCTAGTAGTC
(SEQ ID NO: 444) CCTACGGGAGGCATCAGGCAGATCTCGGTGGAGTCTCATTCGACCAAACACAGTCAGTCAGCCGGATTAGATACCCTAGTAGTC
(SEQ ID NO: 445) CCTACGGGAGGCATCAGGCAGATCTCGGCTCGAAGATTCCCACCCAGTAACAGTCAGTCAGCCGGATTAGATACCCTAGTAGTC
(SEQ ID NO: 446) CCTACGGGAGGCATCAGGCAGATCTCGAGGCTTACGTGTATATCGCGATGAAGTCAGTCAGCCGGATTAGATACCCTAGTAGTC
(SEQ ID NO: 447) CCTACGGGAGGCATCAGGCAGATCTCGTCTCTACCACTCCGCCGGTAATCTAGTCAGTCAGCCGGATTAGATACCCTAGTAGTC
(SEQ ID NO: 448) CCTACGGGAGGCATCAGGCAGATCTCGACTTCCAACTTCCCGATGCCTTGAAGTCAGTCAGCCGGATTAGATACCCTAGTAGTC
(SEQ ID NO: 449) CCTACGGGAGGCATCAGGCAGATCTCGCTCACCTAGGAAAGCAGGCACGAAAGTCAGTCAGCCGGATTAGATACCCTAGTAGTC
(SEQ ID NO: 450) CCTACGGGAGGCATCAGGCAGATCTCGGTGTTGTCGTGCTACGCAGCACTAAGTCAGTCAGCCGGATTAGATACCCTAGTAGTC
(SEQ ID NO: 451) CCTACGGGAGGCATCAGGCAGATCTCGCCACAGATCGATCGCTTAGTGCTGAGTCAGTCAGCCGGATTAGATACCCTAGTAGTC
(SEQ ID NO: 452) CCTACGGGAGGCATCAGGCAGATCTCGTATCGACACAAGCAAAGTTTGCGAAGTCAGTCAGCCGGATTAGATACCCTAGTAGTC
(SEQ ID NO: 453) CCTACGGGAGGCATCAGGCAGATCTCGGATTCCGGCTCATCGAGCCGATCTAGTCAGTCAGCCGGATTAGATACCCTAGTAGTC
(SEQ ID NO: 454) CCTACGGGAGGCATCAGGCAGATCTCGCGTAATTGCCGCCTCATCATGTTCAGTCAGTCAGCCGGATTAGATACCCTAGTAGTC
(SEQ ID NO: 455) CCTACGGGAGGCATCAGGCAGATCTCGGGTGACTAGTTCCCAGGGACTTCTAGTCAGTCAGCCGGATTAGATACCCTAGTAGTC
(SEQ ID NO: 456) CCTACGGGAGGCATCAGGCAGATCTCGATGGGTTCCGTCGCAATCCTTGCGAGTCAGTCAGCCGGATTAGATACCCTAGTAGTC
(SEQ ID NO: 457) CCTACGGGAGGCATCAGGCAGATCTCGTAGGCATGCTTGCCTGCTTCCTTCAGTCAGTCAGCCGGATTAGATACCCTAGTAGTC
(SEQ ID NO: 458) CCTACGGGAGGCATCAGGCAGATCTCGAACTAGTTCAGGCAAGGCACAAGGAGTCAGTCAGCCGGATTAGATACCCTAGTAGTC
(SEQ ID NO: 459) CCTACGGGAGGCATCAGGCAGATCTCGATTCTGCCGAAGGGCCTATAAGTCAGTCAGCCGGATTAGATACCCTAGTAGTC
(SEQ ID NO: 460) CCTACGGGAGGCATCAGGCAGATCTCGAGCATGTCCCGTTCCATTTCATGCAGTCAGTCAGCCGGATTAGATACCCTAGTAGTC
(SEQ ID NO: 461) CCTACGGGAGGCATCAGGCAGATCTCGGTACGATATGACTCGGCGATCATCAGTCAGTCAGCCGGATTAGATACCCTAGTAGTC
(SEQ ID NO: 462) CCTACGGGAGGCATCAGGCAGATCTCGGTGGTGGTTTCCGTTTCACGCGAAAGTCAGTCAGCCGGATTAGATACCCTAGTAGTC
(SEQ ID NO: 463) CCTACGGGAGGCATCAGGCAGATCTCGTAGTATGCGCAAACAAGAACCTTGAGTCAGTCAGCCGGATTAGATACCCTAGTAGTC
(SEQ ID NO: 464) CCTACGGGAGGCATCAGGCAGATCTCGTGCGCTGAATGTTACTCTCTTAGCAGTCAGTCAGCCGGATTAGATACCCTAGTAGTC
(SEQ ID NO: 465) CCTACGGGAGGCATCAGGCAGATCTCGATGGCTGTCAGTAACTGTTCGCGCAGTCAGTCAGCCGGATTAGATACCCTAGTAGTC
(SEQ ID NO: 466) CCTACGGGAGGCATCAGGCAGATCTCGGTTCTCTTCTCGCGAAGCATCTACAGTCAGTCAGCCGGATTAGATACCCTAGTAGTC
(SEQ ID NO: 467) CCTACGGGAGGCATCAGGCAGATCTCGCGTAAGATGCCTGTTTGGCCACACAGTCAGTCAGCCGGATTAGATACCCTAGTAGTC
(SEQ ID NO: 468) CCTACGGGAGGCATCAGGCAGATCTCGGCGTTCTAGCTGTCAGGTTGCCCAAGTCAGTCAGCCGGATTAGATACCCTAGTAGTC
(SEQ ID NO: 469) CCTACGGGAGGCATCAGGCAGATCTCGGTTGTTCTGGGATCATTCCACTCAAGTCAGTCAGCCGGATTAGATACCCTAGTAGTC
(SEQ ID NO: 470) CCTACGGGAGGCATCAGGCAGATCTCGGGACTTCCAGCTGTCACATCACGAAGTCAGTCAGCCGGATTAGATACCCTAGTAGTC
(SEQ ID NO: 471) CCTACGGGAGGCATCAGGCAGATCTCGCTCACAACCGTGCGACATTTCTCTAGTCAGTCAGCCGGATTAGATACCCTAGTAGTC
(SEQ ID NO: 472) CCTACGGGAGGCATCAGGCAGATCTCGCTGCTATTCCTCGGACGTTAACTAAGTCAGTCAGCCGGATTAGATACCCTAGTAGTC
(SEQ ID NO: 473) CCTACGGGAGGCATCAGGCAGATCTCGATGTCACCGCTGTAGCAGTTGCGTAGTCAGTCAGCCGGATTAGATACCCTAGTAGTC
(SEQ ID NO: 474) CCTACGGGAGGCATCAGGCAGATCTCGTGTAACGCCGATCACGCTATTGGAAGTCAGTCAGCCGGATTAGATACCCTAGTAGTC
(SEQ ID NO: 475) CCTACGGGAGGCATCAGGCAGATCTCGAGCAGAACATCTAACTTCACTTCCAGTCAGTCAGCCGGATTAGATACCCTAGTAGTC
(SEQ ID NO: 476) CCTACGGGAGGCATCAGGCAGATCTCGTGGAGTAGGTGGCCAGTGGATATAAGTCAGTCAGCCGGATTAGATACCCTAGTAGTC
(SEQ ID NO: 477) CCTACGGGAGGCATCAGGCAGATCTCGTTGGCTCTATTCTGTGTGTAACGCAGTCAGTCAGCCGGATTAGATACCCTAGTAGTC
(SEQ ID NO: 478) CCTACGGGAGGCATCAGGCAGATCTCGGATCCCACGTACCCAATCGTGCAAAGTCAGTCAGCCGGATTAGATACCCTAGTAGTC
(SEQ ID NO: 479) CCTACGGGAGGCATCAGGCAGATCTCGTACCGCTTCTTCAGGCTAGCAGAGAGTCAGTCAGCCGGATTAGATACCCTAGTAGTC TABLE 3-continued

| | full sequence |
|---|---|
| (SEQ ID NO: 480) | CCTACGGGAGGCATCAGGCAGATCTCGTGTGCGATAACAGTCACTCCGAACAGTCAGTCAGCCGGATTAGATACCCTAGTAGTC |
| (SEQ ID NO: 481) | CCTACGGGAGGCATCAGGCAGATCTCGGATTATCGACGACACCGAAATCTGAGTCAGTCAGCCGGATTAGATACCCTAGTAGTC |
| (SEQ ID NO: 482) | CCTACGGGAGGCATCAGGCAGATCTCGGCCTAGCCCAATTGACGTAGAACTAGTCAGTCAGCCGGATTAGATACCCTAGTAGTC |
| (SEQ ID NO: 483) | CCTACGGGAGGCATCAGGCAGATCTCGGATGTATGTGGTCTATGCCGGCTAAGTCAGTCAGCCGGATTAGATACCCTAGTAGTC |
| (SEQ ID NO: 484) | CCTACGGGAGGCATCAGGCAGATCTCGACTCCTTGTGTTGTGGTATGGGAGAGTCAGTCAGCCGGATTAGATACCCTAGTAGTC |
| (SEQ ID NO: 485) | CCTACGGGAGGCATCAGGCAGATCTCGGTCACGGACATTTGTACCAACCGAAGTCAGTCAGCCGGATTAGATACCCTAGTAGTC |
| (SEQ ID NO: 486) | CCTACGGGAGGCATCAGGCAGATCTCGGCGAGCGAAGTAAGGGTACAGGGTAGTCAGTCAGCCGGATTAGATACCCTAGTAGTC |
| (SEQ ID NO: 487) | CCTACGGGAGGCATCAGGCAGATCTCGATCTACCGAAGCAGAGTGCTAATCAGTCAGTCAGCCGGATTAGATACCCTAGTAGTC |
| (SEQ ID NO: 488) | CCTACGGGAGGCATCAGGCAGATCTCGACTTGGTGTAAGTTGGCGGGTTATAGTCAGTCAGCCGGATTAGATACCCTAGTAGTC |
| (SEQ ID NO: 489) | CCTACGGGAGGCATCAGGCAGATCTCGTCTTGGAGGTCACACGATGGTCATAGTCAGTCAGCCGGATTAGATACCCTAGTAGTC |
| (SEQ ID NO: 490) | CCTACGGGAGGCATCAGGCAGATCTCGTCACCTCCTTGTGTCACCAATCCGAGTCAGTCAGCCGGATTAGATACCCTAGTAGTC |
| (SEQ ID NO: 491) | CCTACGGGAGGCATCAGGCAGATCTCGGCACACCTGATACACTAACAAACGAGTCAGTCAGCCGGATTAGATACCCTAGTAGTC |
| (SEQ ID NO: 492) | CCTACGGGAGGCATCAGGCAGATCTCGGCGACAATTACATTCCAGGCAGATAGTCAGTCAGCCGGATTAGATACCCTAGTAGTC |
| (SEQ ID NO: 493) | CCTACGGGAGGCATCAGGCAGATCTCGTCATGCTCCATTTATGGTACCCAGAGTCAGTCAGCCGGATTAGATACCCTAGTAGTC |
| (SEQ ID NO: 494) | CCTACGGGAGGCATCAGGCAGATCTCGAGCTGTCAAGCTCACGACTTGACAAGTCAGTCAGCCGGATTAGATACCCTAGTAGTC |
| (SEQ ID NO: 495) | CCTACGGGAGGCATCAGGCAGATCTCGGAGAGCAACAGACTTGGAGGCTTAAGTCAGTCAGCCGGATTAGATACCCTAGTAGTC |
| (SEQ ID NO: 496) | CCTACGGGAGGCATCAGGCAGATCTCGTACTCGGGAACTACGTGGTTCCACAGTCAGTCAGCCGGATTAGATACCCTAGTAGTC |
| (SEQ ID NO: 497) | CCTACGGGAGGCATCAGGCAGATCTCGCGTGCTTAGGCTGACGCTTTGCTGAGTCAGTCAGCCGGATTAGATACCCTAGTAGTC |
| (SEQ ID NO: 498) | CCTACGGGAGGCATCAGGCAGATCTCGTACCGAAGGTATACAGGGTTTGTAAGTCAGTCAGCCGGATTAGATACCCTAGTAGTC |
| (SEQ ID NO: 499) | CCTACGGGAGGCATCAGGCAGATCTCGCACTCATCATTCGCCTATGAGATCAGTCAGTCAGCCGGATTAGATACCCTAGTAGTC |
| (SEQ ID NO: 500) | CCTACGGGAGGCATCAGGCAGATCTCGGTATTTCGGACGCAAACCTATGGCAGTCAGTCAGCCGGATTAGATACCCTAGTAGTC |
| (SEQ ID NO: 501) | CCTACGGGAGGCATCAGGCAGATCTCGTATCTATCCTGCATCGCTTAAGGCAGTCAGTCAGCCGGATTAGATACCCTAGTAGTC |
| (SEQ ID NO: 502) | CCTACGGGAGGCATCAGGCAGATCTCGTTGCCAAGAGTCACCATCCAACGAAGTCAGTCAGCCGGATTAGATACCCTAGTAGTC |
| (SEQ ID NO: 503) | CCTACGGGAGGCATCAGGCAGATCTCGAGTAGCGGAAGAGCAATAGGAGGAAGTCAGTCAGCCGGATTAGATACCCTAGTAGTC |
| (SEQ ID NO: 504) | CCTACGGGAGGCATCAGGCAGATCTCGGCAATTAGGTACCCGAACGTCACTAGTCAGTCAGCCGGATTAGATACCCTAGTAGTC |
| (SEQ ID NO: 505) | CCTACGGGAGGCATCAGGCAGATCTCGCATACCGTGAGTACACCAACACCAAGTCAGTCAGCCGGATTAGATACCCTAGTAGTC |
| (SEQ ID NO: 506) | CCTACGGGAGGCATCAGGCAGATCTCGATGTGTGTAGACCCATCACATAGGAGTCAGTCAGCCGGATTAGATACCCTAGTAGTC |
| (SEQ ID NO: 507) | CCTACGGGAGGCATCAGGCAGATCTCGCCTGCGAAGTATCGACACGGAGAAAGTCAGTCAGCCGGATTAGATACCCTAGTAGTC |
| (SEQ ID NO: 508) | CCTACGGGAGGCATCAGGCAGATCTCGTTCTCTCGACATGAACCTATGACAAGTCAGTCAGCCGGATTAGATACCCTAGTAGTC |
| (SEQ ID NO: 509) | CCTACGGGAGGCATCAGGCAGATCTCGGCTCTCCGTAGAATGCCGGTAATAAGTCAGTCAGCCGGATTAGATACCCTAGTAGTC |
| (SEQ ID NO: 510) | CCTACGGGAGGCATCAGGCAGATCTCGGTTAAGCTGACCGAACAGCTCTACAGTCAGTCAGCCGGATTAGATACCCTAGTAGTC |
| (SEQ ID NO: 511) | CCTACGGGAGGCATCAGGCAGATCTCGATGCCATGCCGTGTGAGTCATACCAGTCAGTCAGCCGGATTAGATACCCTAGTAGTC |
| (SEQ ID NO: 512) | CCTACGGGAGGCATCAGGCAGATCTCGGACATTGTCACGTGGCCGTTACTGAGTCAGTCAGCCGGATTAGATACCCTAGTAGTC |
| (SEQ ID NO: 513) | CCTACGGGAGGCATCAGGCAGATCTCGGCCAACAACCATTAGAGCTGCCATAGTCAGTCAGCCGGATTAGATACCCTAGTAGTC |
| (SEQ ID NO: 514) | CCTACGGGAGGCATCAGGCAGATCTCGATCAGTACTAGGATCTAGTGGCAAAGTCAGTCAGCCGGATTAGATACCCTAGTAGTC |
| (SEQ ID NO: 515) | CCTACGGGAGGCATCAGGCAGATCTCGTCCTCGAGCGATCCTTCAATGGGAAGTCAGTCAGCCGGATTAGATACCCTAGTAGTC |
| (SEQ ID NO: 516) | CCTACGGGAGGCATCAGGCAGATCTCGACCCAAGCGTTATTGACGACATCGAGTCAGTCAGCCGGATTAGATACCCTAGTAGTC |
| (SEQ ID NO: 517) | CCTACGGGAGGCATCAGGCAGATCTCGTGCAGCAAGATTACATACTGAGCAAGTCAGTCAGCCGGATTAGATACCCTAGTAGTC |
| (SEQ ID NO: 518) | CCTACGGGAGGCATCAGGCAGATCTCGAGCAACATTGCAGGCTAAACTATGAGTCAGTCAGCCGGATTAGATACCCTAGTAGTC |

TABLE 3-continued full sequence

| | |
|---|---|
| (SEQ ID NO: 519) | CCTACGGGAGGCATCAGGCAGATCTCGGATGTGGTGTTAAAGAGCAGAGCCAGTCAGTCAGCCGGATTAGATACCCTAGTAGTC |
| (SEQ ID NO: 520) | CCTACGGGAGGCATCAGGCAGATCTCGCAGAAATGTGTCGGAGAGATCACGAGTCAGTCAGCCGGATTAGATACCCTAGTAGTC |
| (SEQ ID NO: 521) | CCTACGGGAGGCATCAGGCAGATCTCGGTAGAGGTAGAGTCAACCCGTGAAAGTCAGTCAGCCGGATTAGATACCCTAGTAGTC |
| (SEQ ID NO: 522) | CCTACGGGAGGCATCAGGCAGATCTCGCGTGATCCGCTAGTTTGAAACACGAGTCAGTCAGCCGGATTAGATACCCTAGTAGTC |
| (SEQ ID NO: 523) | CCTACGGGAGGCATCAGGCAGATCTCGGGTTATTTGGCGAGAGAGACAGGTAGTCAGTCAGCCGGATTAGATACCCTAGTAGTC |
| (SEQ ID NO: 524) | CCTACGGGAGGCATCAGGCAGATCTCGGGATCGTAATACTCGCCAGTGCATAGTCAGTCAGCCGGATTAGATACCCTAGTAGTC |
| (SEQ ID NO: 525) | CCTACGGGAGGCATCAGGCAGATCTCGGCATAGCATCAAGCTCAGGACTCTAGTCAGTCAGCCGGATTAGATACCCTAGTAGTC |
| (SEQ ID NO: 526) | CCTACGGGAGGCATCAGGCAGATCTCGGTGTTAGATGTGCACTTTGGGTGCAGTCAGTCAGCCGGATTAGATACCCTAGTAGTC |
| (SEQ ID NO: 527) | CCTACGGGAGGCATCAGGCAGATCTCGTTAGAGCCATGCTCTAGCCTGGCAAGTCAGTCAGCCGGATTAGATACCCTAGTAGTC |
| (SEQ ID NO: 528) | CCTACGGGAGGCATCAGGCAGATCTCGTGAACCCTATGGAATGCAATGCGTAGTCAGTCAGCCGGATTAGATACCCTAGTAGTC |
| (SEQ ID NO: 529) | CCTACGGGAGGCATCAGGCAGATCTCGAGAGTCTTGCCACGAATGAGTCATAGTCAGTCAGCCGGATTAGATACCCTAGTAGTC |
| (SEQ ID NO: 530) | CCTACGGGAGGCATCAGGCAGATCTCGACAACACTCCGACAACGCTAGAATAGTCAGTCAGCCGGATTAGATACCCTAGTAGTC |
| (SEQ ID NO: 531) | CCTACGGGAGGCATCAGGCAGATCTCGCGATGCTGTTGAATCAGAGCCCATAGTCAGTCAGCCGGATTAGATACCCTAGTAGTC |
| (SEQ ID NO: 532) | CCTACGGGAGGCATCAGGCAGATCTCGACGACTGCATAATCTGTAGAGCCAAGTCAGTCAGCCGGATTAGATACCCTAGTAGTC |
| (SEQ ID NO: 533) | CCTACGGGAGGCATCAGGCAGATCTCGACGCGAACTAATCCGACTCTAGGTAGTCAGTCAGCCGGATTAGATACCCTAGTAGTC |
| (SEQ ID NO: 534) | CCTACGGGAGGCATCAGGCAGATCTCGAGCTATGTATGGATCCTACGAGCAAGTCAGTCAGCCGGATTAGATACCCTAGTAGTC |
| (SEQ ID NO: 535) | CCTACGGGAGGCATCAGGCAGATCTCGACGGGTCATCATGACAACGAATCTAGTCAGTCAGCCGGATTAGATACCCTAGTAGTC |
| (SEQ ID NO: 536) | CCTACGGGAGGCATCAGGCAGATCTCGGAAACATCCCACTGCGGTTGACTCAGTCAGTCAGCCGGATTAGATACCCTAGTAGTC |
| (SEQ ID NO: 537) | CCTACGGGAGGCATCAGGCAGATCTCGCGTACTCTCGAGTGAGAAGAAAGGAGTCAGTCAGCCGGATTAGATACCCTAGTAGTC |
| (SEQ ID NO: 538) | CCTACGGGAGGCATCAGGCAGATCTCGTCAGTTCTCGTTTCGGATCTGTGAAGTCAGTCAGCCGGATTAGATACCCTAGTAGTC |
| (SEQ ID NO: 539) | CCTACGGGAGGCATCAGGCAGATCTCGTCGTGCGTGTTGGCCGGTACTCTAAGTCAGTCAGCCGGATTAGATACCCTAGTAGTC |
| (SEQ ID NO: 540) | CCTACGGGAGGCATCAGGCAGATCTCGGTTATCGCATGGCACAGGATTACCAGTCAGTCAGCCGGATTAGATACCCTAGTAGTC |
| (SEQ ID NO: 541) | CCTACGGGAGGCATCAGGCAGATCTCGGATCACGAGAGGCGATATCAGTAGAGTCAGTCAGCCGGATTAGATACCCTAGTAGTC |
| (SEQ ID NO: 542) | CCTACGGGAGGCATCAGGCAGATCTCGGTAAATTCAGGCCATAAGGGAGGCAGTCAGTCAGCCGGATTAGATACCCTAGTAGTC |
| (SEQ ID NO: 543) | CCTACGGGAGGCATCAGGCAGATCTCGAGTGTTTCGGACTGTGTTACTCCTAGTCAGTCAGCCGGATTAGATACCCTAGTAGTC |
| (SEQ ID NO: 544) | CCTACGGGAGGCATCAGGCAGATCTCGACACGCGGTTTAGGTACCTGCAATAGTCAGTCAGCCGGATTAGATACCCTAGTAGTC |
| (SEQ ID NO: 545) | CCTACGGGAGGCATCAGGCAGATCTCGTGGCAAATCTAGTCGCCTATAAGGAGTCAGTCAGCCGGATTAGATACCCTAGTAGTC |
| (SEQ ID NO: 546) | CCTACGGGAGGCATCAGGCAGATCTCGCACCTTACCTTAAGTGGCACTATCAGTCAGTCAGCCGGATTAGATACCCTAGTAGTC |
| (SEQ ID NO: 547) | CCTACGGGAGGCATCAGGCAGATCTCGTTAACCTTCCTGTAACCCGATAGAAGTCAGTCAGCCGGATTAGATACCCTAGTAGTC |
| (SEQ ID NO: 548) | CCTACGGGAGGCATCAGGCAGATCTCGTGCCGTATGCCAGTGTGCTAACGTAGTCAGTCAGCCGGATTAGATACCCTAGTAGTC |
| (SEQ ID NO: 549) | CCTACGGGAGGCATCAGGCAGATCTCGCGTGACAATAGTCTTGCGGCAATCAGTCAGTCAGCCGGATTAGATACCCTAGTAGTC |
| (SEQ ID NO: 550) | CCTACGGGAGGCATCAGGCAGATCTCGCGCTACAACTCGTGAGGTTTGATGAGTCAGTCAGCCGGATTAGATACCCTAGTAGTC |
| (SEQ ID NO: 551) | CCTACGGGAGGCATCAGGCAGATCTCGTTAAGACAGTCGATTGCTGGTCGAAGTCAGTCAGCCGGATTAGATACCCTAGTAGTC |
| (SEQ ID NO: 552) | CCTACGGGAGGCATCAGGCAGATCTCGTCTGCACTGAGCAAGAAGCCGGACAGTCAGTCAGCCGGATTAGATACCCTAGTAGTC |
| (SEQ ID NO: 553) | CCTACGGGAGGCATCAGGCAGATCTCGCGCAGATTAGTAACGGGATACAGGAGTCAGTCAGCCGGATTAGATACCCTAGTAGTC |
| (SEQ ID NO: 554) | CCTACGGGAGGCATCAGGCAGATCTCGTGGGTCCCACATAAGAGTCTCTAGAGTCAGTCAGCCGGATTAGATACCCTAGTAGTC |
| (SEQ ID NO: 555) | CCTACGGGAGGCATCAGGCAGATCTCGCACTGGTGCATATCCGTCATGGGTAGTCAGTCAGCCGGATTAGATACCCTAGTAGTC |
| (SEQ ID NO: 556) | CCTACGGGAGGCATCAGGCAGATCTCGAACGTAGGCTCTAGATCTATGCAGAGTCAGTCAGCCGGATTAGATACCCTAGTAGTC |
| (SEQ ID NO: 557) | CCTACGGGAGGCATCAGGCAGATCTCGAGTTGTAGTCCGGCACAAGGCAAGAGTCAGTCAGCCGGATTAGATACCCTAGTAGTC |

TABLE 3-continued

| | full sequence |
|---|---|
| (SEQ ID NO: 558) | CCTACGGGAGGCATCAGGCAGATCTCGTCGTCAAACCCGCGGCAAACACTTAGTCAGTCAGCCGGATTAGATACCCTAGTAGTC |
| (SEQ ID NO: 559) | CCTACGGGAGGCATCAGGCAGATCTCGTAATCGGTGCCAGCGAGTTCCTGTAGTCAGTCAGCCGGATTAGATACCCTAGTAGTC |
| (SEQ ID NO: 560) | CCTACGGGAGGCATCAGGCAGATCTCGTTGATCCGGTAGTTCCGAATCGGCAGTCAGTCAGCCGGATTAGATACCCTAGTAGTC |
| (SEQ ID NO: 561) | CCTACGGGAGGCATCAGGCAGATCTCGCGGGTGTTTGCTTACCTAGTGAGAAGTCAGTCAGCCGGATTAGATACCCTAGTAGTC |
| (SEQ ID NO: 562) | CCTACGGGAGGCATCAGGCAGATCTCGTTGACCGCGGTTCGTTCTGGTGGTAGTCAGTCAGCCGGATTAGATACCCTAGTAGTC |
| (SEQ ID NO: 563) | CCTACGGGAGGCATCAGGCAGATCTCGGTGCAACCAATCTTGGTCTCCTCTAGTCAGTCAGCCGGATTAGATACCCTAGTAGTC |
| (SEQ ID NO: 564) | CCTACGGGAGGCATCAGGCAGATCTCGGCTTGAGCTTGACTGCATACTGAGAGTCAGTCAGCCGGATTAGATACCCTAGTAGTC |
| (SEQ ID NO: 565) | CCTACGGGAGGCATCAGGCAGATCTCGCGCTGTGGATTACAGGGCCTTTGTAGTCAGTCAGCCGGATTAGATACCCTAGTAGTC |
| (SEQ ID NO: 566) | CCTACGGGAGGCATCAGGCAGATCTCGCTGTCAGTGACCCGATGAATATCGAGTCAGTCAGCCGGATTAGATACCCTAGTAGTC |
| (SEQ ID NO: 567) | CCTACGGGAGGCATCAGGCAGATCTCGACGATTCGAGTCGTCAATTAGTGGAGTCAGTCAGCCGGATTAGATACCCTAGTAGTC |
| (SEQ ID NO: 568) | CCTACGGGAGGCATCAGGCAGATCTCGGGTTCGGTCCATAGTACGCAGTCTAGTCAGTCAGCCGGATTAGATACCCTAGTAGTC |
| (SEQ ID NO: 569) | CCTACGGGAGGCATCAGGCAGATCTCGCTGATCCATCTTAGCAGCTATTGCAGTCAGTCAGCCGGATTAGATACCCTAGTAGTC |
| (SEQ ID NO: 570) | CCTACGGGAGGCATCAGGCAGATCTCGTATGTGCCGGCTCTCGGATAGATCAGTCAGTCAGCCGGATTAGATACCCTAGTAGTC |
| (SEQ ID NO: 571) | CCTACGGGAGGCATCAGGCAGATCTCGTGGTCGCATCGTTTCCCGAAACGAAGTCAGTCAGCCGGATTAGATACCCTAGTAGTC |
| (SEQ ID NO: 572) | CCTACGGGAGGCATCAGGCAGATCTCGTGTAAGACTTGGGAACTTTAGCGCAGTCAGTCAGCCGGATTAGATACCCTAGTAGTC |
| (SEQ ID NO: 573) | CCTACGGGAGGCATCAGGCAGATCTCGCGGATCTAGTGTTCCTTAGAAGGCAGTCAGTCAGCCGGATTAGATACCCTAGTAGTC |
| (SEQ ID NO: 574) | CCTACGGGAGGCATCAGGCAGATCTCGCGATCTTCGAGCGATGGACTTCAAAGTCAGTCAGCCGGATTAGATACCCTAGTAGTC |
| (SEQ ID NO: 575) | CCTACGGGAGGCATCAGGCAGATCTCGGTCGAATTTGCGTACTGAGCCTCGAGTCAGTCAGCCGGATTAGATACCCTAGTAGTC |
| (SEQ ID NO: 576) | CCTACGGGAGGCATCAGGCAGATCTCGGCATCAGAGTTAAGAAGGCCTTATAGTCAGTCAGCCGGATTAGATACCCTAGTAGTC |
| (SEQ ID NO: 577) | CCTACGGGAGGCATCAGGCAGATCTCGGTGGTCATCGTATGGAGCCTTGTCAGTCAGTCAGCCGGATTAGATACCCTAGTAGTC |
| (SEQ ID NO: 578) | CCTACGGGAGGCATCAGGCAGATCTCGCTGAAGGGCGAACTCGATGTAAGCAGTCAGTCAGCCGGATTAGATACCCTAGTAGTC |
| (SEQ ID NO: 579) | CCTACGGGAGGCATCAGGCAGATCTCGCGCTCACAGAATAGCTTCGACAGTAGTCAGTCAGCCGGATTAGATACCCTAGTAGTC |
| (SEQ ID NO: 580) | CCTACGGGAGGCATCAGGCAGATCTCGATTCGGTAGTGCATACGCATCAAGAGTCAGTCAGCCGGATTAGATACCCTAGTAGTC |
| (SEQ ID NO: 581) | CCTACGGGAGGCATCAGGCAGATCTCGCGAGCTGTTACCAGATGTCCGTCAAGTCAGTCAGCCGGATTAGATACCCTAGTAGTC |
| (SEQ ID NO: 582) | CCTACGGGAGGCATCAGGCAGATCTCGCAACACATGCTGGCACCTGTTGAAAGTCAGTCAGCCGGATTAGATACCCTAGTAGTC |
| (SEQ ID NO: 583) | CCTACGGGAGGCATCAGGCAGATCTCGATTCTCTCACGTCCTAGAGAAACTAGTCAGTCAGCCGGATTAGATACCCTAGTAGTC |
| (SEQ ID NO: 584) | CCTACGGGAGGCATCAGGCAGATCTCGCGACTCTAAACGGAGGTTCTTGACAGTCAGTCAGCCGGATTAGATACCCTAGTAGTC |
| (SEQ ID NO: 585) | CCTACGGGAGGCATCAGGCAGATCTCGGTCTTCAGCAAGCTGTAAAGGTTGAGTCAGTCAGCCGGATTAGATACCCTAGTAGTC |
| (SEQ ID NO: 586) | CCTACGGGAGGCATCAGGCAGATCTCGCGGATAACCTCCTGAGTCATTGAGAGTCAGTCAGCCGGATTAGATACCCTAGTAGTC |
| (SEQ ID NO: 587) | CCTACGGGAGGCATCAGGCAGATCTCGAGGGTGACTTTATACGGCAGTTCAAGTCAGTCAGCCGGATTAGATACCCTAGTAGTC |
| (SEQ ID NO: 588) | CCTACGGGAGGCATCAGGCAGATCTCGGACTTCATGCGACTCTAGAAGAGTAGTCAGTCAGCCGGATTAGATACCCTAGTAGTC |
| (SEQ ID NO: 589) | CCTACGGGAGGCATCAGGCAGATCTCGGCCTGTCTGCAATGCACAGTCGCTAGTCAGTCAGCCGGATTAGATACCCTAGTAGTC |
| (SEQ ID NO: 590) | CCTACGGGAGGCATCAGGCAGATCTCGACTGATGGCCTCCATGCGGATCCTAGTCAGTCAGCCGGATTAGATACCCTAGTAGTC |
| (SEQ ID NO: 591) | CCTACGGGAGGCATCAGGCAGATCTCGTTCGATGCCGCATGCTCCGTAGAAAGTCAGTCAGCCGGATTAGATACCCTAGTAGTC |
| (SEQ ID NO: 592) | CCTACGGGAGGCATCAGGCAGATCTCGTGTGGCTCGTGTTGATAGGTACACAGTCAGTCAGCCGGATTAGATACCCTAGTAGTC |
| (SEQ ID NO: 593) | CCTACGGGAGGCATCAGGCAGATCTCGAACTTTCAGGAGCGAGTTCATCGAAGTCAGTCAGCCGGATTAGATACCCTAGTAGTC |
| (SEQ ID NO: 594) | CCTACGGGAGGCATCAGGCAGATCTCGTGCACGTGATAAAAGCAGATTGTCAGTCAGCCGGATTAGATACCCTAGTAGTC |
| (SEQ ID NO: 595) | CCTACGGGAGGCATCAGGCAGATCTCGGTTCGGTGTCCATAGAGGCGTAGGAGTCAGTCAGCCGGATTAGATACCCTAGTAGTC |
| (SEQ ID NO: 596) | CCTACGGGAGGCATCAGGCAGATCTCGAAGACAGCTATCTCAGCGCCGTTAAGTCAGTCAGCCGGATTAGATACCCTAGTAGTC |

TABLE 3-continued

| | full sequence |
|---|---|
| (SEQ ID NO: 597) | CCTACGGGAGGCATCAGGCAGATCTCGATTGACCGGTCATAGACCGACTCCAGTCAGTCAGCCGGATTAGATACCCTAGTAGTC |
| (SEQ ID NO: 598) | CCTACGGGAGGCATCAGGCAGATCTCGTTCTCCATCACAGTCAACGCTGTCAGTCAGTCAGCCGGATTAGATACCCTAGTAGTC |
| (SEQ ID NO: 599) | CCTACGGGAGGCATCAGGCAGATCTCGCGTAGGTAGAGGACAGGAGGGTGTAGTCAGTCAGCCGGATTAGATACCCTAGTAGTC |
| (SEQ ID NO: 600) | CCTACGGGAGGCATCAGGCAGATCTCGATTTAGGACGACGCTGTCGTCAACAGTCAGTCAGCCGGATTAGATACCCTAGTAGTC |
| (SEQ ID NO: 601) | CCTACGGGAGGCATCAGGCAGATCTCGGGATAGCCAAGGATAGAGGCCATTAGTCAGTCAGCCGGATTAGATACCCTAGTAGTC |
| (SEQ ID NO: 602) | CCTACGGGAGGCATCAGGCAGATCTCGTGGTTGGTTACGAAGCTTGAAACCAGTCAGTCAGCCGGATTAGATACCCTAGTAGTC |
| (SEQ ID NO: 603) | CCTACGGGAGGCATCAGGCAGATCTCGGTCGTCCAAATGTAAGCGTCTCGAAGTCAGTCAGCCGGATTAGATACCCTAGTAGTC |
| (SEQ ID NO: 604) | CCTACGGGAGGCATCAGGCAGATCTCGCAACGTGCTCCAATAGCTTCGTGGAGTCAGTCAGCCGGATTAGATACCCTAGTAGTC |
| (SEQ ID NO: 605) | CCTACGGGAGGCATCAGGCAGATCTCGTACACAAGTCGCCGGGATCAAATTAGTCAGTCAGCCGGATTAGATACCCTAGTAGTC |
| (SEQ ID NO: 606) | CCTACGGGAGGCATCAGGCAGATCTCGGCGTCCATGAATAGTCATCGAATGAGTCAGTCAGCCGGATTAGATACCCTAGTAGTC |
| (SEQ ID NO: 607) | CCTACGGGAGGCATCAGGCAGATCTCGGTAATGCGTAACATCTTGGAGTCGAGTCAGTCAGCCGGATTAGATACCCTAGTAGTC |
| (SEQ ID NO: 608) | CCTACGGGAGGCATCAGGCAGATCTCGGTCGCCGTACATAGCACCGGTCTTAGTCAGTCAGCCGGATTAGATACCCTAGTAGTC |
| (SEQ ID NO: 609) | CCTACGGGAGGCATCAGGCAGATCTCGGGAATCCGATTAGCAAATCAGCCTAGTCAGTCAGCCGGATTAGATACCCTAGTAGTC |
| (SEQ ID NO: 610) | CCTACGGGAGGCATCAGGCAGATCTCGCACCCGATGGTTGCAAGCTGTCTCAGTCAGTCAGCCGGATTAGATACCCTAGTAGTC |
| (SEQ ID NO: 611) | CCTACGGGAGGCATCAGGCAGATCTCGTTCTGAGAGGTAAGCGGCCTATTAAGTCAGTCAGCCGGATTAGATACCCTAGTAGTC |
| (SEQ ID NO: 612) | CCTACGGGAGGCATCAGGCAGATCTCGATCCCTACGGAATCTTCAACTACCAGTCAGTCAGCCGGATTAGATACCCTAGTAGTC |
| (SEQ ID NO: 613) | CCTACGGGAGGCATCAGGCAGATCTCGGGTTCCATTAGGTGGAATTCGGCTAGTCAGTCAGCCGGATTAGATACCCTAGTAGTC |
| (SEQ ID NO: 614) | CCTACGGGAGGCATCAGGCAGATCTCGGTGTTCCCAGAATAAGATGCAGTCAGTCAGTCAGCCGGATTAGATACCCTAGTAGTC |
| (SEQ ID NO: 615) | CCTACGGGAGGCATCAGGCAGATCTCGCCGAGGTATAATTGCCGAGTAATCAGTCAGTCAGCCGGATTAGATACCCTAGTAGTC |
| (SEQ ID NO: 616) | CCTACGGGAGGCATCAGGCAGATCTCGAGCGTAATTAGCACCTTGACAAGAAGTCAGTCAGCCGGATTAGATACCCTAGTAGTC |
| (SEQ ID NO: 617) | CCTACGGGAGGCATCAGGCAGATCTCGCTCGTGAATGACGTAACCACCACCAGTCAGTCAGCCGGATTAGATACCCTAGTAGTC |
| (SEQ ID NO: 618) | CCTACGGGAGGCATCAGGCAGATCTCGAGGTGAGTTCTACATAGCTCGGTCAGTCAGTCAGCCGGATTAGATACCCTAGTAGTC |
| (SEQ ID NO: 619) | CCTACGGGAGGCATCAGGCAGATCTCGCCTGTCCTATCTAACCATGCCAACAGTCAGTCAGCCGGATTAGATACCCTAGTAGTC |
| (SEQ ID NO: 620) | CCTACGGGAGGCATCAGGCAGATCTCGGGTTTAACACGCTATGGAGCTAGTAGTCAGTCAGCCGGATTAGATACCCTAGTAGTC |
| (SEQ ID NO: 621) | CCTACGGGAGGCATCAGGCAGATCTCGAGACAGTAGGAGACTACCTCTTCAAGTCAGTCAGCCGGATTAGATACCCTAGTAGTC |
| (SEQ ID NO: 622) | CCTACGGGAGGCATCAGGCAGATCTCGGCCACGACTTACGATGATAACCCAAGTCAGTCAGCCGGATTAGATACCCTAGTAGTC |
| (SEQ ID NO: 623) | CCTACGGGAGGCATCAGGCAGATCTCGATTGTTCCTACCGGCCCAATATAAAGTCAGTCAGCCGGATTAGATACCCTAGTAGTC |
| (SEQ ID NO: 624) | CCTACGGGAGGCATCAGGCAGATCTCGGCCGTAAACTTGTTGTATGACAGGAGTCAGTCAGCCGGATTAGATACCCTAGTAGTC |
| (SEQ ID NO: 625) | CCTACGGGAGGCATCAGGCAGATCTCGGCAGATTTCCAGGGTAAGTTTGACAGTCAGTCAGCCGGATTAGATACCCTAGTAGTC |
| (SEQ ID NO: 626) | CCTACGGGAGGCATCAGGCAGATCTCGAGATGATCAGTCCTACCACGGTACAGTCAGTCAGCCGGATTAGATACCCTAGTAGTC |
| (SEQ ID NO: 627) | CCTACGGGAGGCATCAGGCAGATCTCGGAGACGTGTTCTCGGTCTGTCTGAAGTCAGTCAGCCGGATTAGATACCCTAGTAGTC |
| (SEQ ID NO: 628) | CCTACGGGAGGCATCAGGCAGATCTCGTATCACCGGACGTACATGTCGCCAGTCAGTCAGCCGGATTAGATACCCTAGTAGTC |
| (SEQ ID NO: 629) | CCTACGGGAGGCATCAGGCAGATCTCGTATGCCAGAGATTTCTAGAGTGCGAGTCAGTCAGCCGGATTAGATACCCTAGTAGTC |
| (SEQ ID NO: 630) | CCTACGGGAGGCATCAGGCAGATCTCGAGGTCCAAATCAACGGATGTTATGAGTCAGTCAGCCGGATTAGATACCCTAGTAGTC |
| (SEQ ID NO: 631) | CCTACGGGAGGCATCAGGCAGATCTCGACCGTGCTCACATTGAGGCTACAAAGTCAGTCAGCCGGATTAGATACCCTAGTAGTC |
| (SEQ ID NO: 632) | CCTACGGGAGGCATCAGGCAGATCTCGCTCCCTTTGTGTGTAGGAACCGGAAGTCAGTCAGCCGGATTAGATACCCTAGTAGTC |
| (SEQ ID NO: 633) | CCTACGGGAGGCATCAGGCAGATCTCGAGCTGCACCTAAACATCTAGCAGAAGTCAGTCAGCCGGATTAGATACCCTAGTAGTC |
| (SEQ ID NO: 634) | CCTACGGGAGGCATCAGGCAGATCTCGCCTTGACCGATGCCGACATTGAGAGTCAGTCAGCCGGATTAGATACCCTAGTAGTC |
| (SEQ ID NO: 635) | CCTACGGGAGGCATCAGGCAGATCTCGCTATCATCCTCACATGTAAGGCTCAGTCAGTCAGCCGGATTAGATACCCTAGTAGTC |

TABLE 3-continued

| | full sequence |
|---|---|
| (SEQ ID NO: 636) | CCTACGGGAGGCATCAGGCAGATCTCGACTCTAGCCGGTTGCAAGCTAAGTAGTCAGTCAGCCGGATTAGATACCCTAGTAGTC |
| (SEQ ID NO: 637) | CCTACGGGAGGCATCAGGCAGATCTCGCGATAGGCCTTAGTGTGTGCCATAAGTCAGTCAGCCGGATTAGATACCCTAGTAGTC |
| (SEQ ID NO: 638) | CCTACGGGAGGCATCAGGCAGATCTCGAATGACCTCGTGTGACAACCGAATAGTCAGTCAGCCGGATTAGATACCCTAGTAGTC |
| (SEQ ID NO: 639) | CCTACGGGAGGCATCAGGCAGATCTCGCTTAGGCATGTGTAGGCTCGTGCTAGTCAGTCAGCCGGATTAGATACCCTAGTAGTC |
| (SEQ ID NO: 640) | CCTACGGGAGGCATCAGGCAGATCTCGCCAGATATAGCACTCCTTAAGGCGAGTCAGTCAGCCGGATTAGATACCCTAGTAGTC |
| (SEQ ID NO: 641) | CCTACGGGAGGCATCAGGCAGATCTCGGAGAGTCCACTTTTGCCTGGGTCAAGTCAGTCAGCCGGATTAGATACCCTAGTAGTC |
| (SEQ ID NO: 642) | CCTACGGGAGGCATCAGGCAGATCTCGGAACGGGACGTACAATTCTGCTTCAGTCAGTCAGCCGGATTAGATACCCTAGTAGTC |
| (SEQ ID NO: 643) | CCTACGGGAGGCATCAGGCAGATCTCGACGTGTAGGCTTACTGGCAAACCTAGTCAGTCAGCCGGATTAGATACCCTAGTAGTC |
| (SEQ ID NO: 644) | CCTACGGGAGGCATCAGGCAGATCTCGGGTCTCCTACAGAATCAGAGCTTGAGTCAGTCAGCCGGATTAGATACCCTAGTAGTC |
| (SEQ ID NO: 645) | CCTACGGGAGGCATCAGGCAGATCTCGACTGACTTAAGGCAATGTAGACACAGTCAGTCAGCCGGATTAGATACCCTAGTAGTC |
| (SEQ ID NO: 646) | CCTACGGGAGGCATCAGGCAGATCTCGGATGCTGCCGTTTGGCGATACGTTAGTCAGTCAGCCGGATTAGATACCCTAGTAGTC |
| (SEQ ID NO: 647) | CCTACGGGAGGCATCAGGCAGATCTCGTTCCTAGGCCAGGCCTTACGATAGAGTCAGTCAGCCGGATTAGATACCCTAGTAGTC |
| (SEQ ID NO: 648) | CCTACGGGAGGCATCAGGCAGATCTCGATTAAGCCTGGATACCTGTGTCTTAGTCAGTCAGCCGGATTAGATACCCTAGTAGTC |
| (SEQ ID NO: 649) | CCTACGGGAGGCATCAGGCAGATCTCGTGGCTTTCTATCAACGAGGCAACGAGTCAGTCAGCCGGATTAGATACCCTAGTAGTC |
| (SEQ ID NO: 650) | CCTACGGGAGGCATCAGGCAGATCTCGACAGCTCAAACAGAAGACAGCGACAGTCAGTCAGCCGGATTAGATACCCTAGTAGTC |
| (SEQ ID NO: 651) | CCTACGGGAGGCATCAGGCAGATCTCGGAGCGTATCCATACACCTGCGATCAGTCAGTCAGCCGGATTAGATACCCTAGTAGTC |
| (SEQ ID NO: 652) | CCTACGGGAGGCATCAGGCAGATCTCGATGGGCGAATGGGCGTTGCATTCAGTCAGTCAGCCGGATTAGATACCCTAGTAGTC |
| (SEQ ID NO: 653) | CCTACGGGAGGCATCAGGCAGATCTCGGATCTCTGGGTAACTAGCGTTCAGAGTCAGTCAGCCGGATTAGATACCCTAGTAGTC |
| (SEQ ID NO: 654) | CCTACGGGAGGCATCAGGCAGATCTCGCATCATACGGGTTTGCGACAAAGTAGTCAGTCAGCCGGATTAGATACCCTAGTAGTC |
| (SEQ ID NO: 655) | CCTACGGGAGGCATCAGGCAGATCTCGTACGGATTATGGTGCGAGTATATGAGTCAGTCAGCCGGATTAGATACCCTAGTAGTC |
| (SEQ ID NO: 656) | CCTACGGGAGGCATCAGGCAGATCTCGATAGCGAACTCATACCACAACGAAAGTCAGTCAGCCGGATTAGATACCCTAGTAGTC |
| (SEQ ID NO: 657) | CCTACGGGAGGCATCAGGCAGATCTCGTAACGCTGTGTGTCTGGAACGGTTAGTCAGTCAGCCGGATTAGATACCCTAGTAGTC |
| (SEQ ID NO: 658) | CCTACGGGAGGCATCAGGCAGATCTCGAACCAAACTCGAGTACTACCTCGGAGTCAGTCAGCCGGATTAGATACCCTAGTAGTC |
| (SEQ ID NO: 659) | CCTACGGGAGGCATCAGGCAGATCTCGGCCGTCTCGTAATTCCTGTTAACCAGTCAGTCAGCCGGATTAGATACCCTAGTAGTC |
| (SEQ ID NO: 660) | CCTACGGGAGGCATCAGGCAGATCTCGCTGGGTATCTCGCTATCCAAGTGGAGTCAGTCAGCCGGATTAGATACCCTAGTAGTC |
| (SEQ ID NO: 661) | CCTACGGGAGGCATCAGGCAGATCTCGGACTACCCGTTGCAGTCTAGTACGAGTCAGTCAGCCGGATTAGATACCCTAGTAGTC |
| (SEQ ID NO: 662) | CCTACGGGAGGCATCAGGCAGATCTCGGCGTTGCAAACTGTGTCCGGATTCAGTCAGTCAGCCGGATTAGATACCCTAGTAGTC |
| (SEQ ID NO: 663) | CCTACGGGAGGCATCAGGCAGATCTCGAACCGCATAAGTTGTGGTGATGTAAGTCAGTCAGCCGGATTAGATACCCTAGTAGTC |
| (SEQ ID NO: 664) | CCTACGGGAGGCATCAGGCAGATCTCGACCTTACACCTTCTTTCGTTCAACAGTCAGTCAGCCGGATTAGATACCCTAGTAGTC |
| (SEQ ID NO: 665) | CCTACGGGAGGCATCAGGCAGATCTCGGTAGGTGCTTACCCGAAGATTCTGAGTCAGTCAGCCGGATTAGATACCCTAGTAGTC |
| (SEQ ID NO: 666) | CCTACGGGAGGCATCAGGCAGATCTCGCGCATTTGGATGGTTGGCGTTACAAGTCAGTCAGCCGGATTAGATACCCTAGTAGTC |
| (SEQ ID NO: 667) | CCTACGGGAGGCATCAGGCAGATCTCGATAACATGTGCGGAAGTAGCGAGCAGTCAGTCAGCCGGATTAGATACCCTAGTAGTC |
| (SEQ ID NO: 668) | CCTACGGGAGGCATCAGGCAGATCTCGCTTGAGAAATCGTTGCGGACCCTAAGTCAGTCAGCCGGATTAGATACCCTAGTAGTC |
| (SEQ ID NO: 669) | CCTACGGGAGGCATCAGGCAGATCTCGCTACACAGCACAGCGGAAACATGGAGTCAGTCAGCCGGATTAGATACCCTAGTAGTC |
| (SEQ ID NO: 670) | CCTACGGGAGGCATCAGGCAGATCTCGGAAATGCTACGTAACGTTAGTGTGAGTCAGTCAGCCGGATTAGATACCCTAGTAGTC |
| (SEQ ID NO: 671) | CCTACGGGAGGCATCAGGCAGATCTCGTCTGAGGTTGCCTGCATGACAGTCAGTCAGCCGGATTAGATACCCTAGTAGTC |
| (SEQ ID NO: 672) | CCTACGGGAGGCATCAGGCAGATCTCGGATCATTCTCTCTCAATCGCTTTCAGTCAGTCAGCCGGATTAGATACCCTAGTAGTC |
| (SEQ ID NO: 673) | CCTACGGGAGGCATCAGGCAGATCTCGAGACATACCGTACTACCGATTGCGAGTCAGTCAGCCGGATTAGATACCCTAGTAGTC |
| (SEQ ID NO: 674) | CCTACGGGAGGCATCAGGCAGATCTCGGATCCTCATGCGTCACCCAAGGTAAGTCAGTCAGCCGGATTAGATACCCTAGTAGTC |

TABLE 3-continued

| | full sequence |
|---|---|
| (SEQ ID NO: 675) | CCTACGGGAGGCATCAGGCAGATCTCGATTATCGTCCCTAGCCAGTCATACAGTCAGTCAGCCGGATTAGATACCCTAGTAGTC |
| (SEQ ID NO: 676) | CCTACGGGAGGCATCAGGCAGATCTCGCCAGACCGCTATTAACGGCGCTCTAGTCAGTCAGCCGGATTAGATACCCTAGTAGTC |
| (SEQ ID NO: 677) | CCTACGGGAGGCATCAGGCAGATCTCGAGCTCTAGAAACGTTTGCTCGAGAAGTCAGTCAGCCGGATTAGATACCCTAGTAGTC |
| (SEQ ID NO: 678) | CCTACGGGAGGCATCAGGCAGATCTCGTCCATCGACGTGCAAACGCACTAAAGTCAGTCAGCCGGATTAGATACCCTAGTAGTC |
| (SEQ ID NO: 679) | CCTACGGGAGGCATCAGGCAGATCTCGCGATGTGTGGTTGAACAAAGAGCGAGTCAGTCAGCCGGATTAGATACCCTAGTAGTC |
| (SEQ ID NO: 680) | CCTACGGGAGGCATCAGGCAGATCTCGGCGAAGTTGGGAGCTAAGTGATGTAGTCAGTCAGCCGGATTAGATACCCTAGTAGTC |
| (SEQ ID NO: 681) | CCTACGGGAGGCATCAGGCAGATCTCGGCATTCGGCGTTAAGGGACAAGTGAGTCAGTCAGCCGGATTAGATACCCTAGTAGTC |
| (SEQ ID NO: 682) | CCTACGGGAGGCATCAGGCAGATCTCGCGCCATTGTGCAAGTGTCGATTCGAGTCAGTCAGCCGGATTAGATACCCTAGTAGTC |
| (SEQ ID NO: 683) | CCTACGGGAGGCATCAGGCAGATCTCGTCCAACTGCAGACTATTAAGCGGCAGTCAGTCAGCCGGATTAGATACCCTAGTAGTC |
| (SEQ ID NO: 684) | CCTACGGGAGGCATCAGGCAGATCTCGTAAAGACCCGTACCTACCATTGTTAGTCAGTCAGCCGGATTAGATACCCTAGTAGTC |
| (SEQ ID NO: 685) | CCTACGGGAGGCATCAGGCAGATCTCGTGTATCTTCACCGAGTCCGTTGCTAGTCAGTCAGCCGGATTAGATACCCTAGTAGTC |
| (SEQ ID NO: 686) | CCTACGGGAGGCATCAGGCAGATCTCGGACTGACTCGTCGATAACTGTACGAGTCAGTCAGCCGGATTAGATACCCTAGTAGTC |
| (SEQ ID NO: 687) | CCTACGGGAGGCATCAGGCAGATCTCGTCGTGGATAGCTTAAACCTGGACAAGTCAGTCAGCCGGATTAGATACCCTAGTAGTC |
| (SEQ ID NO: 688) | CCTACGGGAGGCATCAGGCAGATCTCGGACGCACTAACTCCGAATTGACAAAGTCAGTCAGCCGGATTAGATACCCTAGTAGTC |
| (SEQ ID NO: 689) | CCTACGGGAGGCATCAGGCAGATCTCGGGCGATTTACGTCTGGCATCTAGCAGTCAGTCAGCCGGATTAGATACCCTAGTAGTC |
| (SEQ ID NO: 690) | CCTACGGGAGGCATCAGGCAGATCTCGTAAGGCATCGCTGGTGGTCGTTCTAGTCAGTCAGCCGGATTAGATACCCTAGTAGTC |
| (SEQ ID NO: 691) | CCTACGGGAGGCATCAGGCAGATCTCGACCCATACAGCCACTATGGGCTAAAGTCAGTCAGCCGGATTAGATACCCTAGTAGTC |
| (SEQ ID NO: 692) | CCTACGGGAGGCATCAGGCAGATCTCGCGCACTACGCATGCATTGAGTTCGAGTCAGTCAGCCGGATTAGATACCCTAGTAGTC |
| (SEQ ID NO: 693) | CCTACGGGAGGCATCAGGCAGATCTCGCAGTCGTTAAGAGTTGCTGAGTCCAGTCAGTCAGCCGGATTAGATACCCTAGTAGTC |
| (SEQ ID NO: 694) | CCTACGGGAGGCATCAGGCAGATCTCGCTACGAAAGCCTCTATGGTGAACCAGTCAGTCAGCCGGATTAGATACCCTAGTAGTC |
| (SEQ ID NO: 695) | CCTACGGGAGGCATCAGGCAGATCTCGATAATTGCCGAGGGACCAAGGGATAGTCAGTCAGCCGGATTAGATACCCTAGTAGTC |
| (SEQ ID NO: 696) | CCTACGGGAGGCATCAGGCAGATCTCGGGCATGTTATCGGTATTGGTCAGAAGTCAGTCAGCCGGATTAGATACCCTAGTAGTC |
| (SEQ ID NO: 697) | CCTACGGGAGGCATCAGGCAGATCTCGAGGCACAGTAGGAGAACCGTCATAAGTCAGTCAGCCGGATTAGATACCCTAGTAGTC |
| (SEQ ID NO: 698) | CCTACGGGAGGCATCAGGCAGATCTCGCTACTTACATCCAACTGGAACCCTAGTCAGTCAGCCGGATTAGATACCCTAGTAGTC |
| (SEQ ID NO: 699) | CCTACGGGAGGCATCAGGCAGATCTCGCTCTTCTGATCAATACTCGGCTGCAGTCAGTCAGCCGGATTAGATACCCTAGTAGTC |
| (SEQ ID NO: 700) | CCTACGGGAGGCATCAGGCAGATCTCGATGCTAACCACGACGCTTAACGACAGTCAGTCAGCCGGATTAGATACCCTAGTAGTC |
| (SEQ ID NO: 701) | CCTACGGGAGGCATCAGGCAGATCTCGACCAATCTCGGCAGCTTACCGACCAGTCAGTCAGCCGGATTAGATACCCTAGTAGTC |
| (SEQ ID NO: 702) | CCTACGGGAGGCATCAGGCAGATCTCGTATCCAAGCGCAAGGGCTATAGTTAGTCAGTCAGCCGGATTAGATACCCTAGTAGTC |
| (SEQ ID NO: 703) | CCTACGGGAGGCATCAGGCAGATCTCGGTACTGAAGATCTGTCTCGCAAGCAGTCAGTCAGCCGGATTAGATACCCTAGTAGTC |
| (SEQ ID NO: 704) | CCTACGGGAGGCATCAGGCAGATCTCGTCGCCGTGTACACAGCCGCATATCAGTCAGTCAGCCGGATTAGATACCCTAGTAGTC |
| (SEQ ID NO: 705) | CCTACGGGAGGCATCAGGCAGATCTCGAACTGCGATATGGATACGTTCGCAAGTCAGTCAGCCGGATTAGATACCCTAGTAGTC |
| (SEQ ID NO: 706) | CCTACGGGAGGCATCAGGCAGATCTCGCTTCCAACTCATCCAAGATTCGCCAGTCAGTCAGCCGGATTAGATACCCTAGTAGTC |
| (SEQ ID NO: 707) | CCTACGGGAGGCATCAGGCAGATCTCGGAGATCGCCTATGAGGCTGATTTAAGTCAGTCAGCCGGATTAGATACCCTAGTAGTC |
| (SEQ ID NO: 708) | CCTACGGGAGGCATCAGGCAGATCTCGTGTACATCGCCGGAGTTAGCATCAAGTCAGTCAGCCGGATTAGATACCCTAGTAGTC |
| (SEQ ID NO: 709) | CCTACGGGAGGCATCAGGCAGATCTCGTGTTAAGCAGCATGTAGTATAGGCAGTCAGTCAGCCGGATTAGATACCCTAGTAGTC |
| (SEQ ID NO: 710) | CCTACGGGAGGCATCAGGCAGATCTCGACGGCGTTATGTCTCACGCAATGCAGTCAGTCAGCCGGATTAGATACCCTAGTAGTC |
| (SEQ ID NO: 711) | CCTACGGGAGGCATCAGGCAGATCTCGACTTTGCTTTGCGTCCCGTGAAATAGTCAGTCAGCCGGATTAGATACCCTAGTAGTC |
| (SEQ ID NO: 712) | CCTACGGGAGGCATCAGGCAGATCTCGCAAAGCGGTATTGGACAGTGTATTAGTCAGTCAGCCGGATTAGATACCCTAGTAGTC |
| (SEQ ID NO: 713) | CCTACGGGAGGCATCAGGCAGATCTCGCGAAACTACGTAACACGACTATAGAGTCAGTCAGCCGGATTAGATACCCTAGTAGTC |

TABLE 3-continued

| | full sequence |
|---|---|
| (SEQ ID NO: 714) | CCTACGGGAGGCATCAGGCAGATCTCGGAGGACCAGCAAGTGTAGGTGCTTAGTCAGTCAGCCGGATTAGATACCCTAGTAGTC |
| (SEQ ID NO: 715) | CCTACGGGAGGCATCAGGCAGATCTCGAATAGCATGTCGTGAACTAGCGTCAGTCAGTCAGCCGGATTAGATACCCTAGTAGTC |
| (SEQ ID NO: 716) | CCTACGGGAGGCATCAGGCAGATCTCGCGGAGTAATCCTTCCGAGTCACCAAGTCAGTCAGCCGGATTAGATACCCTAGTAGTC |
| (SEQ ID NO: 717) | CCTACGGGAGGCATCAGGCAGATCTCGCTGTGTCCATGGTCCTCTTTGGTCAGTCAGTCAGCCGGATTAGATACCCTAGTAGTC |
| (SEQ ID NO: 718) | CCTACGGGAGGCATCAGGCAGATCTCGCTTCGCGGATGTTCCACCCTCTATAGTCAGTCAGCCGGATTAGATACCCTAGTAGTC |
| (SEQ ID NO: 719) | CCTACGGGAGGCATCAGGCAGATCTCGATAGGCTGTAGTTCGTGACGCTAAAGTCAGTCAGCCGGATTAGATACCCTAGTAGTC |
| (SEQ ID NO: 720) | CCTACGGGAGGCATCAGGCAGATCTCGTGTGTAGCCATGACGGCTAGTTCCAGTCAGTCAGCCGGATTAGATACCCTAGTAGTC |
| (SEQ ID NO: 721) | CCTACGGGAGGCATCAGGCAGATCTCGAAGGGCGCTGAAGCACTGGCATATAGTCAGTCAGCCGGATTAGATACCCTAGTAGTC |
| (SEQ ID NO: 722) | CCTACGGGAGGCATCAGGCAGATCTCGGTTTCCGTGGTGGGCATTAGTTGAAGTCAGTCAGCCGGATTAGATACCCTAGTAGTC |
| (SEQ ID NO: 723) | CCTACGGGAGGCATCAGGCAGATCTCGAGGAACCAGACGCGGTAGTTGATCAGTCAGTCAGCCGGATTAGATACCCTAGTAGTC |
| (SEQ ID NO: 724) | CCTACGGGAGGCATCAGGCAGATCTCGTAATGCCCAGGTTGAAAGCGGCGAAGTCAGTCAGCCGGATTAGATACCCTAGTAGTC |
| (SEQ ID NO: 725) | CCTACGGGAGGCATCAGGCAGATCTCGTATGAACGTCCGGGTTACGGTTACAGTCAGTCAGCCGGATTAGATACCCTAGTAGTC |
| (SEQ ID NO: 726) | CCTACGGGAGGCATCAGGCAGATCTCGCCACATTGGGTCACATCAGGTCACAGTCAGTCAGCCGGATTAGATACCCTAGTAGTC |
| (SEQ ID NO: 727) | CCTACGGGAGGCATCAGGCAGATCTCGTCAGTCAGATGAGTTGATACGATGAGTCAGTCAGCCGGATTAGATACCCTAGTAGTC |
| (SEQ ID NO: 728) | CCTACGGGAGGCATCAGGCAGATCTCGAAGTCACACACACAGACACTTCCGAGTCAGTCAGCCGGATTAGATACCCTAGTAGTC |
| (SEQ ID NO: 729) | CCTACGGGAGGCATCAGGCAGATCTCGGCTGTGATTCGATCACCATCCGAGAGTCAGTCAGCCGGATTAGATACCCTAGTAGTC |
| (SEQ ID NO: 730) | CCTACGGGAGGCATCAGGCAGATCTCGCTAGCTATGGACACCCACCACTAGAGTCAGTCAGCCGGATTAGATACCCTAGTAGTC |
| (SEQ ID NO: 731) | CCTACGGGAGGCATCAGGCAGATCTCGCTTGACGAGGTTCAGAAGGTGTGGAGTCAGTCAGCCGGATTAGATACCCTAGTAGTC |
| (SEQ ID NO: 732) | CCTACGGGAGGCATCAGGCAGATCTCGACCTGGGAATATGAAGCTTGAATCAGTCAGTCAGCCGGATTAGATACCCTAGTAGTC |
| (SEQ ID NO: 733) | CCTACGGGAGGCATCAGGCAGATCTCGCTCTGCCTAATTACTAGGATCAGTAGTCAGTCAGCCGGATTAGATACCCTAGTAGTC |
| (SEQ ID NO: 734) | CCTACGGGAGGCATCAGGCAGATCTCGATATGACCCAGCGCTCCTTAGAAGAGTCAGTCAGCCGGATTAGATACCCTAGTAGTC |
| (SEQ ID NO: 735) | CCTACGGGAGGCATCAGGCAGATCTCGCTCTATTCCACCTCCCATTCCCATAGTCAGTCAGCCGGATTAGATACCCTAGTAGTC |
| (SEQ ID NO: 736) | CCTACGGGAGGCATCAGGCAGATCTCGATTGAGTGAGTCTGGCGTCATTCGAGTCAGTCAGCCGGATTAGATACCCTAGTAGTC |
| (SEQ ID NO: 737) | CCTACGGGAGGCATCAGGCAGATCTCGTTATGGTACGGAAATCCTCGGAGTAGTCAGTCAGCCGGATTAGATACCCTAGTAGTC |
| (SEQ ID NO: 738) | CCTACGGGAGGCATCAGGCAGATCTCGGCTAGTTATGGACTGGACGCATTAAGTCAGTCAGCCGGATTAGATACCCTAGTAGTC |
| (SEQ ID NO: 739) | CCTACGGGAGGCATCAGGCAGATCTCGCAGATTAACCAGACCGATTAGGTAAGTCAGTCAGCCGGATTAGATACCCTAGTAGTC |
| (SEQ ID NO: 740) | CCTACGGGAGGCATCAGGCAGATCTCGGGCTGCATACTCATGTGCTGCTCGAGTCAGTCAGCCGGATTAGATACCCTAGTAGTC |
| (SEQ ID NO: 741) | CCTACGGGAGGCATCAGGCAGATCTCGTTGGTAAAGTGCTACGTACGAAACAGTCAGTCAGCCGGATTAGATACCCTAGTAGTC |
| (SEQ ID NO: 742) | CCTACGGGAGGCATCAGGCAGATCTCGAAGTGGCTATCCATCACATTCTCCAGTCAGTCAGCCGGATTAGATACCCTAGTAGTC |
| (SEQ ID NO: 743) | CCTACGGGAGGCATCAGGCAGATCTCGAACCGATGTACCAGCCTGGTACCTAGTCAGTCAGCCGGATTAGATACCCTAGTAGTC |
| (SEQ ID NO: 744) | CCTACGGGAGGCATCAGGCAGATCTCGTCGATTGGCCGTGCTAAAGTCGTAAGTCAGTCAGCCGGATTAGATACCCTAGTAGTC |
| (SEQ ID NO: 745) | CCTACGGGAGGCATCAGGCAGATCTCGGCATTACTGGACTCTCAGCGCGTAAGTCAGTCAGCCGGATTAGATACCCTAGTAGTC |
| (SEQ ID NO: 746) | CCTACGGGAGGCATCAGGCAGATCTCGTTGGGCCACATAGACCCTAGACCTAGTCAGTCAGCCGGATTAGATACCCTAGTAGTC |
| (SEQ ID NO: 747) | CCTACGGGAGGCATCAGGCAGATCTCGCACACAAAGTCATATTCAGCGGACAGTCAGTCAGCCGGATTAGATACCCTAGTAGTC |
| (SEQ ID NO: 748) | CCTACGGGAGGCATCAGGCAGATCTCGGCCAAGGATAGGGTTCCGGATTAGAGTCAGTCAGCCGGATTAGATACCCTAGTAGTC |
| (SEQ ID NO: 749) | CCTACGGGAGGCATCAGGCAGATCTCGCGCCACGTGTATGCGTGTAATTAGAGTCAGTCAGCCGGATTAGATACCCTAGTAGTC |
| (SEQ ID NO: 750) | CCTACGGGAGGCATCAGGCAGATCTCGGCAACCGATTGTCTGTAGCTTGGCAGTCAGTCAGCCGGATTAGATACCCTAGTAGTC |
| (SEQ ID NO: 751) | CCTACGGGAGGCATCAGGCAGATCTCGCATGTGCTTAGGATGCCTCGTAAGAGTCAGTCAGCCGGATTAGATACCCTAGTAGTC |
| (SEQ ID NO: 752) | CCTACGGGAGGCATCAGGCAGATCTCGGTTCCTCCATTAACCTATGGTGAAAGTCAGTCAGCCGGATTAGATACCCTAGTAGTC |

TABLE 3-continued full sequence

| | |
|---|---|
| (SEQ ID NO: 753) | CCTACGGGAGGCATCAGGCAGATCTCGACCTGTCCTTTCCTGTTACAGCGAAGTCAGTCAGCCGGATTAGATACCCTAGTAGTC |
| (SEQ ID NO: 754) | CCTACGGGAGGCATCAGGCAGATCTCGGTTCACGCCCAACAGTCAGGCCTTAGTCAGTCAGCCGGATTAGATACCCTAGTAGTC |
| (SEQ ID NO: 755) | CCTACGGGAGGCATCAGGCAGATCTCGCGATCGAACACTACTGAGCTGCATAGTCAGTCAGCCGGATTAGATACCCTAGTAGTC |
| (SEQ ID NO: 756) | CCTACGGGAGGCATCAGGCAGATCTCGCATGCCAACATGACGAAGTCTACCAGTCAGTCAGCCGGATTAGATACCCTAGTAGTC |
| (SEQ ID NO: 757) | CCTACGGGAGGCATCAGGCAGATCTCGGAGTACAGTCTAACCGTCTTTCTCAGTCAGTCAGCCGGATTAGATACCCTAGTAGTC |
| (SEQ ID NO: 758) | CCTACGGGAGGCATCAGGCAGATCTCGCCTACATGAGACAGTCTGTCTGCGAGTCAGTCAGCCGGATTAGATACCCTAGTAGTC |
| (SEQ ID NO: 759) | CCTACGGGAGGCATCAGGCAGATCTCGTCCGTGGTATAGCCGCACTCAAGTAGTCAGTCAGCCGGATTAGATACCCTAGTAGTC |
| (SEQ ID NO: 760) | CCTACGGGAGGCATCAGGCAGATCTCGTCTACGGCACGTTGTGGAAACTCCAGTCAGTCAGCCGGATTAGATACCCTAGTAGTC |
| (SEQ ID NO: 761) | CCTACGGGAGGCATCAGGCAGATCTCGATGCTGCAACACTTAGGCAGGTTCAGTCAGTCAGCCGGATTAGATACCCTAGTAGTC |
| (SEQ ID NO: 762) | CCTACGGGAGGCATCAGGCAGATCTCGTTCTCATGGAGGTAAGACTACTGGAGTCAGTCAGCCGGATTAGATACCCTAGTAGTC |
| (SEQ ID NO: 763) | CCTACGGGAGGCATCAGGCAGATCTCGCATAGTGATTGGCGCGAAGTTTCAAGTCAGTCAGCCGGATTAGATACCCTAGTAGTC |
| (SEQ ID NO: 764) | CCTACGGGAGGCATCAGGCAGATCTCGGCTATCAAGACACGATACACTGCCAGTCAGTCAGCCGGATTAGATACCCTAGTAGTC |
| (SEQ ID NO: 765) | CCTACGGGAGGCATCAGGCAGATCTCGCCGTGACAACTCTTGAAATCCCGGAGTCAGTCAGCCGGATTAGATACCCTAGTAGTC |
| (SEQ ID NO: 766) | CCTACGGGAGGCATCAGGCAGATCTCGCGTTCCTTGTTAGTTAGGGAGCGAAGTCAGTCAGCCGGATTAGATACCCTAGTAGTC |
| (SEQ ID NO: 767) | CCTACGGGAGGCATCAGGCAGATCTCGGGAATTATCGGTTTACTGTGGCCGAGTCAGTCAGCCGGATTAGATACCCTAGTAGTC |
| (SEQ ID NO: 768) | CCTACGGGAGGCATCAGGCAGATCTCGCATCAAGCATAGATATAAGGCCCAAGTCAGTCAGCCGGATTAGATACCCTAGTAGTC |

In another embodiment, spike-in control compositions are provided for use in a method that simultaneously 1) controls for cross-contamination and/or sample swapping and 2) allows for quantitation while controlling for different GC content samples (e.g., low, balanced, and high GC content). In this embodiment, nucleic acid constructs are used with barcode sequence fragments, and with GC content fragments where the barcode sequence fragments and the GC content fragments are positioned between universal sequence fragments (see FIG. 11). In one embodiment, the barcode sequence fragment is linked at its 3' end to the 5' end of the GC content fragment, and the barcode sequence fragment is linked at its 5' end to a universal sequence fragment while the GC content fragment is linked at its 3' end to a universal sequence fragment. In this embodiment, the GC content fragment can be used to control for polymerase, transposase, ligase, or repair enzyme GC content bias.

Figure 11:
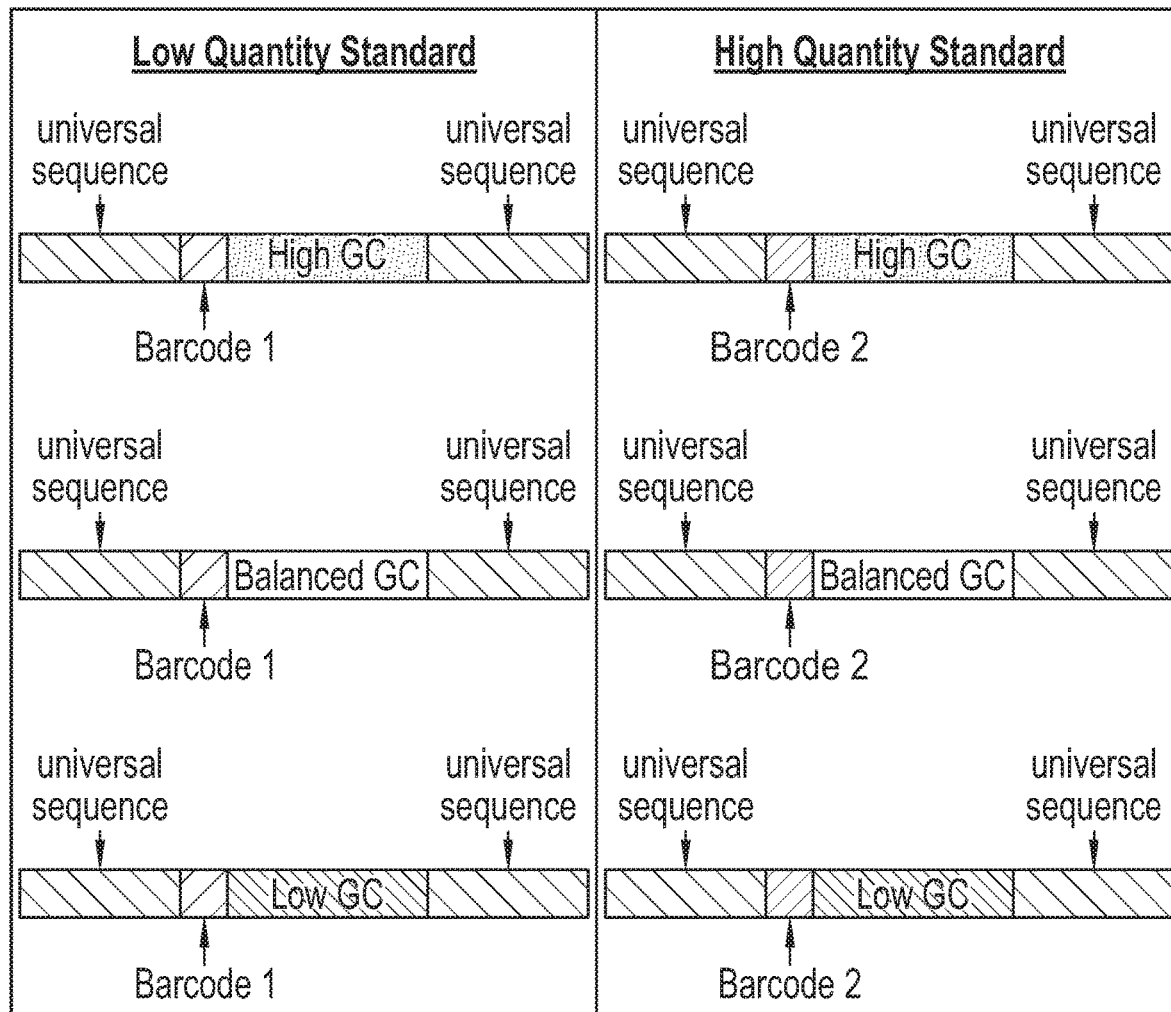
FIG. 11 shows a schematic of exemplary quantification spike-in control nucleic acid constructs where the nucleic acid constructs include universal sequence fragments for bioinformatic analysis, and where exemplary low concentration quantification nucleic acid constructs include a barcode sequence fragment (barcode 1), and exemplary high concentration quantification nucleic acid constructs include a barcode sequence fragment (barcode 2) that is different than the barcode sequence fragment in the low concentration quantification nucleic acid constructs. The schematic also exemplifies nucleic acid constructs with a low GC content fragment, a balanced GC content fragment, and a high GC content fragment.
Figure 12:
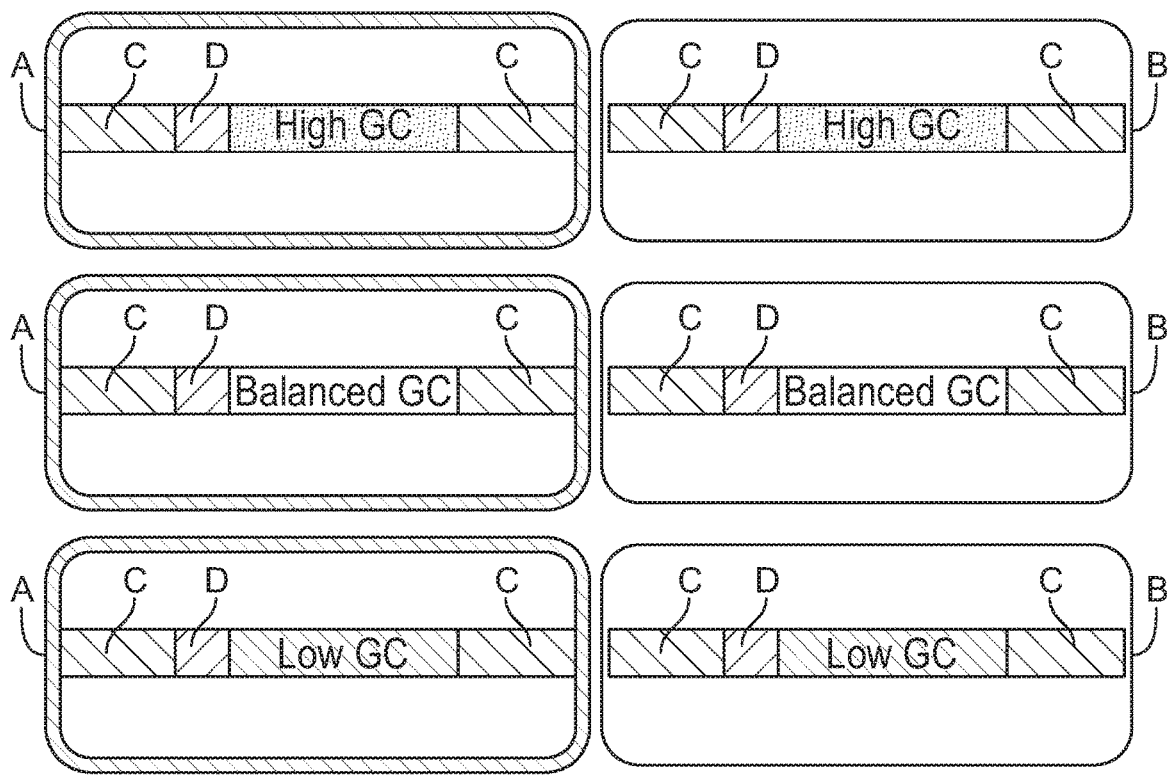
FIG. 12 shows a schematic of exemplary quantification spike-in control nucleic acid constructs encapsulated within simulated cell membranes highly resistant to lysis (A) and within non-resistant (easy to lyse) simulated cell membranes (B). The highly resistant cell membranes (e.g., liposomes) include, for example, lipid formulations with higher crystal transition temperatures, and higher amounts of LPS, PG, teichoic acids, PEG, cholesterol, and/or cationic lipids to condense the nucleic acid constructs. The non-resistant simulated cell membranes may, for example, omit the preceding ingredients or include them to a lesser degree.

By using the same type of nucleic acid construct, but with different barcode sequence fragments, different quantities of the nucleic acid construct can be spiked into samples (see the "Low Quantity Standard" and the "High Quantity Standard" with "Barcode 1" and "Barcode 2", respectively in FIG. 11), and a standard curve for quantitation can be produced. In this quantitation embodiment, the different GC content fragments (e.g., low, balanced, and high GC content) have the same barcode sequence fragment at each GC percentage (e.g., low, balanced, and high GC content), but for each separate concentrations of the nucleic acid constructs used to produce the standard curve (see the "Low Quantity Standard" and the "High Quantity Standard" in FIG. 11), the barcode sequence fragments are different so they can be differentiated post-sequencing. In this quantitation embodiment, the nucleic acid construct can be present at at least two, three, four or five different concentrations for use in generating a standard curve for the quantification of nucleic acids during sequencing.

Various embodiments of the GC content fragments are shown below in Tables 4 through 7.

TABLE 4

| Amplicon based controls | SEQ ID NO: | Forward Primer Binding Site Fragment | 5' Universal Sequence Fragment | Barcode Sequence Fragment | GC Content Fragment | 3' Universal Sequence Fragment | Reverse Primer Binding Site Fragment |
|---|---|---|---|---|---|---|---|
| 20%GC/ 80%ATcontrolseq1 | 2939 | CCTACGGGAGGCAT CAG | GCAGATCTC G | TCCCTTGT CTCCACGA GACTGATT | ATGATTACAGTTAACA GTATCTTAATGATTAC AGTTAACAGTATCTTA | AGTCAGTCA GCC | GGATTAGATACCCTAG TAGTC |
| 50%GC/ 50%ATcontrolseq1 | 2940 | CCTACGGGAGGCAT CAG | GCAGATCTC G | TCCCTTGT CTCCACGA GACTGATT | CTGACTGCAGTTAGCA GTACCTGAATGCTGAC AGTCAGCAGTACCTGA | AGTCAGTCA GCC | GGATTAGATACCCTAG TAGTC |
| 70%GC/ 30%ATcontrolseq1 | 2941 | CCTACGGGAGGCAT CAG | GCAGATCTC G | TCCCTTGT CTCCACGA GACTGATT | CGACGGCTCAGGCCTC AGCGTGGCCGACGGCT GAGGCCTCAGCGTGGC | AGTCAGTCA GCC | GGATTAGATACCCTAG TAGTC |

TABLE 4-continued

| Amplicon based controls | SEQ ID NO: | Forward Primer Binding Site Fragment | 5' Universal Sequence Fragment | Barcode Sequence Fragment | GC Content Fragment | 3' Universal Sequence Fragment | Reverse Primer Binding Site Fragment |
|---|---|---|---|---|---|---|---|
| 20%GC/ 80%ATcontrolseq2 | 2942 | CCTACGGGAGGCAT CAG | GCAGATCTC G | GCTGTACG GATTATCA CCAGGTGT | ATGATTACAGTTAACA GTATCTTAATGATTAC AGTTAACAGTATCTTA | AGTCAGTCA GCC | GGATTAGATACCCTAG TAGTC |
| 50%GC/ 50%ATcontrolseq2 | 2943 | CCTACGGGAGGCAT CAG | GCAGATCTC G | GCTGTACG GATTATCA CCAGGTGT | CTGACTGCAGTTAGCA GTACCTGAATGCTGAC AGTCAGCAGTACCTGA | AGTCAGTCA GCC | GGATTAGATACCCTAG TAGTC |
| 70%GC/ 30%ATcontrolseq2 | 2944 | CCTACGGGAGGCAT CAG | GCAGATCTC G | GCTGTACG GATTATCA CCAGGTGT | CGACGGCTCAGGCCTC AGCGTGGCCGACGGCT GAGGCCTCAGCGTGGC | AGTCAGTCA GCC | GGATTAGATACCCTAG TAGTC |

TABLE 5

| Full sequence |
|---|
| CCTACGGGAGGCATCAGGCAGATCTCGTCCCTTGTCTCCACGAGACTGA TTATGATTACAGTTAACAGTATCTTAATGATTACAGTTAACAGTATCTT AAGTCAGTCAGCCGGATTAGATACCCTAGTAGTC (SEQ ID NO: 2945) |
| CCTACGGGAGGCATCAGGCAGATCTCGTCCCTTGTCTCCACGAGACTGA TTCTGACTGCAGTTAGCAGTACCTGAATGCTGACAGTCAGCAGTACCTG AAGTCAGTCAGCCGGATTAGATACCCTAGTAGTC (SEQ ID NO: 2946) |
| CCTACGGGAGGCATCAGGCAGATCTCGTCCCTTGTCTCCACGAGACTGA TTCGACGGCTCAGGCCTCAGCGTGGCCGACGGCTGAGGCCTCAGCGTGG CAGTCAGTCAGCCGGATTAGATACCCTAGTAGTC (SEQ ID NO: 2947) |
| CCTACGGGAGGCATCAGGCAGATCTCGGCTGTACGGATTATCACCAGGT GTATGATTACAGTTAACAGTATCTTAATGATTACAGTTAACAGTATCTT AAGTCAGTCAGCCGGATTAGATACCCTAGTAGTC (SEQ ID NO: 2948) |
| CCTACGGGAGGCATCAGGCAGATCTCGGCTGTACGGATTATCACCAGGT GTCTGACTGCAGTTAGCAGTACCTGAATGCTGACAGTCAGCAGTACCTG AAGTCAGTCAGCCGGATTAGATACCCTAGTAGTC (SEQ ID NO: 2949) |
| CCTACGGGAGGCATCAGGCAGATCTCGGCTGTACGGATTATCACCAGGT GTCGACGGCTCAGGCCTCAGCGTGGCCGACGGCTGAGGCCTCAGCGTGG CAGTCAGTCAGCCGGATTAGATACCCTAGTAGTC (SEQ ID NO: 2950) |

TABLE 6

| WGS controls | SEQ ID NO: | 5' Universal Sequence Fragment | Barcode Sequence Fragment | GC Content Fragment | 3' Universal Sequence Fragment |
|---|---|---|---|---|---|
| 20%GC/ 80%ATcontrolseq1 | 2951 | GCAGATCTCGTACGCGA A | TCCCTTGTCTCCACGAG ACTGATT | ATGATTACAGTTAACA GTATCTTAATGATTAC AGTTAACAGTATCTTA | GTCATGACAGTCAGTCA GCC |
| 50%GC/ 50%ATcontrolseq1 | 2952 | GCAGATCTCGTACGCGA A | TCCCTTGTCTCCACGAG ACTGATT | CTGACTGCAGTTAGCA GTACCTGAATGCTGAC AGTCAGCAGTACCTGA | GTCATGACAGTCAGTCA GCC |
| 70%GC/ 30%ATcontrolseq1 | 2953 | GCAGATCTCGTACGCGA A | TCCCTTGTCTCCACGAG ACTGATT | CGACGGCTCAGGCCTC AGCGTGGCCGACGGCT GAGGCCTCAGCGTGGC | GTCATGACAGTCAGTCA GCC |
| 20%GC/ 80%ATcontrolseq2 | 2954 | GCAGATCTCGTACGCGA A | GCTGTACGGATTATCAC CAGGTGT | ATGATTACAGTTAACA GTATCTTAATGATTAC AGTTAACAGTATCTTA | GTCATGACAGTCAGTCA GCC |
| 50%GC/ 50%ATcontrolseq2 | 2955 | GCAGATCTCGTACGCGA A | GCTGTACGGATTATCAC CAGGTGT | CTGACTGCAGTTAGCA GTACCTGAATGCTGAC AGTCAGCAGTACCTGA | GTCATGACAGTCAGTCA GCC |
| 70%GC/ 30%ATcontrolseq2 | 2956 | GCAGATCTCGTACGCGA A | GCTGTACGGATTATCAC CAGGTGT | CGACGGCTCAGGCCTC AGCGTGGCCGACGGCT GAGGCCTCAGCGTGGC | GTCATGACAGTCAGTCA GCC |

TABLE 7

Full sequence

GCAGATCTCGTACGCGAATCCCTTGTCTCCACGAGACTGATTATGATTA
CAGTTAACAGTATCTTAATGATTACAGTTAACAGTATCTTAGTCATGAC
AGTCAGTCAGCC
(SEQ ID NO: 2957)

GCAGATCTCGTACGCGAATCCCTTGTCTCCACGAGACTGATTCTGACTG
CAGTTAGCAGTACCTGAATGCTGACAGTCAGCAGTACCTGAGTCATGAC
AGTCAGTCAGCC
(SEQ ID NO: 2958)

GCAGATCTCGTACGCGAATCCCTTGTCTCCACGAGACTGATTCGACGGC
TCAGGCCTCAGCGTGGCCGACGGCTGAGGCCTCAGCGTGGCGTCATGAC
AGTCAGTCAGCC
(SEQ ID NO: 2959)

GCAGATCTCGTACGCGAAGCTGTACGGATTATCACCAGGTGTATGATTA
CAGTTAACAGTATCTTAATGATTACAGTTAACAGTATCTTAGTCATGAC
AGTCAGTCAGCC
(SEQ ID NO: 2960)

GCAGATCTCGTACGCGAAGCTGTACGGATTATCACCAGGTGTCTGACTG
CAGTTAGCAGTACCTGAATGCTGACAGTCAGCAGTACCTGAGTCATGAC
AGTCAGTCAGCC
(SEQ ID NO: 2961)

GCAGATCTCGTACGCGAAGCTGTACGGATTATCACCAGGTGTCGACGGC
TCAGGCCTCAGCGTGGCCGACGGCTGAGGCCTCAGCGTGGCGTCATGAC
AGTCAGTCAGCC
(SEQ ID NO: 2962)

In this quantitation embodiment, the GC content fragment can be from about 100 base pairs in length to about 270 base pairs in length, from about 100 base pairs in length to about 260 base pairs in length, from about 100 base pairs in length to about 250 base pairs in length, from about 100 base pairs in length to about 240 base pairs in length, from about 100 base pairs in length to about 230 base pairs in length, from about 100 base pairs in length to about 220 base pairs in length, from about 100 base pairs in length to about 210 base pairs in length, from about 100 base pairs in length to about 200 base pairs in length, from about 100 base pairs in length to about 190 base pairs in length, from about 100 base pairs in length to about 180 base pairs in length, from about 100 base pairs in length to about 170 base pairs in length, from about 100 base pairs in length to about 160 base pairs in length, from about 100 base pairs in length to about 150 base pairs in length, from about 100 base pairs in length to about 140 base pairs in length, from about 100 base pairs in length to about 130 base pairs in length, from about 100 base pairs in length to about 120 base pairs in length, from about 50 base pairs in length to about 270 base pairs in length, from about 50 base pairs in length to about 260 base pairs in length, from about 50 base pairs in length to about 250 base pairs in length, from about 50 base pairs in length to about 240 base pairs in length, from about 50 base pairs in length to about 230 base pairs in length, from about 50 base pairs in length to about 220 base pairs in length, from about 50 base pairs in length to about 210 base pairs in length, from about 50 base pairs in length to about 200 base pairs in length, from about 50 base pairs in length to about 190 base pairs in length, from about 50 base pairs in length to about 180 base pairs in length, from about 50 base pairs in length to about 170 base pairs in length, from about 50 base pairs in length to about 160 base pairs in length, from about 50 base pairs in length to about 150 base pairs in length, from about 50 base pairs in length to about 140 base pairs in length, from about 50 base pairs in length to about 130 base pairs in length, from about 50 base pairs in length to about 120 base pairs in length, from about 60 base pairs in length to about 120 base pairs in length, from about 70 base pairs in length to about 120 base pairs in length, from about 80 base pairs in length to about 120 base pairs in length, from about 90 base pairs in length to about 120 base pairs in length, or from about 100 base pairs in length to about 120 base pairs in length.

In quantitation embodiments where GC content fragments are present, the GC content of the GC content fragments can vary. As exemplary embodiments, the GC content fragments can have GC contents of about 1 to about 40 percent, about 1 to about 35 percent, about 1 to about 30 percent, about 1 to about 25 percent, about 1 to about 20 percent, about 35 to about 65 percent, about 40 to about 65 percent, about 40 to about 60 percent, about 40 to about 55 percent, about 40 to about 50 percent, about 45 to about 65 percent, about 45 to about 60 percent, about 45 to about 55 percent, about 45 to about 50 percent, about 65 to about 100 percent, about 65 to about 95 percent, about 65 to about 90 percent, about 65 to about 85 percent, about 65 to about 80 percent, about 65 to about 75 percent, about 65 to about 70 percent, about 60 to about 100 percent, about 60 to about 95 percent, about 60 to about 90 percent, about 60 to about 85 percent, about 60 to about 80 percent, about 60 to about 75 percent, or about 60 to about 70 percent. In one aspect, the GC content fragments can have low (e.g., about 1 to about 40 percent), balanced (e.g., about 40 to about 60 percent or about 45 to about 60 percent), or high GC content (e.g., about 60 to about 100 percent or about 65 to about 100 percent). In this quantitation embodiment, the GC content fragments in different nucleic acid constructs can have, for example, at least one, two, three, or four different GC content percentages in the different nucleic acid constructs.

In this quantitation embodiment, the different GC content fragments (e.g., low, balanced, and high GC content) have the same barcode sequence fragment at each GC percentage (e.g., low, balanced, and high GC content), but at each separate concentration of the nucleic acid construct used to produce the standard curve (e.g., "Low Quantity Standard" and the "High Quantity Standard" in FIG. 11), the barcode sequence fragments are unique to each concentration used to produce the standard curve.

In quantitation embodiments for amplicon sequencing, the nucleic acid construct can further comprise at least a first and a second primer binding site fragment. In this aspect, the primers can be any primers of interest. In this embodiment, the first primer binding site fragment is linked at its 3' end to the 5' end of the first universal sequence fragment and the second primer binding site fragment is linked at its 5' end to the 3' end of the second universal sequence fragment. In embodiments for whole genome sequencing, the nucleic acid construct may lack primer binding site fragments. In embodiments where primer binding site fragments are included in the nucleic acid construct, the primer binding site fragments can range in length from about 15 base pairs to about 28 base pairs, from about 15 base pairs to about 26 base pairs, from about 15 base pairs to about 24 base pairs, from about base pairs to about 22 base pairs, from about 15 base pairs to about 20 base pairs, from about 16 base pairs to about 22 base pairs, from about 16 base pairs to about 20 base pairs, from about 17 base pairs to about 20 base pairs, or can be about 18 base pairs.

In an illustrative embodiment of the quantitation embodiment, the nucleic acid construct is a deoxyribonucleic acid construct. In another aspect, the nucleic acid construct is a ribonucleic acid. In another embodiment, the nucleic acid construct is incorporated into a plasmid. In yet another embodiment, the nucleic acid construct is incorporated into the genome of an organism.

In all of the various quantitation embodiments described above, the entire nucleic acid construct, not including plasmid sequence if a plasmid is present, can range in length from about 80 base pairs to about 300 base pairs, from about 80 base pairs to about 290 base pairs, from about 80 base pairs to about 280 base pairs, from about 80 base pairs to about 270 base pairs, from about 80 base pairs to about 260 base pairs, from about 80 base pairs to about 250 base pairs, from about 80 base pairs to about 240 base pairs, from about 80 base pairs to about 230 base pairs, from about 80 base pairs to about 220 base pairs, from about 80 base pairs to about 210 base pairs, from about 80 base pairs to about 200 base pairs, from about 80 base pairs to about 190 base pairs, from about 80 base pairs to about 180 base pairs, from about 80 base pairs to about 170 base pairs, or from about 80 base pairs to about 160 base pairs.

In another embodiment, any of the nucleic acids constructs, incorporated into a plasmid or not incorporated or encapsulated or not encapsulated, can be in the form of a kit. In this illustrative aspect, the kit can further comprise a reagent for nucleic acid extraction, a reagent for nucleic acid purification, a reagent for library preparation, a reagent for amplification, a probe (for example for use in exome/targeted hybridization sequencing as described below), a reagent for sequencing, a reagent for chemical analyses, such as mass spectrometry, and/or instructions for use of the kit. In this illustrative embodiment, the kit can comprise more than one of the control compositions for sequencing or chemical analyses wherein each control composition comprises a different nucleic acid construct wherein the different nucleic acid constructs comprise different barcode sequence fragments (e.g., the 384 barcode sequence fragments contained in SEQ ID NOS:1 to 384 or SEQ ID NOS:384 to 768, or, for example, a subset of 96 of these sequences for use in multiplex sequencing applications).

In yet another illustrative aspect, a kit for quantitation of nucleic acids during sequencing can comprise more than one of any of the control compositions described herein wherein each control composition comprises a different nucleic acid construct wherein the different nucleic acid constructs comprise different barcode sequence fragments. In this quantitation embodiment, the nucleic acid constructs comprising different barcode sequence fragments can be spiked into the sample at different concentrations (see the "Low Quantity Standard" and the "High Quantity Standard" with "Barcode 1" and "Barcode 2", respectively in FIG. 11), and a standard curve for quantitation can be produced. In this quantitation embodiment, each separate concentration of the nucleic acid construct used to produce the standard curve has different barcode sequence fragments so that the different concentrations can be differentiated post-sequencing.

Figure 13A:
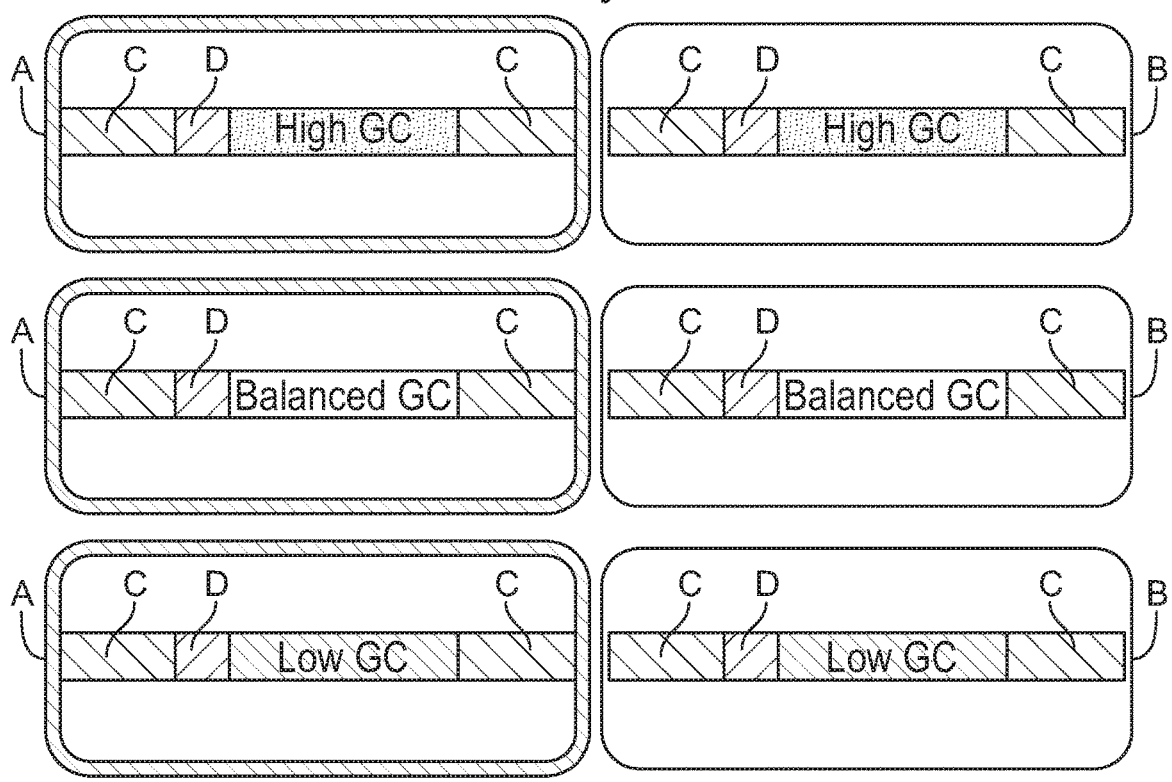
FIGS. 13A and B show a schematic of exemplary low (FIG. 13A) and high (FIG. 13B) concentration quantification nucleic acid constructs encapsulated in different simulated cell membranes to control for differential lysis during sample preparation and processing. Highly resistant (FIG. 13A) and non-resistant (FIG. 13B) simulated cell membranes contain nucleic acid constructs which include universal sequence fragments for bioinformatic analysis (C), a first barcode sequence fragment (barcode 1; D) for the lower concentration constructs, and a second barcode sequence fragment (barcode 2; D) for the higher concentration constructs. The schematic also exemplifies nucleic acid constructs with a low GC content fragment, a balanced GC content fragment, and a high GC content fragment. To apply the quantification standards to amplicon sequencing, a forward primer binding site fragment can be added to the nucleic acid construct on the 5' end of the 5' universal sequence fragment and a reverse primer binding site fragment can be added to the 3' end of the 3' universal sequence fragment. The amplicon sequencing constructs could be either linear or within plasmids.
Figure 13B:
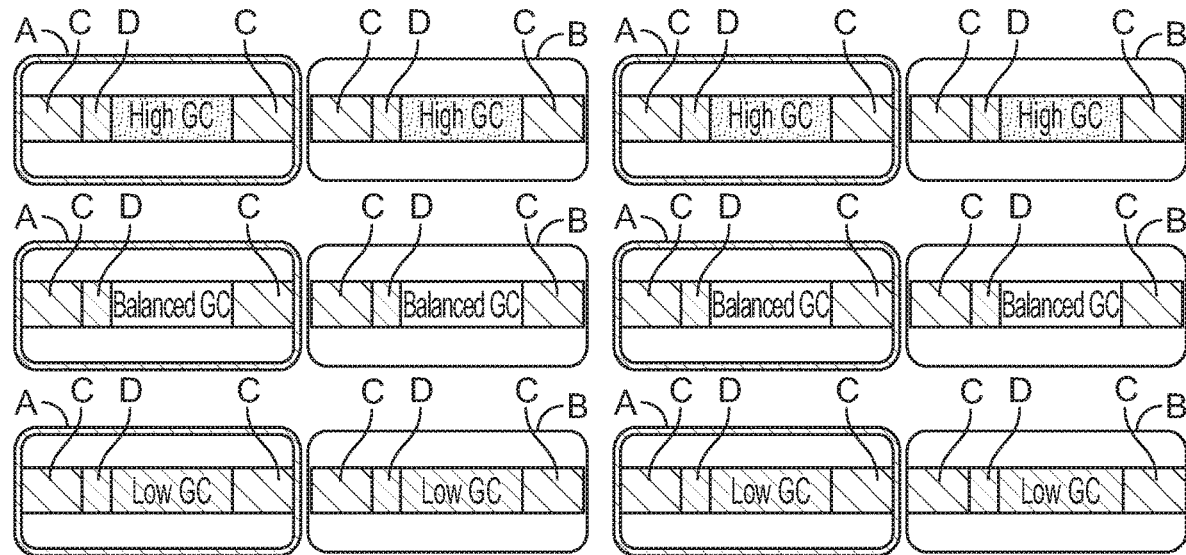
Figure 13B:
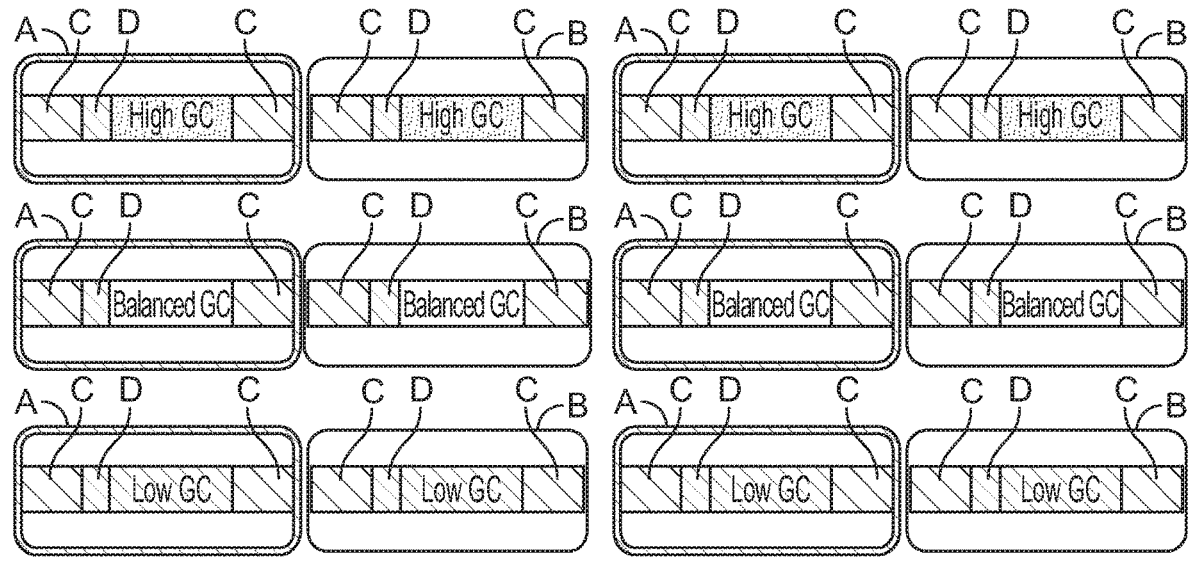

In yet another illustrative aspect, the kits described herein can comprise more than one of any of the control compositions described herein wherein the nucleic acid construct in each control composition is encapsulated in a different type of liposome. In this embodiment, each control composition wherein the nucleic acid construct is encapsulated in a different type of liposome may have a different barcode sequence fragment to differentiate the various types of liposomes post-sequencing (see FIG. 13).

In one embodiment, the probes for use in exome/targeted hybridization sequencing, primers for use in amplicon sequencing, whole genome sequencing, or exome/targeted hybridization sequencing, and the nucleic acid constructs, including nucleic acid constructs incorporated into a plasmid, described herein can be made by methods well-known in the art, including syntheses and recombinant methods. Such techniques are described in Sambrook et al., "Molecular Cloning: A Laboratory Manual", 3rd Edition, Cold Spring Harbor Laboratory Press, (2001), incorporated herein by reference. Plasmids, primers, probes, and the nucleic acid constructs described herein can also be made commercially (e.g., Blue Heron, Bothell, Wash. 98021). Techniques for purifying or isolating the probes, primers, or nucleic acid constructs, including nucleic acid constructs incorporated into a plasmid, described herein are well-known in the art. Such techniques are described in Sambrook et al., "Molecular Cloning: A Laboratory Manual", 3rd Edition, Cold Spring Harbor Laboratory Press, (2001), incorporated herein by reference. The nucleic acid constructs, including nucleic acid constructs incorporated into a plasmid, described herein can be analyzed by techniques known in the art, such as sequencing, to determine if the sequence is correct.

In one illustrative aspect, the nucleic acid construct, incorporated into a plasmid or not incorporated into a plasmid, can be encapsulated. In one exemplary embodiment, the nucleic acid construct, incorporated into a plasmid or not incorporated into a plasmid, can be encapsulated in a liposome, and the liposome can comprise a lipid selected from the group consisting of cholesterol, a cholesterol ester salt, a lipopolysaccharide, a sphingolipid, a peptidoglycan, a phospholipid, any other suitable lipid, and combinations thereof.

In this embodiment, liposomes can be closed, spherical vesicles comprising amphiphilic lipids in proportions such that they arrange themselves into multiple concentric bilayers when hydrated in aqueous solutions. In another aspect, the liposomes can be converted into single bilayer liposomes which are useful carriers of both hydrophilic molecules, which can reside entrapped in the aqueous interior of the liposome, and of hydrophobic molecules, which can reside entrapped in the lipid bilayer. An exemplary hydrophilic chain constituent is polyethylene glycol.

In various embodiments, the lipids can include those having two hydrocarbon chains, typically acyl chains, and a polar head group, such as phospholipids and glycolipids. In this aspect, phospholipids may include any one type of phospholipid or a combination of phospholipids capable of forming liposomes, including, but not limited to, phosphatidylcholines, phosphatidylethanolamine, phosphatidic acid, phosphatidylinositol, and sphingomyelin, where the two hydrocarbon chains are typically between about 14 to 22 carbons in length, and have varying degrees of unsaturation. The glycolipids include, but are not limited to, cerebrosides and gangliosides. Exemplary phosphatidylcholines, include those obtained from natural sources or those that are partially or wholly synthetic, or are of variable chain length and unsaturation.

In various embodiments, the nucleic acid construct can be encapsulated, incorporated into a plasmid or not incorporated into a plasmid, into a simulated cell membrane that mimics the cell membrane of the microorganism or a eukaryotic cell, or another cell of interest. In one illustrative embodiment, lipids with varying crystal transition temperatures, including cholesterol and lipopolysaccharide, can be incorporated during encapsulation to better mimic the mechanical and material characteristics of a microorganism cell wall (e.g., a bacterial cell wall). In this embodiment, variation in liposome production parameters such as the lipid:DNA ratio, the solvent:non-solvent ratio, and the lipid charge can be used to better tune the liposome composition and size to mimic the cell membrane of the microorganism or a eukaryotic cell, or another cell of interest.

For example, membrane rigidity may be increased with increasing amounts of cholesterol. In one embodiment, this allows the production of a range of liposomes that include easy to lyse (i.e., non-resistant liposomes) through difficult to lyse liposomes (i.e., resistant liposomes). In another embodiment, LPS may be used to mimic Gram-negative bacterial membranes. The hydrated saccharide chains can act as a barrier to hydrophobic species while the phospholipid layer can act as a barrier to hydrophilic species. A periplasm layer of water and peptidoglycan (PG) separates the LPS outer membrane from an inner membrane composed of a more conventional phospholipid lipid bilayer. Polyethylene Glycol (PEG) is a hydrophilic, biologically inert, synthetic material that may confer similar membrane robustness. The PEG can assemble into a brush-like layer on the outer membrane of the liposomes, and act as a hydrated barrier while also increasing the apparent size. Although PEG has been extensively used in liposomes for drug delivery, it may not have been demonstrated as an LPS mimic in an artificial cell. PG, teichoic acids, or similar materials can be added to mimic a Gram-positive cell wall, as the thick PG layers increase lysis resistance. In one aspect, after synthesis, liposome size can be adjusted by extruding the liposomes through a filter membrane with well-defined pore sizes. In this embodiment, the final liposome will comprise small, unilamellar vesicles with a size that is determined by the pore size in the membrane used for extrusion. With no extrusion step, the liposomes may be larger, multi-lamellar liposomes.

In one illustrative aspect, direct encapsulation of the nucleic acid construct without a plasmid or genome backbone (shown schematically in FIG. 7A), may be beneficial for whole genome sequencing applications, because there will not be extraneous DNA that could affect whole genome sequencing using non-targeted approaches.

Figure 6A:
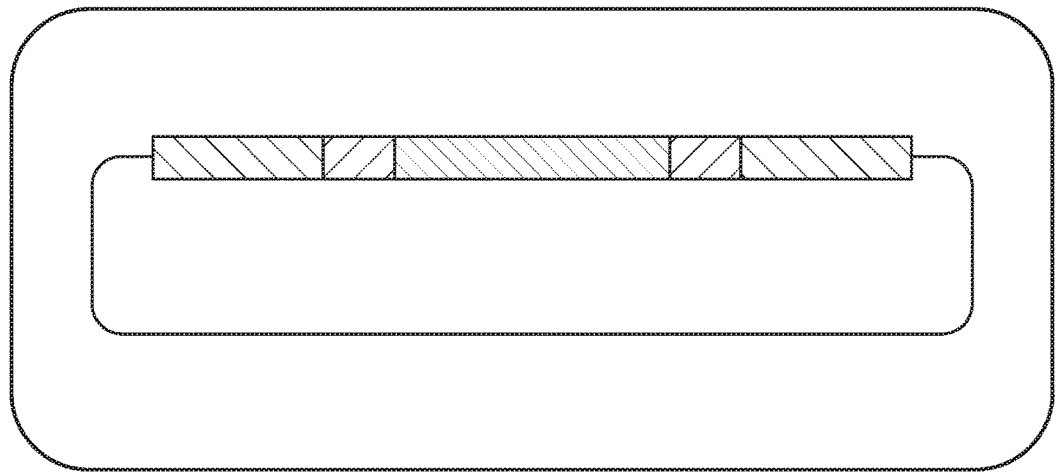
FIG. 6A shows schematically the exemplary nucleic acid construct of FIG. 5 as described herein cloned into a plasmid for amplicon sequencing applications.
Figure 6B:
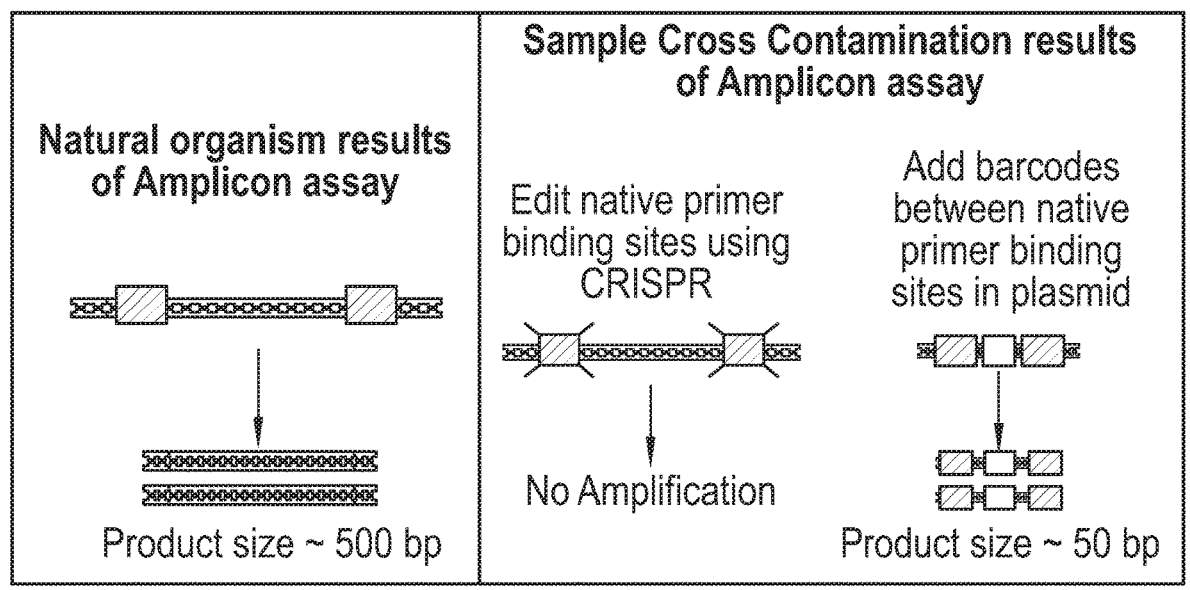
FIG. 6B shows schematically the exemplary nucleic acid construct of FIG. 5 as described herein inserted into the genome of a microorganism. In one aspect, the microorganism could be modified utilizing gene editing (e.g., CRISPR) so that the natural primer binding sites are removed before inserting the nucleic acid construct described herein into the genome of the microorganism.

In all of the encapsulation embodiments described above, encapsulation of the control composition for sequencing or chemical analyses, including the nucleic acid construct, or by incorporation into the genome of a cell (e.g., a bacterial or eukaryotic cell) allows for the control composition for sequencing or chemical analyses to be used in every step of sequencing analysis or chemical analyses of an unknown test sample: from extraction to purification to library preparation, sequencing, or chemical analyses, and data analysis because degradation of the control sample can be avoided so that sample cross-contamination and sample swapping can be effectively monitored throughout the protocol. In another aspect for the quantitation embodiments described herein, the nucleic acid constructs can be encapsulated in a simulated cell membrane to control for differential lysis during sample preparation. In another illustrative aspect, encapsulation of the nucleic acid constructs described herein can enable simultaneous quantification that is controlled for extraction efficiency, cross contamination control, and extraction quality control In embodiments where the nucleic acid construct is not artificially encapsulated in, for example, a liposome, the nucleic acid construct can be incorporated into the genome of a microorganism for use as a control composition for sequencing. This embodiment is shown schematically in FIGS. 6A and B as is applicable to amplicon sequencing. If the primer binding sites are present in the microorganism to be utilized, the microorganism could be modified utilizing gene editing, for example, so that the natural primer binding sites are removed (see FIG. 6B). In another embodiment, the barcode sequence fragment could be inserted into the genome of a microorganism between natural primer binding sites. In one aspect, the microorganism could be modified utilizing gene editing so that the sequence between the natural primer binding sites is replaced with the barcode. In one aspect, the CRISPR/Cas9 system for genome editing could be used as well as other genome editing systems, such as ZFNs, custom designed homing endonucleases, and TALENS systems.

The CRISPR/Cas9 system for genome editing has benefits over other genome editing systems. In this embodiment, the Cas9 endonuclease is capable of introducing a double strand break into a DNA target sequence (e.g., the natural primer binding sites described above). In this aspect, the Cas9 endonuclease is guided by the guide polynucleotide (e.g., guide RNA) to recognize and optionally introduce a double strand break at a specific target site into the genome of a cell, such as a microorganism, a eukaryotic cell, or another cell of interest for use in the methods described herein. The Cas9 endonuclease can unwind the DNA duplex in close proximity to the genomic target site and cleaves both DNA strands upon recognition of a target sequence by a guide polynucleotide (e.g., guide RNA), but only if the correct protospacer-adjacent motif (PAM) is approximately oriented at the 3' end of the target. In this embodiment, the donor polynucleotide construct (e.g., the nucleic acid construct described herein) can then be incorporated into the genomic target site. Methods for using the CRISPR/Cas9 system for genome editing are well-known in the art.

In one illustrative aspect, for sequencing or chemical analyses, the nucleic acids in the sample (e.g., microorganisms such as bacteria or viruses) and the nucleic acids in the control composition for sequencing or chemical analyses (e.g., the nucleic acid construct incorporated or not incorporated into a plasmid or into the genome of a microorganism), are extracted and purified for analysis. In various embodiments, the preparation of the nucleic acids (e.g., DNA or RNA) can involve rupturing the cells that contain the nucleic acids (e.g., cells of a microorganism or the nucleic acid construct in a simulated cell membrane) and isolating and purifying the nucleic acids (e.g., DNA or RNA) from the lysate. Techniques for rupturing cells and for isolation and purification of nucleic acids (e.g., DNA or RNA) are well-known in the art. In one embodiment, for example, nucleic acids may be isolated and purified by rupturing cells using a detergent or a solvent, such as phenol-chloroform. In another aspect, nucleic acids (e.g., DNA or RNA) may be separated from the lysate by physical methods including, but not limited to, centrifugation, pressure techniques, or by using a substance with an affinity for nucleic acids (e.g., DNA or RNA), such as, for example, beads that bind nucleic acids. In one embodiment, after sufficient washing, the isolated, purified nucleic acids may be suspended in either water or a buffer. In another aspect, the nucleic acids (e.g., DNA or RNA) are "isolated" or "purified" before sequencing. In one embodiment, "isolated" means that the nucleic acids are removed from their normal environment. In another aspect, "purified" in the context of the nucleic acids that are sequenced means the nucleic acids are substantially free of other cellular material, or culture medium, or other chemicals used in the extraction process. In other embodiments, commercial kits are available, such as Qiagen™ (e.g., Qiagen DNeasy PowerSoil Kit™), Nuclisensm™, and Wizard™ (Promega), and Promegam™ for extraction and purification of nucleic acids. Methods for preparing nucleic acids for sequencing or chemical analyses and library preparation are also described in Green and Sambrook, "Molecular Cloning: A Laboratory Manual", 4th Edition, Cold Spring Harbor Laboratory Press, (2012), incorporated herein by reference.

In one illustrative aspect, after preparation for sequencing of the nucleic acids in the sample (e.g., in microorganisms such as bacteria or viruses) and the nucleic acid constructs in the control compositions for sequencing or chemical analyses (e.g., nucleic acid construct incorporated or not incorporated into a plasmid or the genome of a microorganism), a library can be prepared, and the nucleic acids can be sequenced using any suitable sequencing method. In one embodiment, Next Generation Sequencing (e.g., using Illumina, ThermoFisher, or PacBio or Oxford Nanopore Technologies sequencing platforms), sequencing by synthesis, pyrosequencing, nanopore sequencing, or modifications or combinations thereof can be used.

In one embodiment, the sequencing can be amplicon sequencing. In another embodiment, the sequencing can be whole genome sequencing. Whole genome sequencing includes, for example, metagenomics, and is utilized heavily in environmental microbial community research, microbiome research, and cancer or human diagnostics. In another embodiment, the sequencing can be exome/targeted hybridization sequencing.

Figure 8A:
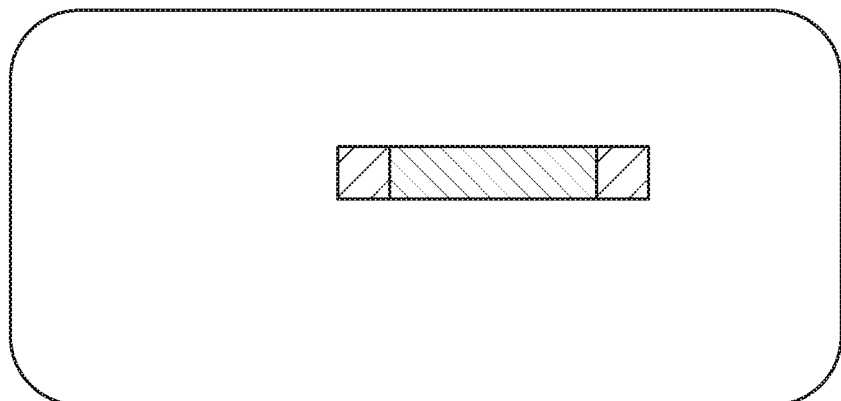
FIG. 8A shows schematically an exemplary construct for exome/targeted hybridization sequencing, encapsulated (e.g., in a liposome). In this example, the nucleic acid construct comprises universal sequence fragments flanking a barcode sequence fragment.
Figure 8B:
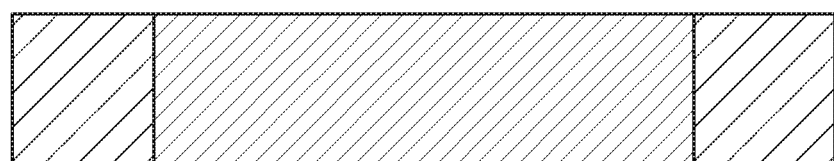
FIG. 8B shows schematically an exemplary probe for exome/targeted hybridization sequencing wherein the probe can be, for example, complementary to the universal sequence fragments (end fragments) with inosines in place of the barcode sequence fragment (middle fragment). Hybridization may occur between the nucleic acid construct of FIG. 8A and the probe of FIG. 8B, and the probe may be a streptavidin sequence probe which binds the sequence of interest, and then is bound to immobilized biotin to enrich the targeted sequences and remove sequences that are not of interest from the library. The targets can then be amplified prior to sequencing.

An exemplary nucleic acid construct and probe for exome/targeted hydridization sequencing is shown schematically in FIGS. 8A and B. In this embodiment, the nucleic acid construct comprises universal sequence fragments and a barcode sequence fragment between the universal sequence fragments (FIG. 8A). In this embodiment, if quantitation is used, GC content fragments can also be included. In this embodiment, the control composition for sequencing can be processed alongside the sample for whole genome sequencing: the control composition for sequencing is spiked into the sample, the DNA is extracted and purified, and a library preparation is conducted. Subsequently a hybridization can occur using streptavidin sequence probes, for example, to bind the nucleic acid construct and other sequences of interest. In this illustrative embodiment, other sequences are removed from the library, and the targets are amplified prior to sequencing. In this embodiment, the probe, at its ends, can be complementary to the universal sequence fragments in the nucleic acid construct, with inosines in the probe in place of the barcode sequence fragment to allow for hybridization of the probe to the universal sequence fragments in the nucleic acid construct. However, no hybridization occurs across the unique barcode sequence fragment to allow for sequencing after the amplification.

In one aspect, libraries can be pooled and concentrated before sequencing. Methods for library preparation and for sequencing are described in Green and Sambrook, "Molecular Cloning: A Laboratory Manual", 4th Edition, Cold Spring Harbor Laboratory Press, (2012), incorporated herein by reference. In one illustrative aspect, after sequencing, the number of reads (i.e., read counts) obtained by sequencing the nucleic acids in the sample or the nucleic acids in the control compositions for sequencing (e.g., nucleic acid construct incorporated or not incorporated into a plasmid or the genome of a microorganism) can be determined.

In various illustrative embodiments, using the control compositions for sequencing or chemical analyses described herein, patient samples or environmental samples (e.g., containing animal, plant, bacteria, viruses, fungi, or archaea) can be analyzed by sequencing or chemical analyses. In accordance with the invention, the term "patient" means a human or an animal, such as a domestic animal (e.g., a dog or a cat). Accordingly, the methods and control compositions for sequencing or chemical analyses described herein can be used, for example, for human clinical medicine (e.g., infectious disease diagnosis, cancer genomics, mendelian genetic testing, and paternity testing), veterinary applications, forensics, environmental or ecological use, and consumer sequencing services such as ancestry DNA, American Gut, or other amplicon sequencing-based technologies that sequence amplicons to determine ancestry or the consumer's microbiome composition.

In various aspects, the patient can be a human, or in the case of veterinary applications, can be a laboratory, agricultural, domestic or wild animal. In one embodiment, the patient can include, but is not limited to, a human, a laboratory animal such as a rodent (e.g., mice, rats, hamsters, etc.), a rabbit, a monkey, a chimpanzee, a domestic animal such as a dog, a cat, and a rabbit, and an agricultural animal such as a cow, a horse, a pig, a sheep, a goat, a chicken, and a wild animal in captivity such as a bear, a panda, a lion, a tiger, a leopard, an elephant, a zebra, a giraffe, a gorilla, a dolphin, and a whale.

In various illustrative embodiments, the samples that can be tested using the control compositions for sequencing or chemical analyses and the methods described herein comprise patient body fluids including, but not limited to, urine, nasal secretions, nasal washes, inner ear fluids, bronchial lavages, bronchial washes, alveolar lavages, spinal fluid, bone marrow aspirates, sputum, pleural fluids, synovial fluids, pericardial fluids, peritoneal fluids, saliva, tears, gastric secretions, stool, reproductive tract secretions, such as seminal fluid, lymph fluid, and whole blood, serum, or plasma, or any other suitable patient sample. In another embodiment, nucleic acids extracted from microorganisms (e.g., bacteria or viruses) isolated or purified from patient samples or environmental samples can be tested using the control compositions for sequencing or chemical analyses and methods described herein. In various embodiments, patient tissue samples that can be tested by using the control compositions for sequencing or chemical analyses and the methods described herein can include tissue biopsies of hospital patients or out-patients and autopsy specimens. As used herein, the term "tissue" includes, but is not limited to, biopsies (including tumor biopsies), autopsy specimens, cell extracts, hair, tissue sections, aspirates, tissue swabs, and fine needle aspirates.

In various illustrative embodiments, environmental samples that can be tested by using the control compositions for sequencing or chemical analyses and the methods described herein can be selected from the group consisting of a soil sample, a water sample, a food sample, an air sample, a plant sample, an industrial waste sample, an agricultural sample, a surface wipe sample, a dust sample, a hair sample, and an animal sample, or any other suitable environmental sample.

In another illustrative embodiment, any of the unencapsulated or encapsulated nucleic acid constructs, incorporated into a plasmid or not incorporated into a plasmid, as described herein may be spiked into a sample that will undergo analysis by an analytical chemistry method, such as mass spectrometry, thermal analysis, electrochemical analysis, chromatographic analysis, and the like. In this embodiment, the analytical chemistry analysis may be quantitative and/or qualitative and the small molecules analyzed may be inorganic or organic compounds. In this aspect, the analysis may be selected from the group consisting of forensic analysis, environmental analysis, industrial analysis (e.g., quality control), or medical analysis. In this illustrative aspect, the nucleic acid construct samples can be extracted and treated in a similar fashion as the analytical chemistry samples, and archived samples, after the analytical chemistry analysis protocol is performed, can be saved for sequencing analysis of the cross-contamination or sample swapping controls. In this embodiment, forensic analysis, for example, may be stomach content analysis, checking blood alcohol content, monitoring substance abuse, toxin analysis, poison analysis, and the like. In this embodiment, the archived samples can be subjected to DNA sequencing to confirm or deny cross-contamination or sample swapping (e.g., at the time of sample collection).

In various illustrative embodiments, the microorganisms present in the patient sample or the environmental sample to be tested can be bacteria or viruses. In this aspect, the bacteria can be selected from Gram-negative and Gram-positive cocci and bacilli, and can comprise antibiotic-resistant bacteria. In another illustrative aspect, the bacteria can be selected from the group consisting of *Pseudomonas* species, *Staphylococcus* species, *Streptococcus* species, *Escherichia* species, *Haemophilus* species, *Neisseria* species, *Chlamydia* species, *Helicobacter* species, *Campylobacter* species, *Salmonella* species, *Shigella* species, *Clostridium* species, *Treponema* species, *Ureaplasma* species, *Listeria* species, *Legionella* species, *Mycoplasma* species, and *Mycobacterium* species, or the group consisting of *S. aureus, P. aeruginosa*, and *E. coli*. In another aspect, the viruses can be selected from DNA and RNA viruses, or can be selected from the group consisting of papilloma viruses, parvoviruses, adenoviruses, herpesviruses, vaccinia viruses, arenaviruses, coronaviruses, rhinoviruses, respiratory syncytial viruses, influenza viruses, picornaviruses, paramyxoviruses, reoviruses, retroviruses, and rhabdoviruses. In another illustrative embodiment, mixtures of any of these microorganisms can be present in the patient sample or the environmental sample. In yet another embodiment, the sample to be tested comprises eukaryotic cells.

In one illustrative aspect, a method is provided using any of the non-quantitation control compositions described herein. The method is for monitoring cross-contamination or sample swapping over all steps of a DNA sequencing protocol including collection of a sample comprising DNA, DNA extraction from the sample, purification of the extracted DNA, library preparation, and sequencing. The method comprises a) spiking the sample with a control composition comprising a nucleic acid construct wherein the nucleic acid construct comprises at least one barcode sequence fragment linked to at least one universal sequence fragment and wherein the nucleic acid construct is a deoxyribonucleic acid construct, b) extracting total DNA wherein total DNA comprises the DNA from the sample and DNA from the nucleic acid construct, c) purifying total DNA, d) preparing a library from total DNA, e) sequencing the extracted, purified total DNA, and f) detecting the nucleic acid construct in total DNA.

In another embodiment, a method is provided using any of the quantitation control compositions described herein that contain GC content fragments, where the method is for monitoring sample cross-contamination and/or sample swapping and for quantification of nucleic acids during sequencing. The method comprises a) extracting DNA from a sample, b) purifying the DNA, c) spiking the sample, after DNA extraction and purification and before library preparation, with a control composition comprising a nucleic acid construct wherein the nucleic acid construct comprises at least one barcode sequence fragment, at least one universal sequence fragment, and at least one GC content fragment, and wherein the nucleic acid construct is a deoxyribonucleic acid construct, wherein total DNA is obtained after spiking the sample, and wherein total DNA comprises the DNA from the sample and the DNA from the nucleic acid construct, d) preparing a library from total DNA, e) sequencing total DNA, and f) detecting and quantifying the nucleic acid construct in total DNA.

In another embodiment, a method is provided using any of the quantitation control compositions described herein that contain GC content fragments. The method is for monitoring sample cross-contamination and/or sample swapping and for quantification of nucleic acids during sequencing. The method comprises a) spiking a sample with a control composition comprising a nucleic acid construct wherein the nucleic acid construct comprises at least one barcode sequence fragment, at least one universal sequence fragment, and at least one GC content fragment and wherein the nucleic acid construct is a deoxyribonucleic acid construct, b) extracting total DNA from the sample wherein total DNA comprises the DNA from the sample and the DNA from the nucleic acid construct, c) purifying total DNA, d) preparing a library from total DNA, e) sequencing total DNA, and f) detecting and quantifying the nucleic acid construct in total DNA.

In another illustrative aspect, a method is provided using any of the non-quantitation control compositions described herein. The method is for monitoring cross-contamination or sample swapping over steps of a DNA sequencing protocol including collection of a sample comprising DNA, DNA extraction from the sample, purification of the extracted DNA, library preparation, and sequencing. The method comprises a) spiking the sample, after DNA extraction and purification and before library preparation, with a control composition comprising a nucleic acid construct wherein the nucleic acid construct comprises at least one barcode sequence fragment, at least one universal sequence fragment, and wherein the nucleic acid construct is a deoxyribonucleic acid construct, wherein total DNA comprises the DNA from the sample and the DNA from the nucleic acid construct, b) extracting total DNA, c) purifying total DNA, d) preparing a library from total DNA, e) sequencing the extracted, purified total DNA, and f) detecting the nucleic acid construct in total DNA.

In another embodiment, a method for monitoring cross-contamination or sample swapping during an analytical chemistry protocol is provided. The method comprises a) spiking an analytical chemistry protocol sample with a control composition comprising a nucleic acid construct wherein the nucleic acid construct comprises at least one barcode sequence fragment linked to at least one universal sequence fragment and wherein the nucleic acid construct is a deoxyribonucleic acid construct; b) performing the analytical chemistry protocol; c) archiving a sample from the analytical chemistry protocol; d) extracting total DNA from the archived sample wherein total DNA comprises the DNA from the nucleic acid construct and DNA from the analytical chemistry protocol sample, if any; e) purifying total DNA; f) preparing a library from total DNA; g) sequencing the extracted, purified total DNA; and h) detecting the nucleic acid construct in total DNA.

Figure 9:
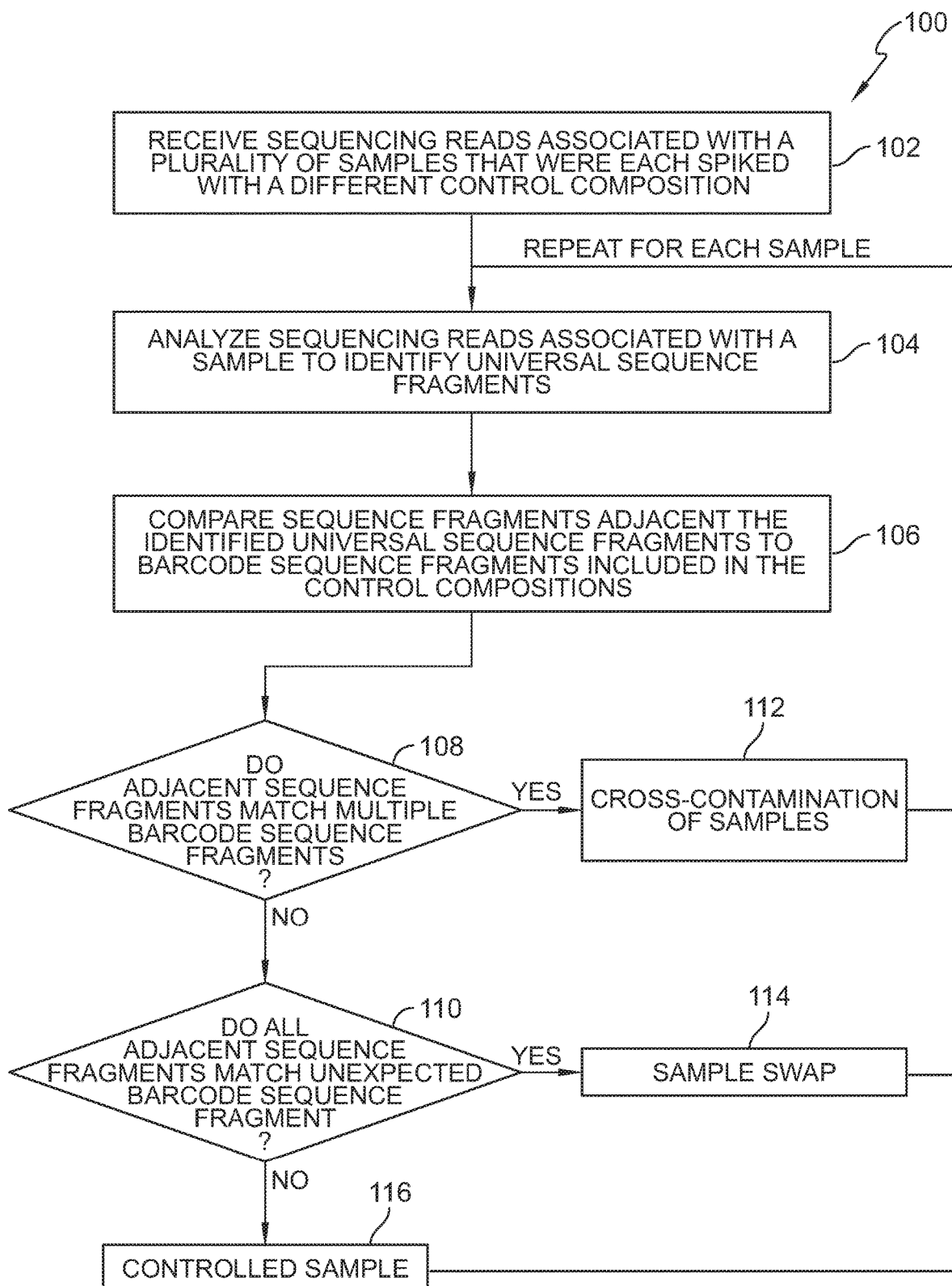
FIG. 9 is a simplified flow diagram illustrating one embodiment of a method for detecting cross-contamination or sample swapping using the presently disclosed control compositions.

Referring now to FIG. 9, an illustrative embodiment of a method 100 for detecting cross-contamination or sample swapping using the presently disclosed control compositions is shown as a simplified flow diagram. The method 100 may be performed by a computing device and, more particularly, a processor of a computing device. As shown in FIG. 9, the method 100 includes a number of steps illustrated as blocks 102-110. It will be appreciated by those of skill in the art that, in other embodiments of the method 100, not all of the blocks 102-110 need be included, the blocks 102-110 may be executed in a different order than that shown in FIG. 9 and described below, and additional or different blocks, other than those shown in FIG. 9, may be included.

In the illustrative embodiment, the method 100 begins with block 102 in which a computing device receives sequencing reads associated a plurality of samples. The sequencing reads received in block 102 will typically have been generated during multiplex sequencing of the plurality of samples. As discussed above, each of the plurality of samples is spiked with a different control composition comprising a different nucleic acid construct, with each different nucleic acid construct comprising a different barcode sequence fragment, to allow for monitoring cross-contamination or sample swapping over all steps of a DNA sequencing protocol being applied to the plurality of samples. As such, the sequencing reads received in block 102 will include sequencing reads of the DNA found in each sample and DNA from the nucleic acid constructs of the control compositions spiked into the samples. Each sequencing read is associated with the sample from which it was read, either by the use of a tag or by grouping in a distinct data structure. Block 102 may involve receiving the sequencing reads in the form of one or more FASTA, FASTQ, or similar files.

After block 102, the method 100 proceeds to block 104 in which the computing device analyzes the sequencing reads associated with a particular sample to identify the presence of one or more universal sequence fragments. As discussed above, universal sequence fragments may be linked to the 5' end and/or the 3' end of the barcode sequence fragment to assist the bioinformatic software in locating and processing the barcode sequence fragments found in the nucleic acid constructs of the control compositions. In some embodiments, block 104 may involve using a text-matching algorithm to identify the presence of one or more universal sequence fragments in the sequencing reads. By way of example, if a 10-base pair universal sequence fragment is included in the nucleic acid constructs of the control compositions, block 104 may involve utilizing a text-matching algorithm to compare each string of 10 characters present in the sequencing reads to the 10 characters representing that 10-base pair universal sequence fragment. In some embodiments, block 104 may also involve referencing a database of universal sequence fragments that may be included in the nucleic acid constructs of the control compositions. In such embodiments, each text string present in the sequencing reads being analyzed may be compared to each of the text strings representing a universal sequence fragment in the database to identify any matches.

After block 104, the method 100 proceeds to block 106 in which the computing device compares sequence fragments that are adjacent the universal sequence fragments identified in block 104 to the barcode sequence fragments included in the nucleic acid constructs of the control compositions spiked into the samples. In some embodiments, where the barcode sequence fragments are linked to two universal sequence fragments (one at the 5' end of the barcode sequence fragment and another at the 3' end of the barcode sequence fragment), block 106 may involve comparing each sequence fragment located between two universal sequence fragments in a sequencing read (identified in block 104) to the barcode sequence fragments included in the nucleic acid constructs of the control compositions. In some embodiments, block 106 may involve using a text-matching algorithm to identify the barcode sequence fragment adjacent the universal sequence fragment(s). By way of example, block 106 may involve utilizing a text-matching algorithm to compare the text string representing the sequence fragment adjacent the universal sequence fragment(s) to a plurality of text strings representing the different barcode sequence fragments included in the nucleic acid constructs of the control compositions spiked into the samples. In some embodiments, block 106 may involve referencing a database of barcode sequence fragments that may be included in the nucleic acid constructs of the control compositions for this purpose.

After block 106, the method 100 proceeds to block 108 in which the computing device determines whether the sequence fragments analyzed in block 106 collectively match multiple barcode sequence fragments included in the nucleic acid constructs of the control compositions spiked into the samples. If no cross-contamination between samples has occurred, all of the barcode sequence fragments found in the sequencing reads associated with a particular sample will be identical and match only the barcode sequence fragment included in the nucleic acid construct of the control composition spiked into that sample. As such, if block 108 determines that the sequence fragments analyzed in block 106 collectively match multiple barcode sequence fragments, the method 100 proceeds to block 112 in which the computing device identifies a cross-contamination condition. If block 108 determines that all of the sequence fragments analyzed in block 106 are identical, the method 100 instead proceeds to block 110.

In block 110 of the method 100, the computing device determines whether the sequence fragments analyzed in block 106 all match an unexpected barcode sequence fragment included in the nucleic acid constructs of the control compositions spiked into the samples. The sequencing reads associated with each sample will be expected to include a particular barcode sequence fragment based upon the nucleic acid construct of the control composition spiked into that sample. As such, if block 110 determines that the sequence fragments analyzed in block 106 all match an unexpected barcode sequence fragment, the method 100 proceeds to block 114 in which the computing device identifies a sample swap condition. If block 110 determines that all of the sequence fragments analyzed in block 106 are identical and match the expected barcode sequence fragment, the method 100 instead proceeds to block 116 in which the computing device identifies a (normal) controlled sample condition.

After reaching any of blocks 112, 114, or 116 for each sample, the method returns to block 104 and repeats blocks 104-116 for the sequencing reads associated with another sample of the plurality of samples. This process repeats until the sequencing reads associated with each of the plurality of samples has been analyzed. As such, at the conclusion of the method 100, each of the plurality of samples will have been identified as subject to a cross-contamination condition, a sample swap condition, or a controlled sample condition.

Figure 10:
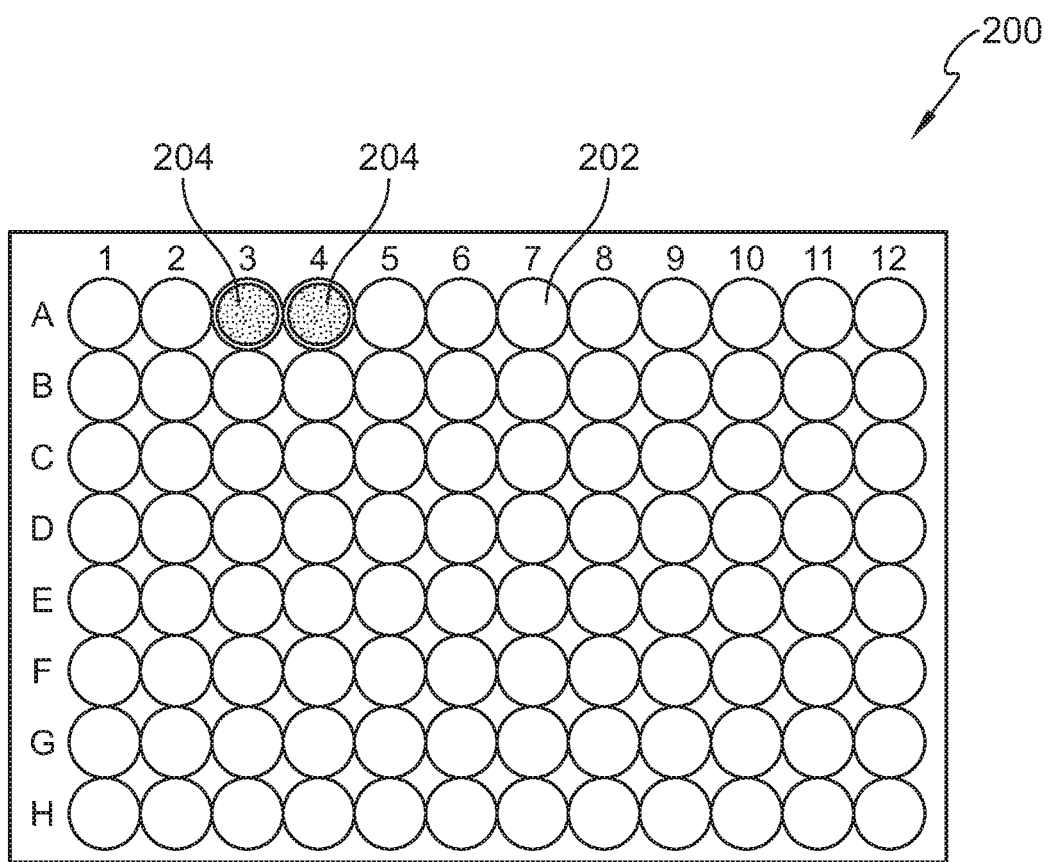
FIG. 10 is one embodiment of a graphic for displaying the results of the method of FIG. 9. Wells that have cross contamination are highlighted. This type of visual aid would enable researchers to identify cross-contamination or sample swapping, and to decide if a full plate will need to be re-run or only a few wells. The darker color in wells 3 and 4 indicates cross-contamination between wells A3 and A4.

FIG. 10 illustrates a simple graphic 200 that may be used for displaying the results of the method 100. In the illustrative embodiment shown in FIG. 10, the graphic 200 appears as a top-down view of 96-well sample plate. As will be appreciated by those skilled in the art, such samples plates are commonly used for multiplex processing and sequencing of a plurality of samples. In FIG. 10, the graphic 200 includes 96 icons 202, 204 (only three of which are labelled for clarity), with each icon 202, 204 representing one of the wells of a 96-well sample plate. It is contemplated that, in other embodiments, the graphic 200 may include greater or fewer icons 202, 204 to represent larger or smaller sample plates and/or a different number of samples being processed.

For each sample identified as subject to a controlled sample condition by the method 100, the graphic 200 includes a first icon 202 at a location corresponding to the well containing that sample. For each sample identified as subject to a cross-contamination condition by the method 100, the graphic 200 includes a second icon 204 at a location corresponding to the well containing that sample. For each sample identified as subject to a sample swap condition by the method 100, the graphic 200 may include a third icon (not shown) at a location corresponding to the well containing that sample. The first icon 202, second 204, and third icon may each be visually distinct from one another, allowing a user observing graphic 200 to quickly identify which samples are subject to which conditions. It is contemplated that in some embodiments, the graphic 200 may provide additional information on each sample, particularly in response to user interaction with the graphic 200. For instance, where a user clicks on and/or hovers over one of the icons 202, 204 with a mouse pointer, the graphic 200 may display additional information related to the sample represented by that icon, such as the barcode sequence fragment(s) found in that sample and their amounts (e.g., in number of reads or percentage of total reads).

The following examples are for illustrative purposes only. The examples are not intended to limit the invention in any way.

Example 1

Protocol for Use of Control Compositions for Sequencing

The goal was to encapsulate the CCC-1 and CCC-2 DNA (see description below) in a synthetic cell wall-like membrane that would mimic a natural bacterium, and to verify the encapsulation through spectrophotometric analysis (UV absorbance, or fluorescence), and then to test the encapsulated CCC-1 and CCC-2 DNA molecules for use as control compositions for sequencing (as described herein) in a spiked soil sample using amplicon sequencing.

Encapsulation Protocol

The Thin Film Hydration method is a viable liposome production method due to its applicability to the small volumes used for pDNA (plasmid DNA—CCC-1 and CCC-2 DNA) samples. Stock pDNA (plasmid DNA—CCC-1 and CCC-2 DNA) was purchased (see below), and only 5 µL of pDNA (at 10 µg/mL) is required for an amplicon sequencing test. The thin film hydration method (without extrusion) yields a small volume of liposomes with good yield.

Materials

| Item | Abbr. |
|---|---|
| Dipalmitoyl-sn-glycero-3-phosphocholine (DPPC) | DPPC |
| Cholesterol | CHOL |
| 1,2-dipalmitoyl-sn-glycero-3-phosphoethanolamine-N-[methoxy(poly(ethylene glycol))]- 2000] (ammonium salt) | DPPE-PEG |
| Lipopolysaccharides (rough strains) from *Escherichia coli* EH100 (Ra mutant) | LPS-Ra |

The encapsulation methods involved generating a standard calibration curve of pDNA in a UV transparent 96-well plate and reading the absorbance at 260 nm. To a micro-vial, 781 µL of ethanol was added. Then 16 µL of pDNA at 841 mg/mL (i.e. ng/µL) was added. The resulting solution was 98% ethanol with 20 µg/mL pDNA. This is the standard solution. CCC-1 and CCC-2 DNA was quantitated as described in FIG. 1 before encapsulation.

200 µL of ethanol was then added to wells B-H of columns 1 and 2 of a 96-well plate. Then 400 µL of the pDNA standard solution was added to well A of columns 1 and 2 of the plate. A 2-fold, 8-step serial dilution was performed, leaving row H as pure ethanol. The absorbance at 260 nm was then read.

To three separate 1-dram glass vials, the mass of lipids shown in Table 8 below was weighed. The actual masses were recorded and the required volume of chloroform was calculated to bring each lipid solution to its target concentration. The required volume of chloroform to add is shown under Vol solvent, add. Then the three lipid solutions were mixed by combining 1.25 mL of each in a single container.

TABLE 8

| Lipid Type | Target mass, $M_{Target}$ (mg) | Target Concentration, $C_{Target}$ (mg/mL) | Actual Mass, $M_{Actual}$ (mg) | $V_{solvent, add}$ (mL) | $V_{stock, add}$ (mL) |
|---|---|---|---|---|---|
| DPPC | 30.9 | 24.701 | 32.5 | 1.316 | 1.25 |
| CHOL | 9.5 | 7.590 | 11 | 1.449 | 1.25 |
| PEG 2000 | 9.6 | 7.710 | 11.6 | 1.505 | 1.25 |
| Chloroform | | | | | 1.25 |

The lipid solution was added to the round bottom flask and the chloroform was removed to yield a thin film. To a 1-dram glass vial, 2.5 mL of Tris-EDTA buffer was added. Then 59 µL of pDNA at 841.7 µg/mL (i.e. ng/µL) was added to the vial, and vortexed briefly to disperse the DNA. Then the pDNA solution (2.5 mL) was added to the flask, and the flask was vortexed at room temperature until the lipid film dissolved. This yielded a white turbid dispersion of pDNA encapsulated in liposomes. The solution was stored in the refrigerator until use.

Spike-In Protocol

Each 0.25 gram soil sample was spiked with either 12.5 ng of CCC-1 DNA, CCC-2 DNA, or a mixture of CCC-1 and CCC-2 DNA, encapsulated as described above. The average size of the encapsulated CCC-1 DNA or CCC-2 DNA (each include a plasmid) was 8±2 µm in diameter, and encapsulation efficiency was demonstrated to be ~85%. The CCC-1 and CCC-2 DNA molecules are plasmids comprising a barcode sequence fragment and were purchased from Blue Heron, Bothell, Wash. 98021. The CCC-1 DNA and CCC-2 DNA sequences, including the plasmid, are shown below as SEQ ID NOS:769 and 770, respectively. The nucleic acid construct sequence within the CCC-1 DNA and CCC-2 DNA sequences are shown below as SEQ ID NOS:771 and 772, respectively.

(SEQ ID NO: 769)
gtaacactggcagagcattacgctgacttgacgggacggcgcaagctcat gaccaaaatcccttaacgtgagttttcgttccactgagcgtcagacccg tagaaaagatcaaaggatcttcttgagatcctttttttctgcgcgtaatc tgctgcttgcaaacaaaaaaaccaccgctaccagcggtggatgatgccgg atcaagagctaccaactcataccgaaggtaactggcttcagctcttatgg -continued tttcccaagctgcggtatcattgcagcactggggccagatggtaagccct cccgtatcgtagttatctacacgacggggagtcaggcaactatggatgaa cgaaatagacagatcgctgagataggtgcctcactgattaagcattggta actgtcagaccaagtttactcatatatacatagattgatttaaaacttca tattaatttaaaaggatctaggtgaagatccatttgataatctcatgacc aaaatcccttaacgtgagattcgaccactgagcgtcagaccccgtagaaa agatcaaaggatcacttgagatcattattctgcgcgtaatctgctgcttg caaacaaaaaaaccaccgctaccagcggtggatgatgccggatcaagagc taccaactattaccgaaggtaactggcttcagcagagcgcagataccaaa tactgttcttctagtgtagccgtagttaggccaccacttcaagaactctg tagcaccgcctacatacctcgctctgctaatcctgttaccagtggctgct gccagtggcgataagtcgtgtcttaccgggttggactcaagacgatagtt accggataaggcgcagcggtcgggctgaacggggggacgtgcacacagcc cagatggagcgaacgacctacaccgaactgagatacctacagcgtgagct atgagaaagcgccacgcacccgaagggagaaaggcggacaggtatccgt aagcggcagggtcggaacaggagagcgcacgagggagcttccaggggaa acgcctggtatctttatagtcctgtcgggtttcgccacctctgacttgag cgtcgatttttgtgatgctcgtcagggggcggagcctatggaaaaacgc cagcaacgcggccatttacggacctggccattgctggccattgctcacat gactacctgcgttatcccctgattctgtggataaccgtattaccgcattg agtgagctgataccgctcgccgcagccgaacgaccgagcgcagcgagtca gtgagcgaggaagcggaagagcgcccaatacgcaaaccgcctctccccgc gcgttggccgattcattaatgcagctggcacgacaggtttcccgactgga aagcgggcagtgagcgcaacgcaattaatgtgagttagctcactcattag gcaccccaggattacactttatgcttccggctcgtatgttgtgtggaatt gtgagcggataacaatttcacacaggaaacagctatgaccatgattacgc caagctgcgatccggatctggatccagatcgggatctggatcaagcagga tcctatctcattccctacgggaggcatcaggcagatctcgtcccagtctc cacgagactgattagtcagtcagccggattagataccctagtagtcgaaa gttgagaccatggaattcgatctggatcttgatccggatcacgatctcga tcaattcactggccgtcgattacaacgtcgtgactgggaaaaccctggcg ttacccaacttaatcgccttgcagcacatccccattcgccagctggcgta atagcgaagaggcccgcaccgatcgccatcccaacagagcgcagcctgaa tggcgaatggcgcctgatgcggtattactccttacgcatctgtgcggtat ttcacaccgcatacgtcaaagcaaccatagtacgcgccctgtagcggcgc attaagcgcggcgggtgtggtggttacgcgcagcgtgaccgctacacttg ccagcgccttagcgcccgctcattcgattcaccatcctactcgcacgtt cgccggcatcccgtcaagctctaaatcggggggctcccataggggaccgat ttagtgattacggcacctcgaccccaaaaaacttgatttgggtgatggtt cacgtagtgggccatcgccctgatagacggtattcgcccatgacgaggag -continued tccacgttattaatagtggactatgaccaaactggaacaacactcaactc tatctcggtcttatggtacccaagctggcctcgtgatacgcctatttta taggttaatgtcatgggggggggggggaaagccacgttgtgtctcaaaat ctctgatgttacattgcacaagataaaaatatatcatcatgaacaataaa actgtctgcttacataaacagtaatacaaggggtgttatgagccatattc aacgggaaacgtcgaggccgcgattaaattccaacatggatgctgattta tatgggtataaatgggctcgcgataatgtcgggcaatcaggtgcgacaat ctatcgcttgtatgggaagcccgatgcgccagagttgtttctgaaacatg gcaaaggtagcgttgccaatgatgttacagatgagatggtcagactaaac tggctgacggaatttatgcctcaccgaccatcaagcatatatccgtactc ctgatgatgcatggttactcaccactgcgatccccggaaaaacagcattc caggtattagaagaatatcctgattcaggtgaaaatattgagatgcgctg gcagtgacctgcgccggagcattcgattcctgatgtaattgtccattaac agcgatcgcgtatttcgtcttgctcaggcgcaatcacgaatgaataacgg tttggttgatgcgagtgattttgatgacgagcgtaatgctggcctgaga acaagtctggaaagaaatgcataaacattgccattctcaccggattcagt cgtcactcatggtgatactcacttgataaccttatattgacgagggaaa ttaataggttgtattgatgttggacgagtcggaatcgcagaccgatacca ggatcttgccatcctatggaactgcctcggtgagattctcatcattacag aaacggctattcaaaaatatggtattgataatcctgatgtgaataaattg cagtttcatttgatgctcgatgagttttctaatcagaattggttaattg gtt (SEQ ID NO: 770)

gtaacactggcagagcattacgctgacttgacgggacggcgcaagctcat gaccaaaatcccttaacgtgagttttcgttccactgagcgtcagaccccg tagaaaagatcaaaggatcttcttgagatcctttttttctgcgcgtaatc tgctgcttgcaaacaaaaaaaccaccgctaccagcggtggatgatgccgg atcaagagctaccaactcataccgaaggtaactggcttcagctcttatgg tttcccaagctgcggtatcattgcagcactggggccagatggtaagccct cccgtatcgtagttatctacacgacggggagtcaggcaactatggatgaa cgaaatagacagatcgctgagataggtgcctcactgattaagcattggta actgtcagaccaagtttactcatatatacatagattgatttaaaacttca tattaatttaaaaggatctaggtgaagatccatttgataatctcatgacc aaaatcccttaacgtgagattcgaccactgagcgtcagaccccgtagaaa agatcaaaggatcacttgagatcattattctgcgcgtaatctgctgcttg caaacaaaaaaaccaccgctaccagcggtggatgatgccggatcaagagc taccaactattaccgaaggtaactggcttcagcagagcgcagataccaaa tactgttcttctagtgtagccgtagttaggccaccacttcaagaactctg tagcaccgcctacatacctcgctctgctaatcctgttaccagtggctgct gccagtggcgataagtcgtgtcttaccgggttggactcaagacgatagtt accggataaggcgcagcggtcgggctgaacggggggacgtgcacacagcc -continued

```
cagatggagcgaacgacctacaccgaactgagatacctacagcgtgagct
atgagaaagcgccacgcacccgaagggagaaaggcggacaggtatccggt
aagcggcagggtcggaacaggagagcgcacgagggagcttccaggggaa
acgcctggtatctttatagtcctgtcgggtttcgccacctctgacttgag
cgtcgattttttgtgatgctcgtcaggggggcggagcctatggaaaaacgc
cagcaacgcggccatttacggacctggccttttgctggccttttgctcac
atgttctttcctgcgttatccctgattctgtggataaccgtattaccgc
attgagtgagctgataccgctcgccgcagccgaacgaccgagcgcagcga
gtcagtgagcgaggaagcggaagagcgcccaatacgcaaaccgcctctcc
ccgcgcgttggccgattcattaatgcagctggcacgacaggtttcccgac
tggaaagcgggcagtgagcgcaacgcaattaatgtgagttagctcactca
ttaggcaccccaggattacactttatgcttccggctcgtatgttgtgtgg
aattgtgagcggataacaatttcacacaggaaacagctatgaccatgatt
acgccaagctgcgatccggatctggatccagatcgggatctggatcaagc
ttggatcctatctcctttccctacgggaggcatcaggcagatctcggctg
tacggattatcaccaggtgtagtcagtcagccggattagatacccctagta
gtcgaaagttgagaccatggaattcgatctggatcttgatccggatcacg
atctcgatcaattcactggccgtcgattacaacgtcgtgactgggaaaac
cctggcgttacccaacttaatcgccttgcagcacatccccattcgccagc
tggcgtaatagcgaagaggcccgcaccgatcgccatcccaacagagcgca
gcctgaatggcgaatggcgcctgatgcggtattactccttacgcatctgt
gcggtatttcacaccgcatacgtcaaagcaaccatagtacgcgccctgta
gcggcgcattaagcgcggcgggtgtggtggttacgcgcagcgtgaccgct
acacttgccagcgccttagcgcccgctcattcgattcaccatcctactcg
ccacgttcgccggcatcccgtcaagctctaaatcgggggctcccatagg
gaccgatttagtgattacggcacctcgaccccaaaaaacttgatttgggt
gatggttcacgtagtgggccatcgccctgatagacggtattcgcccatga
cgaggagtccacgttattaatagtggactatgaccaaactggaacaacac
tcaactctatctcggtcttatggtacccaagctggcctcgtgatacgcct
atttttataggttaatgtcatgggggggggggggaaagccacgttgtgtc
tcaaaatctctgatgttacattgcacaagataaaaatatatcatcatgaa
caataaaactgtctgcttacataaacagtaatacaagggggtgttatgagc
catattcaacgggaaacgtcgaggccgcgattaaattccaacatggatgc
tgatttatatgggtataaatgggctcgcgataatgtcgggcaatcaggtg
cgacaatctatcgcttgtatgggaagcccgatgcgccagagttgtttctg
aaacatggcaaaggtagcgttgccaatgatgttacagatgagatggtcag
actaaactggctgacggaatttatgcctcaccgaccatcaagcatatatc
cgtactcctgatgatgcatggttactcaccactcgcatccccggaaaaac
agcattccaggtattagaagaatatcctgattcaggtgaaaatattgaga
tgcgctggcagtgacctgcgccggagcattcgattcctgatgtaattgtc
cattaacagcgatcgcgtatttcgtcttgctcaggcgcaatcacgaatga
```

```
ataacggtttggttgatgcgagtgattttgatgacgagcgtaatggctgg
cctgagaacaagtctggaaagaaatgcataaacattgccattctcaccgg
attcagtcgtcactcatggtgatactcacttgataaccttatattgacga
ggggaaattaataggttgtattgatgttggacgagtcggaatcgcagacc
gataccaggatcttgccatcctatggaactgcctcggtgagattctcatc
attacagaaacggctattcaaaaatatggtattgataatcctgatgtgaa
taaattgcagtttcatttgatgctcgatgagttttttctaatcagaattgg
ttaattggtt
```

(SEQ ID NO: 771)
CCTACGGGAGGCATCAGGCAGATCTCGTCCCTTGTCTCCACGAGACTGAT
TAGTCAGTCAGCCGGATTAGATACCCTAGTAGTC (SEQ ID NO: 772)
CCTACGGGAGGCATCAGGCAGATCTCGGCTGTACGGATTATCACCAGGTG
TAGTCAGTCAGCCGGATTAGATACCCTAGTAGTC

Extraction and Purification Protocol

The DNA in the spiked soil samples was then extracted using the Qiagen DNeasy PowerSoil Kit™. The Agilent Bioanalyzer confirmed that samples contained amplicon products from both the soil microorganisms of the sample and the nucleic acid construct described herein, based on the different amplicon sizes: 16S (soil sample)=~600 bp and the nucleic acid construct=200 bp (FIGS. 2A and B).

Library Preparation and Sequencing Protocol

Figure 3A:
FIGS. 3A-C show the Krona plot of all soil bacteria present in the CCC-1 DNA-spiked sample (FIG. 3A), the CCC-2 DNA spiked sample (FIG. 3B), and the CCC-1 and CCC-2 DNA mixed spiked sample (FIG. 3C). The figures demonstrate that the spike-in controls do not interfere with the target (i.e., bacterial DNA) amplification or sequencing.
Figure 3B:
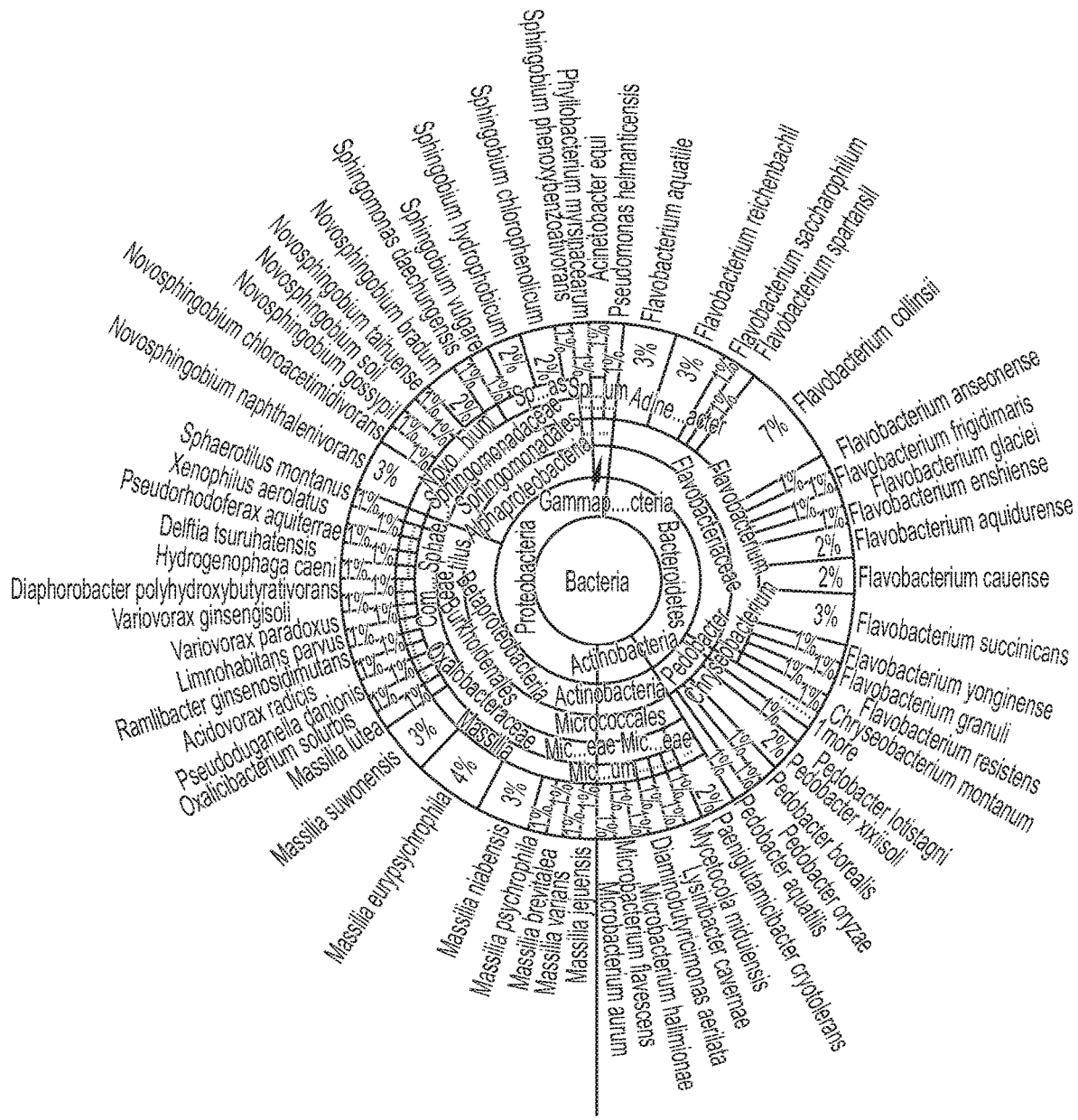
Figure 3C:
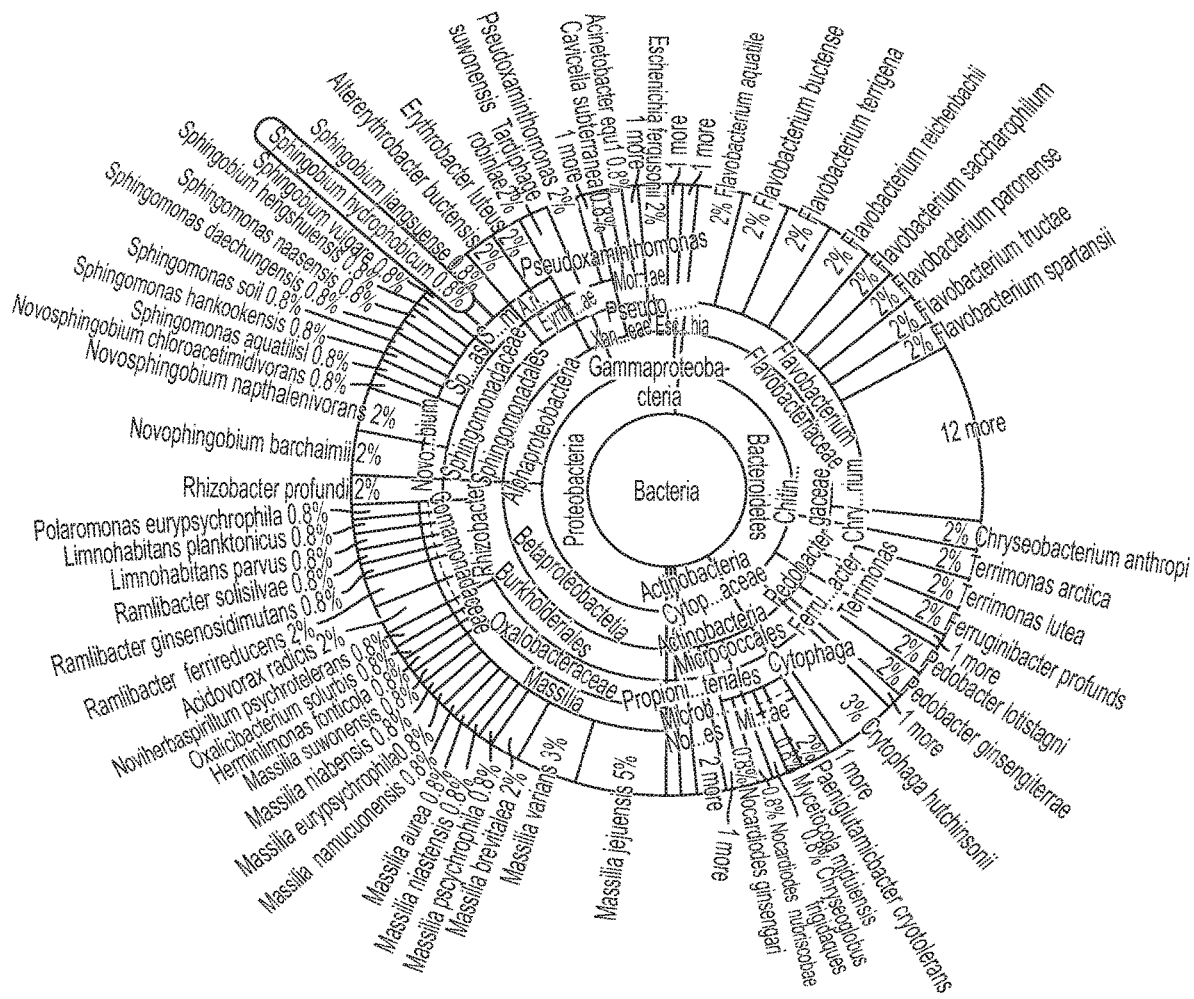

The 16S DNA was amplified and prepared for Illumina NGS sequencing on an Illumina MiSeq. The bead based clean-ups were replaced with MinElute PCR clean up columns. After library preparation, the libraries were visualized on the Agilent Bioanalyzer using the DNA High Sensitivity Assay to check the amplification and size. The libraries were then sequenced on an Illumina MiSeq 300 cycle nanoflow cell. The data was processed and sequencing results showed that the expected microorganisms (FIGS. 3A and B), and both nucleic acid constructs comprising barcode sequence fragments (within CCC-1 DNA and CCC-2 DNA; FIG. 4) were successfully sequenced and present in their specific samples.

Figure 2A:
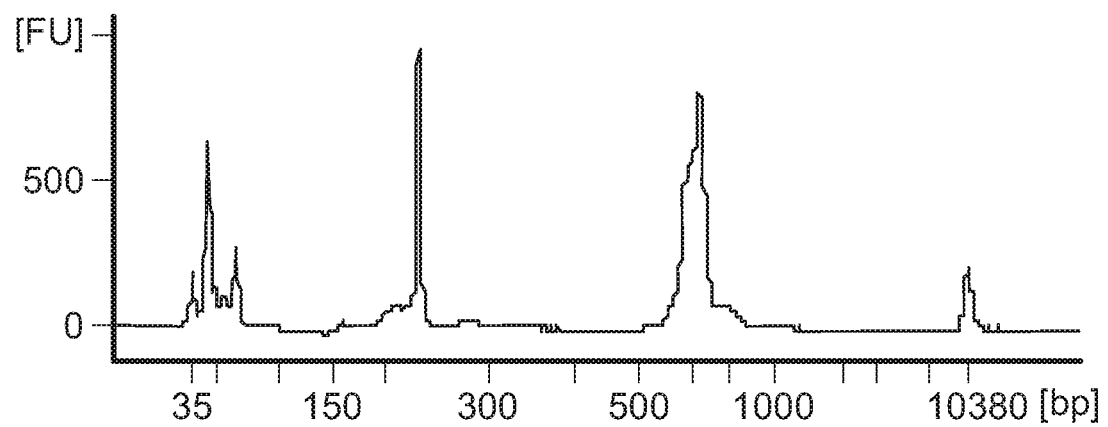
FIGS. 2A-B show the bioanalyzer results of CCC-1 DNA spike-in controls post soil extraction and library preparation (FIG. 2A) and the bioanalyzer results of CCC-1 DNA and CCC-2 DNA (for a description see Example 1) mixed spike-in controls post soil extraction and library preparation (FIG. 2B). Barcoded DNA peaks for the CCC-1 DNA and CCC-2 DNA controls can be seen at ~200 bp and 16S soil sample DNA libraries can be seen ~600 bp.
Figure 2B:
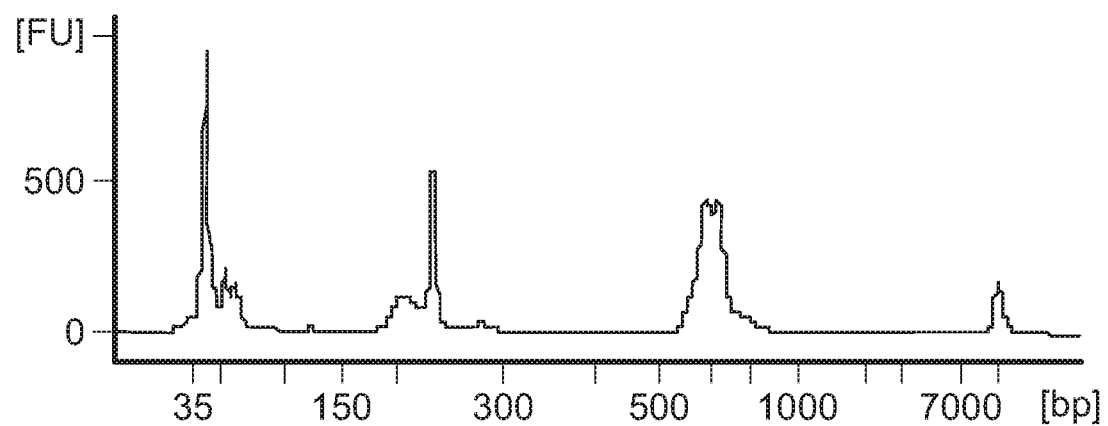

The data shown in FIGS. 2A and B, 3A, B, and C, and 4 are from soil sample DNA extraction assays where the spike-in protocol, the DNA extraction protocol, and the library preparation and sequencing protocols were performed according to the general protocols described above.

Example 2

Exemplary Scale-Up Encapsulation Protocol

Ethanol Injection Method
1. Solvent to be used is ethanol
2. Weigh lipids into 1 dram vials using Table 9 below. Target the mass in column 2 (at least). Record the actual mass in column 3. Calculate the volume of chloroform to add to each lipid as $V_{EtOH,Add}$ (mL)=$M_{Actual}$ (mg)/$[(4*M_{Target}$ (mg)/2 (mL)] and enter it in column 4 (stock volumes). The final result would be a 2 mL sample of a 10 mg/mL lipids solution with a 60:35:5 mole ratio of DPPC:Chol:PEG 2000.

TABLE 9

| Lipid Type | Target mass, $M_{Target}$ (mg) | Actual mass, $M_{Actual}$ (mg) | $V_{solvent, add}$ (mL) | $V_{stock, add}$ (mL) |
|---|---|---|---|---|
| DPPC | 12.4 | | | 0.5 |
| CHOL | 3.8 | | | 0.5 |
| PEG 2000 | 3.8 | | | 0.5 |
| LPS | 0 | | | 0 |
| EtOH | | | | 0.5 |

3. Dissolve lipids in the indicated volumes of ethanol. Then, to a 4 dram vial, add the volumes of each stock solution shown in column 5 of Table 2.
4. In a second 4 dram vial, add 2 mL of 20 mM Citrate buffer, pH 6.0.
5. Heat both to 45° C. in a water bath.
6. Draw both samples into separate 3 mL syringes and connect them to the t-connectors.
7. Using 2 syringe pumps, inject the two solutions into the t-connector a 1 mL/s (60 mL/hr). Collect the mixed solution in a stirred 4 dram vial containing 4 mL of 20 mM Citrate Buffer with 300 mM NaCl.
8. Incubate the resulting solution in a water bath at 37° C. for 30 minutes.
9. Separate the liposomes from free DNA by using sephadex columns.

Example 3

Protocol for Use of Control Compostions for Mass Spectrometry

Analytical chemistry analysis of unknown materials can be confounded by identification of compounds that do not seem to fit with what is expected. These unexpected compounds could be the result of a cross contamination event or may actually be present in the sample. Therefore, the next generation sequencing (NGS) cross contamination controls described herein were tested in a mass spectrometry protocol.

Chemical Sample Composition and Analysis

Mock chemical samples composed of 10 mL MilliQ water spiked with Cannabigerol at 10 ng/mL and Dicamba at 10 ng/mL were prepared for analysis. Two replicates (1A and 1B) were spiked with 20 μL. (240 ng) of cross contamination control 1 (CCC1). Two replicates (2A and 2B) were spiked with 20 μL (240 ng) of cross contamination control 2 (CCC2), and two replicates (3A and 3B) were spiked with 20 μL (240 ng) of CCC1 and 20 μL (240 ng) of CCC2 for a total of six samples for analysis. A negative control blank of water was also prepared and tested. A positive control spiked with Cannabigerol at 10 ng/mL and Dicamba at 10 ng/mL in water was run concurrently with the mock contamination samples. Chemical analysis was performed on a Waters Xevo TQ-XS triple quadrupole mass spectrometer following standard analytical methods for both spiked compounds. The pertinent instrument conditions are shown in Table 10.

TABLE 10

UPLC-MS/MS System Description

| UPLC | Waters Acquity |
|---|---|
| Tandem Mass Spectrometer | Waters Xevo TQ-S |
| Mass Spec Source | Electrospray, negative ion mode |
| Mass Spec Software | Waters MassLynx |
| HPLC Column | Phenomenex Prodigy ODS-3 100 Å 3 μm 2 × 100 mm |
| HPLC Column Temperature | 50° C. |
| Mobile Phase Components | A = 0.1% Formic Acid in Milli-Q Water<br>B = 0.1% Formic Acid in Acetonitrile |

| Gradient Profile | Time, min | % B | Flow rate, mL/min | Curve |
|---|---|---|---|---|
| | 0 | 90 | 0.3 | — |
| | 1 | 90 | 0.3 | 2 |
| | 6 | 10 | 0.3 | 6 |
| | 6.1 | 0 | 0.3 | 6 |
| | 7.0 | 0 | 0.3 | 6 |
| | 7.01 | 90 | 0.4 | 6 |
| | 8 | 90 | 0.4 | 1 |

| Injection Volume | 5 μL |
|---|---|
| Capillary | 0.5 kV |
| Source Temperature | 110° C. |
| Desolvation, nebulizer gas | Nitrogen @ 1000 1/hr and 600° C. |
| Collision gas | Argon @ 0.15 mL/min |
| Mass Resolution | Unit in both quadrupoles |
| Run Time | Approximately 8 min |

Ions

| Compound | Precursor | Cone (V) | Product | Collision (eV) |
|---|---|---|---|---|
| Cannabigerol | 317.2 | 30 | 69.2 | 20 |
| | | | 95.2 | 20 |
| Dicamba | 219 | 10 | 175 | 10 |
| | | | 177 | 10 |

Nucleic Acid Extraction

Encapsulated DNA from the cross-contamination control spike-in mock chemical samples were captured using a 0.22 μM nylon membrane filter (Agilent, Cat. No. R000038111) within a filtration system. The cross-contamination controls were extracted from the nylon membranes using a DNeasy PowerWater Kit (Qiagen, 14900-50-NF) and the DNA was eluted in molecular biology grade water. One tenth of the filtrate volume of 3M sodium acetate pH 5.2 was added to each filtrate. Twice the volume of the filtrate volume of ethanol (Fisher; Cat. No. BP2818-500) was added and incubated overnight at −20° C. Each sample was centrifuged at 16,000×g for 20 minutes at 4° C. and the supernatant was discarded. The DNA pellet was washed with 10 mL of 70% ethanol and centrifuged at 16,000×g for 2 minutes. The alcohol was removed, and the nucleic acid pellet air dried in a BSC until visibly dry (~15-30 minutes). The DNA pellet was suspended using the 100 μL of PowerWater DNA sample prepared using the PowerWater Kit. The extracted DNA was cleaned using a OneStep PCR Inhibitor Removal Kit (Zymo Research; Cat. No. D6030).

Sequencing

The extracted DNA samples, and a non-encapsulated CCC-1 positive control, were amplified using a KAPA HiFi Hot Start Ready Mix (KAPA Biosystems; Cat. No. 07958935001) following the Illumina 16S Metagenomic Sequencing Library Preparation guideline. The thermocycler conditions were as follows: one cycle of 95° C. for 3 minutes, 25 cycles of 95° C. for 0.5 minutes, 55° C. for 0.5 minutes, and 72° C. for 0.5 minutes; and one cycle of 72° C. for 5 minutes. The following 16S rRNA gene-specific primers coupled to Illumina adapter overhang nucleotide sequences were used:

16S Forward Primer =
(SEQ ID NO: 773)
5' TCGTCGGCAGCGTCAGATGTGTATAAGAGACAGCCTACGGGNGGCWG
CAG 3'

16S Reverse Primer =
(SEQ ID NO: 774)
5' GTCTCGTGGGCTCGGAGATGTATATAAGAGACAGGACTACHVGGGTA
TCTAATCC 3'

After amplification, the products were purified using a MinElute PCR Purification Kit (Qiagen; Cat. No. 28006) followed with a SPRISelect (Beckman Coulter; Cat. No. B23317) bead size selection (0.9X Beads). Nextera Dual-index adapters (Illumina; Cat. No. 15055293) were added to the PCR products through amplification with the KAPA HiFi Hot Start Ready Mix (KAPA Biosystems; Cat. No. 07958935001) with the following thermocycler conditions: one cycle of 95° C. for 3 minutes, 8 cycles of 95° C. for 0.5 minutes, 55° C. for 0.5 minutes, and 72° C. for 0.5 minutes; and one cycle of 72° C. for 5 minutes. The libraries were purified using a MinElute PCR Purification Kit (Qiagen; Cat. No. 28006) followed with a SPRISelect (Beckman Coulter; Cat. No. B23317) bead size selection (1.4X Beads). Libraries were quantified using a Qubit dsDNA High Sensitivity kit (Invitrogen; Cat. No. Q32854), analyzed on an Agilent High Sensitivity DNA chip (Agilent; Cat. No. 5067-4627) using a 2100 Bioanalyzer and pooled and normalized to 1 nM with 10 mM Tris-HCl (pH 8.5). Pooled library was denatured using 0.2N NaOH, neutralized with 200 mM Tris-HCl pH 7, diluted to 10 pM with hybridization buffer, and combined with 5% PhiX volume (10 pM). The denatured Phi-X and amplicon library pool was heat denatured at 96° C. before loading onto a 500 cycles MiSeq Nano Kit V2 (Cat. No. MS-103-1003) and was sequenced on an Illumina MiSeq instrument using the 250×250 bp paired-end reads.

Bioinformatics

Data files were downloaded and unzipped for analysis. Cutadapt was run to remove adapters prior to analysis. A Grep search was conducted to identify and count the custom control sequences in each file.

Results

Mock chemical samples containing Cannabigerol and Dicamba were analyzed on a Waters Xevo TQ-XS triple quadrupole mass spectrometer. The MilliQ water negative control came back blank on the MS and the chemical samples all matched the positive control showing there was no influence in the spectra from the presence of the cross-contamination controls (Table 11).

TABLE 11

Spectra results from the spiked chemical samples

| Sample | CBG Concentration (% Recovery) | Dicamba Concentration (% Recovery) |
|---|---|---|
| Blank | Not Detected | Not Detected |
| Positive Control | 8.4 ng/mL (−16.0%) | 8.3 ng/mL (−17.2%) |
| Blank | Not Detected | Not Detected |
| 1A | 14.7 ng/mL (+46.7%) | 8.9 ng/mL (−11.0%) |
| 1B | 15.4 ng/mL (+53.5%) | 8.7 ng/mL (−12.6%) |
| 2A | 12.5 ng/mL (+25.3%) | 10.7 ng/mL (+7.1%) |
| 2B | 9.2 ng/mL (−7.7%) | 10.2 ng/mL (+2.2%) |
| 3A | 9.2 ng/mL (−8.5%) | 11.0 ng/mL (+10.0%) |
| 3B | 17.5 ng/mL (+75.4%) | 11.1 ng/mL (+10.7%) |
| Blank | Not Detected | Not Detected |
| Positive Control | 11.6 ng/mL (+16.0%) | 11.7 ng/mL (+17.2%) |

Results showed acceptable variance at this concentration, which was specifically chosen to be at the lower detection limit of the mass spectrometer. There were no detectable interferences from the mock cross contamination compounds that would suppress or enhance chromatography, or otherwise influence result interpretation by an analyst.

Aliquots from each sample along with a control of CCC1 in water were prepared and sequenced. Adapter sequences, short and low-quality reads were removed prior to data analysis. The reads that passed quality control were counted for CCC1 or CCC2. The number of reads for each cross-contamination control are shown in Table 12.

TABLE 12

Read counts for each cross-contamination control

| Sample | # of CCC1 reads (%) | # of CCC2 reads |
|---|---|---|
| CCC1 | 10768 (99.5%) | 51 (0.4%) |
| 1A | 10502 (99.4%) | 67 (0.6%) |
| 1B | 1808 (99.7%) | 5 (0.2%) |
| 2A | 57 (1.0%) | 5457 (99.0%) |
| 2B | 23 (1.1%) | 1921 (98.8%) |
| 3A | 7559 (75.6%) | 2444 (24.4%) |
| 3B | 6696 (74.1%) | 2343 (25.9%) |

The results show that the cross-contamination controls spiked into the chemical samples do not interfere with chemical analysis and the controls can be detected in analytical chemistry samples when the solvent is water.

SEQUENCE LISTING

The patent contains a lengthy sequence listing. A copy of the sequence listing is available in electronic form from the USPTO web site (https://seqdata.uspto.gov/?pageRequest=docDetail&DocID=US11702653B2). An electronic copy of the sequence listing will also be available from the USPTO upon request and payment of the fee set forth in 37 CFR 1.19(b)(3).

What is claimed is:

1. A method for monitoring sample cross-contamination and/or sample swapping, and for quantitation of nucleic acids during sequencing, the method comprising,
   a) spiking a first sample comprising prokaryotic or eukaryotic cells with a first control composition comprising a first nucleic acid construct wherein the first nucleic acid construct comprises at least one barcode sequence fragment, at least one universal sequence fragment, and at least one GC content fragment, and wherein the first nucleic acid construct is a deoxyribonucleic acid construct;
   b) extracting total DNA from the first sample wherein total DNA comprises the DNA from the first sample and the DNA from the first nucleic acid construct;
   c) purifying total DNA;
   d) preparing a library from total DNA;
   e) sequencing total DNA;
   f) detecting and quantifying the first nucleic acid construct in total DNA;
   g) spiking a second sample comprising the prokaryotic or eukaryotic cells with a second control composition, wherein the second control composition comprises a different nucleic acid construct than the first control composition with a different barcode sequence fragment linked to at least one universal sequence fragment and then performing steps b) to f) for the second sample wherein the second nucleic acid construct is detected and quantified in step f), and wherein detection of the different barcode sequence fragments in the first sample and the second sample is used to determine if cross-contamination between the first sample and the second sample or sample swapping between the first sample and the second sample occurred during sample preparation or processing and wherein the quantification of the GC content fragments in the first sample and the second sample is used to control for enzyme GC content bias; and
   h) comparing the extraction efficiency of the first and second nucleic acid constructs with the extraction efficiency of the DNA in the first and second samples to control for extraction efficiency wherein the first nucleic acid construct and the second nucleic acid construct are separately encapsulated in a simulated cell membrane that mimics the cell membrane of the prokaryotic or eukaryotic cells in the first sample and the second sample to control for extraction efficiency.

2. The method of claim 1 wherein sample cross-contamination and/or sample swapping can be monitored over all steps of a DNA sequencing protocol including collection of the first and second sample, extraction of total DNA, purification of the extracted total DNA, library preparation, and sequencing.

3. The method of claim 1 wherein the first and second control composition comprises nucleic acid constructs with GC content fragments with at least two, at least three, or at least four different percent GC contents.

4. The method of claim 3 wherein the GC content fragment is used to control for polymerase, transposase, ligase, or repair enzyme GC content bias.

5. The method of claim 1 wherein the GC content fragment is used to control for polymerase, transposase, ligase, or repair enzyme GC content bias.

6. The method of claim 1 wherein the first and second nucleic acid construct is present at at least two, at least three, at least four, or at least five different concentrations for use in generating a standard curve for the quantification of nucleic acids during sequencing.

7. The method of claim 1 wherein detecting and quantifying the first and second nucleic acid constructs in total DNA comprises:
   a) identifying each universal sequence fragment in sequencing reads generated by sequencing the total DNA;
   b) identifying the barcode sequence fragment in each sequencing read identified as including a universal sequence fragment; and
   c) counting the number of occurrences of each of the first and second barcode sequence fragments identified in the sequencing reads generated by sequencing the total DNA.

8. The method of claim 7, wherein the identifying steps are performed using a textmatching algorithm.

9. The method of claim 8 wherein identifying each universal sequence fragment comprises referencing a database of universal sequence fragments that may be included in the nucleic acid construct of the control composition.

10. The method of claim 8 wherein each universal sequence fragment comprises referencing a database of universal sequence fragments that may be included in the nucleic acid construct of the control composition.

11. The method of claim 8 further comprising comparing the number of occurrences of each of the first and second barcode sequence fragments identified in the sequencing reads generated by sequencing the total DNA to a known concentration of the nucleic acid constructs comprising the first and second barcode sequence fragments in the control compositions that were used to spike the first and second samples.

12. The method of claim 11 wherein the comparing step comprises referencing a database of barcode sequence fragments that may be included in the nucleic acid construct of the control composition.

13. The method of claim 8 further comprising determining that cross-contamination or sample swapping has occurred in response to identifying the second barcode sequence fragment in the sequencing reads generated by sequencing the total DNA of the first sample or identifying the first barcode sequence fragment in the sequencing reads generated by sequencing the total DNA of the second sample.

14. The method of claim 8 further comprising identifying the GC content fragment in each sequencing read identified as including a universal sequence fragment and counting the number of occurrences of each unique GC content fragment identified in the sequencing reads generated by sequencing the total DNA.

15. The method of claim 14, further comprising comparing the number of occurrences of each unique GC content fragment identified in the sequencing reads generated by sequencing the total DNA to a known concentration of the nucleic acid construct comprising that GC content fragment in the control composition that was used to spike the sample.

16. The method of claim 1 wherein the universal sequence fragment adds length to the nucleic acid construct and is a marker for bioinformatic analysis to identify the beginning and end of the barcode sequence fragment after sequencing.

* * * * *